US007847088B2

(12) United States Patent
Bezerra

(10) Patent No.: US 7,847,088 B2
(45) Date of Patent: Dec. 7, 2010

(54) CLASSIFICATION AND DIAGNOSIS OF THE MOLECULAR BASIS OF CHOLESTASIS

(75) Inventor: Jorge Bezerra, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 12/011,628

(22) Filed: Jan. 28, 2008

(65) Prior Publication Data
US 2008/0254994 A1 Oct. 16, 2008

Related U.S. Application Data

(63) Continuation of application No. PCT/US2006/029372, filed on Jul. 28, 2006.

(60) Provisional application No. 60/703,703, filed on Jul. 29, 2005.

(51) Int. Cl.
C07H 21/04 (2006.01)
C12N 15/11 (2006.01)
C12Q 1/68 (2006.01)

(52) U.S. Cl. .................. 536/24.33; 435/6; 536/23.1; 536/24.3

(58) Field of Classification Search ............... None
See application file for complete search history.

(56) References Cited

U.S. PATENT DOCUMENTS 6,812,339 B1 11/2004 Venter et al.
6,979,557 B2 12/2005 Isogai et al.

FOREIGN PATENT DOCUMENTS

WO PCT/US2006/029372 7/2008

OTHER PUBLICATIONS

Boyer, "Expression of JAGGED1 alleles in patients with Alagille syndrome", Human Genetics, Mar. 2005, p. 445-53, 116(6).
Carlton, "Molecular Basis of Intrahepatic Cholestasis", Annals of Medecine. 2004, p. 606-17, 36(8).
Cutler, "High-Throughput Variation Detection and Genotyping Using Microarrays", Genome Research, Nov. 2001, p. 1913-1925, 11.
Jurkiewicz, "Twelve Novel JAG1 Gene Mutations in polish Alagille syndrome patients", Human Mutations, Mar. 2005, p. 321, 25-3.
Klomp, "Characterization of mutations in ATP8B1 associated with hereditary cholestasis", Hepatology, Jul. 2004, p. 27-38, 40-1.
Lamoril, "Neonatal Hemolytic Anemia Due to Inherited Harderoporphyria: Clinical Characteristics and Molecular Basis", Blood, Feb. 15, 1998, p. 1453-1457, 91-4.
Maitra, "The Human MitoChip: A High-Throughout Sequencing Microarray for Mitochondrial Mutation Detection", Genome Research, 2004, p. 812-819, 14.
Mullenbach, "ATP8B1 mutations in British cases with intrahepatic cholestasis of pregnancy", Gut, Jun. 2005, p. 829-834, 54-6.
Pauli-Magnus, "Sequencing analysis of bile salt export pump (ABCB11) and multidrug resistance p-glycoprotein 3 (ABCB4, MDR3) in patients with intrahepatic cholestasis of pregnancy", Pharmacognetics, Feb. 2004, p. 91-102, 14-2.
Painter, "Sequence variation in ATP8B1 gene and intrahepatic cholestasis of pregnancy", Eur. J. Hum Genet. Apr. 2005, p. 435-439, 13-4.
Trauner, "Genetic disorders and molecular mechanisms in cholestatic liver disease- a clinical approach", Semin Gastrointes Dis. Apr. 2001, p. 66-68, 12-2, Abstract.
Vanberge-Henegouwen, "Relevance of hereditary defects in lipid transport proteins for the pathogenesis of cholesterol gallstone disease", Scand J Gastroenterol Suppl, 2004, p. 60-69, 241.Abstract.
Van Mil, "Benign recurrent intrahepatic cholestasis type 2 is caused by mutations in ABCB11", Gastroenterology, Aug. 2004, p. 379-384, 127-2.
Database Entrez Nucleotide "Homo sapiens chromosome 20" Accession number NC_000020, (2004).
Database Entrez Nucleotide "Homo sapiens chromosome 7" Accession number NC_000007, (2004).
Database EntrezGene "Homo sapiens ATP8B1" (2005).
Database EntrezGene "Homo sapiens ABCB11" (2005).
Database EntrezGene "Homo sapiens SERPINA1" (2005).
GeneChip CustomSeq Resequencing Arrays, Affymetrix, Apr. 2004.
CustomSeq Custom Resequencing Array Design Guide, Affymetrix, (c) 2002-2003.
GeneChip CustomSeq Resequencing Array Protocol version 2.0, Affymetrix (c) 2003-2004.
Bull, "A gene encoding a P-type ATPase mutated in two forms of hereditary cholestasis", Nature Genetics, Mar. 18, 1998, p. 219-224, 18.

Primary Examiner—James Martinell
(74) Attorney, Agent, or Firm—Taft Stettinius & Hollister LLP

(57) ABSTRACT

The methods and compositions of the invention find use in the clinical diagnosis of cholestasis related syndromes, particularly PFIC types 1, 2, and 3; BRIC types 1 and 2; Alagille syndrome, and alpha1-antitrypsin deficiency. The compositions of the invention include isolated nucleic acid molecules and oligonucleotide pairs suitable for use in amplifying regions of cholestasis related genes. Compositions of the invention include a cholestasis related gene resequencing microarray suitable for determining the nucleotide sequence of a region of a cholestasis related gene. Knowledge of the nucleotide sequence of one or more regions of a patient's cholestasis related gene allows diagnosis of the patient's syndrome.

7 Claims, 5 Drawing Sheets

| AMPLICON | ATP8B1 | Regions | TARGET Length | Amplicon Length | Forward Primer | Reverse Primer |
|---|---|---|---|---|---|---|
| 8B1#1 | C20 | Promoter/Exon 1 | 483 | 1601 | B1_3389 | B1_4989 |
| 8B1#2 | C1 | Exon 2-5 | 5593 | 7038 | 8B1_E2-5_L | 8B1_E2-5_R |
| 8B1#3 | C2 | Exon 6-10 | 3330 | 5712 | B1_32900 | B1_38611 |
| 8B1#4 | C3 | Exon 11-14 | 8006 | 8942 | 8B1_E11-14_L | 8B1_E11-14_R |
| 8B1#5 | C19 | Exon 15 | 277 | 1515 | B1_60572f | B1_62086r |
| 8B1#6 | C30 | Exon 16-17 | 2307 | 3289 | B1_64486 | B1_67774 |
| 8B1#7 | C27 | Exon 18-19 | 1493 | 2338 | B1_67745f | B1_70082r |
| 8B1#8 | C23 | Exon 20-21 | 1486 | 2926 | B1_72527f | B1_75452r |
| 8B1#9 | C4 | Exon 22-27 | 6974 | 7946 | B1_80366f | B1_88311r |

FIG. 1A

| | | | SEQ ID NO. |
|---|---|---|---|
| 1 | B1_3389 | CTAGGGAGTGTTCCTGGGAAGTCAGTAAAC | 1 |
| | B1_4989 | GTCAGATATGCTCTCCCAGCCCTTCTTACT | 2 |
| 2 | 8B1_E2-5_L | CTGAGAGCTACAAGGGAGAGATCTGTTCTAGG | 3 |
| | 8B1_E2-5_R | TACCTACCTACACTGGTAAAGAGGAGCTCTGG | 4 |
| 3 | B1_32900 | CCAGAGCTCCTCTTTACCAGTGTAGGTAGGTA | 5 |
| | B1_38611 | GGAGGCTTGCTTCTAAGAGAACTGCCTCTATG | 6 |
| 4 | 8B1_E11-14_L | GTAATCCCAGCTACTCAGGAGGCTGAAGCATA | 7 |
| | 8B1_E11-14_R | GAAGTGAGGGAATGAAGTGAAGGCAGACTACG | 8 |
| 5 | B1_60572f | CTACATGGGAAGATGAGGTAGGAGGATCAC | 9 |
| | B1_62086r | AGATACTGTGGCTACCCCTTTGAGTAGGGAAC | 10 |
| 6 | B1_64486 | TAGCTGGGTGTGGTAACTCACATCTGTAATC | 11 |
| | B1_67774 | CTAATTATACATCCTGGTTGCTGCTCTCCTG | 12 |
| 7 | B1_67745f | AGGAGAGCAGCAACCAGGATGTATAATTAGC | 13 |
| | B1_70082r | CCCACCTAGACTAGATTACAGGGGACCTACAT | 14 |
| 8 | B1_72527f | GGTGGAAGAATAGCTTGAACCTAGGAGGTG | 15 |
| | B1_75452r | CAGAAGCCCTGTCAGTGATACTCTTTCCTC | 16 |
| 9 | B1_80366f | AGGTAGCTGGAAAGTAGATATGAGCTCTGCTG | 17 |
| | B1_88311r | CTGCTTCAGCTTCTCAAATAGGTGGGATTAC | 18 |

FIG. 1B

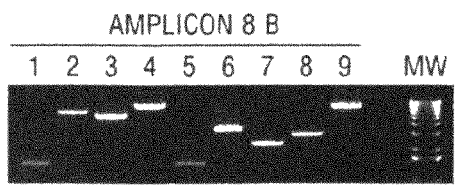

| AMPLICON | ABCB11 | REGIONS | TARGET LENGTH | AMPLICON LENGTH | FORWARD PRIMER | REVERSE PRIMER |
|---|---|---|---|---|---|---|
| B11_#1 | C21 | PROMOTE/EXON 1 | 401 | 2453 | B11_2914 | B11_5366r |
| B11_#2 | C5 | EXON 2-5 | 4925 | 6527 | B11_17390 | B11_23916 |
| B11_#3 | F35 | EXON 6-7 | 1418 | 3450 | B11_38021 | B11_41470 |
| B11_#4 | F36 | EXON 8-9 | 3126 | 4158 | B11_41440 | B11_45597 |
| B11_#5 | C6 | EXON 10-11 | 6463 | 8837 | B11_48005 | B11_56841 |
| B11_#6 | F37 | EXON 12 | 155 | 2101 | B11_58038 | B11_60138 |
| B11_#7 | F20 | EXON 13-17 | 5458 | 7940 | B11_61931 | B11_69870 |
| B11_#8 | C7 | EXON 18-19 | 6389 | 7953 | B11_71757 | B11_79709 |
| B11_#9 | C32 | EXON 20-23 | 9822 | 13583 | B11_88489 | B11_102071 |
| B11_#10 | C33 | EXON 24-28 | 9640 | 14808 | B11_102042 | B11_116849 |

FIG. 2B

| | | | SEQ ID NO. |
|---|---|---|---|
| 1 | B11_2914 | CTCTCTCTCACACAGCATACGTACACACACTC | 19 |
| | B11_5366r | CACCCATGTACACCACTCTCTCTCTCTCTAAG | 20 |
| 2 | B11_17390 | CTGTGCTCTGCTTACTCTTCGGTACTTCTCTG | 21 |
| | B11_23916 | GTGACTGTGTCTGTGTGAGTTCTGGCTACTTC | 22 |
| 3 | B11_38021 | CACTGCTCTTCCCAGCCTCTGTTAACTACT | 23 |
| | B11_41470 | CTCAAGGTCACAGTAAGGAGCAGAGTAAGTGC | 24 |
| 4 | B11_41440 | CACTTACTCTGCTCCTTACTGTGACCTTGAGC | 25 |
| | B11_45597 | GCACAAACTGAGAGACTCAGGGTACTATGC | 26 |
| 5 | B11_48005 | AGAGAGCAGAACAGTGGTTACCAGGGACTT | 27 |
| | B11_56841 | GTGCATACTTCTTTACTGCCTGTCCTCTCC | 28 |
| 6 | B11_58038 | ATAGTCCCAGCTAGTCAGGAGGCTGATATG | 29 |
| | B11_60138 | CTCAGTGTCTTCCACTTTCTGCAGTCTCTG | 30 |
| 7 | B11_61931 | AAGACCTACTAGCCAGCATTCAGCCTCTAC | 31 |
| | B11_69870 | GCTAGGCAGGTTTACCTCTCTCATCCACTAGA | 32 |
| 8 | B11_71757 | CTCTTTCTCCCTCCCTGACTACACTCTGAATC | 33 |
| | B11_79709 | GTGATGGGATTATCTAGTCTCCCCTCTCTC | 34 |
| 9 | B11_88489 | TTAGAGACTTAAGGGCTGCAGGACCAGAGTAG | 35 |
| | B11_102071 | GGAGTGGGAGAGAAGTGCTGAAAGAGATAC | 36 |
| 10 | B11_102042 | GTATCTCTTTCAGCACTTCTCTCCCACTCC | 37 |
| | B11_116849 | ATCTAGCTGACTACTTCCTCTGGGTACAGCAC | 38 |

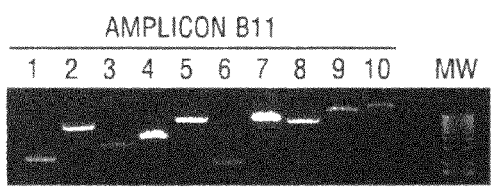

| AMPLICON | ABCB4 | REGIONS | TARGET LENGTH | AMPLICON LENGTH | FORWARD PRIMER | REVERSE PRIMER |
|---|---|---|---|---|---|---|
| B4#1 | C24 | PRO-A1 | 1780 | 2231 | B4_2070 | B4_4300 |
| B4#2 | C28 | EXON A2 TO E2 | 2240 | 2769 | B4_5468f | B4_8236r |
| B4#3 | C29 | EXON 3 | 99 | 1067 | B4_9789 | B4_10855 |
| B4#4 | C8 | EXON 4-5 | 8418 | 9685 | B4_16965f | B4_26649b |
| B4#5 | C9 | EXON 6-9 | 6146 | 7248 | B4_29028f | B4_36275r |
| B4#6 | C10 | EXON 10-14 | 5353 | 8780 | B4_33842f | B4_42621r |
| B4#7 | C31 | EXON 15-18 | 9489 | 11342 | B4_47444f | B4_58785b |
| B4#8 | C11 | EXON 19-23 | 8227 | 9952 | B4_60112f | B4_70063b |
| B4#9 | C12 | EXON 24-28 | 7387 | 8741 | B4_70243f | B4_78983b |

FIG. 3B

| | | | SEQ ID NO. |
|---|---|---|---|
| 1 | B4_2070 | ACCTTAGCCCAGGTCCTTGCACATAGTAAG | 39 |
| | B4_4300 | CACAACCCTCTAGCCCTCTCTCTTTATCAG | 40 |
| 2 | B4_5468f | CTCAGACAGACAGACAGGCAAATACACCTC | 41 |
| | B4_8236r | GGAGGGGTAAGACAAGGAGGAAGAGACATAAC | 42 |
| 3 | B4_9789 | GGGAGTAGGGATGTGGTCAGAGAGGAAATA | 43 |
| | B4_10855 | CATAACTCACTGCAGCCTCAGACTCCTAAGAC | 44 |
| 4 | B4_16965f | TCCCCTCTGTAGGTAGTACTGTGTCCAAGATT | 45 |
| | B4_26649b | AGACACCTTTCAGGCCTTTTAGCATACAGAC | 46 |
| 5 | B4_29028f | CTAAAAGGCCTGAAAGGTGTCTATCTGGAAG | 47 |
| | B4_36275r | GTATATACTAGAAAGTCAGCTCTGCCCACTGGA | 48 |
| 6 | B4_33842f | GTCCAGTGGGCAGAGCTGACTTTCTAGTAT | 49 |
| | B4_42621r | AACCTAGACTCCAGGGCTGAATAGGACTCT | 50 |
| 7 | B4_47444f | AGAGAGCTGTGTTCTAGCCTCTCTCTCTTTCC | 51 |
| | B4_58785b | GAAGTCACACTTCCCCCTGATAAGGAGTCTAC | 52 |
| 8 | B4_60112f | CACCTGTGTCAGAATACTAGCAACTGTTACCC | 53 |
| | B4_70063b | TTTACCCATCTCTACCTTCTATCCCCCTACTC | 54 |
| 9 | B4_70243f | CCTAGAAGACAGCTTTAGGCAGTACAGGGAAG | 55 |
| | B4_78983b | GTCTACCCAACCCATTCAGGACCATAAGAC | 56 |

FIG. 3C

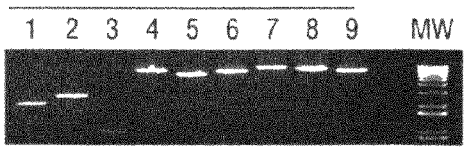

| AMPLICON | JAG1 | REGIONS | TARGET LENGTH | AMPLICON LENGTH | FORWARD PRIMER | REVERSE PRIMER |
|---|---|---|---|---|---|---|
| JAG1#1 | C26 | PROMOTER/EXON 1-2 | 1832 | 2693 | Jag_3779 | Jag_6471 |
| JAG1#2 | C25 | C1-C2 | 1793 | 2980 | Jag_10988 | Jag_13967 |
| JAG1#3 | C13 | EXON 3-5 | 7661 | 8368 | Jag_14531f | Jag_22898b |
| JAG1#4 | C14 | EXON 6-15 | 6672 | 7431 | Jag26030f | Jag33460b |
| JAG1#5 | C15 | EXON 16-26 | 7828 | 8658 | Jag33005f | Jag41662b |

FIG. 4A

| | | | SEQ ID NO. |
|---|---|---|---|
| 1 | Jag_3779 | CTGCAGGACATACCTACTATTAGGGCCAAAAC | 57 |
| | Jag_6471 | ACTACCCCAGCCGAGATCTAACTATAGTGTCC | 58 |
| 2 | Jag_10988 | AGTCAAACATGCAGAGTCCTCTACCAGCTC | 59 |
| | Jag_13967 | AGGTGGGGTAGACAAGGAACATGAACTAGG | 60 |
| 3 | Jag_14531f | CCCCTCGGTACAAATACCTGGTTAGGTTAG | 61 |
| | Jag_22898b | CCATCTAGCCCATCAGCACTATAAGGGAAG | 62 |
| 4 | Jag26030f | CACCGAGAGAGTCCTTTCCTCTATAGTCTGTC | 63 |
| | Jag33460b | GAGAGCCAAGCCTTTCCTACTGCTTACATC | 64 |
| 5 | Jag33005f | CTACTGTGAAACCAGTGAGTCTGCCACTCT | 65 |
| | Jag41662b | ACTCTGGAACCTCACAGAAGACCAGAACAC | 66 |

FIG. 4B

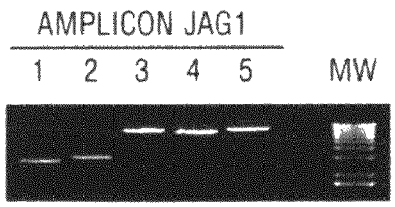

FIG. 4C

| AMPLICON | SERPINA1 | Regions | TARGET Length | Amplicon Length | Forward Primer | Reverse Primer |
|---|---|---|---|---|---|---|
| A1#1 | C22 | Promoter/Exon 1-3 | 2435 | 3367 | A1_4194f | A1_7560b |
| A1#2 | C16 | Exon 4-7 | 4881 | 6001 | A1_12102f | A1_18102b |

| | | | SEQ ID NO. |
|---|---|---|---|
| 1 | A1_4194f | CCTTACTCATGACCAGCTCACAGGATCTTC | 67 |
| | A1_7560b | CAGTAGGAGAGGTGGTGAGGCTTATAGGAGAC | 68 |
| 2 | A1_12102f | GGATTCTGGTTCTGCTACTTCCTCAGTGAC | 69 |
| | A1_18102b | GACTAGGGAGGAGAAGGGATATAGGGTAATGG | 70 |

CLASSIFICATION AND DIAGNOSIS OF THE MOLECULAR BASIS OF CHOLESTASIS

CROSS-REFERENCE TO RELATED APPLICATIONS

This application is a continuation of and claims priority to and benefit of PCT U.S. 2006/29372, filed on Jul. 28, 2006 which application claimed priority to U.S. Provisional Patent Application No. 60/703,703 filed on Jul. 29, 2005, the disclosures of which are incorporated herein by reference in their entirety.

FIELD OF THE INVENTION

The field of this invention relates to the field of genetic diagnostic assays for cholestasis related syndromes.

BACKGROUND OF THE INVENTION

Pathological jaundice (here used as a synonym for cholestasis) is the most frequent presenting syndrome in children and adults with liver disease. It results from the impaired excretion of bile from the liver, with a range of underlying causes including genetic, metabolic, inflammatory, and drug- or toxin-induced disorders. Therefore, physicians are challenged to identify the cause of jaundice in order to initiate specific treatment and supportive measures to prevent progression and/or complications of liver disease. The prognosis and treatment course for these cholestasis related syndromes differ widely. Thus, identifying the precise cause of cholestasis or jaundice allows appropriate treatment to be provided to a patient exhibiting cholestasis.

Progressive familial intrahepatic cholestasis (PFIC), benign recurring intrahepatic cholestasis (BRIC), alpha1-antitrypsin deficiency, and Alagille disease constitute approximately 45% of neonatal jaundice cases. These diseases can be difficult to clinically define. The number and size of the cholestasis related genes underlying PFIC, BRIC, alpha1-antitrypsin deficiency, and Alagille disease has impaired the use of mutation detection as a diagnostic criterion. Cholestasis related genes underlying PFIC, BRIC, alpha1-antitrypsin deficiency, and Alagille disease include, but are not limited to, ATP8B1 (SEQ ID NO:71), ABCB11 (SEQ ID NO:72), ABCB4 (SEQ ID NO:73), JAG1 (SEQ ID NO:74), and SERPINA1 (SEQ ID NO:75). ATP8B1 is located on the long arm of chromosome 18 at 18q21.31. ABCB11 is located on the long arm of chromosome 2 at 2q24. ABCB4 is located on the long arm of chromosome 7 at 7q21.1. JAG1 is located on the short arm of chromosome 20 at 20p12.1-p11.23. SERPINA1 is located on the long arm of chromosome 14 at 14q32.1.

Development of efficient, accurate, sensitive methods of detecting mutations in the genes associated with cholestasis, particularly PFIC, BRIC, alpha1-antitrypsin deficiency, and Alagille syndrome is desirable. It is of importance to develop a method of predicting disease outcome with respect to treatment course. It is of particular importance to develop a method of determining cholestasis classification that would identify subjects likely to benefit from early aggressive treatment.

SUMMARY OF THE INVENTION

Compositions and methods for diagnosing cholestasis related syndromes are provided. The inventions are based on identification of nucleotide sequences for amplifying and sequencing the 5' regulatory regions, exons, and exon-intron boundaries of several cholestasis related genes: ATP8B1 (SEQ ID NO:71); ABCB11 (SEQ ID NO:72); ABCB4 (SEQ ID NO:73); JAG1 (SEQ ID NO:74); and SERPIN-1 (SEQ ID NO:75). The compositions of the invention allow amplification of the cholestasis related gene exons; exon-intron boundaries; and 5' regulatory regions and sequencing of the cholestasis related gene exons, exon-intron boundaries, and the 5' upstream region. The cholestasis related gene exon, exon-intron boundary, and the 5' upstream region nucleotide sequences provide prognostic and diagnostic information for cholestasis related syndromes.

Compositions of the invention include isolated nucleic acid molecules comprising the nucleotide sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, and variants thereof. Variant nucleotide sequences of the invention differ by one nucleotide alteration from the nucleotide sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or hybridize under stringent conditions to a complement of a nucleotide sequence of the invention.

Compositions of the invention include an oligonucleotide pair library comprised of at least one oligonucleotide pair. Compositions of the invention further include oligonucleotide pairs comprising a first nucleic acid molecule and a second nucleic acid molecule. Oligonucleotide pairs of the invention allow amplification of a region of a cholestasis related gene. Nucleotide sequences of the first nucleic acid molecule in an oligonucleotide pair are set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, and variants thereof. Nucleotide sequences of the second nucleic acid molecule in an oligonucleotide pair are set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, and variants thereof.

In an embodiment, an oligonucleotide pair of the invention comprises a first nucleic acid molecule having the nucleotide sequence set forth in SEQ ID NO:1 or a variant thereof and a second nucleic acid molecule having the nucleotide sequence set forth in SEQ ID NO:2 or a variant thereof. In an embodiment, an oligonucleotide pair of the invention comprises a first nucleic acid molecule having the nucleotide sequence set forth in SEQ ID NO:3 or a variant thereof and a second nucleic acid molecule having the nucleotide sequence set forth in SEQ ID NO:4 or a variant thereof. In an embodiment, an oligonucleotide pair of the invention comprises a first nucleic acid molecule having the nucleotide sequence set forth in SEQ ID NO:5 or a variant thereof and a second nucleic acid molecule having the nucleotide sequence set forth in SEQ ID NO:6 or a variant thereof. In an embodiment, an oligonucleotide pair of the invention comprises a first nucleic acid molecule having the nucleotide sequence set forth in SEQ ID NO:7 or a variant thereof and a second nucleic acid molecule having the nucleotide sequence set forth in SEQ ID NO:8 or a variant thereof. In an embodiment, an oligonucleotide pair of the invention comprises a first nucleic acid molecule having the nucleotide sequence set forth in SEQ ID NO:9 or a variant thereof and a second nucleic acid molecule having the nucleotide sequence set forth in SEQ ID NO:10 or a variant thereof. In an embodiment, an oligonucleotide pair of the invention comprises a first nucleic acid molecule having the nucleotide sequence set forth in SEQ ID NO:11 or a variant thereof and a second nucleic acid molecule having the nucleotide sequence set forth in SEQ ID NO:12 or a variant thereof. In an embodiment, an oligonucleotide pair of the invention comprises a first nucleic acid molecule having the nucleotide sequence set forth in SEQ ID NO:13 or a variant thereof and a second nucleic acid molecule having the nucleotide sequence set forth in SEQ ID NO:14 or a variant thereof. In an embodiment, an oligonucleotide pair of the invention comprises a first nucleic acid molecule having the nucleotide sequence set forth in SEQ ID NO:15 or a variant thereof and a second nucleic acid molecule having the nucleotide sequence set forth in SEQ ID NO:16 or a variant thereof. In an embodiment, an oligonucleotide pair of the invention comprises a first nucleic acid molecule having the nucleotide sequence set forth in SEQ ID NO:17 or a variant thereof and a second nucleic acid molecule having the nucleotide sequence set forth in SEQ ID NO:18 or a variant thereof. In an embodiment an oligonucleotide pair of the invention allows amplification of a region of the ATP8B1 protein gene (SEQ ID NO:71).

In an embodiment, an oligonucleotide pair of the invention comprises a first nucleic acid molecule having the nucleotide sequence set forth in SEQ ID NO:19 or a variant thereof and a second nucleic acid molecule having the nucleotide sequence set forth in SEQ ID NO:20 or a variant thereof. In an embodiment, an oligonucleotide pair of the invention comprises a first nucleic acid molecule having the nucleotide sequence set forth in SEQ ID NO:21 or a variant thereof and a second nucleic acid molecule having the nucleotide sequence set forth in SEQ ID NO:22 or a variant thereof. In an embodiment, an oligonucleotide pair of the invention comprises a first nucleic acid molecule having the nucleotide sequence set forth in SEQ ID NO:23 or a variant thereof and a second nucleic acid molecule having the nucleotide sequence set forth in SEQ ID NO:24 or a variant thereof. In an embodiment, an oligonucleotide pair of the invention comprises a first nucleic acid molecule having the nucleotide sequence set forth in SEQ ID NO:25 or a variant thereof and a second nucleic acid molecule having the nucleotide sequence set forth in SEQ ID NO:26 or a variant thereof. In an embodiment, an oligonucleotide pair of the invention comprises a first nucleic acid molecule having the nucleotide sequence set forth in SEQ ID NO:27 or a variant thereof and a second nucleic acid molecule having the nucleotide sequence set forth in SEQ ID NO:28 or a variant thereof. In an embodiment, an oligonucleotide pair of the invention comprises a first nucleic acid molecule having the nucleotide sequence set forth in SEQ ID NO:29 or a variant thereof and a second nucleic acid molecule having the nucleotide sequence set forth in SEQ ID NO:30 or a variant thereof. In an embodiment, an oligonucleotide pair of the invention comprises a first nucleic acid molecule having the nucleotide sequence set forth in SEQ ID NO:31 or a variant thereof and a second nucleic acid molecule having the nucleotide sequence set forth in SEQ ID NO:32 or a variant thereof. In an embodiment, an oligonucleotide pair of the invention comprises a first nucleic acid molecule having the nucleotide sequence set forth in SEQ ID NO:33 or a variant thereof and a second nucleic acid molecule having the nucleotide sequence set forth in SEQ ID NO:34 or a variant thereof. In an embodiment, an oligonucleotide pair of the invention comprises a first nucleic acid molecule having the nucleotide sequence set forth in SEQ ID NO:35 or a variant thereof and a second nucleic acid molecule having the nucleotide sequence set forth in SEQ ID NO:36 or a variant thereof. In an embodiment, an oligonucleotide pair of the invention comprises a first nucleic acid molecule having the nucleotide sequence set forth in SEQ ID NO:37 or a variant thereof and a second nucleic acid molecule having the nucleotide sequence set forth in SEQ ID NO:38 or a variant thereof. In an embodiment an oligonucleotide pair of the invention allows amplification of a region of the ABCB11 protein gene (SEQ ID NO:72).

In an embodiment, an oligonucleotide pair of the invention comprises a first nucleic acid molecule having the nucleotide sequence set forth in SEQ ID NO:39 or a variant thereof and a second nucleic acid molecule having the nucleotide sequence set forth in SEQ ID NO:40 or a variant thereof. In an embodiment, an oligonucleotide pair of the invention comprises a first nucleic acid molecule having the nucleotide sequence set forth in SEQ ID NO:41 or a variant thereof and a second nucleic acid molecule having the nucleotide sequence set forth in SEQ ID NO:42 or a variant thereof. In an embodiment, an oligonucleotide pair of the invention comprises a first nucleic acid molecule having the nucleotide sequence set forth in SEQ ID NO:43 or a variant thereof and a second nucleic acid molecule having the nucleotide sequence set forth in SEQ ID NO:44 or a variant thereof. In an embodiment, an oligonucleotide pair of the invention comprises a first nucleic acid molecule having the nucleotide sequence set forth in SEQ ID NO:45 or a variant thereof and a second nucleic acid molecule having the nucleotide sequence set forth in SEQ ID NO:46 or a variant thereof. In an embodiment, an oligonucleotide pair of the invention comprises a first nucleic acid molecule having the nucleotide sequence set forth in SEQ ID NO:47 or a variant thereof and a second nucleic acid molecule having the nucleotide sequence set forth in SEQ ID NO:48 or a variant thereof. In an embodiment, an oligonucleotide pair of the invention comprises a first nucleic acid molecule having the nucleotide sequence set forth in SEQ ID NO:49 or a variant thereof and a second nucleic acid molecule having the nucleotide sequence set forth in SEQ ID NO:50 or a variant thereof. In an embodiment, an oligonucleotide pair of the invention comprises a first nucleic acid molecule having the nucleotide sequence set forth in SEQ ID NO:51 or a variant thereof and a second nucleic acid molecule having the nucleotide sequence set forth in SEQ ID NO:52 or a variant thereof. In an embodiment, an oligonucleotide pair of the invention comprises a first nucleic acid molecule having the nucleotide sequence set forth in SEQ ID NO:53 or a variant thereof and a second nucleic acid molecule having the nucleotide sequence set forth in SEQ ID NO:54 or a variant thereof. In an embodiment, an oligonucleotide pair of the invention comprises a first nucleic acid molecule having the nucleotide sequence set forth in SEQ ID NO:55 or a variant thereof and a second nucleic acid molecule having the nucleotide sequence set forth in SEQ ID NO:56 or a variant thereof. In an embodiment an oligonucleotide pair of the invention allows amplification of a region of the ABCB4 protein gene (SEQ ID NO:73).

In an embodiment, an oligonucleotide pair of the invention comprises a first nucleic acid molecule having the nucleotide sequence set forth in SEQ ID NO:57 or a variant thereof and a second nucleic acid molecule having the nucleotide sequence set forth in SEQ ID NO:58 or a variant thereof. In an embodiment, an oligonucleotide pair of the invention comprises a first nucleic acid molecule having the nucleotide sequence set forth in SEQ ID NO:59 or a variant thereof and a second nucleic acid molecule having the nucleotide sequence set forth in SEQ ID NO:60 or a variant thereof. In an embodiment, an oligonucleotide pair of the invention comprises a first nucleic acid molecule having the nucleotide sequence set forth in SEQ ID NO:61 or a variant thereof and a second nucleic acid molecule having the nucleotide sequence set forth in SEQ ID NO:62 or a variant thereof. In an embodiment, an oligonucleotide pair of the invention comprises a first nucleic acid molecule having the nucleotide sequence set forth in SEQ ID NO:63 or a variant thereof and a second nucleic acid molecule having the nucleotide sequence set forth in SEQ ID NO:64 or a variant thereof. In an embodiment, an oligonucleotide pair of the invention comprises a first nucleic acid molecule having the nucleotide sequence set forth in SEQ ID NO:65 or a variant thereof and a second nucleic acid molecule having the nucleotide sequence set forth in SEQ ID NO:66 or a variant thereof. In an embodiment an oligonucleotide pair of the invention allows amplification of a region of the JAG1 protein gene (SEQ ID NO:74).

In an embodiment, an oligonucleotide pair of the invention comprises a first nucleic acid molecule having the nucleotide sequence set forth in SEQ ID NO:67 or a variant thereof and a second nucleic acid molecule having the nucleotide sequence set forth in SEQ ID NO:68 or a variant thereof. In an embodiment, an oligonucleotide pair of the invention comprises a first nucleic acid molecule having the nucleotide sequence set forth in SEQ ID NO:69 or a variant thereof and a second nucleic acid molecule having the nucleotide sequence set forth in SEQ ID NO:70 or a variant thereof. In an embodiment an oligonucleotide pair of the invention allows amplification of a region of the SERPINA-1 protein gene (SEQ ID NO:75).

Compositions of the invention include a resequencing microarray consisting of nucleic acid probes having a nucleotide sequence derived from the nucleotide sequences set forth in SEQ ID NO:71, SEQ ID NO:72, SEQ ID NO:73, SEQ ID NO:74, and SEQ ID NO:75. The nucleic acid probes are of a predetermined length, such as 25 nucleotides. Each probe has a predetermined nucleotide sequence that is a segment of the nucleotide sequence set forth in nucleotides 1 to 483 of SEQ ID NO:71; nucleotides 25,479 to 25,620 of SEQ ID NO:71; nucleotides 27,398 to 27,555 of SEQ ID NO:71; nucleotides 30,753 to 30,895 of SEQ ID NO:71; nucleotides 30,966 to 31,071 of SEQ ID NO:71; nucleotides 34,199 to 34,315 of SEQ ID NO:71; nucleotides 34,378 to 34,492 of SEQ ID NO:71; nucleotides 36,534 to 36,660 of SEQ ID NO:71; nucleotides 36,737 to 36,939 of SEQ ID NO:71; nucleotides 37,396 to 37,528 of SEQ ID NO:71; nucleotides 40,069 to 40,303 of SEQ ID NO:71; nucleotides 43,559 to 43,811 of SEQ ID NO:71; nucleotides 46,951 to 47,038 of SEQ ID NO:71; nucleotides 47,874 to 48,074 of SEQ ID NO:71; nucleotides 57,044 to 57,276 of SEQ ID NO:71; nucleotides 60,486 to 60,642 of SEQ ID NO:71; nucleotides 62,584 to 62,792 of SEQ ID NO:71; nucleotides 63,526 to 63,681 of SEQ ID NO:71; nucleotides 64,899 to 65,018 of SEQ ID NO:71; nucleotides 69,451 to 69,627 of SEQ ID NO:71; nucleotides 70,604 to 70,936 of SEQ ID NO:71; nucleotides 76,649 to 76,916 of SEQ ID NO:71; nucleotides 77,991 to 78,118 of SEQ ID NO:71; nucleotides 79,337 to 79,626 of SEQ ID NO:71; nucleotides 79,894 to 80,076 of SEQ ID NO:71; nucleotides 81,569 to 81,743 of SEQ ID NO:71; nucleotides 83,354 to 83,756 of SEQ ID NO:71; nucleotides 1 to 401 of SEQ ID NO:72; nucleotides 13,430 to 13,576 of SEQ ID NO:72; nucleotides 14,783 to 14,848 of SEQ ID NO:72; nucleotides 17,228 to 17,323 of SEQ ID NO:72; nucleotides 18,072 to 18,354 of SEQ ID NO:72; nucleotides 34,860 to 34,991 of SEQ ID NO:72; nucleotides 36,100 to 36,277 of SEQ ID NO:72; nucleotides 37,700 to 37,915 of SEQ ID NO:72; nucleotides 40,657 to 40,825 of SEQ ID NO:72; nucleotides 45,298 to 45,516 of SEQ ID NO:72; nucleotides 51,603 to 51,760 of SEQ ID NO:72; nucleotides 54,895 to 55,049 of SEQ ID NO:72; nucleotides 57,742 to 57,911 of SEQ ID NO:72; nucleotides 59,532 to 59,779 of SEQ ID NO:72; nucleotides 61,367 to 61,581 of SEQ ID NO:72; nucleotides 62,031 to 62,276 of SEQ ID NO:72; nucleotides 63,092 to 63,199 of SEQ ID NO:72; nucleotides 67,274 to 67,420 of SEQ ID NO:72; nucleotides 73,454 to 73,662 of SEQ ID NO:72; nucleotides 86,621 to 86,769 of SEQ ID NO:72; nucleotides 86,816 to 87,021 of SEQ ID NO:72; nucleotides 95,149 to 95,396 of SEQ ID NO:72; nucleotides 96,157 to 96,442 of SEQ ID NO:72; nucleotides 99,049 to 99,249 of SEQ ID NO:72; nucleotides 100,720 to 100,961 of SEQ ID NO:72; nucleotides 104,220 to 104,470 of SEQ ID NO:72; nucleotides 106,779 to 106,969 of SEQ ID NO:72; nucleotides 107,760 to 108,687 of SEQ ID NO:72; nucleotides 1 to 1,802 of SEQ ID NO:73; nucleotides 1,803 to 2,186 of SEQ ID NO:73; nucleotides 2,299 to 2,400 of SEQ ID NO:73; nucleotides 3,075 to 3,254 of SEQ ID NO:73; nucleotides 3,611 to 3,760 of SEQ ID NO:73; nucleotides 3,879 to 4,008 of SEQ ID NO:73; nucleotides 6,675 to 6,773 of SEQ ID NO:73; nucleotides 16,442 to 16,636 of SEQ ID NO:73; nucleotides 24,758 to 24,859 of SEQ ID NO:73; nucleotides 26,215 to 26,450 of SEQ ID NO:73; nucleotides 27,556 to 27,771 of SEQ ID NO:73; nucleotides 29,258 to 29,426 of SEQ ID NO:73; nucleotides 32,145 to 32,360 of SEQ ID NO:73; nucleotides 34,375 to 34,532 of SEQ ID NO:73; nucleotides 35,577 to 35,731 of SEQ ID NO:73; nucleotides 35,906 to 36,075 of SEQ ID NO:73; nucleotides 38,948 to 39,195 of SEQ ID NO:73; nucleotides 39,513 to 39,721 727 of SEQ ID NO:73; nucleotides 47,785 to 47,990 of SEQ ID NO:73; nucleotides 52,430 to 52,644 of SEQ ID NO:73; nucleotides 55,298 to 55,488 of SEQ ID NO:73; nucleotides 57,125 to 57,273 of SEQ ID NO:73; nucleotides 59,275 to 59,396 of SEQ ID NO:73; nucleotides 60,730 to 60,857 of SEQ ID NO:73; nucleotides 61,835 to 62,082 of SEQ ID NO:73; nucleotides 65,633 to 65,777 of SEQ ID NO:73; nucleotides 67,317 to 67,501 of SEQ ID NO:73; nucleotides 69,958 to 70,158 of SEQ ID NO:73; nucleotides 71,116 to 71,357 of SEQ ID NO:73; nucleotides 72,835 to 73,106 of SEQ ID NO:73; nucleotides 76,069 to 76,259 of SEQ ID NO:73; nucleotides 77,048 to 77,349 of SEQ ID NO:73; nucleotides 1 to 1,015 of SEQ ID NO:74; nucleotides 1,415 to 1,764 of SEQ ID NO:74; nucleotides 6,490 to 6,689 of SEQ ID NO:74; nucleotides 8,080 to 8,239 of SEQ ID NO:74; nucleotides 10,407 to 10,502 of SEQ ID NO:74; nucleotides 15,699 to 15,997 of SEQ ID NO:74; nucleotides 17,963 to 18,067 of SEQ ID NO:74; nucleotides 21,823 to 21,997 of SEQ ID NO:74; nucleotides 22,171 to 22,334 of SEQ ID NO:74; nucleotides 22,727 to 22,884 of SEQ ID NO:74; nucleotides 24,061 to 24,218 of SEQ ID NO:74; nucleotides 24,786 to 24,943 of SEQ ID NO:74; nucleotides 25,314 to 25,404 of SEQ ID NO:74; nucleotides 25,699 to 25,916 of SEQ ID NO:74; nucleotides 26,311 to 26,505 of SEQ ID NO:74; nucleotides 27,318 to 27,526 of SEQ ID NO:74; nucleotides 28,337 to 28,494 of SEQ ID NO:74; nucleotides 28,952 to 29,109 of SEQ ID NO:74; nucleotides 29,165 to 29,322 of SEQ ID NO:74; nucleotides 29,442 to 29,602 of SEQ ID NO:74; nucleotides 30,037 to 30,108 of SEQ ID NO:74; nucleotides 30,558 to 30,687 of SEQ ID NO:74; nucleotides 31,820 to 31,977 of SEQ ID NO:74; nucleotides 32,529 to 32,682 of SEQ ID NO:74; nucleotides 32,728 to 33,005 of SEQ ID NO:74; nucleotides 33,177 to 33,352 of SEQ ID NO:74; nucleotides 33,488 to 33,682 of SEQ ID NO:74; nucleotides 34,466 to 36,779 of SEQ ID NO:74; nucleotides 1 to 538 of SEQ ID NO:75; nucleotides 539 to 792 of SEQ ID NO:75; nucleotides 886 to 1,033 of SEQ ID NO:75; nucleotides 6,308 to 7,001 of SEQ ID NO:75; nucleotides 8,408 to 8,722 of SEQ ID NO:75; nucleotides 9,938 to 10,129 of SEQ ID NO:75; or nucleotides 10,909 to 11,232 of SEQ ID NO:75 or differs by one predetermined nucleotide alteration from a segment of the nucleotide sequence set forth in nucleotides 1 to 483 of SEQ ID NO:71; nucleotides 25,479 to 25,620 of SEQ ID NO:71; nucleotides 27,398 to 27,555 of SEQ ID NO:71; nucleotides 30,753 to 30,895 of SEQ ID NO:71; nucleotides 30,966 to 31,071 of SEQ ID NO:71; nucleotides 34,199 to 34,315 of SEQ ID NO:71; nucleotides 34,378 to 34,492 of SEQ ID NO:71; nucleotides 36,534 to 36,660 of SEQ ID NO:71; nucleotides 36,737 to 36,939 of SEQ ID NO:71; nucleotides 37,396 to 37,528 of SEQ ID NO:71; nucleotides 40,069 to 40,303 of SEQ ID NO:71; nucleotides 43,559 to 43,811 of SEQ ID NO:71; nucleotides 46,951 to 47,038 of SEQ ID NO:71; nucleotides 47,874 to 48,074 of SEQ ID NO:71; nucleotides 57,044 to 57,276 of SEQ ID NO:71; nucleotides 60,486 to 60,642 of SEQ ID NO:71; nucleotides 62,584 to 62,792 of SEQ ID NO:71; nucleotides 63,526 to 63,681 of SEQ ID NO:71; nucleotides 64,899 to 65,018 of SEQ ID NO:71; nucleotides 69,451 to 69,627 of SEQ ID NO:71; nucleotides 70,604 to 70,936 of SEQ ID NO:71; nucleotides 76,649 to 76,916 of SEQ ID NO:71; nucleotides 77,991 to 78,118 of SEQ ID NO:71; nucleotides 79,337 to 79,626 of SEQ ID NO:71; nucleotides 79,894 to 80,076 of SEQ ID NO:71; nucleotides 81,569 to 81,743 of SEQ ID NO:71; nucleotides 83,354 to 83,756 of SEQ ID NO:71; nucleotides 1 to 401 of SEQ ID NO:72; nucleotides 13,430 to 13,576 of SEQ ID NO:72; nucleotides 14,783 to 14,848 of SEQ ID NO:72; nucleotides 17,228 to 17,323 of SEQ ID NO:72; nucleotides 18,072 to 18,354 of SEQ ID NO:72; nucleotides 34,860 to 34,991 of SEQ ID NO:72; nucleotides 36,100 to 36,277 of SEQ ID NO:72; nucleotides 37,700 to 37,915 of SEQ ID NO:72; nucleotides 40,657 to 40,825 of SEQ ID NO:72; nucleotides 45,298 to 45,516 of SEQ ID NO:72; nucleotides 51,603 to 51,760 of SEQ ID NO:72; nucleotides 54,895 to 55,049 of SEQ ID NO:72; nucleotides 57,742 to 57,911 of SEQ ID NO:72; nucleotides 59,532 to 59,779 of SEQ ID NO:72; nucleotides 61,367 to 61,581 of SEQ ID NO:72; nucleotides 62,031 to 62,276 of SEQ ID NO:72; nucleotides 63,092 to 63,199 of SEQ ID NO:72; nucleotides 67,274 to 67,420 of SEQ ID NO:72; nucleotides 73,454 to 73,662 of SEQ ID NO:72; nucleotides 86,621 to 86,769 of SEQ ID NO:72; nucleotides 86,816 to 87,021 of SEQ ID NO:72; nucleotides 95,149 to 95,396 of SEQ ID NO:72; nucleotides 96,157 to 96,442 of SEQ ID NO:72; nucleotides 99,049 to 99,249 of SEQ ID NO:72; nucleotides 100,720 to 100,961 of SEQ ID NO:72; nucleotides 104,220 to 104,470 of SEQ ID NO:72; nucleotides 106,779 to 106,969 of SEQ ID NO:72; nucleotides 107,760 to 108,687 of SEQ ID NO:72; nucleotides 1 to 1,802 of SEQ ID NO:73; nucleotides 1,803 to 2,186 of SEQ ID NO:73; nucleotides 2,299 to 2,400 of SEQ ID NO:73; nucleotides 3,075 to 3,254 of SEQ ID NO:73; nucleotides 3,611 to 3,760 of SEQ ID NO:73; nucleotides 3,879 to 4,008 of SEQ ID NO:73; nucleotides 6,675 to 6,773 of SEQ ID NO:73; nucleotides 16,442 to 16,636 of SEQ ID NO:73; nucleotides 24,758 to 24,859 of SEQ ID NO:73; nucleotides 26,215 to 26,450 of SEQ ID NO:73; nucleotides 27,556 to 27,771 of SEQ ID NO:73; nucleotides 29,258 to 29,426 of SEQ ID NO:73; nucleotides 32,145 to 32,360 of SEQ ID NO:73; nucleotides 34,375 to 34,532 of SEQ ID NO:73; nucleotides 35,577 to 35,731 of SEQ ID NO:73; nucleotides 35,906 to 36,075 of SEQ ID NO:73; nucleotides 38,948 to 39,195 of SEQ ID NO:73; nucleotides 39,513 to 39,727 of SEQ ID NO:73; nucleotides 47,785 to 47,990 of SEQ ID NO:73; nucleotides 52,430 to 52,644 of SEQ ID NO:73; nucleotides 55,298 to 55,488 of SEQ ID NO:73; nucleotides 57,125 to 57,273 of SEQ ID NO:73; nucleotides 59,275 to 59,396 of SEQ ID NO:73; nucleotides 60,730 to 60,857 of SEQ ID NO:73; nucleotides 61,835 to 62,082 of SEQ ID NO:73; nucleotides 65,633 to 65,777 of SEQ ID NO:73; nucleotides 67,317 to 67,501 of SEQ ID NO:73; nucleotides 69,958 to 70,158 of SEQ ID NO:73; nucleotides 71,116 to 71,357 of SEQ ID NO:73; nucleotides 72,835 to 73,106 of SEQ ID NO:73; nucleotides 76,069 to 76,259 of SEQ ID NO:73; nucleotides 77,048 to 77,349 of SEQ ID NO:73; nucleotides 1 to 1,015 of SEQ ID NO:74; nucleotides 1,415 to 1,764 of SEQ ID NO:74; nucleotides 6,490 to 6,689 of SEQ ID NO:74; nucleotides 8,080 to 8,239 of SEQ ID NO:74; nucleotides 10,407 to 10,502 of SEQ ID NO:74; nucleotides 15,699 to 15,997 of SEQ ID NO:74; nucleotides 17,963 to 18,067 of SEQ ID NO:74; nucleotides 21,823 to 21,997 of SEQ ID NO:74; nucleotides 22,171 to 22,334 of SEQ ID NO:74; nucleotides 22,727 to 22,884 of SEQ ID NO:74; nucleotides 24,061 to 24,218 of SEQ ID NO:74; nucleotides 24,786 to 24,943 of SEQ ID NO:74; nucleotides 25,314 to 25,404 of SEQ ID NO:74; nucleotides 25,699 to 25,916 of SEQ ID NO:74; nucleotides 26,311 to 26,505 of SEQ ID NO:74; nucleotides 27,318 to 27,526 of SEQ ID NO:74; nucleotides 28,337 to 28,494 of SEQ ID NO:74; nucleotides 28,952 to 29,109 of SEQ ID NO:74; nucleotides 29,165 to 29,322 of SEQ ID NO:74; nucleotides 29,442 to 29,602 of SEQ ID NO:74; nucleotides 30,037 to 30,108 of SEQ ID NO:74; nucleotides 30,558 to 30,687 of SEQ ID NO:74; nucleotides 31,820 to 31,977 of SEQ ID NO:74; nucleotides 32,529 to 32,682 of SEQ ID NO:74; nucleotides 32,728 to 33,005 of SEQ ID NO:74; nucleotides 33,177 to 33,352 of SEQ ID NO:74; nucleotides 33,488 to 33,682 of SEQ ID NO:74; nucleotides 34,466 to 36,779 of SEQ ID NO:74; nucleotides 1 to 538 of SEQ ID NO:75; nucleotides 539 to 792 of SEQ ID NO:75; nucleotides 886 to 1,033 of SEQ ID NO:75; nucleotides 6,308 to 7,001 of SEQ ID NO:75; nucleotides 8,408 to 8,722 of SEQ ID NO:75; nucleotides 9,938 to 10,129 of SEQ ID NO:75; or nucleotides 10,909 to 11,232 of SEQ ID NO:75.

Compositions of the invention include a kit comprising a cholestasis related gene resequencing microarray and at least one oligonucleotide pair of the invention. In an aspect, the kit further comprises a standard sequence profile.

Methods of the invention include methods of determining the nucleotide sequence of a region of a cholestasis related gene of a human subject. The method involves the steps of obtaining a biological sample from the subject, providing an oligonucleotide pair of the invention, performing enzymatic amplification of a region of a cholestasis related gene, providing amplified DNA, and determining the nucleotide sequence of a region of a cholestasis related gene. In an aspect, the method involves the step of providing a cholestasis related gene resequencing microarray. In an aspect, the nucleotide sequence of one or multiple amplified regions is determined. In an aspect the nucleotide sequence of a region of at least one, two, three, four, or five cholestasis related genes is compared with a standard sequence profile. In an aspect of the invention, the cholestasis related gene is selected from the group consisting of ATP8B1 (SEQ ID NO:71), ABCB4 (SEQ ID NO:73), ABCB11 (SEQ ID NO:72), JAG1 (SEQ ID NO:74), and SERPINA-1 (SEQ ID NO:75).

Methods of the invention include methods of diagnosing a cholestasis related syndrome. The methods involve the steps of obtaining a biological sample from a human subject exhibiting cholestasis, performing enzymatic amplification of a region of a cholestasis related gene, providing amplified DNA having the nucleotide sequence of a region of a cholestasis related gene, determining the nucleotide sequence of the amplified DNA, and comparing the nucleotide sequence of the amplified DNA with a standard sequence profile. In an aspect, the method comprises the step of providing a cholestasis related gene resequencing microarray. Cholestasis related syndromes include, but are not limited to, cholestasis, neonatal cholestasis, progressive familial intrahepatic cholestasis, benign recurrent intrahepatic cholestasis, alpha-1 anti-trypsin deficiency, Alagille syndrome, intrahepatic cholestasis of pregnancy, primary sclerosing cholangitis, biliary atresia, cholelithiasis, cirrhosis of the liver, and septicemia. In an aspect, the method comprises the step of providing at least one oligonucleotide pair of the invention. In an aspect, enzymatic amplification of multiple regions, including regions of multiple cholestasis related genes, occurs. In an aspect, the nucleotide sequences of multiple amplified DNA are determined.

Methods of the invention include methods of determining the cholestasis classification of a subject exhibiting cholestasis. The methods comprise the steps of obtaining a biological sample from the subject, determining the nucleotide sequence of a region of a cholestasis related gene of the human subject, and comparing the nucleotide sequence of the region with a standard sequence profile. In an aspect of the method, the step of determining the nucleotide sequence further comprises the steps of performing enzymatic amplification of a region of a cholestasis related gene, providing amplified DNA having the nucleotide sequence of a region of a cholestasis related gene, and providing a cholestasis related gene resequencing microarray.

Methods of the invention include methods of predicting the prognosis for a subject exhibiting cholestasis. The methods comprise the steps of obtaining a biological sample from the subject, determining the nucleotide sequence of a region of a cholestasis related gene of the human subject, and comparing the nucleotide sequence of the region with a standard sequence profile. In an aspect of the method, the step of determining the nucleotide sequence further comprises the steps of performing enzymatic amplification of a region of a cholestasis related gene, providing amplified DNA having the nucleotide sequence of a region of a cholestasis related gene, and providing a cholestasis related gene resequencing microarray.

BRIEF DESCRIPTION OF THE DRAWINGS

FIG. 1 presents the ATP8B1 oligonucleotide primer pairs, the amplicon size, the relative genomic location of the amplicon, and the size of the targets tiled on the resequencing microarray in Panel A. Panel B presents working oligonucleotide names, the nucleotide sequence of each primer, and the SEQ ID NO. Panel C presents a photograph of the PCR amplification products. PCR reactions were performed with the indicated oligonucleotide pair: Lane 1 (SEQ ID NO:1 and SEQ ID NO:2), Lane 2 (SEQ ID NO:3 and SEQ ID NO:4), Lane 3 (SEQ ID NO:5 and SEQ ID NO:6), Lane 4 (SEQ ID NO:7 and SEQ ID NO:8), Lane 5 (SEQ ID NO:9 and SEQ ID NO:10), Lane 6 (SEQ ID NO:11 and SEQ ID NO:12), Lane 7 (SEQ ID NO:13 and SEQ ID NO:14), Lane 8 (SEQ ID NO:15 and SEQ ID NO:16), Lane 9 (SEQ ID NO:17 and SEQ ID NO:18), and size markers (MW).

FIG. 2 presents the ABCB11 oligonucleotide primer pairs, the amplicon size, the relative genomic location of the amplicon, and the size of the targets tiled on the resequencing microarray in Panel A. Panel B presents working oligonucleotide names, the nucleotide sequence of each primer, and the SEQ ID NO. Panel C presents a photograph of the PCR amplification products. PCR reactions were performed with the indicated oligonucleotide pair: Lane 1 (SEQ ID NO:19 and SEQ ID NO:20), Lane 2 (SEQ ID NO:21 and SEQ ID NO:22), Lane 3 (SEQ ID NO:23 and SEQ ID NO:24), Lane 4 (SEQ ID NO:25 and SEQ ID NO:26), Lane 5 (SEQ ID NO:27 and SEQ ID NO:28), Lane 6 (SEQ ID NO:29 and SEQ ID NO:30), Lane 7 (SEQ ID NO:31 and SEQ ID NO:32), Lane 8 (SEQ ID NO:33 and SEQ ID NO:34), Lane 9 (SEQ ID NO:35 and SEQ ID NO:36), Lane 10 (SEQ ID NO:37 and SEQ ID NO:38), and size markers (MW).

FIG. 3 presents the ABCB4 oligonucleotide primer pairs, the amplicon size, the relative genomic location of the amplicon, and the size of the targets tiled on the resequencing microarray in Panel A. Panel B presents working oligonucleotide names, the nucleotide sequence of each primer, and the SEQ ID NO. Panel C presents a photograph of the PCR amplification products. PCR reactions were performed with the indicated oligonucleotide pair: Lane 1 (SEQ ID NO:39 and SEQ ID NO:40), Lane 2 (SEQ ID NO:41 and SEQ ID NO:42), Lane 3 (SEQ ID NO:43 and SEQ ID NO:44), Lane 4 (SEQ ID NO:45 and SEQ ID NO:46), Lane 5 (SEQ ID NO:47 and SEQ ID NO:48), Lane 6 (SEQ ID NO:49 and SEQ ID NO:50), Lane 7 (SEQ ID NO:51 and SEQ ID NO:52), Lane 8 (SEQ ID NO:53 and SEQ ID NO:54), Lane 9 (SEQ ID NO:55 and SEQ ID NO:56), and size markers (MW).

FIG. 4 presents the JAG1 oligonucleotide primer pairs, the amplicon size, the relative genomic location of the amplicon, and the size of the targets tiled on the resequencing microarray in Panel A. Panel B presents working oligonucleotide names, the nucleotide sequence of each primer, and the SEQ ID NO. Panel C presents a photograph of the PCR amplification products. PCR reactions were performed with the indicated oligonucleotide pair: Lane 1 (SEQ ID NO:57 and SEQ ID NO:58), Lane 2 (SEQ ID NO:59 and SEQ ID NO:60), Lane 3 (SEQ ID NO:61 and SEQ ID NO:62), Lane 4 (SEQ ID NO:63 and SEQ ID NO:64), Lane 5 (SEQ ID NO:65 and SEQ ID NO:66), and size markers (MW).

DETAILED DESCRIPTION OF THE INVENTION

Figures 5A, 5B, 5C:
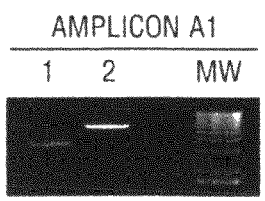
FIG. 5 presents the SERPINA 1 oligonucleotide primer pairs, the amplicon size, the relative genomic location of the amplicon, and the size of the targets tiled on the resequencing microarray in Panel A. Panel B presents working oligonucleotide names, the nucleotide sequence of each primer, and the SEQ ID NO. Panel C presents a photograph of the PCR amplification products. PCR reactions were performed with the indicated oligonucleotide pair: Lane 1 (SEQ ID NO:67 and SEQ ID NO:68), Lane 2 (SEQ ID NO:69 and SEQ ID NO:70), and size markers (MW).

The present invention provides methods of determining the nucleotide sequence of a region of a cholestasis related gene, classifying disease, particularly cholestasis related syndromes, diagnosing a cholestasis related syndrome, and predicting the prognosis of a cholestasis related syndrome. The invention provides methods of amplifying a region or regions of various cholestasis related genes, and methods of determining the nucleotide sequence of a region or regions of various cholestasis related genes. Compositions of the invention include isolated nucleic acid molecules and oligonucleotide pairs useful in amplifying a region or regions of various cholestasis related genes as well as kits for performing the methods of the invention. Compositions of the invention include a resequencing microarray useful in determining the nucleotide sequence of the promoter region, exon regions, and exon/intron boundaries of various cholestasis related genes as well as kits for performing the methods of the invention. The invention relates to identification of genomic nucleotide alterations in a cholestasis related gene in various cholestasis related syndromes.

Cholestasis related syndromes are characterized by an impaired excretion of bile from the liver resulting in elevated bilirubin levels in the bloodstream. Cholestasis related syndromes include, but are not limited to, pathological jaundice, cancer, obstruction of the biliary duct by gall stones, inflammatory masses, or tumors, cholecystitis, pancreatic carcinoma, cholestasis, Gilbert's disease, acetaminophen overdose, hepatitis B infection, hemolysis, hereditary spherocytosis, conjugated hyperbilirubinemia, acholuric jaundice, breastfeeding jaundice, breast milk jaundice, cholestatic jaundice, congenital jaundice, hematogenous jaundice, hemolytic jaundice, hemorrhagic jaundice, hepatocellular jaundice, infectious jaundice, jaundice of the newborn, non-hemolytic jaundice, obstructive jaundice, pathological jaundice of the newborn, parenchymatous jaundice, retention jaundice, Alagille disease, biliary atresia, progressive familial intrahepatic cholestasis (PFIC), PFIC type 1, PFIC type II, and PFIC type III, benign recurring intrahepatic cholestasis (BRIC), BRIC type I, BRIC type II, alpha1-antitrypsin deficiency, Alagille syndrome, intrahepatic cholestasis of pregnancy, primary sclerosing cholangitis, neonatal cholestasis, cholelithiasis, cirrhosis of the liver, cholangitis, Byler Disease, Byler Syndrome, cholelithiasis, liver disease related to total parenteral nutrition, chronic lung disease, congenital heart disease, exocrine pancreatic deficiency, and septicemia.

Cholestasis related phenotypes include, but are not limited to, jaundice, altered enzyme levels, growth failure, discolored urine, discolored stools, pruritus, abnormal bleeding, steatorrhea, elevated alkaline phosphatase levels, altered bilirubin levels, clotting rate, fatigue, loss of appetite, asthma-like symptoms, hyperlipidemia, xanthoma formation, and cirrhosis.

Methods of measuring cholestasis related phenotypes include, but are not limited to, physical examination, bilirubin assays, ultrasounds, computed tomography, liver biopsy, endoscopy, magnetic resonance imaging, enzymatic assays including, but not limited to, alanine transaminase, albumin, alkaline phosphatase, alpha-fetoprotein, aspartate transaminase, gamma-glutamyl transpeptidase, lactic dehydrogenase, mitochondrial antibodies, 5'-nucleotidase, and prothrombin assays; endoscopic retrograde cholangiopancreatography, percutaneous transhepatic cholangiography, and operative cholangiography.

Compositions of the invention include isolated nucleic acid molecules having the nucleotide sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, and SEQ ID NO:70, or a fragment or variants thereof. Isolated nucleic acid molecules of the invention anneal to a nucleotide sequence of interest.

Nucleotide sequences of interest in the present invention include numerous cholestasis related compounds. Cholestasis related genes include, but are not limited to, ATP8B1 (SEQ ID NO:71); ABCB11 (SEQ ID NO:72); ABCB4 (SEQ ID NO:73); JAG1 (SEQ ID NO:74); and SERPINA-1 or SERPIN-1 (SEQ ID NO:75). Portions of the first intron sequence of ABCB4 (SEQ ID NO:73) and SERPINA-1 (SEQ ID NO:75) are not included in the sequence listing. The invention particularly pertains to nucleotide sequence alterations in the 5' upstream regions, exons, and exon-intron boundary regions of the cholestasis related genes, thus selected regions of ATP8B1 (SEQ ID NO:71); ABCB11 (SEQ ID NO:72); ABCB4 (SEQ ID NO:73); JAG1 (SEQ ID NO:74); and SERPINA-1 (SEQ ID NO:75) are of particular interest.

Nucleic acid molecules having a nucleotide sequence set forth in SEQ ID NOS:1-18 anneal to the ATP8B1 gene (SEQ ID NO:71). Nucleic acid molecules having a nucleotide sequence set forth in SEQ ID NOS:19-38 anneal to the ABCB11 gene (SEQ ID NO:72). Nucleic acid molecules having a nucleotide sequence set forth in SEQ ID NOS:39-56 anneal to the ABCB4 gene (SEQ ID NO:73). Nucleic acid molecules having a nucleotide sequence set forth in SEQ ID NOS:57-66 anneal to the JAG1 gene (SEQ ID NO:74). Nucleic acid molecules having a nucleotide sequence set forth in SEQ ID NOS:67-70 anneal to the SERPINA-1 gene (SEQ ID NO:75).

The invention encompasses isolated or substantially purified nucleic acid compositions. An "isolated" or substantially "purified" nucleic acid molecule is substantially free of other cellular material, or culture medium when produced by recombinant techniques or substantially free of chemical precursors or other chemicals when chemically synthesized. A substantially purified preparation of nucleic acid molecules, particularly isolated nucleic acid molecules as used herein, means a preparation of nucleic acid molecules in which at least 70% of the nucleic acid molecules, preferably at least 80% of the nucleic acid molecules, more preferably at least 85% of the nucleic acid molecules, yet more preferably 90%, most preferably at least 91%, 92%, 93%, 94%, 95%, 96%, 97%, 98%, 99% or more of the nucleic acid molecules are the subject sequence.

By fragments or variants thereof is intended isolated nucleic acid molecules having a nucleotide sequence that differs by one nucleotide alteration from that set forth in SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 or a nucleotide sequence that hybridizes under stringent conditions to a complement of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70. A fragment or variant that differs by one nucleotide alteration from a nucleotide sequence set forth in SEQ ID NO:1, 2, 3, 4, 5, 6, 7, 8, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 differs from that nucleotide sequence by the addition, insertion, deletion, removal, subtraction, or substitution of one nucleotide. Fragments or variants include isolated nucleic acid molecules having a nucleotide sequence that hybridizes under stringent conditions to a complement of SEQ ID NO:1, 2, 3, 4, 5, 6, 7, 8, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70.

By "stringent conditions" or "stringent hybridization conditions" is intended conditions under which a molecule will hybridize to its target sequence to a detectably greater degree than to other sequences (e.g., at least 2-fold over background). Microarray hybridization conditions are discussed elsewhere herein. Stringent conditions are sequence-dependent and will be different in different circumstances. By controlling the stringency of the hybridization and/or washing conditions, target sequences that are 100% complementary can be identified (homologous probing). Alternatively, stringency conditions can be adjusted to allow some mismatching in sequences so that lower degrees of similarity are detected (heterologous probing). Generally, a hybridization fragment is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

By "region" is intended a portion of the entire nucleotide sequence of interest, such as the genomic ATP8B1 gene, ABCB11 gene, ABCB4 gene, JAG1 gene, and SERPINA-1 gene. A region of a nucleotide sequence of interest, such as a genomic cholestasis related gene may range from 16, 20, 50, 75, 100, 150, 200, 250, 300, 350, 400, 450, 500, 550, 600, 650, 700, 800, 900, 1,000, 1,100, 1,200, 1,300, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 4000, 4050, 4100, 4150, 4200, 4300, 4400, 4500, 4600, 4700, 4800, 4900, 5000, 6000, 7000, 8000, 9000, 10000, 20000, 30000, 40000, 50000, 60000, 70000, 80000, 90000, 100000, 108687 nucleotides, or up to the total number of nucleotides present in a full-length nucleotide sequence of interest disclosed herein. Such a region contains nucleotide sequence from the 5' regulatory control sequence, one or more exons, one or more exon-intron boundaries, or one or more introns of a cholestasis related nucleotide sequence of interest. The oligonucleotide pairs of the invention each amplify a different region of a cholestasis related gene. A region may comprise multiple smaller regions. For example, oligonucleotide pair of the invention may amplify a region comprising multiple regions of particular interest.

Regions of particular interest include, but are not limited to, the nucleotide sequences set forth in nucleotides 1 to 483 of SEQ ID NO:71; nucleotides 25,479 to 25,620 of SEQ ID NO:71; nucleotides 27,398 to 27,555 of SEQ ID NO:71; nucleotides 30,753 to 30,895 of SEQ ID NO:71; nucleotides 30,966 to 31,071 of SEQ ID NO:71; nucleotides 34,199 to 34,315 of SEQ ID NO:71; nucleotides 34,378 to 34,492 of SEQ ID NO:71; nucleotides 36,534 to 36,660 of SEQ ID NO:71; nucleotides 36,737 to 36,939 of SEQ ID NO:71; nucleotides 37,396 to 37,528 of SEQ ID NO:71; nucleotides 40,069 to 40,303 of SEQ ID NO:71; nucleotides 43,559 to 43,811 of SEQ ID NO:71; nucleotides 46,951 to 47,038 of SEQ ID NO:71; nucleotides 47,874 to 48,074 of SEQ ID NO:71; nucleotides 57,044 to 57,276 of SEQ ID NO:71; nucleotides 60,486 to 60,642 of SEQ ID NO:71; nucleotides 62,584 to 62,792 of SEQ ID NO:71; nucleotides 63,526 to 63,681 of SEQ ID NO:71; nucleotides 64,899 to 65,018 of SEQ ID NO:71; nucleotides 69,451 to 69,627 of SEQ ID NO:71; nucleotides 70,604 to 70,936 of SEQ ID NO:71; nucleotides 76,649 to 76,916 of SEQ ID NO:71; nucleotides 77,991 to 78,118 of SEQ ID NO:71; nucleotides 79,337 to 79,626 of SEQ ID NO:71; nucleotides 79,894 to 80,076 of SEQ ID NO:71; nucleotides 81,569 to 81,743 of SEQ ID NO:71; nucleotides 83,354 to 83,756 of SEQ ID NO:71;

nucleotides 1 to 401 of SEQ ID NO:72; nucleotides 13,430 to 13,576 of SEQ ID NO:72; nucleotides 14,783 to 14,848 of SEQ ID NO:72; nucleotides 17,228 to 17,323 of SEQ ID NO:72; nucleotides 18,072 to 18,354 of SEQ ID NO:72; nucleotides 34,860 to 34,991 of SEQ ID NO:72; nucleotides 36,100 to 36,277 of SEQ ID NO:72; nucleotides 37,700 to 37,915 of SEQ ID NO:72; nucleotides 40,657 to 40,825 of SEQ ID NO:72; nucleotides 45,298 to 45,516 of SEQ ID NO:72; nucleotides 51,603 to 51,760 of SEQ ID NO:72; nucleotides 54,895 to 55,049 of SEQ ID NO:72; nucleotides 57,742 to 57,911 of SEQ ID NO:72; nucleotides 59,532 to 59,779 of SEQ ID NO:72; nucleotides 61,367 to 61,581 of SEQ ID NO:72; nucleotides 62,031 to 62,276 of SEQ ID NO:72; nucleotides 63,092 to 63,199 of SEQ ID NO:72; nucleotides 67,274 to 67,420 of SEQ ID NO:72; nucleotides 73,454 to 73,662 of SEQ ID NO:72; nucleotides 86,621 to 86,769 of SEQ ID NO:72; nucleotides 86,816 to 87,021 of SEQ ID NO:72; nucleotides 95,149 to 95,396 of SEQ ID NO:72; nucleotides 96,157 to 96,442 of SEQ ID NO:72; nucleotides 99,049 to 99,249 of SEQ ID NO:72; nucleotides 100,720 to 100,961 of SEQ ID NO:72; nucleotides 104,220 to 104,470 of SEQ ID NO:72; nucleotides 106,779 to 106,969 of SEQ ID NO:72; nucleotides 107,760 to 108,687 of SEQ ID NO:72; nucleotides 1 to 1,802 of SEQ ID NO:73; nucleotides 1,803 to 2,186 of SEQ ID NO:73; nucleotides 2,299 to 2,400 of SEQ ID NO:73; nucleotides 3,075 to 3,254 of SEQ ID NO:73; nucleotides 3,611 to 3,760 of SEQ ID NO:73; nucleotides 3,879 to 4,008 of SEQ ID NO:73; nucleotides 6,675 to 6,773 of SEQ ID NO:73; nucleotides 16,442 to 16,636 of SEQ ID NO:73; nucleotides 24,758 to 24,859 of SEQ ID NO:73; nucleotides 26,215 to 26,450 of SEQ ID NO:73; nucleotides 27,556 to 27,771 of SEQ ID NO:73; nucleotides 29,258 to 29,426 of SEQ ID NO:73; nucleotides 32,145 to 32,360 of SEQ ID NO:73; nucleotides 34,375 to 34,532 of SEQ ID NO:73; nucleotides 35,577 to 35,731 of SEQ ID NO:73; nucleotides 35,906 to 36,075 of SEQ ID NO:73; nucleotides 38,948 to 39,195 of SEQ ID NO:73; nucleotides 39,513 to 39,727 of SEQ ID NO:73; nucleotides 47,785 to 47,990 of SEQ ID NO:73; nucleotides 52,430 to 52,644 of SEQ ID NO:73; nucleotides 55,298 to 55,488 of SEQ ID NO:73; nucleotides 57,125 to 57,273 of SEQ ID NO:73; nucleotides 59,275 to 59,396 of SEQ ID NO:73; nucleotides 60,730 to 60,857 of SEQ ID NO:73; nucleotides 61,835 to 62,082 of SEQ ID NO:73; nucleotides 65,633 to 65,777 of SEQ ID NO:73; nucleotides 67,317 to 67,501 of SEQ ID NO:73; nucleotides 69,958 to 70,158 of SEQ ID NO:73; nucleotides 71,116 to 71,357 of SEQ ID NO:73; nucleotides 72,835 to 73,106 of SEQ ID NO:73; nucleotides 76,069 to 76,259 of SEQ ID NO:73; nucleotides 77,048 to 77,349 of SEQ ID NO:73; nucleotides 1 to 1,015 of SEQ ID NO:74; nucleotides 1,415 to 1,764 of SEQ ID NO:74; nucleotides 6,490 to 6,689 of SEQ ID NO:74; nucleotides 8,080 to 8,239 of SEQ ID NO:74; nucleotides 10,407 to 10,502 of SEQ ID NO:74; nucleotides 15,699 to 15,997 of SEQ ID NO:74; nucleotides 17,963 to 18,067 of SEQ ID NO:74; nucleotides 21,823 to 21,997 of SEQ ID NO:74; nucleotides 22,171 to 22,334 of SEQ ID NO:74; nucleotides 22,727 to 22,884 of SEQ ID NO:74; nucleotides 24,061 to 24,218 of SEQ ID NO:74; nucleotides 24,786 to 24,943 of SEQ ID NO:74; nucleotides 25,314 to 25,404 of SEQ ID NO:74; nucleotides 25,699 to 25,916 of SEQ ID NO:74; nucleotides 26,311 to 26,505 of SEQ ID NO:74; nucleotides 27,318 to 27,526 of SEQ ID NO:74; nucleotides 28,337 to 28,494 of SEQ ID NO:74; nucleotides 28,952 to 29,109 of SEQ ID NO:74; nucleotides 29,165 to 29,322 of SEQ ID NO:74; nucleotides 29,442 to 29,602 of SEQ ID NO:74; nucleotides 30,037 to 30,108 of SEQ ID NO:74; nucleotides 30,558 to 30,687 of SEQ ID NO:74; nucleotides 31,820 to 31,977 of SEQ ID NO:74; nucleotides 32,529 to 32,682 of SEQ ID NO:74; nucleotides 32,728 to 33,005 of SEQ ID NO:74; nucleotides 33,177 to 33,352 of SEQ ID NO:74; nucleotides 33,488 to 33,682 of SEQ ID NO:74; nucleotides 34,466 to 36,779 of SEQ ID NO:74; nucleotides 1 to 538 of SEQ ID NO:75; nucleotides 539 to 792 of SEQ ID NO:75; nucleotides 886 to 1,033 of SEQ ID NO:75; nucleotides 6,308 to 7,001 of SEQ ID NO:75; nucleotides 8,408 to 8,722 of SEQ ID NO:75; nucleotides 9,938 to 10,129 of SEQ ID NO:75; or nucleotides 10,909 to 11,232 of SEQ ID NO:75.

Compositions of the invention include oligonucleotide pairs. An oligonucleotide pair of the invention consists of a first isolated nucleic acid molecule of the invention and a second isolated nucleic acid molecule of the invention with different nucleotide sequences. An oligonucleotide pair of the invention is suitable for use as a primer pair or primer set in an enzymatic amplification reaction such as, but not limited to, a PCR reaction. In an embodiment, an oligonucleotide pair comprises a first nucleic acid molecule having the nucleotide sequence set forth in SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, or a fragment or variant thereof and a second nucleic acid molecule having the nucleotide sequence set forth in SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or a fragment or variant thereof. The first and second nucleic acid molecules of an oligonucleotide pair anneal to opposite strands of a cholestasis related gene such that they allow amplification of a region of a cholestasis related gene bracketed by the primer pair.

In an embodiment, an oligonucleotide pair of the invention comprises a first nucleic acid molecule having the nucleotide sequence set forth in SEQ ID NO:1 or a variant thereof and a second nucleic acid molecule having the nucleotide sequence set forth in SEQ ID NO:2 or a variant thereof. In an embodiment, an oligonucleotide pair of the invention comprises a first nucleic acid molecule having the nucleotide sequence set forth in SEQ ID NO:3 or a variant thereof and a second nucleic acid molecule having the nucleotide sequence set forth in SEQ ID NO:4 or a variant thereof. In an embodiment, an oligonucleotide pair of the invention comprises a first nucleic acid molecule having the nucleotide sequence set forth in SEQ ID NO:5 or a variant thereof and a second nucleic acid molecule having the nucleotide sequence set forth in SEQ ID NO:6 or a variant thereof. In an embodiment, an oligonucleotide pair of the invention comprises a first nucleic acid molecule having the nucleotide sequence set forth in SEQ ID NO:7 or a variant thereof and a second nucleic acid molecule having the nucleotide sequence set forth in SEQ ID NO:8 or a variant thereof. In an embodiment, an oligonucleotide pair of the invention comprises a first nucleic acid molecule having the nucleotide sequence set forth in SEQ ID NO:9 or a variant thereof and a second nucleic acid molecule having the nucleotide sequence set forth in SEQ ID NO:10 or a variant thereof. In an embodiment, an oligonucleotide pair of the invention comprises a first nucleic acid molecule having the nucleotide sequence set forth in SEQ ID NO:11 or a variant thereof and a second nucleic acid molecule having the nucleotide sequence set forth in SEQ ID NO:12 or a variant thereof. In an embodiment, an oligonucleotide pair of the invention comprises a first nucleic acid molecule having the nucleotide sequence set forth in SEQ ID NO:13 or a variant thereof and a second nucleic acid molecule having the nucleotide sequence set forth in SEQ ID NO:14 or a variant thereof. In an embodiment, an oligonucleotide pair of the invention comprises a first nucleic acid molecule having the nucleotide sequence set forth in SEQ ID NO:15 or a variant thereof and a second nucleic acid molecule having the nucleotide sequence set forth in SEQ ID NO:16 or a variant thereof. In an embodiment, an oligonucleotide pair of the invention comprises a first nucleic acid molecule having the nucleotide sequence set forth in SEQ ID NO:17 or a variant thereof and a second nucleic acid molecule having the nucleotide sequence set forth in SEQ ID NO:18 or a variant thereof. In an embodiment an oligonucleotide pair of the invention allows amplification of a region of the ATP8B1 protein gene (SEQ ID NO:71).

In an embodiment, an oligonucleotide pair of the invention comprises a first nucleic acid molecule having the nucleotide sequence set forth in SEQ ID NO:19 or a variant thereof and a second nucleic acid molecule having the nucleotide sequence set forth in SEQ ID NO:20 or a variant thereof. In an embodiment, an oligonucleotide pair of the invention comprises a first nucleic acid molecule having the nucleotide sequence set forth in SEQ ID NO:21 or a variant thereof and a second nucleic acid molecule having the nucleotide sequence set forth in SEQ ID NO:22 or a variant thereof. In an embodiment, an oligonucleotide pair of the invention comprises a first nucleic acid molecule having the nucleotide sequence set forth in SEQ ID NO:23 or a variant thereof and a second nucleic acid molecule having the nucleotide sequence set forth in SEQ ID NO:24 or a variant thereof. In an embodiment, an oligonucleotide pair of the invention comprises a first nucleic acid molecule having the nucleotide sequence set forth in SEQ ID NO:25 or a variant thereof and a second nucleic acid molecule having the nucleotide sequence set forth in SEQ ID NO:26 or a variant thereof. In an embodiment, an oligonucleotide pair of the invention comprises a first nucleic acid molecule having the nucleotide sequence set forth in SEQ ID NO:27 or a variant thereof and a second nucleic acid molecule having the nucleotide sequence set forth in SEQ ID NO:28 or a variant thereof. In an embodiment, an oligonucleotide pair of the invention comprises a first nucleic acid molecule having the nucleotide sequence set forth in SEQ ID NO:29 or a variant thereof and a second nucleic acid molecule having the nucleotide sequence set forth in SEQ ID NO:30 or a variant thereof. In an embodiment, an oligonucleotide pair of the invention comprises a first nucleic acid molecule having the nucleotide sequence set forth in SEQ ID NO:31 or a variant thereof and a second nucleic acid molecule having the nucleotide sequence set forth in SEQ ID NO:32 or a variant thereof. In an embodiment, an oligonucleotide pair of the invention comprises a first nucleic acid molecule having the nucleotide sequence set forth in SEQ ID NO:33 or a variant thereof and a second nucleic acid molecule having the nucleotide sequence set forth in SEQ ID NO:34 or a variant thereof. In an embodiment, an oligonucleotide pair of the invention comprises a first nucleic acid molecule having the nucleotide sequence set forth in SEQ ID NO:35 or a variant thereof and a second nucleic acid molecule having the nucleotide sequence set forth in SEQ ID NO:36 or a variant thereof. In an embodiment, an oligonucleotide pair of the invention comprises a first nucleic acid molecule having the nucleotide sequence set forth in SEQ ID NO:37 or a variant thereof and a second nucleic acid molecule having the nucleotide sequence set forth in SEQ ID NO:38 or a variant thereof. In an embodiment an oligonucleotide pair of the invention allows amplification of a region of the ABCB11 protein gene (SEQ ID NO:72).

In an embodiment, an oligonucleotide pair of the invention comprises a first nucleic acid molecule having the nucleotide sequence set forth in SEQ ID NO:39 or a variant thereof and a second nucleic acid molecule having the nucleotide sequence set forth in SEQ ID NO:40 or a variant thereof. In an embodiment, an oligonucleotide pair of the invention comprises a first nucleic acid molecule having the nucleotide sequence set forth in SEQ ID NO:41 or a variant thereof and a second nucleic acid molecule having the nucleotide sequence set forth in SEQ ID NO:42 or a variant thereof. In an embodiment, an oligonucleotide pair of the invention comprises a first nucleic acid molecule having the nucleotide sequence set forth in SEQ ID NO:43 or a variant thereof and a second nucleic acid molecule having the nucleotide sequence set forth in SEQ ID NO:44 or a variant thereof. In an embodiment, an oligonucleotide pair of the invention comprises a first nucleic acid molecule having the nucleotide sequence set forth in SEQ ID NO:45 or a variant thereof and a second nucleic acid molecule having the nucleotide sequence set forth in SEQ ID NO:46 or a variant thereof. In an embodiment, an oligonucleotide pair of the invention comprises a first nucleic acid molecule having the nucleotide sequence set forth in SEQ ID NO:47 or a variant thereof and a second nucleic acid molecule having the nucleotide sequence set forth in SEQ ID NO:48 or a variant thereof. In an embodiment, an oligonucleotide pair of the invention comprises a first nucleic acid molecule having the nucleotide sequence set forth in SEQ ID NO:49 or a variant thereof and a second nucleic acid molecule having the nucleotide sequence set forth in SEQ ID NO:50 or a variant thereof. In an embodiment, an oligonucleotide pair of the invention comprises a first nucleic acid molecule having the nucleotide sequence set forth in SEQ ID NO:51 or a variant thereof and a second nucleic acid molecule having the nucleotide sequence set forth in SEQ ID NO:52 or a variant thereof. In an embodiment, an oligonucleotide pair of the invention comprises a first nucleic acid molecule having the nucleotide sequence set forth in SEQ ID NO:53 or a variant thereof and a second nucleic acid molecule having the nucleotide sequence set forth in SEQ ID NO:54 or a variant thereof. In an embodiment, an oligonucleotide pair of the invention comprises a first nucleic acid molecule having the nucleotide sequence set forth in SEQ ID NO:55 or a variant thereof and a second nucleic acid molecule having the nucleotide sequence set forth in SEQ ID NO:56 or a variant thereof. In an embodiment an oligonucleotide pair of the invention allows amplification of a region of the ABCB4 protein gene (SEQ ID NO:73).

In an embodiment, an oligonucleotide pair of the invention comprises a first nucleic acid molecule having the nucleotide sequence set forth in SEQ ID NO:57 or a variant thereof and a second nucleic acid molecule having the nucleotide sequence set forth in SEQ ID NO:58 or a variant thereof. In an embodiment, an oligonucleotide pair of the invention comprises a first nucleic acid molecule having the nucleotide sequence set forth in SEQ ID NO:59 or a variant thereof and a second nucleic acid molecule having the nucleotide sequence set forth in SEQ ID NO:60 or a variant thereof. In an embodiment, an oligonucleotide pair of the invention comprises a first nucleic acid molecule having the nucleotide sequence set forth in SEQ ID NO:61 or a variant thereof and a second nucleic acid molecule having the nucleotide sequence set forth in SEQ ID NO:62 or a variant thereof. In an embodiment, an oligonucleotide pair of the invention comprises a first nucleic acid molecule having the nucleotide sequence set forth in SEQ ID NO:63 or a variant thereof and a second nucleic acid molecule having the nucleotide sequence set forth in SEQ ID NO:64 or a variant thereof. In an embodiment, an oligonucleotide pair of the invention comprises a first nucleic acid molecule having the nucleotide sequence set forth in SEQ ID NO:65 or a variant thereof and a second nucleic acid molecule having the nucleotide sequence set forth in SEQ ID NO:66 or a variant thereof. In an embodiment an oligonucleotide pair of the invention allows amplification of a region of the JAG1 protein gene (SEQ ID NO:74).

In an embodiment, an oligonucleotide pair of the invention comprises a first nucleic acid molecule having the nucleotide sequence set forth in SEQ ID NO:67 or a variant thereof and a second nucleic acid molecule having the nucleotide sequence set forth in SEQ ID NO:68 or a variant thereof. In an embodiment, an oligonucleotide pair of the invention comprises a first nucleic acid molecule having the nucleotide sequence set forth in SEQ ID NO:69 or a variant thereof and a second nucleic acid molecule having the nucleotide sequence set forth in SEQ ID NO:70 or a variant thereof. In an embodiment an oligonucleotide pair of the invention allows amplification of a region of the SERPINA-1 protein gene (SEQ ID NO:75).

Additional oligonucleotide pairs comprising the isolated nucleic acid molecules of the invention are encompassed by the invention.

By "amplification" is intended an increase in the amount of nucleic acid molecules in a sample. Amplifying DNA increases the amount of acid precipitable nucleic acid molecules. The amount of acid precipitable material increases by 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, or more. Methods of quantifying nucleic acid molecules are known in the art and include, but are not limited to, UV absorption spectra, radiolabel incorporation, agarose gel electrophoresis, bisbenzimide staining and ethidium bromide staining. See, for example, Ausubel et al., eds. (2003) *Current Protocols in Molecular Biology*, (John Wiley & Sons, New York) and Sambrook et al. (2001) *Molecular Cloning: A Laboratory Manual* (3d ed., Cold Spring Harbor Laboratory Press, Plainview, N.Y., herein incorporated by reference.

Enzymatic amplification is the process of using enzymes to perform amplification. A common type of enzymatic amplification is the polymerase chain reaction (PCR). Known methods of PCR include, but are not limited to, methods using paired primers, nested primers, single specific primers, degenerate primers, gene-specific primers, vector-specific primers, partially-mismatched primers, and the like. Known methods of PCR include, but are not limited to, methods using DNA polymerases from extremophiles, engineered DNA polymerases, and long-range PCR. It is recognized that it is preferable to use high fidelity PCR reaction conditions in the methods of the invention. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Long range PCR amplification methods include methods such as those described in the TaKaRa LA PCR guide, Takara Shuzo Co., Ltd.

By "amplified DNA" is intended the product of enzymatic amplification.

Any method of DNA sequencing known in the art can be used in the methods of the invention. Methods of sequencing DNA are known in the art and are described in Graham & Hill eds. (2001) *DNA Sequencing Protocols* (Humana Press, Totowa N.J.), Kieleczawa ed (2004) *DNA Sequencing: Optimizing the Process and Analysis* (Jones & Bartlett Publishers, Ontario), Ausubel et al., eds. (2003) *Current Protocols in Molecular Biology*, (John Wiley & Sons, New York) and Sambrook et al. (2001) *Molecular Cloning: A Laboratory Manual* (3d ed., Cold Spring Harbor Laboratory Press, Plainview, N.Y., herein incorporated by reference in their entirety).

In an embodiment a resequencing microarray is used in the methods of the invention. By "resequencing microarray" or "variation detection array" is intended a microarray of nucleic acid probes arranged on a chip wherein each nucleic acid probe is of a predetermined length and sequence. Regions of a nucleotide sequence of interest are divided into segments of predetermined length and nucleic acid probes based on the sequence of each segment are arranged on a chip. Each nucleic acid probe contains a single query base. For each segment, four nucleic acid probes of identical sequence with the exception of the query base are tiled on the chip. A predetermined nucleotide is inserted at the query base location, and each nucleotide is presented in one of the four nucleic acid probes. Thus, each possible nucleotide sequence is represented. The sequence of each nucleic acid probe is identical to a segment of a nucleotide sequence of interest or differs by one predetermined nucleotide alteration from a segment of a nucleotide sequence of interest. See Warrington et al. (2002) *Hum Mutat* 19:402-409 and Cutler et al. (2001) *Genome Res* 11: 1913-1925, herein incorporated by reference in their entirety.

A cholestasis related gene resequencing microarray of the invention consists of nucleic acid probes having a nucleotide sequence derived from the nucleotide sequences set forth in SEQ ID NOS:71-75. In particular the nucleic acid probes have a nucleotide sequence derived from a segment of the nucleotide sequence set forth in nucleotides 1 to 483 of SEQ ID NO:71; nucleotides 25,479 to 25,620 of SEQ ID NO:71; nucleotides 27,398 to 27,555 of SEQ ID NO:71; nucleotides 30,753 to 30,895 of SEQ ID NO:71; nucleotides 30,966 to 31,071 of SEQ ID NO:71; nucleotides 34,199 to 34,315 of SEQ ID NO:71; nucleotides 34,378 to 34,492 of SEQ ID NO:71; nucleotides 36,534 to 36,660 of SEQ ID NO:71; nucleotides 36,737 to 36,939 of SEQ ID NO:71; nucleotides 37,396 to 37,528 of SEQ ID NO:71; nucleotides 40,069 to 40,303 of SEQ ID NO:71; nucleotides 43,559 to 43,811 of SEQ ID NO:71; nucleotides 46,951 to 47,038 of SEQ ID NO:71; nucleotides 47,874 to 48,074 of SEQ ID NO:71; nucleotides 57,044 to 57,276 of SEQ ID NO:71; nucleotides 60,486 to 60,642 of SEQ ID NO:71; nucleotides 62,584 to 62,792 of SEQ ID NO:71; nucleotides 63,526 to 63,681 of SEQ ID NO:71; nucleotides 64,899 to 65,018 of SEQ ID NO:71; nucleotides 69,451 to 69,627 of SEQ ID NO:71; nucleotides 70,604 to 70,936 of SEQ ID NO:71; nucleotides 76,649 to 76,916 of SEQ ID NO:71; nucleotides 77,991 to 78,118 of SEQ ID NO:71; nucleotides 79,337 to 79,626 of SEQ ID NO:71; nucleotides 79,894 to 80,076 of SEQ ID NO:71; nucleotides 81,569 to 81,743 of SEQ ID NO:71; nucleotides 83,354 to 83,756 of SEQ ID NO:71; nucleotides 1 to 401 of SEQ ID NO:72; nucleotides 13,430 to 13,576 of SEQ ID NO:72; nucleotides 14,783 to 14,848 of SEQ ID NO:72; nucleotides 17,228 to 17,323 of SEQ ID NO:72; nucleotides 18,072 to 18,354 of SEQ ID NO:72; nucleotides 34,860 to 34,991 of SEQ ID NO:72; nucleotides 36,100 to 36,277 of SEQ ID NO:72; nucleotides 37,700 to 37,915 of SEQ ID NO:72; nucleotides 40,657 to 40,825 of SEQ ID NO:72; nucleotides 45,298 to 45,516 of SEQ ID NO:72; nucleotides 51,603 to 51,760 of SEQ ID NO:72; nucleotides 54,895 to 55,049 of SEQ ID NO:72; nucleotides 57,742 to 57,911 of SEQ ID NO:72; nucleotides 59,532 to 59,779 of SEQ ID NO:72; nucleotides 61,367 to 61,581 of SEQ ID NO:72; nucleotides 62,031 to 62,276 of SEQ ID NO:72;

nucleotides 63,092 to 63,199 of SEQ ID NO:72; nucleotides 67,274 to 67,420 of SEQ ID NO:72; nucleotides 73,454 to 73,662 of SEQ ID NO:72; nucleotides 86,621 to 86,769 of SEQ ID NO:72; nucleotides 86,816 to 87,021 of SEQ ID NO:72; nucleotides 95,149 to 95,396 of SEQ ID NO:72; nucleotides 96,157 to 96,442 of SEQ ID NO:72; nucleotides 99,049 to 99,249 of SEQ ID NO:72; nucleotides 100,720 to 100,961 of SEQ ID NO:72; nucleotides 104,220 to 104,470 of SEQ ID NO:72; nucleotides 106,779 to 106,969 of SEQ ID NO:72; nucleotides 107,760 to 108,687 of SEQ ID NO:72; nucleotides 1 to 1,802 of SEQ ID NO:73; nucleotides 1,803 to 2,186 of SEQ ID NO:73; nucleotides 2,299 to 2,400 of SEQ ID NO:73; nucleotides 3,075 to 3,254 of SEQ ID NO:73; nucleotides 3,611 to 3,760 of SEQ ID NO:73; nucleotides 3,879 to 4,008 of SEQ ID NO:73; nucleotides 6,675 to 6,773 of SEQ ID NO:73; nucleotides 16,442 to 16,636 of SEQ ID NO:73; nucleotides 24,758 to 24,859 of SEQ ID NO:73; nucleotides 26,215 to 26,450 of SEQ ID NO:73; nucleotides 27,556 to 27,771 of SEQ ID NO:73; nucleotides 29,258 to 29,426 of SEQ ID NO:73; nucleotides 32,145 to 32,360 of SEQ ID NO:73; nucleotides 34,375 to 34,532 of SEQ ID NO:73; nucleotides 35,577 to 35,731 of SEQ ID NO:73; nucleotides 35,906 to 36,075 of SEQ ID NO:73; nucleotides 38,948 to 39,195 of SEQ ID NO:73; nucleotides 39,513 to 39,727 of SEQ ID NO:73; nucleotides 47,785 to 47,990 of SEQ ID NO:73; nucleotides 52,430 to 52,644 of SEQ ID NO:73; nucleotides 55,298 to 55,488 of SEQ ID NO:73; nucleotides 57,125 to 57,273 of SEQ ID NO:73; nucleotides 59,275 to 59,396 of SEQ ID NO:73; nucleotides 60,730 to 60,857 of SEQ ID NO:73; nucleotides 61,835 to 62,082 of SEQ ID NO:73; nucleotides 65,633 to 65,777 of SEQ ID NO:73; nucleotides 67,317 to 67,501 of SEQ ID NO:73; nucleotides 69,958 to 70,158 of SEQ ID NO:73; nucleotides 71,116 to 71,357 of SEQ ID NO:73; nucleotides 72,835 to 73,106 of SEQ ID NO:73; nucleotides 76,069 to 76,259 of SEQ ID NO:73; nucleotides 77,048 to 77,349 of SEQ ID NO:73; nucleotides 1 to 1,015 of SEQ ID NO:74; nucleotides 1,415 to 1,764 of SEQ ID NO:74; nucleotides 6,490 to 6,689 of SEQ ID NO:74; nucleotides 8,080 to 8,239 of SEQ ID NO:74; nucleotides 10,407 to 10,502 of SEQ ID NO:74; nucleotides 15,699 to 15,997 of SEQ ID NO:74; nucleotides 17,963 to 18,067 of SEQ ID NO:74; nucleotides 21,823 to 21,997 of SEQ ID NO:74; nucleotides 22,171 to 22,334 of SEQ ID NO:74; nucleotides 22,727 to 22,884 of SEQ ID NO:74; nucleotides 24,061 to 24,218 of SEQ ID NO:74; nucleotides 24,786 to 24,943 of SEQ ID NO:74; nucleotides 25,314 to 25,404 of SEQ ID NO:74; nucleotides 25,699 to 25,916 of SEQ ID NO:74; nucleotides 26,311 to 26,505 of SEQ ID NO:74; nucleotides 27,318 to 27,526 of SEQ ID NO:74; nucleotides 28,337 to 28,494 of SEQ ID NO:74; nucleotides 28,952 to 29,109 of SEQ ID NO:74; nucleotides 29,165 to 29,322 of SEQ ID NO:74; nucleotides 29,442 to 29,602 of SEQ ID NO:74; nucleotides 30,037 to 30,108 of SEQ ID NO:74; nucleotides 30,558 to 30,687 of SEQ ID NO:74; nucleotides 31,820 to 31,977 of SEQ ID NO:74; nucleotides 32,529 to 32,682 of SEQ ID NO:74; nucleotides 32,728 to 33,005 of SEQ ID NO:74; nucleotides 33,177 to 33,352 of SEQ ID NO:74; nucleotides 33,488 to 33,682 of SEQ ID NO:74; nucleotides 34,466 to 36,779 of SEQ ID NO:74; nucleotides 1 to 538 of SEQ ID NO:75; nucleotides 539 to 792 of SEQ ID NO:75; nucleotides 886 to 1,033 of SEQ ID NO:75; nucleotides 6,308 to 7,001 of SEQ ID NO:75; nucleotides 8,408 to 8,722 of SEQ ID NO:75; nucleotides 9,938 to 10,129 of SEQ ID NO:75; nucleotides 10,909 to 11,232 of SEQ ID NO:75 or differs by one predetermined nucleotide alteration from a segment of the nucleotide sequence set forth in nucleotides 1 to 483 of SEQ ID NO:71; nucleotides 25,479 to 25,620 of SEQ ID NO:71; nucleotides 27,398 to 27,555 of SEQ ID NO:71; nucleotides 30,753 to 30,895 of SEQ ID NO:71; nucleotides 30,966 to 31,071 of SEQ ID NO:71; nucleotides 34,199 to 34,315 of SEQ ID NO:71; nucleotides 34,378 to 34,492 of SEQ ID NO:71; nucleotides 36,534 to 36,660 of SEQ ID NO:71; nucleotides 36,737 to 36,939 of SEQ ID NO:71; nucleotides 37,396 to 37,528 of SEQ ID NO:71; nucleotides 40,069 to 40,303 of SEQ ID NO:71; nucleotides 43,559 to 43,811 of SEQ ID NO:71; nucleotides 46,951 to 47,038 of SEQ ID NO:71; nucleotides 47,874 to 48,074 of SEQ ID NO:71; nucleotides 57,044 to 57,276 of SEQ ID NO:71; nucleotides 60,486 to 60,642 of SEQ ID NO:71; nucleotides 62,584 to 62,792 of SEQ ID NO:71; nucleotides 63,526 to 63,681 of SEQ ID NO:71; nucleotides 64,899 to 65,018 of SEQ ID NO:71; nucleotides 69,451 to 69,627 of SEQ ID NO:71; nucleotides 70,604 to 70,936 of SEQ ID NO:71; nucleotides 76,649 to 76,916 of SEQ ID NO:71; nucleotides 77,991 to 78,118 of SEQ ID NO:71; nucleotides 79,337 to 79,626 of SEQ ID NO:71; nucleotides 79,894 to 80,076 of SEQ ID NO:71; nucleotides 81,569 to 81,743 of SEQ ID NO:71; nucleotides 83,354 to 83,756 of SEQ ID NO:71; nucleotides 1 to 401 of SEQ ID NO:72; nucleotides 13,430 to 13,576 of SEQ ID NO:72; nucleotides 14,783 to 14,848 of SEQ ID NO:72; nucleotides 17,228 to 17,323 of SEQ ID NO:72; nucleotides 18,072 to 18,354 of SEQ ID NO:72; nucleotides 34,860 to 34,991 of SEQ ID NO:72; nucleotides 36,100 to 36,277 of SEQ ID NO:72; nucleotides 37,700 to 37,915 of SEQ ID NO:72; nucleotides 40,657 to 40,825 of SEQ ID NO:72; nucleotides 45,298 to 45,516 of SEQ ID NO:72; nucleotides 51,603 to 51,760 of SEQ ID NO:72; nucleotides 54,895 to 55,049 of SEQ ID NO:72; nucleotides 57,742 to 57,911 of SEQ ID NO:72; nucleotides 59,532 to 59,779 of SEQ ID NO:72; nucleotides 61,367 to 61,581 of SEQ ID NO:72; nucleotides 62,031 to 62,276 of SEQ ID NO:72; nucleotides 63,092 to 63,199 of SEQ ID NO:72; nucleotides 67,274 to 67,420 of SEQ ID NO:72; nucleotides 73,454 to 73,662 of SEQ ID NO:72; nucleotides 86,621 to 86,769 of SEQ ID NO:72; nucleotides 86,816 to 87,021 of SEQ ID NO:72; nucleotides 95,149 to 95,396 of SEQ ID NO:72; nucleotides 96,157 to 96,442 of SEQ ID NO:72; nucleotides 99,049 to 99,249 of SEQ ID NO:72; nucleotides 100,720 to 100,961 of SEQ ID NO:72; nucleotides 104,220 to 104,470 of SEQ ID NO:72; nucleotides 106,779 to 106,969 of SEQ ID NO:72; nucleotides 107,760 to 108,687 of SEQ ID NO:72; nucleotides 1 to 1,802 of SEQ ID NO:73; nucleotides 1,803 to 2,186 of SEQ ID NO:73; nucleotides 2,299 to 2,400 of SEQ ID NO:73; nucleotides 3,075 to 3,254 of SEQ ID NO:73; nucleotides 3,611 to 3,760 of SEQ ID NO:73; nucleotides 3,879 to 4,008 of SEQ ID NO:73; nucleotides 6,675 to 6,773 of SEQ ID NO:73; nucleotides 16,442 to 16,636 of SEQ ID NO:73; nucleotides 24,758 to 24,859 of SEQ ID NO:73; nucleotides 26,215 to 26,450 of SEQ ID NO:73; nucleotides 27,556 to 27,771 of SEQ ID NO:73; nucleotides 29,258 to 29,426 of SEQ ID NO:73; nucleotides 32,145 to 32,360 of SEQ ID NO:73; nucleotides 34,375 to 34,532 of SEQ ID NO:73; nucleotides 35,577 to 35,731 of SEQ ID NO:73; nucleotides 35,906 to 36,075 of SEQ ID NO:73; nucleotides 38,948 to 39,195 of SEQ ID NO:73; nucleotides 39,513 to 39,727 of SEQ ID NO:73; nucleotides 47,785 to 47,990 of SEQ ID NO:73; nucleotides 52,430 to 52,644 of SEQ ID NO:73; nucleotides 55,298 to 55,488 of SEQ ID NO:73; nucleotides 57,125 to 57,273 of SEQ ID NO:73; nucleotides 59,275 to 59,396 of SEQ ID NO:73; nucleotides 60,730 to 60,857 of SEQ ID NO:73; nucleotides 61,835 to 62,082 of SEQ ID NO:73; nucleotides 65,633 to 65,777 of SEQ ID NO:73; nucleotides 67,317 to 67,501 of SEQ ID NO:73;

nucleotides 69,958 to 70,158 of SEQ ID NO:73; nucleotides 71,116 to 71,357 of SEQ ID NO:73; nucleotides 72,835 to 73,106 of SEQ ID NO:73; nucleotides 76,069 to 76,259 of SEQ ID NO:73; nucleotides 77,048 to 77,349 of SEQ ID NO:73; nucleotides 1 to 1,015 of SEQ ID NO:74; nucleotides 1,415 to 1,764 of SEQ ID NO:74; nucleotides 6,490 to 6,689 of SEQ ID NO:74; nucleotides 8,080 to 8,239 of SEQ ID NO:74; nucleotides 10,407 to 10,502 of SEQ ID NO:74; nucleotides 15,699 to 15,997 of SEQ ID NO:74; nucleotides 17,963 to 18,067 of SEQ ID NO:74; nucleotides 21,823 to 21,997 of SEQ ID NO:74; nucleotides 22,171 to 22,334 of SEQ ID NO:74; nucleotides 22,727 to 22,884 of SEQ ID NO:74; nucleotides 24,061 to 24,218 of SEQ ID NO:74; nucleotides 24,786 to 24,943 of SEQ ID NO:74; nucleotides 25,314 to 25,404 of SEQ ID NO:74; nucleotides 25,699 to 25,916 of SEQ ID NO:74; nucleotides 26,311 to 26,505 of SEQ ID NO:74; nucleotides 27,318 to 27,526 of SEQ ID NO:74; nucleotides 28,337 to 28,494 of SEQ ID NO:74; nucleotides 28,952 to 29,109 of SEQ ID NO:74; nucleotides 29,165 to 29,322 of SEQ ID NO:74; nucleotides 29,442 to 29,602 of SEQ ID NO:74; nucleotides 30,037 to 30,108 of SEQ ID NO:74; nucleotides 30,558 to 30,687 of SEQ ID NO:74; nucleotides 31,820 to 31,977 of SEQ ID NO:74; nucleotides 32,529 to 32,682 of SEQ ID NO:74; nucleotides 32,728 to 33,005 of SEQ ID NO:74; nucleotides 33,177 to 33,352 of SEQ ID NO:74; nucleotides 33,488 to 33,682 of SEQ ID NO:74; nucleotides 34,466 to 36,779 of SEQ ID NO:74; nucleotides 1 to 538 of SEQ ID NO:75; nucleotides 539 to 792 of SEQ ID NO:75; nucleotides 886 to 1,033 of SEQ ID NO:75; nucleotides 6,308 to 7,001 of SEQ ID NO:75; nucleotides 8,408 to 8,722 of SEQ ID NO:75; nucleotides 9,938 to 10,129 of SEQ ID NO:75; or nucleotides 10,909 to 11,232 of SEQ ID NO:75.

Methods of using and analyzing microarrays are known in the art. Hybridization and wash protocols are described extensively in GeneChip® CustomSeq™ Resequencing Array Protocol, (2004) V.2.0, revision 3, Affymetrix. Microarray analysis is discussed extensively in Cutler et al. (2001) Genome Res 11: 1913-1925 and GeneChip® CustomSeq™ Resequencing Array Protocol, (2004) V.2.0, revision 3, Affymetrix, herein incorporated by reference in their entirety.

In an embodiment, the invention provides kits for performing the methods of the invention. Such kits comprise an isolated nucleic acid molecule of the invention, particularly multiple isolated nucleic acid molecules of the invention, and an oligonucleotide pair of the invention, particularly multiple oligonucleotide pairs of the invention. A kit of the invention may further comprise a cholestasis related gene resequencing microarray. Additionally a kit of the invention may comprise a standard sequence profile or a means of accessing a standard sequence profile.

By "standard sequence profile" is intended a listing of the consensus nucleotide sequence of at least one nucleotide sequence of interest. A standard sequence profile may contain additional information including but not limited to, a correlation of at least one nucleotide sequence variation with a disease, syndrome, prognosis, or treatment protocol. A standard sequence profile may exist in printed or electronic form, a remotely accessible form, in a database, or in any other means known in the art. In an embodiment a standard sequence profile is a cholestasis related standard sequence profile. For instance, an exemplary cholestasis related standard sequence profile correlates certain nucleotide alterations in ATP8B1 with either PFIC Type I or BRIC Type 1; ABCB11 with either PFIC Type II or BRIC Type II; ABCB4 with PFIC Type III or MDR deficiency; JAG1 with Alagille Syndrome; or SERPINA-1 with alpha1-antitrypsin deficiency.

By "disease classification", "disease type", or "disease subtype" is intended a set of diseases limited by certain shared characteristics, phenotypes, genotypes, or traits. Disease classification for various diseases and disorders are known in the art. Typically cholestasis related syndromes are classified based on the location of cause of the cholestasis, that is, within the liver or outside the liver.

By "subject" is intended a human, human tissue, or human cells. Suitable subjects include, but are not limited to, humans exhibiting cholestasis, tissue obtained from a human exhibiting cholestasis, cells obtained from a human exhibiting cholestasis, cells cultured from a human exhibiting cholestasis, and healthy humans.

By "biological sample" is intended a sample collected from a subject including, but not limited to, whole blood, tissue, cells, mucosa, fluid, scrapings, hairs, cell lysates, and secretions. Biological samples such as blood samples can be obtained by any method known to one skilled in the art. Further, biological samples can be enriched, purified, isolated, or stabilized by any method known to one skilled in the art.

The invention encompasses isolated or substantially purified nucleic acid or protein compositions.

By "disease progression" or "disease course" is intended the physiological events related to a disease or disorder that occur during the period after the initial presentation in a subject or patient exhibiting a disease or disorder. With respect to cholestasis, the duration and degree of the cholestasis are used to describe the disease course or progression. For instance, benign recurrent intrahepatic cholestasis presents and regresses, typically without the development of cirrhosis. Progressive familial intrahepatic cholestasis presents early in infancy and typically continues with the development of cirrhosis and eventual lethality. Identifying the disease course or disease progression that an untreated patient would experience allows practitioners to identify those patients who would benefit most from aggressive early intervention.

The following examples are offered by way of illustration and not limitation.

EXPERIMENTAL

Example 1

Enzymatic Amplification of Multiple Regions of Cholestasis Related Genes

Genomic DNA was purified from whole blood samples obtained from subjects exhibiting jaundice. An enzymatic amplification master mix was prepared following the polymerase manufacturer's standard protocol. The master mix was aliquoted into thermocycler tubes. The isolated nucleic acid molecules of the invention were diluted and added in pairs to each tube. The purified genomic DNA was diluted and added into each tube. The reaction mixtures were placed in a thermocycler and subjected to incubations suitable for long-range PCR. Aliquots of each reaction mixture were loaded on agarose gels and subjected to electrophoresis. Typical results obtained with oligonucleotide pairs specific to ATP8B1 are shown in FIG. 1, Panel C; ABCB11 in FIG. 2, Panel C; ABCB4 in FIG. 3, Panel C; JAG1 in FIG. 4, Panel C; and SERPINA-1 in FIG. 5, Panel C.

Example 2

Resequencing Microarray Analysis

Amplified DNA obtained as described above was utilized in resequencing microarray analysis with a cholestasis related gene resequencing microarray of the invention. Microarray analysis was performed according to the manufacturer's recommended protocol.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

That which is claimed:

1. An oligonucleotide pair library comprising at least one oligonucleotide pair, said oligonucleotide pair comprising a first nucleic acid molecule and a second nucleic acid molecule wherein said oligonucleotide pair is selected from the group consisting of:
   (a) the oligonucleotide pair consisting of a first nucleic acid molecule having the nucleotide sequence set forth in SEQ ID NO:1 and a second nucleic acid molecule having the nucleotide sequence set forth in SEQ ID NO:2;
   (b) the oligonucleotide pair consisting of a first nucleic acid molecule having the nucleotide sequence set forth in SEQ ID NO:3 and a second nucleic acid molecule having the nucleotide sequence set forth in SEQ ID NO:4;
   (c) the oligonucleotide pair consisting of a first nucleic acid molecule having the nucleotide sequence set forth in SEQ ID NO:5 and a second nucleic acid molecule having the nucleotide sequence set forth in SEQ ID NO:6;
   (d) the oligonucleotide pair consisting of a first nucleic acid molecule having the nucleotide sequence set forth in SEQ ID NO:7 and a second nucleic acid molecule having the nucleotide sequence set forth in SEQ ID NO:8;
   (e) the oligonucleotide pair consisting of a first nucleic acid molecule having the nucleotide sequence set forth in SEQ ID NO:9 and a second nucleic acid molecule having the nucleotide sequence set forth in SEQ ID NO:10;
   (f) the oligonucleotide pair consisting of a first nucleic acid molecule having the nucleotide sequence set forth in SEQ ID NO:11 and a second nucleic acid molecule having the nucleotide sequence set forth in SEQ ID NO:12;
   (g) the oligonucleotide pair consisting of a first nucleic acid molecule having the nucleotide sequence set forth in SEQ ID NO:13 and a second nucleic acid molecule having the nucleotide sequence set forth in SEQ ID NO:14;
   (h) the oligonucleotide pair consisting of a first nucleic acid molecule having the nucleotide sequence set forth in SEQ ID NO:15 and a second nucleic acid molecule having the nucleotide sequence set forth in SEQ ID NO:16;
   (i) the oligonucleotide pair consisting of a first nucleic acid molecule having the nucleotide sequence set forth in SEQ ID NO:17 and a second nucleic acid molecule having the nucleotide sequence set forth in SEQ ID NO:18;
   (j) the oligonucleotide pair consisting of a first nucleic acid molecule having the nucleotide sequence set forth in SEQ ID NO:19 and a second nucleic acid molecule having the nucleotide sequence set forth in SEQ ID NO:20;
   (k) the oligonucleotide pair consisting of a first nucleic acid molecule having the nucleotide sequence set forth in SEQ ID NO:21 and a second nucleic acid molecule having the nucleotide sequence set forth in SEQ ID NO:22;
   (l) the oligonucleotide pair consisting of a first nucleic acid molecule having the nucleotide sequence set forth in SEQ ID NO:23 and a second nucleic acid molecule having the nucleotide sequence set forth in SEQ ID NO:24;
   (m) the oligonucleotide pair consisting of a first nucleic acid molecule having the nucleotide sequence set forth in SEQ ID NO:25 and a second nucleic acid molecule having the nucleotide sequence set forth in SEQ ID NO:26;
   (n) the oligonucleotide pair consisting of a first nucleic acid molecule having the nucleotide sequence set forth in SEQ ID NO:27 and a second nucleic acid molecule having the nucleotide sequence set forth in SEQ ID NO:28;

(o) the oligonucleotide pair consisting of a first nucleic acid molecule having the nucleotide sequence set forth in SEQ ID NO:29 and a second nucleic acid molecule having the nucleotide sequence set forth in SEQ ID NO:30;

(p) the oligonucleotide pair consisting of a first nucleic acid molecule having the nucleotide sequence set forth in SEQ ID NO:31 and a second nucleic acid molecule having the nucleotide sequence set forth in SEQ ID NO:32;

(q) the oligonucleotide pair consisting of a first nucleic acid molecule having the nucleotide sequence set forth in SEQ ID NO:33 and a second nucleic acid molecule having the nucleotide sequence set forth in SEQ ID NO:34;

(r) the oligonucleotide pair consisting of a first nucleic acid molecule having the nucleotide sequence set forth in SEQ ID NO:35 and a second nucleic acid molecule having the nucleotide sequence set forth in SEQ ID NO:36;

(s) the oligonucleotide pair consisting of a first nucleic acid molecule having the nucleotide sequence set forth in SEQ ID NO:37 and a second nucleic acid molecule having the nucleotide sequence set forth in SEQ ID NO:38;

(t) the oligonucleotide pair consisting of a first nucleic acid molecule having the nucleotide sequence set forth in SEQ ID NO:39 and a second nucleic acid molecule having the nucleotide sequence set forth in SEQ ID NO:40;

(u) the oligonucleotide pair consisting of a first nucleic acid molecule having the nucleotide sequence set forth in SEQ ID NO:41 and a second nucleic acid molecule having the nucleotide sequence set forth in SEQ ID NO:42;

(v) the oligonucleotide pair consisting of a first nucleic acid molecule having the nucleotide sequence set forth in SEQ ID NO:43 and a second nucleic acid molecule having the nucleotide sequence set forth in SEQ ID NO:44;

(w) the oligonucleotide pair consisting of a first nucleic acid molecule having the nucleotide sequence set forth in SEQ ID NO:45 and a second nucleic acid molecule having the nucleotide sequence set forth in SEQ ID NO:46;

(x) the oligonucleotide pair consisting of a first nucleic acid molecule having the nucleotide sequence set forth in SEQ ID NO:47 and a second nucleic acid molecule having the nucleotide sequence set forth in SEQ ID NO:48;

(y) the oligonucleotide pair consisting of a first nucleic acid molecule having the nucleotide sequence set forth in SEQ ID NO:49 and a second nucleic acid molecule having the nucleotide sequence set forth in SEQ ID NO:50;

(z) the oligonucleotide pair consisting of a first nucleic acid molecule having the nucleotide sequence set forth in SEQ ID NO:51 and a second nucleic acid molecule having the nucleotide sequence set forth in SEQ ID NO:52;

(aa) the oligonucleotide pair consisting of a first nucleic acid molecule having the nucleotide sequence set forth in SEQ ID NO:53 and a second nucleic acid molecule having the nucleotide sequence set forth in SEQ ID NO:54;

(ab) the oligonucleotide pair consisting of a first nucleic acid molecule having the nucleotide sequence set forth in SEQ ID NO:55 and a second nucleic acid molecule having the nucleotide sequence set forth in SEQ ID NO:56;

(ac) the oligonucleotide pair consisting of a first nucleic acid molecule having the nucleotide sequence set forth in SEQ ID NO:57 and a second nucleic acid molecule having the nucleotide sequence set forth in SEQ ID NO:58;

(ad) the oligonucleotide pair consisting of a first nucleic acid molecule having the nucleotide sequence set forth in SEQ ID NO:59 and a second nucleic acid molecule having the nucleotide sequence set forth in SEQ ID NO:60;

(ae) the oligonucleotide pair consisting of a first nucleic acid molecule having the nucleotide sequence set forth in SEQ ID NO:61 and a second nucleic acid molecule having the nucleotide sequence set forth in SEQ ID NO:62;

(af) the oligonucleotide pair consisting of a first nucleic acid molecule having the nucleotide sequence set forth in SEQ ID NO:63 and a second nucleic acid molecule having the nucleotide sequence set forth in SEQ ID NO:64;

(ag) the oligonucleotide pair consisting of a first nucleic acid molecule having the nucleotide sequence set forth in SEQ ID NO:65 and a second nucleic acid molecule having the nucleotide sequence set forth in SEQ ID NO:66;

(ah) the oligonucleotide pair consisting of a first nucleic acid molecule having the nucleotide sequence set forth in SEQ ID NO:67 and a second nucleic acid molecule having the nucleotide sequence set forth in SEQ ID NO:68;

(ai) the oligonucleotide pair consisting of a first nucleic acid molecule having the nucleotide sequence set forth in SEQ ID NO:69 and a second nucleic acid molecule having the nucleotide sequence set forth in SEQ ID NO:70;

(aj) an oligonucleotide pair comprising a first nucleic acid molecule having a nucleotide sequence that differs by one nucleotide alteration from that set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69; and (ak) an oligonucleotide pair comprising a second nucleic acid molecule having a nucleotide sequence that differs by one nucleotide alteration from that set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70.

2. The oligonucleotide pair library of claim 1, wherein said first and second nucleic acid molecules of said oligonucleotide pair, allow amplification of a region of the ATP8B1 protein gene (SEQ ID NO:71) and wherein said oligonucleotide pair is selected from the group consisting of:
   (a) the oligonucleotide pair consisting of a first nucleic acid molecule having the nucleotide sequence set forth in SEQ ID NO:1 and a second nucleic acid molecule having the nucleotide sequence set forth in SEQ ID NO:2;
   (b) the oligonucleotide pair consisting of a first nucleic acid molecule having the nucleotide sequence set forth in SEQ ID NO:3 and a second nucleic acid molecule having the nucleotide sequence set forth in SEQ ID NO:4;
   (c) the oligonucleotide pair consisting of a first nucleic acid molecule having the nucleotide sequence set forth in SEQ ID NO:5 and a second nucleic acid molecule having the nucleotide sequence set forth in SEQ ID NO:6;
   (d) the oligonucleotide pair consisting of a first nucleic acid molecule having the nucleotide sequence set forth in SEQ ID NO:7 and a second nucleic acid molecule having the nucleotide sequence set forth in SEQ ID NO:8;
   (e) the oligonucleotide pair consisting of a first, nucleic acid molecule having the nucleotide sequence set forth in SEQ ID NO:9 and a second nucleic acid molecule having the nucleotide sequence set forth in SEQ ID NO:10;
   (f) the oligonucleotide pair consisting of a first nucleic acid molecule having the nucleotide sequence set forth in SEQ ID NO:11 and a second nucleic acid molecule having the nucleotide sequence set forth in SEQ ID NO:12;
   (g) the oligonucleotide pair consisting of a first nucleic acid molecule having the nucleotide sequence set forth in SEQ ID NO:13 and a second nucleic acid molecule having the nucleotide sequence set forth in SEQ ID NO:14;
   (h) the oligonucleotide pair consisting of a first nucleic acid molecule having the nucleotide sequence set forth in SEQ ID NO:15 and a second nucleic acid molecule having the nucleotide sequence set forth in SEQ ID NO:16; and
   (i) the oligonucleotide pair consisting of a first nucleic acid molecule having the nucleotide sequence set forth in SEQ ID NO:17 and a second nucleic, acid molecule having the nucleotide sequence set forth in SEQ ID NO:18.

3. The oligonucleotide pair library of claim 1, wherein said, first and second nucleic acid molecules of said oligonucleotide pair allow amplification of a region of the ABCB11 protein gene (SEQ ID NO:72) and wherein said oligonucleotide pair is selected from the group consisting of:
   (a) the oligonucleotide pair consisting of a first nucleic acid molecule having the nucleotide sequence set forth in SEQ ID NO:19 and a second nucleic acid molecule having the nucleotide sequence set forth in SEQ ID NO:20;
   (b) the oligonucleotide pair consisting of a first nucleic acid molecule having the nucleotide sequence set forth in SEQ ID NO:21 and a second nucleic acid molecule having the nucleotide sequence set forth in SEQ ID NO:22;
   (c) the oligonucleotide pair consisting of a first nucleic acid molecule having the nucleotide sequence set forth in SEQ ID NO:23 and a second nucleic acid molecule having the nucleotide sequence set forth in SEQ ID NO:24;
   (d) the oligonucleotide pair consisting of a first nucleic acid molecule having the nucleotide sequence set forth in SEQ ID NO:25 and a second nucleic acid molecule having the nucleotide sequence set forth in SEQ ID NO:26;
   (e) the oligonucleotide pair consisting of a first nucleic acid molecule having the nucleotide sequence set forth in SEQ ID NO:27 and a second nucleic acid molecule having the nucleotide sequence set forth in SEQ ID NO:28;
   (f) the oligonucleotide pair consisting of a first nucleic acid molecule having the nucleotide sequence set forth in SEQ ID NO:29 and a second nucleic acid molecule having the nucleotide sequence set forth in SEQ ID NO:30;
   (g) the oligonucleotide pair consisting of a first nucleic acid molecule having the nucleotide sequence set forth in SEQ ID NO:31 and a second nucleic acid molecule having the nucleotide sequence set forth in SEQ ID NO:32;
   (h) the oligonucleotide pair consisting of a first nucleic acid molecule having the nucleotide sequence set forth in SEQ ID NO:33 and a second nucleic acid molecule having the nucleotide sequence set forth in SEQ ID NO:34;
   (i) the oligonucleotide pair consisting of a first nucleic acid molecule having the nucleotide sequence set forth in SEQ ID NO:35 and a second nucleic acid molecule having the nucleotide sequence set forth in SEQ ID NO:36; and
   (j) the oligonucleotide pair consisting of a first nucleic acid molecule having the nucleotide sequence set forth in SEQ ID NO:37 and a second nucleic acid molecule having the nucleotide sequence set forth in SEQ ID NO:38.

4. The oligonucleotide pair library of claim 1, wherein said first and second nucleic acid molecules of said oligonucleotide pair allow amplification of a region of the ABCB4 protein gene (SEQ ID NO:73) wherein said oligonucleotide pair is selected from the group consisting of:
   (a) the oligonucleotide pair consisting of a first nucleic acid molecule having the nucleotide sequence set forth in SEQ ID NO:39 and a second nucleic acid molecule having the nucleotide sequence set forth in SEQ ID NO:40;
   (b) the oligonucleotide pair consisting of a first nucleic acid molecule having the nucleotide sequence set forth in SEQ ID NO:41 and a second nucleic acid molecule having the nucleotide sequence set forth in SEQ ID NO:42;
   (c) the oligonucleotide, pair consisting of a first nucleic acid molecule having the nucleotide sequence set forth in SEQ ID NO:43 and a second nucleic acid molecule having the nucleotide sequence set forth in SEQ ID NO:44;
   (d) the oligonucleotide pair consisting of a first nucleic acid molecule having the nucleotide sequence set forth in SEQ ID NO:45 and a second nucleic acid molecule having the nucleotide sequence set forth in SEQ ID NO:46;
   (e) the oligonucleotide pair consisting of a first nucleic acid molecule nucleotide sequence set forth in SEQ ID NO:47 and a second nucleic acid molecule having the nucleotide sequence set forth in SEQ ID NO:48;
(f) the oligonucleotide pair consisting of a first nucleic acid molecule having the nucleotide sequence set forth in SEQ ID NO:49 and a second nucleic acid molecule having the nucleotide sequence set forth in SEQ ID NO:50;
(g) the oligonucleotide pair consisting of a first nucleic acid molecule having the nucleotide sequence set forth in SEQ ID NO:51 and a second nucleic acid molecule having the nucleotide sequence set forth in SEQ ID NO:52;
(h) the oligonucleotide pair consisting of a first nucleic acid molecule having the nucleotide sequence set forth in SEQ ID NO:53 and a second nucleic acid molecule having the nucleotide sequence set forth in SEQ ID NO:54; and
(i) the oligonucleotide pair consisting of a first nucleic acid molecule having the nucleotide sequence set forth in SEQ ID NO:55 and a second nucleic acid molecule having the nucleotide sequence set forth in SEQ ID NO:56.

5. The oligonucleotide pair library of claim 1, wherein said first and second nucleic acid molecules of said oligonucleotide pair allow amplification of a region of the JAG1 protein gene (SEQ ID NO:74) and wherein said oligonucleotide pair is selected from the group consisting of:
(a) the oligonucleotide pair consisting of a first nucleic acid molecule having the nucleotide sequence set forth in SEQ ID NO:57 and a second nucleic acid molecule having the nucleotide sequence set forth in SEQ ID NO:58;
(b) the oligonucleotide pair consisting of a first nucleic acid molecule having the nucleotide sequence set forth in SEQ ID NO:59 and a second nucleic acid molecule having the nucleotide sequence set forth in SEQ ID NO:60;
(c) the oligonucleotide pair consisting of a first nucleic acid molecule having the nucleotide sequence set, forth in SEQ ID NO:61 and a second nucleic acid molecule having the nucleotide sequence set forth in SEQ ID NO:62;
(d) the oligonucleotide pair consisting of a first nucleic acid molecule having the nucleotide sequence set forth in SEQ ID NO:63 and a second nucleic acid molecule having the nucleotide sequence set forth in SEQ ID NO:64; and
(e) the oligonucleotide pair consisting of a first nucleic acid molecule having the nucleotide sequence set forth in SEQ ID NO:65 and a second nucleic acid molecule having the nucleotide sequence set forth in SEQ ID NO:66.

6. The oligonucleotide pair library of claim 1, wherein said first and second nucleic acid molecules of said oligonucleotide pair allow amplification of a region of the SERPINA1 protein gene (SEQ ID NO:75) and wherein said oligonucleotide pair is selected from the group consisting of:
(a) the oligonucleotide pair consisting of a first nucleic acid molecule having the nucleotide sequence set forth in SEQ ID NO:67 and a second nucleic acid molecule having the nucleotide sequence set forth in SEQ ID NO:68; and
(b) the oligonucleotide pair consisting of a first nucleic acid molecule having the nucleotide sequence set forth in SEQ ID NO:69 and a second nucleic acid molecule having the nucleotide sequence set forth in SEQ ID NO:70.

7. A kit comprising a cholestasis related gene resequencing microarray and at least one oligonucleotide pair selected from the group consisting of:
(a) the oligonucleotide pair consisting of a first nucleic acid molecule having the nucleotide sequence set forth in SEQ ID NO:1 and a second nucleic acid molecule having the nucleotide sequence set forth in SEQ ID NO:2;
(b) the oligonucleotide pair consisting of a first nucleic acid molecule having the nucleotide sequence set forth in SEQ ID NO:3 and a second nucleic acid molecule having the nucleotide sequence set forth in SEQ ID NO:4;
(c) the oligonucleotide pair consisting of a first nucleic acid molecule having the nucleotide sequence set forth in SEQ ID NO:5 and a second nucleic acid molecule having the nucleotide sequence set forth in SEQ ID NO:6;
(d) the oligonucleotide pair consisting of a first nucleic acid molecule having the nucleotide sequence set forth in SEQ ID NO:7 and a second nucleic acid molecule having the nucleotide sequence set forth in SEQ ID NO:8;
(e) the oligonucleotide pair consisting of a first nucleic acid molecule having the nucleotide sequence set forth in SEQ ID NO:9 and a second nucleic acid molecule having the nucleotide sequence set forth in SEQ ID NO:10;
(f) the oligonucleotide pair consisting of a first nucleic acid molecule having the nucleotide sequence set forth in SEQ ID NO:11 and a second nucleic acid molecule having the nucleotide sequence set forth in SEQ ID NO:12;
(g) the oligonucleotide pair consisting of a first nucleic acid molecule having the nucleotide sequence set forth in SEQ ID NO:13 and a second nucleic acid molecule having the nucleotide sequence set forth in SEQ ID NO:14;
(h) the oligonucleotide pair consisting of a first nucleic acid molecule having the nucleotide sequence set forth in SEQ ID NO:15 and a second nucleic acid molecule having the nucleotide sequence set forth in SEQ ID NO:16;
(i) the oligonucleotide pair consisting of a first nucleic acid molecule having the nucleotide sequence set forth in SEQ ID NO:17 and a second nucleic acid molecule having the nucleotide sequence set forth in SEQ ID NO:18;
(j) the oligonucleotide pair consisting of a first nucleic acid molecule having the nucleotide sequence set forth in SEQ ID NO:19 and a second nucleic acid molecule having the nucleotide sequence set forth in SEQ ID NO:20;
(k) the oligonucleotide pair consisting of a first nucleic acid molecule having the nucleotide sequence set forth in SEQ ID NO:21 and a second nucleic acid molecule having the nucleotide sequence set forth in SEQ ID NO:22;
(l) the oligonucleotide pair consisting of a first nucleic acid molecule having the nucleotide sequence set forth in SEQ ID NO:23 and a second nucleic acid molecule having the nucleotide sequence set forth in SEQ ID NO:24;
(m) the oligonucleotide pair consisting of a first nucleic acid molecule having the nucleotide sequence set forth in SEQ ID NO:25 and a second nucleic acid molecule having the nucleotide sequence set forth in SEQ ID NO:26;
(n) the oligonucleotide pair consisting of a first nucleic acid molecule having the nucleotide sequence set forth in SEQ ID NO:27 and a second nucleic acid molecule having the nucleotide sequence set forth in SEQ ID NO:28;

(o) the oligonucleotide pair consisting of a first nucleic acid molecule having the nucleotide sequence set forth in SEQ ID NO:29 and a second nucleic acid molecule having the nucleotide sequence set forth in SEQ ID NO:30;

(p) the oligonucleotide pair consisting of a first nucleic acid molecule having the nucleotide sequence set forth in SEQ ID NO:31 and a second nucleic acid molecule having the nucleotide sequence set forth in SEQ ID NO:32;

(q) the oligonucleotide pair consisting of a first nucleic acid molecule having the nucleotide sequence set forth in SEQ ID NO:33 and a second nucleic acid molecule having the nucleotide sequence set forth in SEQ ID NO:34;

(r) the oligonucleotide pair consisting of a first nucleic acid molecule having the nucleotide sequence set forth in SEQ ID NO:35 and a second nucleic acid molecule having the nucleotide sequence set forth in SEQ ID NO:36;

(s) the oligonucleotide pair consisting of a first nucleic acid molecule having the nucleotide sequence set forth in SEQ ID NO:37 and a second nucleic acid molecule having the nucleotide sequence set forth in SEQ ID NO:38;

(t) the oligonucleotide pair consisting of a first nucleic acid molecule having the nucleotide sequence set forth in SEQ ID NO:39 and a second nucleic acid molecule having the nucleotide sequence set forth in SEQ ID NO:40;

(u) the oligonucleotide pair consisting of a first nucleic acid molecule having the nucleotide sequence set forth in SEQ ID NO:41 and a second nucleic acid molecule having the nucleotide sequence set forth in SEQ ID NO:42;

(v) the oligonucleotide pair consisting of a first nucleic acid molecule having the nucleotide sequence set forth in SEQ ID NO:43 and a second nucleic acid molecule having the nucleotide sequence set forth in SEQ ID NO:44;

(w) the oligonucleotide pair consisting of a first nucleic acid molecule having the nucleotide sequence set forth in SEQ ID NO:45 and a second nucleic acid molecule having the nucleotide sequence set forth in SEQ ID NO:46;

(x) the oligonucleotide pair consisting of a first nucleic acid molecule having the nucleotide sequence set forth in SEQ ID NO:47 and a second nucleic acid molecule having the nucleotide sequence set forth in SEQ ID NO:48;

(y) the oligonucleotide pair consisting of a first nucleic acid molecule having the nucleotide sequence set forth in SEQ ID NO:49 and a second nucleic acid molecule having the nucleotide sequence set forth in SEQ ID NO:50;

(z) the oligonucleotide pair consisting of a first nucleic acid molecule having the nucleotide sequence set forth in SEQ ID NO:51 and a second nucleic acid molecule having the nucleotide sequence set forth in SEQ ID NO:52;

(aa) the oligonucleotide pair consisting of a first nucleic acid molecule having the nucleotide sequence set forth in SEQ ID NO:53 and a second nucleic acid molecule having the nucleotide sequence set forth in SEQ ID NO:54;

(ab) the oligonucleotide pair consisting of a first nucleic acid molecule having the nucleotide sequence set forth in SEQ ID NO:55 and a second nucleic acid molecule having the nucleotide sequence set forth in SEQ ID NO:56;

(ac) the oligonucleotide pair consisting of a first nucleic acid molecule having the nucleotide sequence set forth in SEQ ID NO:57 and a second nucleic acid molecule having the nucleotide sequence set forth in SEQ ID NO:58;

(ad) the oligonucleotide pair consisting of a first nucleic acid molecule having the nucleotide sequence set forth in SEQ ID NO:59 and a second nucleic acid molecule having the nucleotide sequence set forth in SEQ ID NO:60;

(ae) the oligonucleotide pair consisting of a first nucleic acid molecule having the nucleotide sequence set forth in SEQ ID NO:61 and a second nucleic acid molecule having the nucleotide sequence set forth in SEQ ID NO:62;

(af) the oligonucleotide pair consisting of a first nucleic acid molecule having the nucleotide sequence set forth in SEQ ID NO:63 and a second nucleic acid molecule having the nucleotide sequence set forth in SEQ ID NO:64;

(ag) the oligonucleotide pair consisting of a first nucleic acid molecule having the nucleotide sequence set forth in SEQ ID NO:65 and a second nucleic acid molecule having the nucleotide sequence set forth in SEQ ID NO:66;

(ah) the oligonucleotide pair consisting Of a first, nucleic acid molecule having the nucleotide sequence set forth in SEQ ID NO:67 and a second nucleic acid molecule having the nucleotide sequence set forth in SEQ ID NO:68;

(ai) the oligonucleotide pair consisting of a first nucleic acid molecule having the nucleotide sequence set forth in SEQ ID NO:69 and a second nucleic acid molecule having the nucleotide sequence set forth in SEQ ID NO:70;

(aj) an oligonucleotide pair comprising a first nucleic acid molecule having a nucleotide sequence that differs by one nucleotide alteration from that set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69; and (ak) an oligonucleotide pair comprising a second nucleic acid molecule having a nucleotide sequence that differs by one nucleotide alteration from that set forth in SEQ ID NO:2, SEQ ID NO:4, SEQ ID NO:6, SEQ ID NO:8, SEQ ID NO:10, SEQ NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or SEQ ID NO:70.

\* \* \* \* \*

```
                            SEQUENCE LISTING

<160> NUMBER OF SEQ ID NOS: 75

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 1
ctagggagtg ttcctgggaa gtcagtaaac                                     30

<210> SEQ ID NO 2
<211> LENGTH: 30
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 2
gtcagatatg ctctcccagc ccttcttact                                     30

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 3
ctgagagcta caagggagag atctgttcta gg                                  32

<210> SEQ ID NO 4
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 4
tacctaccta cactggtaaa gaggagctct gg                                  32

<210> SEQ ID NO 5
<211> LENGTH: 32
<212> TYPE: DNA
<213> ORGANISM: Artificial Sequence
<220> FEATURE:
<223> OTHER INFORMATION: Oligonucleotide Primer for Amplification of
```

-continued

ATP8B1

<400> SEQUENCE: 5
ccagagctcc tctttaccag tgtaggtagg ta                32

<210> SEQ ID NO 6
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 6
ggaggcttgc ttctaagaga actgcctcta tg                32

<210> SEQ ID NO 7
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 7
gtaatcccag ctactcagga ggctgaagca ta                32

<210> SEQ ID NO 8
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 8
gaagtgaggg aatgaagtga aggcagacta cg                32

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 9
ctacatggga agatgaggta ggaggatcac                   30

<210> SEQ ID NO 10
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 10
agatactgtg gctacccctt tgagtaggga ac                32

<210> SEQ ID NO 11
<211> LENGTH: 31
<212> TYPE: DNA
<213> ORGANISM: Artificial Sequence
<220> FEATURE:
<223> OTHER INFORMATION: Oligonucleotide Primer for Amplification of
      ATP8B1

```
<400> SEQUENCE: 11
tagctgggtg tggtaactca catctgtaat c                                    31

<210> SEQ ID NO 12
<211> LENGTH: 31
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 12
ctaattatac atcctggttg ctgctctcct g                                    31

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 13
aggagagcag caaccaggat gtataattag c                                    31

<210> SEQ ID NO 14
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 14
cccacctaga ctagattaca ggggacctac at                                   32

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 15
ggtggaagaa tagcttgaac ctaggaggtg                                      30

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 16
cagaagccct gtcagtgata ctctttcctc                                      30

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide Primer for Amplification of
      ATP8B1
```

```
<400> SEQUENCE: 17
aggtagctgg aaagtagata tgagctctgc tg                                32

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide Primer for Amplification of
      ATP8B1

<400> SEQUENCE: 18
ctgcttcagc ttctcaaata ggtgggatta c                                 31

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 19
ctctctctca cacagcatac gtacacacac tc                                32

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 20
cacccatgta caccactctc tctctctcta ag                                32

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 21
ctgtgctctg cttactcttc ggtacttctc tg                                32

<210> SEQ ID NO 22
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 22
gtgactgtgt ctgtgtgagt tctggctact tc                                32

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 23
```
cactgctctt cccagcctct gttaactact                                              30

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 24
ctcaaggtca cagtaaggag cagagtaagt gc                                           32

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 25
cacttactct gctccttact gtgaccttga gc                                           32

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 26
gcacaaactg agagactcag ggtactatgc                                              30

<210> SEQ ID NO 27
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 27
agagagcaga acagtggtta ccagggactt                                              30

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 28
gtgcatactt ctttactgcc tgtcctctcc                                              30

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 29

-continued atagtcccag ctagtcagga ggctgatatg                                            30

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 30
ctcagtgtct tccactttct gcagtctctg                                            30

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 31
aagacctact agccagcatt cagcctctac                                            30

<210> SEQ ID NO 32
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 32
gctaggcagg tttacctctc tcatccacta ga                                         32

<210> SEQ ID NO 33
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 33
ctctttctcc ctccctgact acactctgaa tc                                         32

<210> SEQ ID NO 34
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 34
gtgatgggat tatctagtct cccctctctc tc                                         32

<210> SEQ ID NO 35
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB11

<400> SEQUENCE: 35
ttagagactt aagggctgca ggaccagagt ag                                         32

<210> SEQ ID NO 36
<211> LENGTH: 30
<212> TYPE: DNA
<213> ORGANISM: Artificial Sequence
<220> FEATURE:
<223> OTHER INFORMATION: Oligonucleotide Primer for Amplification of ABCB11

<400> SEQUENCE: 36
ggagtgggag agaagtgctg aaagagatac                                        30

<210> SEQ ID NO 37
<211> LENGTH: 30
<212> TYPE: DNA
<213> ORGANISM: Artificial Sequence
<220> FEATURE:
<223> OTHER INFORMATION: Oligonucleotide Primer for Amplification of ABCB11

<400> SEQUENCE: 37
gtatctcttt cagcacttct ctcccactcc                                        30

<210> SEQ ID NO 38
<211> LENGTH: 32
<212> TYPE: DNA
<213> ORGANISM: Artificial Sequence
<220> FEATURE:
<223> OTHER INFORMATION: Oligonucleotide Primer for Amplification of ABCB11

<400> SEQUENCE: 38
atctagctga ctacttcctc tgggtacagc ac                                     32

<210> SEQ ID NO 39
<211> LENGTH: 30
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 39
accttagccc aggtccttgc acatagtaag                                        30

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 40
cacaaccctc tagccctctc tctttatcag                                        30

<210> SEQ ID NO 41
<211> LENGTH: 30
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 41
ctcagacaga cagacaggca aatacacctc                                        30

```
<210> SEQ ID NO 42
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 42 ggagggtaa gacaaggagg aagagacata ac                                    32

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 43
gggagtaggg atgtggtcag agaggaaata                                      30

<210> SEQ ID NO 44
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 44
cataactcac tgcagcctca gactcctaag ac                                   32

<210> SEQ ID NO 45
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 45
tcccctctgt aggtagtact gtgtccaaga tt                                   32

<210> SEQ ID NO 46
<211> LENGTH: 31
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 46
agacaccttt caggccttt agcatacaga c                                    31

<210> SEQ ID NO 47
<211> LENGTH: 31
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 47
ctaaaaggcc tgaaaggtgt ctatctggaa g                                    31
```

<210> SEQ ID NO 48
<211> LENGTH: 33
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 48
gtatatacta gaaagtcagc tctgcccact gga        33

<210> SEQ ID NO 49
<211> LENGTH: 30
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 49
gtccagtggg cagagctgac tttctagtat        30

<210> SEQ ID NO 50
<211> LENGTH: 30
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 50
aacctagact ccagggctga ataggactct        30

<210> SEQ ID NO 51
<211> LENGTH: 32
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 51
agagagctgt gttctagcct ctctctcttt cc        32

<210> SEQ ID NO 52
<211> LENGTH: 32
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 52
gaagtcacac ttccccctga taaggagtct ac        32

<210> SEQ ID NO 53
<211> LENGTH: 32
<212> TYPE: DNA
<213> ORGANISM: Artificial Sequence
<220> FEATURE:
<223> OTHER INFORMATION: Oligonucleotide Primer for Amplification of ABCB4

<400> SEQUENCE: 53
cacctgtgtc agaatactag caactgttac cc        32

<210> SEQ ID NO 54

```
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 54
tttacccatc tctaccttct atcccctac tc                                    32

<210> SEQ ID NO 55
<211> LENGTH: 32
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 55
cctagaagac agctttaggc agtacaggga ag                                    32

<210> SEQ ID NO 56
<211> LENGTH: 30
<212> TYPE: DNA
<213> ORGANISM: Artificial Sequence
<220> FEATURE:
<223> OTHER INFORMATION: Oligonucleotide Primer for Amplification of
      ABCB4

<400> SEQUENCE: 56
gtctacccaa cccattcagg accataagac                                       30

<210> SEQ ID NO 57
<211> LENGTH: 32
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 57
ctgcaggaca tacctactat tagggccaaa ac                                    32

<210> SEQ ID NO 58
<211> LENGTH: 32
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 58 actacccag ccgagatcta actatagtgt cc                                     32

<210> SEQ ID NO 59
<211> LENGTH: 30
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 59
agtcaaacat gcagagtcct ctaccagctc                                       30

<210> SEQ ID NO 60
<211> LENGTH: 30
```

-continued

```
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 60
aggtggggta gacaaggaac atgaactagg                                      30

<210> SEQ ID NO 61
<211> LENGTH: 30
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 61
cccctcggta caaatacctg gttaggttag                                      30

<210> SEQ ID NO 62
<211> LENGTH: 30
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 62
ccatctagcc catcagcact ataagggaag                                      30

<210> SEQ ID NO 63
<211> LENGTH: 32
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 63
caccgagaga gtcctttcct ctatagtctg tc                                   32

<210> SEQ ID NO 64
<211> LENGTH: 30
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 64
gagagccaag cctttcctac tgcttacatc                                      30

<210> SEQ ID NO 65
<211> LENGTH: 30
<212> TYPE: DNA
<213> ORGANISM: Artificial Sequence
<220> FEATURE:
<223> OTHER INFORMATION: Oligonucleotide Primer for Amplification of
      JAG1

<400> SEQUENCE: 65
ctactgtgaa accagtgagt ctgccactct                                      30

<210> SEQ ID NO 66
<211> LENGTH: 30
<212> TYPE: DNA
```

<213> ORGANISM: Artificial Sequence
<220> FEATURE:
<223> OTHER INFORMATION: Oligonucleotide Primer for Amplification of JAG1

<400> SEQUENCE: 66
actctggaac ctcacagaag accagaacac         30

<210> SEQ ID NO 67
<211> LENGTH: 30
<212> TYPE: DNA
<213> ORGANISM: Artificial Sequence
<220> FEATURE:
<223> OTHER INFORMATION: Oligonucleotide Primer for Amplification of SERPINA1

<400> SEQUENCE: 67
ccttactcat gaccagctca caggatcttc         30

<210> SEQ ID NO 68
<211> LENGTH: 32
<212> TYPE: DNA
<213> ORGANISM: Artificial Sequence
<220> FEATURE:
<223> OTHER INFORMATION: Oligonucleotide Primer for Amplification of SERPINA1

<400> SEQUENCE: 68
cagtaggaga ggtggtgagg cttataggag ac         32

<210> SEQ ID NO 69
<211> LENGTH: 30
<212> TYPE: DNA
<213> ORGANISM: Artificial Sequence
<220> FEATURE:
<223> OTHER INFORMATION: Oligonucleotide Primer for Amplification of SERPINA1

<400> SEQUENCE: 69
ggattctggt tctgctactt cctcagtgac         30

<210> SEQ ID NO 70
<211> LENGTH: 32
<212> TYPE: DNA
<213> ORGANISM: Artificial Sequence
<220> FEATURE:
<223> OTHER INFORMATION: Oligonucleotide Primer for Amplification of SERPINA1

<400> SEQUENCE: 70
gactagggag gagaagggat atagggtaat gg         32

<210> SEQ ID NO 71
<211> LENGTH: 83756
<212> TYPE: DNA
<213> ORGANISM: Homo sapiens

<400> SEQUENCE: 71
tatatatata cccttgttta aaataaaag gtttgcagct ccatattttt taaaaaaatc         60
ttacccaagc atttaatcag tactgaatgg ttttgttctt gtcttcatgt caagttgaat         120
ttgggggtac tattccagaa tatttacatg ttagacaatg ttctgtaaaa ggggcattgt         180
agcagcatgc aggcagtatt caaccaaaaa ctgggcaaga gtcataattc actctggttt         240
ctctttcctt ttaagcaggt agttccaatt tgccagcaga atgagtacag aaagagactc         300

```
agaaacgaca tttgacgagg attctcagcc taatgacgaa gtggttccct acagtgatga    360
tgaaacagaa gatgaacttg atgaccaggg gtctgctgtt gaaccagaac aaaaccgagt    420
caacagggaa gcagaggaga accgggagcc attcagaaaa ggtaaccaca tgaagtcccg    480
gtgactaggt cgcttataaa tcctcatgtg ggtcatggcc acacgtgcca aagatgatcg    540
gtctattttg cgtggtctag agagaatct tctctgatct cttcttagga tgcgactgac    600
agaatggtgg atgggcttgg acaagtaccc attgtcctta gtaagaaggg ctgggagagc    660
atatctgaca agttctgcag agaaaataca ttaaggtctt tgttagtgtg tgtatatata    720
tatatatata tatatatata tatatatata tatatatata tatatatata tatatatatt    780
ttgaggcagg gtctcactgt gtctccccag ctggagtcca gtggtgtgaa ctcggctcac    840
tgcagccttg acctcctgga ctcaagtgat cctcctacct cagcctcctg agtagctgga    900
ctacaggcat gcaccagtat gtccaactaa ttttttgtatt tgtgtgtgtg tttgtgtgtg    960
tagatggtat ttcactatgt tgcccaggct cgtctcaaac tcctgagctc aagggatctg   1020
cccacctcaa cctctcaaac tcctggaatt acaggcatga gctacgatgc gtagccagtg   1080
tatatattct aaaatggag ttatgcgggc aagaatctgc atgttactgc acccagaaat   1140
ttttaaagga tacatatcaa tcagtcttag atgttaacta ttagtattgt taaattggcg   1200
gtatgagtta tataaataac catccttgtg tatgtgtgtg tgtgtgtgtg tgtatatata   1260
tatatatata tatatatata tatatgtata tggtctgccc agggtcaggc cagcatcaga   1320
ggcagggtct agaccaaggc cagcaaactt tttctgtaaa gggccagcaa gtaaacattt   1380
taggctttgt ggaccacgtg gtctctgcca atgttgagtg taagtgaccg cagacagtac   1440
atcactgaag gcagtagaac atggcttgct tttaccatga tgccttttct tttgtggctt   1500
ttctatttca tctcctgctg gttctcccac cctggcaaac agatgtgggc ttctcttgta   1560
gctcttctcc atgagcaagc tgagactttt ctctctggac cccagatttg atatcaggct   1620
gaaaatattt cctccatggt gttccctaaa attctagccg aacaacctta gcatcacatt   1680
cacagaaatc attatcatag tgttctggtt tcagcgctcc agacacgcct ccctgcagcc   1740
ttagtcagag aagcctcgga ttttagctgg ttttcccgag gtctctgtta ctgccattct   1800
gcccttgaag gctttctaga agcctctttt tccccсcatgc caaacccccc ctctagtttc   1860
tctttcttgg gttctgctat ctggatgagc tattttttc taataatttt aacctgtaga   1920
agatgtgata tgcatgaaat cccatttctg caatgattct tcctgttctg gtcacagaat   1980
ctgcctgtgg ggagattctc agtgtgggga gtgcatgcac cccgcgagcc ccatctcacc   2040
caaatgtggg gaggccattg actcctgtat gttgtgtgtc cgctaccttt ccatagcaaa   2100
catttagatg gattacctct tagagtgggt ttctggtttt gatttcaagc tgttgaggat   2160
tgagcttaag tgccttctgc cttgaatcag aaggtactaa actcatgata cttgaccaaa   2220
attaaagtga aattccctgc cgggcacagt ggctcacgcc tgcaatccca gcactttggg   2280
agactgaggt gagtggatca cctgaggtca ggagttcaag accagccaga ccaacatggt   2340
gaaaccccgt ctctactaaa aatacaaaaa ttagccaggc gtggtggcaa gtgcctgtag   2400
tcccagctat ttgggaggct gaggcaggag aatcactaga acccggcagg cagaggtggc   2460
agtgagctga gatggtgcca ttgcactcca gcctgggcaa caagagtgaa actccaactc   2520
aaaaaaaaaa aaaaaaaaga aagaaagaaa atggaattcc caccaatctg aacaggaagg   2580
tggcctctgt cataacaggt ccagactgga tattggtgaa ctagctaaag ctgaagcagc   2640
cagacaagtt acaaggaagt tctagttgat tgcccaaaca gtgaataaaa catgcttctt   2700
```

```
cctcattcct ttccccgcta attgcactgc ttagtctcct atcacaattt tggaatctct    2760
accaaatgta gatatctgat ggggtggcag gagaattggc tccatggggt ccagggtcaa    2820
ctttgctctt ggtgcttggt ggcacgccat cagacgtgta gtccgagaca cagcaaaggg    2880
accgggattg ggtgcctgca gaaatgtcag agacgcatgt agtgggtgga aactctcatc    2940
ccctgttttt ttacaactct gcctgcccat tctggtggtt aggatccttt cctgatcatt    3000
cagtttgcag gtcatatgtt ttgtagattt ctaccctcgg tatatgggca ttaaaagagc    3060
tcagtcttgg ccgggtgcgg cgactcatgc ctgtaatccc agcactttgg gaggccaagg    3120
aagttgaatc gcctgaggtc aggagttcga gaccagcctg gccaacatag tgaaacccca    3180
tctctattaa aaatacaaaa attagccggg catggtggtg cacacctata atcccagcta    3240
ctcgggaggc tgaggcagga gaatcgcttg aacctgggaa atggaggttg cagtgaacca    3300
agatcccacc actacacgcc atcctgggtg acaaagtgag actccatctc aaaaaaaaaa    3360
aaaaaatgct cagtcttgaa tcttagtcat gttttccaag ggtgatttat attcctaggg    3420
gatttgggtg gttctcgctt ctcaaaaccc atatcaaatg actttgcctg tgactttta    3480 caaaaattct tattctaata cctctctgcg cccttcccaa gcacacagat gatgttcagt    3540
aaatgccaga cctcttttcct cccatttccc atgtgcctg cctccctcac agccagtctg    3600
ctctccttct ttcctcctt cctctctttg ccctcttcat ccctcttcc tttcccacta    3660 tattctcatt tgtgcaattt cccagttaag gtcagtgtca ccctgacttc tcttctttt    3720 tttaatcatc atctgtcttt cttgacattt cacatcctga ataatttcct tcagagaatc    3780
agttctttaa gacatcagaa catgagtcac cctgcgaggt accaccagac taacaccagg    3840
gaccagcacc cattctagca aaacactgcc taagcagcct gaactcgct agtttcttta    3900 atgagggttg tagcacagaa agttgctttc ttttttttt aaagaaagga atcctctag    3960 cccaactaag ctttcctgtt aaacaagtgc tttgagagac ccattcagag tacttttcac    4020
tagaaggacc tttattgtgt tttgtgagaa ggaaggacag gcacaaacat gctgttagaa    4080
tgtgccatgg agaaagataa gcccacaggt tcgagtggag taactttacc ctttgtgtaa    4140
agattcagca aagattctca gaaatgagcg ggaatgtttt cagtgctatg ggatgagctc    4200
tgtcgtttcc tgatgaacac acttctcagc atgtgttctg ggaaacacta gttttgtat    4260 ttttggagtt ttcttgttgt ttgtttgttt gtttttgttt tgagatggag tctctctctg    4320
tcgcccagac tggagagcag aggcgcgata tcggctcact gcaaccccgc tcctgggttc    4380
aagcgattct cctgcctcag cctcccaagt agctgggatt acaggcgtat gctaccacgc    4440
ctggctaatt tttgtatttt tagtagagac agagtttcac catgttggcc aggatggtct    4500
cgatctcctg aacttgtgat ccaccagcct cagcctccca aagtgctggg attataggcg    4560
tgagctacca cacccggcct aaagtgata tcttcataaa ataatctgga attaagaatg    4620
tggggtcttt agcgcatcta tgaattaata tttagttgga accaaaacac agataaagat    4680
ggctcattga aacgtatcaa tcgtaggata tcctagggaa tctgtgaaaa gtgctgaggg    4740
agctgttcca cttaataaga tgaattttcc attttcggca cataccacat atgggagtct    4800
actctggcta cttatttct ttctttctct gatcggttgt aaattaccat ccacctccac    4860
agcctaaaaa caccagagta attgatgctt gtaaagccgc agggtgaggg gtattcctgc    4920
actgagtgat tactgatggg gaagggtggt gatactgtgc catctcattt tatttttattc    4980 tttttattta tttgttat tatttatttg acagaatctc gctcttgttg cccaggctgg    5040
```

```
agtgaagtgg cgtgatctca gctcactgca acctccgcct cccgggttca agtgattctc    5100
ctgcctcagc ctcccgagta gctgggatta ccggcgcccg ccatcacgcc cagctaattt    5160
ttgtatttt agtaaggacg aattttgcc atgttggcca ggcttgtctt gaactcctga    5220
cctaaggtga ttcgcccacc ctggcctccc aaagtgctgg gattacaggc atgaaccact    5280
gtgcccggcc tattctattt attttaaga tcttgggcaa catgctcatt ttagagaatt    5340
tgctttcaag tcatgtaatt tatgattgaa ccttgggtaa gaatctcttg ctcatggaaa    5400
cctaactcag ctggtggttt tcttcctgct actttgcagc ccaagttcag aagtagattt    5460
ttaatgatag aagtcaccat aggaagacac tctcctttgc actaactggg ggttctcagt    5520
cctgcctgta catcagaacc tcttgtggaa tttttacaaa ctctctaggt gcctggaccc    5580
agcccctgaa gatacagagt ggttctggga tgaggcaagg ggaagaatct atcatttaaa    5640
atgaattcag tggcctgaat attttctccc attctgttgt ctctttactt tgttgattgt    5700
ttcctttgct ttacagaagc ttttaactt gtgatctcat ttgtccgttt ttgctttggt    5760
tgcctgtgct tgtgaagtat tactcaagaa atctttgccc agtttagtgt cctggagagt    5820
ttcccaagtg gttttttgt tgttgttgtt tgttttgtt tgaggcagag tcttgctctg    5880
tcaccaggct gaagtgcagt ggcacaatct ggctcactg caacctcaac ttcttgagtt    5940
caagcaattc ccttgcctca gcctcccgag tagctgggac tacaggtatg taccaccatg    6000
ctcggctaac tttttgtatt ttagtagaga cagggtttca ccatgttggc caggatggtc    6060
tccatctctt gaccttgtga tccacccacc ttggcttccc aaagtgctgg aattacaggc    6120
gtgagccacc atgctcagac ttccccaggg ttttcttgga gtagtttcat agtttgaggt    6180
cttagattta agtctgtaat ccatttgat tcaattttg catatgacaa gagatggggt    6240
ctactttcat tcatctacat ataaatatgc agttttcct tgcatcattt attgaagaga    6300
ctgccttttc ccaatgtatg ttcttggcac ctttgttgaa aacaagttta ctaaggatgt    6360
atgaattat ctctgagttc tcttttctgt tccattgatc tgtgtgtctg ttttatgcc    6420
aataccacgt tgttttggtt attatagctc tgtcatataa tttgaagtca ggtagtgtga    6480
ttcctacagt tctgttctt tggcttagat tagctgtggc tttctgggt cttctgtggt    6540
tcccatacaa atttaggat tttttttcta tttctgtgaa gacagtcatt ggtattttca    6600
tagagattgc attgaatctg tagattgctt tgggcagtgt ggacatttta acaatattcc    6660
aatccatgag catggaatat cattccattt ttctggtgtc ctctttagtt tcttgcatca    6720
ttgcaatcaa tttatagttt tgattgcaga gatcttttac ttctttggta aacttaattc    6780
ttagctattt tattcatagc tattataaat gggattattt tttttctttt tttttatta    6840
tactttaagt tttagggtac atgtgcacat tgtgcaggt agttacatat gtatacatgt    6900
gccatgctgg tgcgctgcac ccactaactc atcatctagc attaggtata tctcccaatg    6960
ctatccctcc ccctccccc cacccacca cagtccccag agtgtgatat tccccttcct    7020
gtgtccatgt gatctcattg ttcaattccc acctatgagt gagaatatgc ggtgtttggt    7080
ttttgttct tgcgatagtt tactgagaat gatgatttcc aatttcatcc atgtccctac    7140
aaaggacatg aactcatcct tttatggc tgcatagtat tccatggtgt atatgtgcca    7200
catttcttta atccagtcta tcattgttgg acatttgggt tggttccaag tctttgctat    7260
tgtgaataat gccgcaataa acatacgtgt gcatgtgtct ttatagcagc atgatttata    7320
gtcatttggg tgtataccca gtaatgggat ggctgggtca atggtatttt ctagttctag    7380
atccctgagg aatcgccaca ctgacttcca caatggttga actagtttac agtcccacca    7440
```

```
acagtgtaaa agtgttccta tttctccaca tcctctccag cacctgttgt ttcctggctt    7500
tttaatgatt gccattctaa ctggtgtgag atggtatctc acagtggttt tgatttgcat    7560
ttctctgatg gccagtgatg atgagcattt tttcatgtgt tttttggctg cataaatgtc    7620
ttcttttgat tagtgtctgt tcatgtcctt cgcccacttt ttgatggggt tgtttgtttt    7680
tttcttgtaa atttgtttga gttcattgta gattctggat attagcctt tgtcagatga    7740
gtaggttgcg aaaattttct cccatttttgt aggttgcctg ttcactctga tggtagtttc    7800
ttttgctgtg cagaagctct ttagtttaat tagatcccat ttgtcaattt tgtcttttgt    7860
tgccattgct tttggtgttt tggacatgaa gtccttgccc atgcctatgt cctgaatggt    7920
aatgcctagg ttttcttcta gggtttttat ggttttaggt ctaacgttta aatctttaat    7980
ccatcttgaa ttgattttgg tataaggtgt agggaaggga tccagtttca gtttcctaca    8040
tatggctagc cagttttccc agcaccattt attaaatagg gaatcctttc cccattgctt    8100
gttttctca ggtttgtcaa aggtcagata gttctaggta tgcggcatta tttctgaggg    8160
ctctgttctg ttccattgat ctatatttct gttttggtac cagtaccatg ctgttttggt    8220
tactgtagcc ttgtagtata gtttgaagtc aggtagtgtg atgcctccag cttttgttctt    8280
ttggcttagg attgacttgg caatccgggc tctttttttgg ttccatatga actttaaagt    8340
agttttttcc aattctgtga agaaagtcat tggtagcttg atgggatgg cattgaatct    8400
gtaaattacc ttgggcagta tggccatttt cacgatattg attcttccta cccatgagca    8460
tggaatgttc ttccatttgt ttgtatcctc ttttatttcc ttgagcagtg gtttgtagtt    8520
ctccttgaag aggtccttca catcccttgt aagttggatt cctaggtatt ttattctctt    8580
tgaagcaatt gtgaatggga gttcactcat gatttggctc tctgtttgtc tgttgttggt    8640
gtataagaat gcttgtgatt tttgtacatt gattttgtat cctgagactt tgctgaagtt    8700
gcttatcagc ttaaggagat tttgggctga acaatgggg ttttctagat atacaatcat    8760
gtcatctgca aacagagaca atttgacttc ctcttttcct aactgaatac cctttatttc    8820
cttctcctgc ctaattgccc gggccagaac ttccaacact atgttgaata ggagtggtga    8880
gagagggcat ccctgacttg tgccagtttt caaagggaat gcttccagtt tttcccatt    8940
cagtatgata ttggctgtgg gtttgtcata gatagctctt attattttga aatacgtccc    9000
atcaatacct aatttactga gagttttag catgaagggt tgttgaattt tgtcaaaggc    9060
tttttctgca tctattgaga taatcatgtg gttttttgtct ttggctctgt ttatatgctg    9120
gattacattt atcgatttgc gtatattgaa ccagccttgc atcccaggga tgaagcccac    9180
ttgatcatgg tggataagct ttttgatgtg ttgctggatt cggtttgcca gtattttatt    9240
gaggattttt gcatcaatgt tcatcaagga tattggtcta aaattctctt ttttggttgt    9300
gtctctgccc ggctttggta tcagaatgat gctggcctca taaatgagt tagggaggat    9360
tccctctttt tctattgatt ggaatagttt cagaaggaat ggtaccagtt cctccttgta    9420
cctctggtag aattcggctg tgaatccatc tggtcctgga ctcttttttgg ttggtaaact    9480
attgattatt gccacaattt cagatcctgt tattggtcta ttcagagatt caacttcttc    9540
ctggtttagt cttgggagag tgtatgtgtc caggaattta tccatttctt ctagattttc    9600
tagtttattt gcgtagaggt gtttgtagta ttctctgatg gtagtttgta tttctgtggg    9660
atcggtggtg atatcccctt tatcattttt tattgtgtct atttgattct tctctcttt    9720
tttctttatt aatcttgcta gcggtctatc aattttgttg atccttcaa aaaaccagct    9780
```

```
cctggattca ctgattttt gaagggtttt ttgtgtctct atttccttca gttctgctct    9840
gattttagtt atttcttgcc ttctgctaac ttttgaatgt gtttgctctt gcttttctac    9900
ttcttttaat tgtgatgtta gggtgtcaat tttggatctt tcctgctttc tcttgtgggc    9960
atttagtgct ataaatttcc ctctacacac tgctttgaat gcgtcccaga gattctggta   10020
tgttgtgtct ttgttctcgt tggttttcaaa gaacatcttt atttctgcct tcatttcgtt   10080
atgtacccag tagtcattca ggagcaggtt gttcagtttc cacgtagttg agcggctttg   10140
agtgagattc ttaatcctga gttctagttt gattgcactg tggtctgaga gatagtttgt   10200
tataatttct gttcttttac atttgctgag gagagcttta cttccaacta tgtggtcaat   10260
tttggaatag gtgtggtgtg gtgctgaaaa aaatgtatat tctgttgatt tggggtggag   10320
agttctgtag atgtctatta ggtccgcttg gtgcagagct gagttcaatt cctgggtatc   10380
cttgttgact ttctgtctcg ttgatctgtc taatgttgac agtggggtgt taaagtctcc   10440
cattattaat gtgtgggagt ctaagtctct ttgtaggtca ctcaggattt gctttatgaa   10500
tctgggtgct cctgtattgg gtgcatatat atttaggaga gttagctctt cttgtcgaat   10560
tgatcccttt accattatgt aatggccttc tttgtctctt ttgatctttg ttggtttaaa   10620
gtctgtttta tcagagacta ggattgcaac ccctgccttt ttttgttttc catttgcttg   10680
gtagatcttc ctccatcctt ttattttgag cctgtgtgtg tctctgcacg tgagatgggt   10740
ttcctgaata cagcacactg atgggtcttg actctttatc caatttgcca gtctgtgtct   10800
tttaattgga gaatttagtc catttacatt taaagtgaat attgttatgt gtgaatttga   10860
tcctgtcatt atgatgttag ctggtgattt tgctcgttag ttgatgcagt ttcttcctag   10920
tctcaatggt ctttacattt tggcatgatt ttgcagcggc tggtaccggt tgttcctttc   10980
catgtttagt gcttccttca ggagctcttt tagggcaggc ctggtggtga caaaatctct   11040
cagcatttgc ttgtctgtaa agtatttgat ttctccttca cttatgaagc ttagtttggc   11100
tggatatgaa attctgggtt gaaaattctt ttctttaaga atgttgaata ctggcccca   11160
ctctcttctg gcttgtaggg tttctgccga gagatccgct gttagtctga tgggcttccc   11220
tttgagggta acccaacctt tctctctggg tgcccttaac attttttctt tcatttcaac   11280
tttggtgaat ctgacaatta tgtgtcttgg agttgctctt ctcgaggagt atctttgtgg   11340
cgttctctgt atttcctgaa tctgaacgtt ggcctgcctt gctagattgg ggaagttctc   11400
ctggataata tcctgcagag tgttttccaa cttggttcca ttctccccat cactttcagg   11460
tacaccaatc agacgtagat ttggtctttt cacatagtcc catatttctt ggaggctttg   11520
ctcatttctt tttattcttt tttctctaaa gttcccttct cgcttcattt cattcatttc   11580
atcttccatt gctgataccc tttcttccag ttgatcgcat cggctcctga ggcttctgca   11640
ttcttcacgt agttctcgag ccttggtttt cagctccatc agctccttta agcacttctc   11700
tgtattggtt attctagtta tacattcttc taaattttt tcaaagtttt caacttcttt   11760
gcctttggtt tgaatgtcct cccgtagctc agagtaattt gatcgtctga agccttcttc   11820
tctcagctcg tcaaagtcat tctccatcca gctttgttct gttgctggtg aggaactgcg   11880
ttcctttgga ggaggagaga cgctctgcgt tttagagttt ccagttttc tgttctgttt   11940
tttccccatc tttgtggttt tatctacttt tggtctttga tgatggtgat gtacagatgg   12000
gttttctgtg tggatgtcct ttctgtttgt tagttttcct tctaacagac aggaccctca   12060
gctgcaggtc tgttggaata ccctgccgtg tgaggtgtca gtgtgcccct gctgggggt   12120
gcctcccagt taggctgctc gggggtcagg ggtcagggac ccacttgaag aggcagtctg   12180
```

```
ttggttctca gatctccagc tgcgtgctgg gagaaccact gctctcttca aagctgtcag    12240
acagggacat ttaagtctgc agaggttact gctgtctgta ccctgccccc agaggtggag    12300
cctacagtgg caggcaggcc tctgagctgt ggtgggctcc acccagttcg agcttcccgg    12360
ctgctttgtt tacctaagca agcctgggca atggcgggca cctctccccc agcctcgctg    12420
ccgccttgca gtttgatctc agactgctgt gctagcaatc agtgagattc cgtgggcgta    12480
ggaccctccg agccaggtgt gggatatagt ctctaggtgc gccgttttc aagccggtct    12540
gaaaagcgca atattcgggt gggagtgacc cgattttcca ggtgcgtccg tcaccccttt    12600
ctttgactcg gaaagggaac tccctgaccc cttgcgcttc ccaggtgagg caatgcctcg    12660
ccttgcttcg gctcgcgcac agtgcgcgca cccactggcc tgcgcccact gtctggcact    12720
ccctagtgag atgaacccgg tacctcagat ggaaatggag aaatcaccgg tcttctgtgt    12780
ctctcacgct gggagctgta gaccggagct gttcctattc ggccatcttg gctcctccca    12840
atgggattat tttcttgatt tcttttcag attgtttgct gttggcatac agaaaggcta    12900
ctgatttctg tatgttgatt ttgtatcttg caaccttaca gaatttgttt accagttctg    12960
atagtttttt ggtggagtct ttaggttttt ccaaatatga gatcatatca tccgcaaaca    13020
aggataattt gacttattcc tttccaattt ggatgccgtt tatttctttc tcttgtccga    13080
ttgctctagc taggacttct ggtgaaagta ggcatccttg acatgttcca gatctaagag    13140
gaaaggcttt tagttttcc ccattcagtt tgatactagc tatgggtctg tcatatatgg    13200
cttttattat actgaggtat gttgttctgt acccagtttt tgaggatttt ttttatcat    13260
gaagtgatgt tgaattgtat caaattcttt ttcagcatca attgaaatga tcatatggtt    13320
tttgcccttc attctgttga catgacatat cacattaatt gatttgtgta tgttaacaa    13380
tctttgcatt tctgggataa atcccacttg atcatgatga atgatctttt taatgtgttg    13440
ttgaattcaa ttttctagta ttttgttgag gattttttgca tcaacattca tcaatgatat    13500
tggcctatag gtcttttgt ttttgttttt gttttttgat gtgtctttgt ctggttttgg    13560
catcagggta atactggcct tgtagaatga gtttggaagt atttcctcct gtttatttta    13620
gaatagattg agtaggattg gtattagttc ttctttaaat gcttggtagt attcagtagt    13680
gaagccattg ggtcctggga ttttctttgc tgagagactt tttattatgg ctttgatctc    13740
attacttgtt attcatctgt ttgggttttg gatttcttta tgattcaatc ttggtaggtt    13800
ttatgtatct aggaatttat ccattttttt ctacattttc caattattg gcaaatagtt    13860
gctcatagta gccactaatg atctttgaat ttctgtggta acagttgtaa tgtcttcttt    13920
ttcagctctg attttattta tttgggtctc tcttttttg cttttttttt ttttttttt    13980
ttttagttag tccagctaaa ggtttgtcaa ttttgtttat cttttcaaga aactaacttc    14040
ttggccaggc acagtggctc acacctgtaa tcccagcact ttgggaggct gaggtaggtg    14100
gatcacttga gggcaggagt ttgagaccag cctggccaac acagtggaac cctgtctcta    14160
ctaaaactac aaaaattagc caggtgtggt ggcacatgcc tatagtcctg gctactccta    14220
gctactcagg agactgaggc acaagaattg cttgaacctg ggaggcggag gttgcagtga    14280
gccaagatcg caccactgca ctccagcctg ggcaacagag tgagactctg tctccaaaaa    14340
aaaaccaaac caaaccaaac caaaacaaaa aaccgttttt gtttcattga tcttttgtat    14400
tgttttcttt gtttcaatgt catttatctc tgctttgatc tttattattt cttttcttct    14460
agtaactttg ggtttggttt gctcttgctt ttctagttct tttttttttt tttttttttt    14520
```

```
tttttttttt tttttttttt gagacagagt cttgctctgt tacccaggtt ggagtgcagt   14580
ggtgtgatct cggcttactg caagctccgc ctcccgggtt catgccattc tcctgcctca   14640
gcctccccag cagctgggac tacaggtgcc cgccactgtg cccacctaag ttttttgtat   14700 tttttagta gcaatggggt ttcagtgtgt tagccaggat ggtctcgatc tcctgacctc   14760
atgatctgcc cacctcggcc tcccaaagtg ttgggattac aggcgtgagc cactgcacct   14820
ggctctagtt cttttagatg catcatcagg ttgtttgaag ttttctttat tttttgatgt   14880
aggcacgtat agctataaac ttccctccta gtactgcttt cactgtgtcc cacaggtttt   14940
ggtttatcat gtttccatta tcatttgttt gaagaaattt ttcagtttcc tgtttaattt   15000
cttcattgac ccactggtca tttaggaaca tattgtttaa tttccatgtt tttgtatagt   15060
ttccaaaatt cctcttatta ttgatttcta gttttactca ttgtggtcag tcagatgttt   15120
gatattattt caatttattt gaatgtttta agactcgttc tgtgacttaa tatacgttct   15180
gtctttgaga atgatccacg tgctgaggaa aagaatgtgt attctacagc tgttgtatga   15240
aatattttat aaatatctat ttggtctata gtgcagatta agtcccatgt ttctttgttg   15300
attttctgtc tggaagatct gtccagtgct gaaagtgtag tgttgatgtc tccagctatt   15360
attttactgg ggtctatcac tctctttagc tctagtaata tttgctttat atatctgggt   15420
gctccagtgt aaggtggata aatatttaaa actattatat cctcttgctg aactgacctc   15480
tttatcatta tatagtgact ttgtctcttc ttatagtttt gtcttgaaat ctattttgtc   15540
tgatataaat ataggtatcc tgttcttttt tgctttccat tggcatggaa tatcttcttc   15600
aatcccttca ttttcagtcc aggtggagtg tctgttgtag gcaacagatc actgggtctt   15660
tttttttttt aaatctattc agccactcta tatcttttga ttgacagttt agcccattta   15720
cattcgatgt tatattgata agtaaggact tactcttgcc attttgttat gttttccggt   15780
ggctttgtgg tcttctcttc cttctttcct cccttccctt ctgcctttta gtgaaggtgg   15840
ttttctcttg tggtgtgctt taatttcctg cttttttattt tgtatatatc cattgtatgt   15900
ttttgatttt gaggttacca tgaggcttgt aagtactgtc taataactca ttattttaag   15960
ctaaaagaaa actaataaac tctacacttt aacttcctcc ctctgctttt taactttta   16020 ttgtttctat ttatatctta ttgtactatg tcttgaaaag ttgttctagt cactattttt   16080
tatcagttaa tcttttagtc attttactga agagtagttt acatgtcaca gtcacagtgt   16140
tatactattc tgggttttc tgtatactta actgttacca gtgagttttg tgccttcagg   16200
tgatttctta ttgctcacta acatcgttta ctttctgatt aatgtactct gtttagcatt   16260
tcctgtagga caggtctagt gttgatgaaa tccctcagct tttgtttgtc tgggaaggtc   16320
ttcatttctc ctttatgctt gaatatattt tccttcagca ctttaaatat gtcatgccac   16380
tctctcctgg cctataaggt ttccactgaa aagtctgctg ccagacgtat tggagtgcca   16440
ttgtatttta tttgttcttt ttcttttgct gcttttagga tccttccttt tatccttgac   16500
ttttaggaat ttgattacta aatgcctgag gtagtcttct ttgggttaat ctgcttggtg   16560
ttctacaacc ttcttgttct tggatattga tatcttcctc taggtttggg aagttctctg   16620
ttattatcct ttgaataaac tttctacccc tgtctctttc tctacctcca ctttaatgcc   16680
aataactctt agatttgctt ttttaagtct attttctaga tcttgtaggt gtacttcttt   16740
cttttttatt cttttttctt ctgtctcctc tgaccatatt ttccaatagc ttaccttcca   16800
gctcactaat tctttgttcc acttattcaa tcctggtatt aaaagtctct gatgcattct   16860
tcagtatgtc ggttgcattt ttcaactccg gaatttcagc ttgactcttt ttaattattt   16920
```

```
caatctctgt tacatttatc tgatagaatt ctaaactttt tctgtgttgt cttgaatttc    16980
tttgagtttc ctctttgtta agtttatctg atagagttct gaatgtcttc tctgtgctat    17040
cttgaatttc tttgagtttc ctcaaaatgg caattttgaa ttttctgtct gaaaggtcat    17100
atagttttgt ttctgcaggt ttggcccctg gtgtcttatt tagtttgttt ggtgaagtca    17160
tgttttcctg gatgttcttg atgcttgtgg atgttcatca atgtctgggc attgaagagt    17220
tagatattta ttgtagctct cacagtctgg gcttgtttat acccatcctt cttgggaagg    17280
atttccaggt attcaaaaga acttggatat tatgattgaa cccatatctg cattaggggg    17340
catcccaagc tcaataacgc tgcatttctt gcagactatc tggaagaatt atctggatta    17400
tcaagcccac actcttgttc ttgttgctta ctttctccca aacagaatca atctctctct    17460
ctctcttttt ttgctctttc tctctccccc ttcccccctc cctcctctcc ctttctcctt    17520
ctctctctcc ctctgttctg ggccacccag agctagggg gtggagatac aagcaccaat     17580
atggccatca ccactgagaa tgtactgggt cagacatgaa gctggcacca cactgggtct    17640
cgccatggcc cactgtaacc atgatctggc tgcctatgtt ccctcaatgc cctgttgtga    17700
agccagccag gctagcttca agccagtgag ttccccagg ctgcagccag atccagagat     17760
gccatctggg agccatggac tggagtccaa aaccttagaa atctgcttgg tgtcctatct    17820
attctactgt ggctgagctg cactcaaac cattagccag tcctttccac tattctgccc     17880
tttccacagg ctcagggcc tctcccatg tccaccacca ccacaggcct atgaggagtg      17940
ctgccaggtt actgctgatg ttcggtaaag gcctatggcc tcttcagtca gcttgtggta    18000
aatcctttca gtcacccttc agggcagtga gctcccctct ggcaaaaagc aagtccagag    18060
atgtcatcca agaacctaag gcctagactc agggacccca agaggggtct ctatttgttg    18120
ctttacccca ctgtggccaa ggtggtagca agtgcaaggc aggctgggcg cagtgtctca    18180
tgcctgtaat cccagcactt tgggaggctg aggcgggcag atcacttgag gccaggagtt    18240
agagaccagc ctggccaaca tggcgaaacc ctgtctctac taaaaataaa aaaaattagg    18300
ccgggcgcgg tggctcactc ctgtaatccc agcatgttgg gaggtcaagg tgggtggaac    18360
acttgaggtc aggagttcaa gactggcctg accaacatgg tgcaaccca tctctactaa    18420 aaatacaaaa ttagccaagc atggtggcac acacctctaa tcccagctac tcggaggct    18480 gaggcaggag aattgcttga acccggtagg tggaggttgc agtgagctga gatcgcacca    18540
ctgcactcca tcctgggtga cagagtgaga aaccatctca aataaaataa aataaaataa    18600
aataaaataa aaaattttta aaaattagct gggcatggtg gtacatgcct gtaatcccag    18660
ctactcagga ggctgaggca tgagaattgc ttgaacccag gaggcacagg ttgcagtgag    18720
ctgagatgac accattgcac tccagcctgg gcaaaatagc aagactctat ctctgaaaag    18780
aaagaaagag agagagagag aaagaaaaaa gaaagaaaga aagagaaaga aagaaagaaa    18840
gaaagaagga aggaaggaag gaaggaagga aggaaggaag gaaggaagga aagaaagaaa    18900
gaaagaaaga aagaaagaaa gaaagaaaga gaaagatcaa gagcaagaca aagcacccttt   18960 taatttttcct tctgctttc tcaagcggaa ggaatctctc accatggcca ccacagctgg    19020
gaatgtgctg ggtcacaact aaagccgaaa tatcttagcc tcaattaagg cccacagcct    19080
tggatattaa ctgggtatca ctactgttta ttcagggctc aagggctctt tcatcagcag    19140
gtgatggatc ctgccagagc tgggtccttg ccctgcaagg cagcaggctc ccttctgatc    19200
caggattgtc tagaaatgtt gtctgggaac tagggcctga aacagcctca tgaccctgcc    19260
```

```
tggtgcccta tcctactgtg gctgagctgg tatccaagat gcaagacaaa gttctcttta   19320
ctcctccctc tcatctcctc aagcagaagg aagaggtctc ttttggagca gtgaggttgg   19380
cggggagggg ccgagcaagc attccactag ctgctctggc tggtgtctca gtaggtcatg   19440
tgcctgctaa gtcaactggc tccaagtcca gctcagcact aggacttgcc taagagttgt   19500
agttcatggg gcctacactg cctttcaatt ttatttagag ccccagggca ctttggccct   19560
cggtgacgag gtttgccaga attcaagttc tgaccaaggt acaggagatt ccctctggc    19620 tagggctggt ctaaatgctc cctctatggt ctggcatcag ctgagttcag cctgcttttg   19680 cttttctactg tctgtaacag ggcagcactg agttcagtgc aaagcctcac aatcgctgca   19740
ctgtccctct cccaagcgta cagattttct ctccatgcca cacatctggt gctgggctg    19800 ggggaggggt ggcattggca attcaagact attttttccta ccctcttcag tccttttca   19860 gcaatataaa gttaaaacca ggtactgtga gtgcctgatt ttttggtttt tataaaggtg   19920
cttttttgtt tgtagatagt tgttaaattt gatgttccta tgggaattac aattcgtgcg   19980
agcttctatt tggccacctt gctcctctcc atattcgcca tatatatata tatatatatg   20040
ccaatagagg gaaggagagg aatcacaaac attgctttaa aacagtaata catgtaaatg   20100
atccaattag aaaagggtcc agaatgaaaa tgaagttttc cttcctgcct ctcctgtccc   20160
tcagtcatgc agtttccttt ccaaaaaaaa tactgctggt ctgggcacgg tggctcacac   20220
ctgtaatccc ggcactctgg gaggccaagg caggaggata gcttgtgggc agcagttcaa   20280
gaccagcctg gtctgcaaag caagacctca tctttacaaa aaaatttaaa aattaggtac   20340
gatggcgtgc actttagtct cagctactcc agaagttgag gtgggaggat cacttgagcc   20400
caggagttca gaggctgcag tgagctatga gcatgccact gcactccagc ccaggtgcca   20460
cagtgagact ttgtctttta aaaaaatgac aaaaagaaat tacggttacc agtttctcaa   20520
aatatgtcct tccagagaga tacacgtttg tatgcgcaaa gaatgcttgc aaacttgctt   20580
cctcatatac ccatacacat atgcagaaac agatgtgcac gtgtgtgtac atatatgcat   20640
tcatattgtg tatgaattct atgcatcaca cagctgaaag cacaagatgg tagataccct   20700
tctgcttttg tctcttaaca gtgtaatttg gaggtaattc ctaccatatt tatggggtca   20760
cctcattctt ttttttgctga ctgcataggc tatcattgta atcgtgttta actggctgtt   20820
cccagtaggc atttggggttg tttctagtcg ttctgataaa tagggctgca ttgaaaatcc   20880
ctgcagtagg tacatggggg atatttccta gaagtgtgat tatttggtca gtgcatgtgt   20940
gtgttaaatt ttgagatctg gccaaattac tctccataaa ggctacctca gagtgtctgt   21000
ttctctgctc tcttttgaac ctagaatgtc atcccaagca ttaccatgtg ccaatgtttt   21060
gctattatag gataaaaact actatctcag tgaagaattg catttctctt ttaggaaccc   21120
aaatatcttc tcacaggttt aagagccatt tgaggccagg tacagtggct catgcccatt   21180
atcccggcac tttgggaggc cgaggtgggc agatcacctg aggtcaggag ttcaagacca   21240
gtctggccaa catgatgaaa cccggtctct actaaaaata caaaaattag ccgggcatga   21300
tggtgggcgc ctgtaacccc agctactcag gagagtgagg caggagaatc tcttgaaccc   21360
aggagacgga agttgcagtg agctgagatc gcatcattgg actccagcct cagcgagaac   21420
agcattgaat ttcccttgt atgaactgtc ttttcatgtc ctttagccat tctctcttca    21480
attgttccta tggttttttt ttctttttga tgttggactt tttatctact tgttttcctt   21540
gtttgctgca gtgtgtacca accagtgcag cttcttggtt gttggtgggt ctgtaagcaa   21600
gcgttcggag ccagcacaga gaggatgaga ggagggctgc actcatctgc tcttccagat   21660
```

```
ggcactgatc aaaggacgtg gtgatcatgg gaacactctg gagagcacgt agccatattt   21720
agatatattg acaacacaac catttagtag actcagggtg actttaagcc acatgtcaca   21780
tggcagctgt taaaatcatc tctgtacatg tacatggata gttctgatgg cacacccttg   21840
ttagctttgt agcttttagc taaagggcca tatggtgaag gtgcattttt tgcatttctt   21900
atttcttctc ttttctttgt caatatatcc attctagaaa atgagatgag ccaggcacag   21960
tgtggtgcat gcctgtaatc ccagctactc tgaaggctga ggcaggagga tcacttgagc   22020
ccaggaattt gaggccagcc taggcactgg gcaacatagt gagactccgt ctcttaaaaa   22080
aaaaaaaaaa gaaaagaaaa gaaaagtgg ccaggcatgg tgactcaagc ctgtaatccc    22140
agcactttgg gaggtcgagg caggtggacc acctgaggtt aggagtttga gaacagcctg   22200
atcaatatgg tgaaaccctg tctctactaa aaatacaaaa attagccggg cgtggtggtg   22260
tgcacctgta gtcccagcta ctcgggaggc tgagatagga gaactgcttg aacctgggag   22320
gcagaggctg cagtgagctg agatcgcacc actgcactcc accctggatg acagaacaag   22380
actgtctcaa acaaaaaaaa aatgaaaaaa gaaagaaaaa aggacaaaaa aagaaaatgg   22440
ggcaagatgc ttactctttc tgtaaattat ctttgtagtt caagtgtcca gtaaagttct   22500
ctgttccaag cagacactta aaataaatat ttgctcaaaa aggtcaattc ctccacgtgc   22560
tgttttgctg cccttcctaa aggcatgtgt atcagtgcag cacttcttaa ctgatgttaa   22620
taagtgttct gtgattttt aaaaagtgcc tatgattata ttaattttgg aaaagctatt    22680
ttaaatatta aagcatttta acatttaac ttataaaata aaatcagttt atttactaca    22740
ggacttctca cagcctttaa tgtacaagca aatccaccga acttccaaga gagggttgca   22800
aggtgctgtc ttctgcaagt gtgtctgtcc atggagctct gttttcatat tttcatggta   22860
tctcattgaa atacagctca agcaattagc ctaaactcat agatgaataa agagtagaca   22920
tcaatttgtt tgtcccctga tttgtctgaa ttaggccaaa caaggatctt taactggaaa   22980
tagggttatt gattacttga ctgcagtcag atttctaaaa ttgagtaaaa acgtgtttgc   23040
ggttcaattg cagacaaaga catactggtt actttctcca ggctcccac agtattggca    23100 gaagtgtaaa attaagagat caaggtcatt tctggtaacc cctcactgca cctactcgag   23160
gtctgatgcc accctctctg tctgaatcat ccaaatcaaa attggccagg atgagggta    23220 tagtgctggg accagacaga gccaccacca gctggtggct taattatgaa gcaaatttat   23280
agagccacaa gggggatgga ccagaagtgg actgggaaag atcattatgt ccagctcctt   23340
aacagggcag tttcttcttt ccacttgagt tatttctaaa attgactttt taaaaatccc   23400
ttattggcct tttctgtctt cttgagaaat cttgtctgtt tttcttctca gccttcctga   23460
aatgcgtaac agtggttctg aacagtgttc tagaaccctg gtggtgggga tgtgtcacaa   23520
gtcatctgtg tgctaaagta aaccattaaa agcacatgca tttgcaaatt accaccaaat   23580
agaatggatt caagagtacc ttatgtaagg tcttatctac ctactttgag aacgcctttt   23640
tgagtggaat gagctgttct gattgcctat gtgattacag tgcttatgag tggctttata   23700
tttccatttt tattttccct tttgataaga ttgcacttga gctacaaaga taccaggaac   23760
attttcattt gtaataacac aactgttatg attacccgat gaaaggcagc caaaatgatg   23820
cgagaaaaat gttcaatagt gatattgtgg ctttaaaaaa gcaatcaggt taattatttg   23880
cattcctcaa tagtctacac ttgttacttt tttttttttt tttttttttt gagacagagt   23940
ttccgtctgt cgcccaggct ggagtgcagt ggcactatct cggctcactg caacctctgc   24000
```

```
ctcccaggtt caagagattc tcctgcctca gcctcctgag tagctgggat tacaggcatg   24060
caccaccatg ccccattact tttttgtgtt tttagtagag acggggtttc accatgttgg   24120
ccaggctggt tttgaactcc tgacctcaag tgatccatcc acctcggcct cccaaagtgc   24180
taggattaca ggcatgagcc accatgctcg gcctacactt gttactcttg ccatattgtc   24240
tatatttcct ttggagtagg agtctagaaa atacatcatt ttgccaggca cagtggctca   24300
cgcctgtaat cccaggactt tgggaggcca aggctggtgg atcaccaggt cagaagttca   24360
agaccagact ggccaatatg gtgaaacccc gtctctacta aaaatacaaa aattagccgg   24420
gtgtggtggc aggcacctgt aatcccagct actcaggagg ctgaggcaga agaatcactt   24480
gaacccggga ggcagaggtt gcagtgagcc gagatcacac aatctttatt attatagttg   24540
ttaagactga tatttttgta attttttact ttcaagtgtc ttttaatata ttcccatctc   24600
caaaaatagt tgtgccacac tcattgttaa tttctcttct ctgccaattt ggtggggatt   24660
catcaacacc tagttctctc cattatgtgc gtcactcaag ggagcttcat ccagcatgca   24720
tgttcatgga gaacttggtg ccaaagaggt gcttcctcat tctcttttct tttcttttct   24780
gtttgttttt ttgagatgga gtcttgctct gtcgcccagg ctagagtgca gtggcgcaat   24840
ctcagctcac tgcaacctcc acctcccggg ttcaaacaat tttcctgcct cagcctcctg   24900
agaagctggg attacaggtg cccgccactg cacctggcta ttttttagtag agacggggtt   24960 tcaccacctt ggccaggctg gtcttgaact cctgacctcg tgattcaccc gccttggcct   25020
cccaaagtgc tgggattaca ggcgtgagcc accgcgcccg gcctgcttcc tcattttctt   25080
cctgatttat agcatgcttg cctccagctt tcatagcagc agcatgctta tgccttcctc   25140
gaggcatcaa gatgtcagca ggatcgattc cttctgagag ctacaaggga gagatctgtt   25200
ctaggcttct ctccttggct tgcagatggc cattttctcc ctgtgacttc gcatcgtctt   25260
ccatctatct ctgtgtccaa atttcccttt ttgtaaaggt atcagtcatg ttgaattagg   25320
gtcctctcta atgacttcac tttaatttga ttacatctgc aatgagcagt ttccaaataa   25380
ggtcacattc tgagggatgg aggtttagga cttcaacatt tgaatctggg gaagacacaa   25440
ttcaactcat aacaacatgt taatttgcta cttacgaact tttctcccct ttttttaaag   25500
aatgtacatg gcaagtcaaa gcaaacgatc gcaagtacca cgaacaacct cactttatga   25560
acacaaaatt cttgtgtatt aaggagagta aatatgcggt gagttgttaa ctttctgaat   25620
tgttttcatt aaaatgcagt tttttccagt agctggcatg cttactacct tcatgctaca   25680
cctgccttcc acgtaaccac ctgcctgggg ctactgataa tcatcattgt ttctatagaa   25740
tgtcattttt attgatgttt acctttgggg tgggtagcgg gtgacttgaa acaaaacaga   25800
attatgtaga ttgaaattt ctctctcttt tttaaatttt aagctctctt agaaatgttt   25860
tatgaaagaa tatacaatga tggcacagaa gcctcctgtt tgaaagtaat gagtttgaaa   25920
ggaatctctt aagaacttat cttccccttc tctgcctgga atggatttag agattttaaa   25980 catattttg actcaaaaat gcttattacc tttggaatgt gataaagaat gcttaaagat   26040
taaatgcgaa atacaaaaat tagcctggag tggtggcatg tgcccacagt tcagctact   26100 tgggaggctg agccaagaga atcgcttgag cccaggaggc agaggtttca gtgagctgaa   26160
attgtgccat tgcactccag cttgggtgac aggagtgaga ctctgtctca ataataataa   26220
taataataaa tattaagtgt gggcttaaat gttgtaagat gtgtgtttta atgccaaggg   26280
cttccatagc agagtaccac aactggatgg cttaaaacaa cagaagttta ctctctcctg   26340
atgcagggat cagaagtctg aaatcttggt gttggcaggg ttggctcctt ctggagcctc   26400
```

```
tgcaggagaa tctgttccct gcctctcccc tggcttctgg tggccactgg caatccttgg   26460
agttccttgg cttacagatg aagtcacccc aatctctgct tccatcttca aggggcactc   26520
ttcctgtgtg tgtctgtgtg caactttcct cttataggga ccccagtccg aataagcacc   26580
tcattaaatt agagcctgtc ctaatcacgt atgacttcat cttgattatc tctgcgaaga   26640
tcctatttcc aaataagatc ccattcatag atattagtgt taagacctga acatatcttt   26700
tgcaggacac aatgcaaccc actacagtac cttttgctct ttcttacata gtaggctctg   26760
tctcctcact taaataaaag cctcactttt cctggctttg ccatgttgt tgtctacctt     26820 taccctgttt tctaacagtc tctaatgggt caaggaatct gacagcagga tttatttggt   26880
cacagtctga tgtctgtttc ttgttactgc ctctgtcata agactccaag tagtcatttt   26940
gaggcttggc tgcttggcta gaattaaaag cttaaagaa atatcagtat ctttctttct     27000
tcttttcttt tttaaggcag agtctcactc tgtcactcag gctggagtgc agtggggcga   27060
tctgcaactt ctgcctccct ggttcaagcg attctcctgc ctcagcctcc caagtatctg   27120
ggattacagg tgcaggccac cacgcctggc taatttttgt attttagta gaggtggggt     27180 ttcaccatgt tggctaggct ggtctcaaac tcctaggctc aggtgatcca cccacctcgg   27240
tctcccaaag cgctgggatt gcaggcataa gccaccgcac ccagacaaaa tcctcaatat   27300 cttttctgaca gatgatgttc ctttgtcact gtaagctgtg ggacttgtga cttttgcaga   27360
tgtgtataca ttgtgataaa tacagcatca tttagaatga ctcttatttt ttccaacaga   27420
ataatgcaat taaacatac aagtacaacg catttacctt tataccaatg aatctgtttg     27480
agcagtttaa gagagcagcc aatttatatt tcctggctct tcttatctta caggtaatgc   27540
cctttgctat cttaaatctg tttgaattat agtgactcga taacatttaa gctgtagaca   27600
catataatgt gaataatctt gaaagtgttt tatattagca tcagggttct gtacataaag   27660
gaacagtgcc tcatacacag aaccagctca atcagtgtta tatgaacagg gaaagggagc     27720
aaatggaaat attattctaa ttctgtattt taaaaaattt catgttatac tgatatgggt   27780
gttaaaattg gtatccctga agtgaataaa actaaaatcc agccaggctc agtggcccac   27840
gcctataatc ccagcacttt gggaggccga ggcgggtgga tcacctcggg tgaggagttc   27900
cagaccaccc tggctaacat ggttaaaccc cgtttctact aaaaatacaa aaaattagcc   27960
aggcgtgatg gtgcatgcct ataatcccag ctactcggga gactgaggca agagaatcgc   28020
ttgaacccag gaggcggagg ttgcagtgag ccgagatcac accattgcac tccagcttgg   28080
acaacaagag ctaaactcca tcttaaaaaa aaataaaata aaatccttac tttgtaaaat   28140
tatttgcacc ttaaaattaa agctattttg tgcttgtctt ttatcattgt agttagatgc   28200
tgaatttccc ccccaaaaag atcattgatt ttttattaaa attttggtca taaatttcag   28260
taagttattt ttgtgaactg ttttttacatt ttaaaaggcc tacttaaaaa ttttttttcc   28320
taattgtggc aaagcatcca gttatccaga gagcatgagt ttagctgtgc aagaactgtt   28380
gctgtaaccg agggaactct acacacacta gttagcgcca gaatcaacct ttagtgtctg   28440
ccgtgcggat tacatagctt aagctcagaa tatccacctg gttttttcag attcttttt     28500 tttttttttt tgagaccgtg tttcgctctt gtcgtccagg ctggagtgca gtggcaccat   28560
cttggctcac tgcaacctcc tcctccttct cttgggttca gcgattctc ctgcctcagc     28620 cccctgagta gctgggatca cagttgccag ccaccacgcc cagctaattt ttgtattttt   28680
agtagagaca gggtttcacc atgttgacca ggctggtctc aaactcctga attcaggtga   28740
```

```
tccacccgcc tcagcctccc caagtgctgg gattacaagc atgagccact gcgcccggca    28800
ctttatcaga ttctttacgg caagcattgg atttggaaaa gttatacctg ctgggattga    28860
ccctttaagg ttttatgaaa atggggtaga atgtgtgtct aggtggggat ggaggatgcg    28920
tggagaggag agaaaaagaa gagacgatgg taaggagaaa tggataggca atgatttagg    28980
aaactgtaag accttcaagt cagatagtaa aggatggccc tgttatcaaa ggagatgctt    29040
agaaaggtgt gtgtagaggt tagcactgca aactccaagg tgctgctctg taggaagtag    29100 accatttttcc cttacttcct tctagcaggg aagaggagtt tcacatattc actgtgatgt    29160
gggaagaagg atcttttttgt cttctaactg caccccagtt atcttctctc tctctttttt    29220
tttttttttt gagatggagt ttcgctcctg ttatcaaggc tggagtgcaa tggcgtgatc    29280
tcagctcacc aaaacctctg cctcccaggt tcaagctatt ctcctgcctc agcctcctga    29340
gtagctggga ttacaggcat gcgccaccac acctggctaa ttttgtattt ttagtagaga    29400
cggcgtttct ctatgttggt caggctggtc tcgaacttcc aacctcaggt gatccgccca    29460
cctcggcctc ccaaagtgtt gggattacaa gcatgagcta ccgtgcctgg cgcagttatc    29520
ttctcttaag gtcagcaatc caaattaggg taacagtaat agccgtaggc agcttcttaa    29580
cttgtgttgt cactacactt aattcttcta gtctagaagg tcaggcctgg catgacctcc    29640
attttgcaga gaaaagctga ggcctagtaa gctaaagtaa cttgctcaaa gtcccataag    29700
ccataaatga tagagctgac caagacttgg atctaggagt tgactccaaa gcctgtcatt    29760
ttaaccacta cattatacag cccagtgatc aggaggatgg ttatgaaata actttattaa    29820
acttgcatcc caatctttgt tcaaacttag aggctgtctt gatggaggaa ggccagctca    29880 cttttcttgga taggccaata gtgatgatca tgaaggaagc actttcttct aatgccctca    29940
gagatgctct ccctaatccc tcactttcag aggcagctag tacctcttgc catcattgcc    30000
ttcagcatgg gatcctcaga aaccactgac tgagaaacct gcagtataga acctactatg    30060
catgcattcc ttaaaagtta agatgacttt ggccaggcac ggtggctcac acctgtaatc    30120
ccggcacttt gggaggctga ggcaggagga ttgcctgagg tcaggagttc gagaccagcc    30180
tggccaacat ggtgaaaacc catctctact aaaaatacaa aaaattagc cgggggtggt    30240 ggcacacacc tgtaatccca gctactcagg aggctgaagc aggagaatcg cttgagcctg    30300
ggaggcggag gttgcattga gccaaaattg tgccactgca ctccagcctg ggtgacagag    30360
ggagactctg tctcaaaaaa aaaaaagaa aaaaaagtt aagacgagac ttctcccttg    30420
ccactcctac cccctcaccc ccagttaaat atgattttca caaagatttt agagcaactc    30480
ttttttaggt atcataatac aaaacttcct tggtgtccag ttaagtttgc aatgagataa    30540
tttcaggagc cactgccctc taggctctgt tccaggtatc cagaagctag agagaaccac    30600
tagaaggagg ttgtccaaat gcttgaagag cctttcctat atactctgca ggatgtagac    30660
ttatgtgatg acggtgatga gacttggaat tagcaagctt agaattagca ataagttacc    30720
tgtaagcttg atatgccttc atggacacac acataagccc ttttattctt ttaggcagtt    30780
cctcaaatct ctaccctggc ttggtacacc acactagtgc cctgcttgt ggtgctgggc    30840 gtcactgcaa tcaaagacct ggtggacgat gtggtgagga tttctcatac aacgttctac    30900
tcattgcttt gagttgactt taagttctcg tgccttcctt ctctattgag atgttttaaaa    30960 cagcatttcc ccatcttcct tctcaaggct cgccataaaa tggataagga aatcaacaat    31020
aggacgtgtg aagtcattaa ggatggcagg tactgtgtct aattagtaac tgagtttcaa    31080
ggatgtaatg cataactctg cctagaaaca cattcagaga taattattac aatgtagaag    31140
```

```
gctattagta cattaactgt ttatttttt  cgagatagag tctcgctctg tcgcccaggc  31200
tggagtgcag tagcgttatc tcggctcact gcaacttcca cctcccaggt tcaagcaatt  31260
ttcctgcctc agcctccgag tagatgggat tacaggcgtg caccaccatg ctcagctaat  31320
tttgtacttt tagtagagat ggggtttcac catgttggcc aggctggtct caaactcctg  31380
acctcaagtt atcctccttg atctcccaaa gtgttgggat tacaggtgta agccaccatg  31440
cctggcctta aattatcttt taatgagta  tgtaccctg  ttgtaataaa tctaataagg  31500
atagtgataa aaatagataa aaagatgact attttgagta ctaaattcca taggaaatat  31560
tcattaaaat ttttaacata tcaacacttt taaaagtttt aaactataat attgttttaa  31620
agattttcac atatacaaat gatataccca gtggacgtaa tgaacctgct ataaataata  31680
aacttaattt cactggaggc agtcgtctaa tcactatgtg tttatctgcc attcatttat  31740
ggccaaaaat gacttggaga tttaaaatac ttttttaaata tatgtttatg ccccagttcc  31800
cctaatgaat ttagtataca attcttaact ccagcattaa aaaaaaaatt tggcttatct  31860
ttcaattgac gaaattgtag atgttttaca tttcagtatt tctgaaattt taaaatagaa  31920
atttgcatgt aagtccgaaa tgacaaatgg ataggccagc accttcttag cagggctact  31980
ggaaggcaat tctgaatact gaaatattgg aggcaattct gttagattct tctatccgat  32040
gttccagttt cctctgagga ggcccccctgt gctctaccct gctaatgctc aagttcctat  32100
aggtgtgacc ccactgcagg ggctgctcag gccatggccc tgccagacat gcaccctaga  32160
cttccaaatt caaggcaacc cagagctcct ctttaccagt gtaggtaggt atggtacagg  32220
ctaaacatat gggttggcca ggcacggtgg ctcacgcctg taatctcagc actttgggag  32280
gccgaggcag gaggatcact tgaggccagg agttcgaggc cagcctggaa aacttagtga  32340
gactcctgtc ttttttttta ttttttgag  acggagtctc gctctgtcgc ccaggctgga  32400
gtgcagtggc gcgatctccg ctcactgcaa gctccgcctc ccgggttcac agcatcctgc  32460
ctcagcttcc cgagtagctg ggactacagg cgcccgccac tgcacctggc taatttttg   32520
tatttttagt agagatgggg tttcaccgtg gtcttaatct cctgacctca tgatccactc  32580
acctcggcct cccaaagtgc tgggattaca ggcgtgagcc accgggcccg gccgagactc  32640
ctgtcttaac aacaacaacc tcctctgcta ggctcattgg gacacttatt ctatttact  32700
gaatgaagtg tttcctaatc ctagaattgt aaataaagcc aattaagatc tttaaattgt  32760
tgtgattttg tcttttgaca cttgaaaggt aactttggaa cataaattttc ttatttgcaa  32820
aggaaaaaaa gccatctaaa catatttata gcttggtata gtctatattt gcattagagt  32880
ggaagtacgg ctgtaagtca ggttactttc ctcagtgttg acacataaaa agtcttggaa  32940
tgaggcctta gttactattt ttagcacttg aatttgcagt tctgcctgaa gcctcctgct  33000
caaaaaacaa ctcattactg atccctgagt tggtgctttc gtcacagttg actacgttaa  33060
tttaacaaac acttatggag tactttctgc atgttggagg caggacagta tccttgagaa  33120
atttatagtt caagacagaa gatgagacac ctacacacat cattctaata aaatccatat  33180
cagaataaaa aagataaaaa caaaatgctc tgacagtaca gggaagggaa aattcacttt  33240
agcgagggaa tgtggggaaa gatgtcaaga cgtgagcaaa gccctgaaaa tgatgcccta  33300
gggaggctga aggggctgtg taaacacaag ttgtggtgac aacacaaagc tccatcagac  33360
aactgaccat aatccaattt gagtgtagcc tcagggcctt aaaggggaata cagtgtcttt  33420
gtcagttaag cctttacaat taagaagtta accggccagg tgaggtggct catgcctata  33480
```

```
atcccagcac tttgggaggc cgaggtgggt ggatcacctg aggtcaggag ttcgagacca    33540
gcctggccaa tatggtaaaa actcatctct aaaaaattag tcaggcgtga aggcacgtgc    33600
ctgtagtccc agctactcgg gaggctgagg caggaggatc tcttgaaccc caggaggcag    33660
aagttgcagt gagctgagat cgtgccactg cactccagcc tgggcaacag agcaagactc    33720
tgtctcaatg aaaaaaaaaa ttaataaata aataataaag ataatttaaa cagcagagag    33780
taggcaagct ctgaagcccc acgaagactc tgggaggccc aggtgggtgc cataatgtag    33840
gtgcttctgt cctgggacca gcatggagca agtgatgggt cactgagaag gaacacagca    33900
gggaggcaag ttgacataa gcaaaaacaa aaggggtgg caagtatttc cctgccacgc    33960
acataagtgg cccccataaa ctcttcctta catgacctag atgaaaagaa tgtatcaaag    34020
tcattcatca ttgcttcctt cagaggtcaa tacaattttc atgccccct ttaatatgtt    34080 tacatccatt aaagagcaaa attttagcat tttctctgtg acttgcatat tttccagaat    34140
ctataacatc cagaaagaat agtaattccc ttgcctgtaa cttaaaatgt caataaatcc    34200
tcattatttt taatccttag gttcaaagtt gctaagtgga agaaattca agttggagac    34260 gtcattcgtc tgaaaaaaaa tgattttgtt ccagtaagtg aacaaattct gcttctcttg    34320
ttccttgttc tcccccagcc cctgtgctcg gcttttccct cagggtctcg gtgttatttg    34380
tgtgttttgt tttggacagg ctgacattct cctgctgtct agctctgagc ctaacagcct    34440
ctgctatgtg gaaacagcag aactggatgg gtaagtgtgt ctcgatgggc ctgatttaaa    34500
gctggccttt gaaggcacat tcattccact gaaatcgggg cattgtggac cagacggctt    34560
gatatctggc cttgcctctg ccacctgctg ctgtccctac tgatctcacc tttgcgcctc    34620
tgtgaagtgg agctcttact acctgcgttt ctccacctct cagggaaggt aaaaggatca    34680
gacaggagca tatgtgtctg agccctttat caactgctga gcagcgtcca gacagatatg    34740
aataatatcg aggttattat ctgtgtcaga gaaaggaaca gatttttaaa gtctttacca    34800
ataggcaatt tatttattta tttttgagac agagtctcac tctgtcgccc aggctggagt    34860
gtagtggtgc tatctcagct cactgcaacc tccacacccc ctgggttcaa acaattctcc    34920
tgcctcagcc tcttgagtaa ctgagattac aggctccagc cccacaccc agctaatttt    34980 tgcatttta gtagagatgg ggtttcacca tgttagccag gctggtctcg aactcctgat    35040
ctcaagtgat ctgcccacct tggcctgcca aattgctggg attacagggg tgagccacag    35100
cagctggccc caggaggcaa ttttgaattc tccttgtgtt ggttttggtt actatgctat    35160
catttaaaag agaatgaagt tctgtttttg accagttttc tgaccagttt tcaaggcatt    35220
tattgagtgc tcacgaggtt gccggcactt tacatattag ctcatttaat cctctaaacg    35280
accatgtgag acgaatatta ttcgtctgta ttacccatga ggaatcggag gcccaggag    35340 gtgcagcagc ccgcccaagg tcacacagta agtggtagag tcgggacatt gctccctctg    35400
ctcctcgcgc ctcacgctcc agatgtgcat acactgcttt acagagagcg gaaatcatga    35460
gactgaaaac tagggctgtc attgcttcat agatcaggca attgactgtt ggaaatctat    35520
cacacttttt ttttttttt ggcggaaaaa aatacttaaa gccaattaac cacttcttaa    35580
ttgtacaggc taattggtta aaaaccaatt aaccacttct taattgtaaa ggcttaactg    35640
acaaagacac tgcattctct ttaaggcccc gaggctatac ccaaattgga ttatgggcag    35700
ttgcctgata gagctttctg ttgtcaggtt ggtctcaaac tcctgacctc aagtgatctg    35760
cctgcctctg cctcccaaag tgctgccatt acatgcgtga gccgcggcgc ccgactgttt    35820
attctcaact ataaaactgc tattatttcc atgagagatt ctaaagcttt acaaagacat    35880
```

```
aagatcctaa catgccctgc cagaacagaa tggtgaggtt gagaatgaac ttccctaggg    35940
aaaattcctg agtattcgtg aatcctatat aaagccttca gtcgtgagac ggcagcctca    36000
cccttgagag cacctgcccc ggcctgccct tgtgcccacc cacgacctta ccttgcacta    36060
tggtggggca gttgggagta aagctaagac ttccttttcc aaataaaatt gtctttcaaa    36120
aacatgtgat ccagttattc actctggaaa agaatttgac agaggcgaaa cagaatttct    36180
gtaacaaata tgtgttatag aatcatttta atgtgattaa atattagaca ctacattttc    36240
aaacagcact ttggtagtcc tagctgatgg taaagttaaa gttaatgaga aggatgtttg    36300
tgggtacctc tgtcctaacc ttcacaacaa caaacagtga agggaaccaa catttcccaa    36360
ggtcagaaat tttctcgact tcaggggata accttttcca aacctgaagt tccaaggtga    36420
acagagtttg aaaatagaaa cagctaatta tttaggcttc atgtccaggt atggctaatg    36480
taactttgga tgattaactt ccactttgaa ctcaaaaatt tgttcattta attcattttt    36540
tccccattcc tttagagaaa ccaatttaaa atttaagatg tcacttgaaa tcacagacca    36600
gtacctccaa agagaagata cattggctac atttgatggt ttgtaccaaa catgtcttac    36660
tttgctttaa attttagttg cttggttcaa ttcctattga ttaaaaccag aaagactttt    36720
gtatgtgatt aattatgtga atcttatatt ttttaaaggt tttattgaat gtgaagaacc    36780
caataacaga ctagataagt ttacaggaac actattttgg agaaacacaa gttttccttt    36840
ggatgctgat aaaattttgt tacgtggctg tgtaattagg aacaccgatt tctgccacgg    36900
cttagtcatt tttgcaggta cgttcagagt ttcttgggaa attaatcagc tatgatcttt    36960
aaagacttag aggggattgc tttttctgtc ctttgtccatc aaaaccaaaa gaagagtaat    37020
agcatcatga gctttttttt ttttttttttt tttttttga cacagagtct cactctgtag    37080
cccaggctgg agtgcagtgg cataatctca gctcactgca acctctgtct cctgggttca    37140
agtgattctc ctgtctcagg ctccagagta gttgggatta taggcatgtg ccaccatgcc    37200
cagataattt ttgtattttt agtagagaca gggttttgcc atgttggcca ggctggcctc    37260 gaaccctga cctcaggtga tccgcccaac tcagcctcca aaactgctgg gattacaggc    37320
gtaagccacc atgcctggcc aagaagagta attttattgg tgagctagtg aattgatttt    37380
tcccaactga tgactacatt gaattttcca ttttcaggtg ctgacactaa aataatgaag    37440
aatagtggga aaaccagatt taaagaact aaaattgatt acttgatgaa ctacatggtt    37500
tacacggtat ttatttttca tctcagtaga tctctcatct agattgctgt cttttgcact    37560
aatattatcg tatgttttc taatacaaaa tcttacctct ttaggtggaa tagaaaaatt    37620
attgggcact ccaagcttca aatgcaggaa gaagggattt ttttttccag aaatgcctta    37680
ctttttctca gaaatgccac acttttaaca ggagaattcc cttgggaagg gaaatttcgg    37740
ttgtagggtg ccctgagtgc tttgatgacg ggaactggaa aaccaggaag ccctagataa    37800
attagtgaag ctggactcct gaagtcaatg tagggttgat ttcattgctg ttactttccc    37860
atagaggcag ttctcttaga agcaagcctc ccccagcacc cccaacatat actgtatagc    37920
tccaaataca aggcaaggct aaaaataaag tatgtcgagg acactcaaga ccactcccag    37980
gtttgatgat tcactggaag gactcatagg cctcagcaca tagtcgtatt cacagctgtg    38040
agtcattaca acaaaaggac acagagcaag atcaccaaag actcatggag caaagtgcaa    38100
aggaaaccag gcacaagctt ccaaaagtcg gccgtcctgc ccccactccc caccaaacca    38160
cacacacaat aggcacttaa ttctcccagc agcaattaat gacaccacat gtgaaatgtt    38220
```

```
gtctatacca gggaagctca tgagagactc agtgtcaaag gttttaaca aaaaaactct    38280 agactcccca aaagaatgca gatggtcagc ataaaccatg ctgtttgcac agttaggcat    38340
catgagtttt tttattatta ttattatttg tttttttttg agattgagtt tcactcttgt    38400
tgcccaggct ggagtacaat ggcatgatct tggctcactg caatctccgt ctcccaggtt    38460
caagtgattc tcctgcctca gcctcccaag tagctgggat tacaggcacc tgccaccaca    38520
cctggctaat ttttgtattt ttagtagaga cggggtttca ccatgttggc caggctggtc    38580
tcgaacccct gacctcaagt gatctgcctg cctcggcctc ccaaagtgct tggattacaa    38640
gcatgagcca ctgcacccgg cccatgagct attcttatca gagaataaaa ataactggg    38700 aaatcctcca aacatctaag ttaccagata ccagcccagg gcgaaccttg caagccggcc    38760
ttcggaggaa gcagtctcag acctgctatg tttgctcttt tctgcccacg tggtgacccc    38820
aaatattaag cactccttct atttcccaat gaaaaatttt ttcaagtatt taattcaatt    38880
tgaatgcata cttctaaaac ttattctttg attgcatata catgtttaaa atcacataaa    38940
aataataatt taagaaacat tttcccctgc tttctcattt catgaaaatt gtatttgaac    39000
ttttcacatt catctttggt gtcatggttg tggttatcca ctctcaaaga gcctgtttgg    39060
cactctgctc tttccacgac aaagttgtga gatatagcac ttttggactc catgtccaga    39120
aatttaaatt tgtctctgga aatttttattc ccacttgcga atctccaagt accactagga    39180
tggttgactt tttattcctt ccataaatat atgctcataa cttctacaac ataatactta    39240
tcatattgct tcttaagtga tcttatttta caatgtcatg caatacttat gacattacac    39300
cttaaggaat aatcgcccaa ataggtgaa attttcttg ccctgaaaaa aaaattctgg    39360
ctgggtgagg gccacctgta atcccagcag tttgggagac tgaggcatgc agatcacttg    39420
aggacaagag ttcgagacca gcctggccaa catggtgaaa ctcgtctcta ctaaaaagac    39480
aaaaattagc cggccttggt ggcgcgtgcc tgtaatccca gctactcagg aggctgaagc    39540
ataagaattg tttgaaccag ggaggtggag gttgtagtga gccacaatgg caccactgca    39600
ctccagcctg ggtgatacag tgagacgctg tctaaaaaaa aaaaaaaaaa aaaaaaaaaa    39660
aatctgttga atatcttcta taagcattcc agttttccag ttcagccttg ttggaagttg    39720
tttcatgcta agtaagatat cttccccaaa cagtatgtta ttgttcaaag taaacgtaat    39780
tgagagaatg ccctgtaata taagattctt caaggatttg aatataagac accaccttct    39840
ctttggagag ataattttgg gaacaaaacc ttaccttcta tgggagatgt aggatacatc    39900
agtcaattgc agcaatcaaa tagactttca aagcgttatg atagtgctgt ttttatttga    39960
catatattat ttttcagact actaaattct caatcatatg aagtattgag taaggttaat    40020
tagcatctag gaaatgcaag aggttggaaa tccatcttca gaatgcattt aaatgttttc    40080
tgtcttctag atctttgttg ttcttattct gctttctgct ggtcttgcca tcggccatgc    40140
ttattgggaa gcacaggtgg gcaattcctc ttggtacctc tatgatggag aagacgatac    40200
accctcctac cgtggattcc tcattttctg gggctatatc attgttctca acaccatggt    40260
acccatctct ctctatgtca ggtaaggctg tcctctctgg cattttgctt taatggaaga    40320
atgttgtacc ttctcccaac atagtgcctt catttctagt gatcactgtt tcaaaggtca    40380
caaagaacag gtaagaaaat cacgttcatt tcagaattga gggtaagaga ggaaaaggaa    40440 attaacatt gagtatccac tctgtgccag gcaccttta tctcatcctg tttgcagata    40500
agggtaggga atttcaaaga tcgattgcta ctcctgtagt cattgtctta ttagtaaggt    40560
tcccttctca ccgggttcca aagcccagac ttcagaaagg gactgggagg agggaagat    40620
```

```
ttagcaggtg atggaaaaac ttagttttcc cttttggaag tggtcctcac ctcttatctg    40680
agcctttatt atcatctgcc acacccaagg tggagaactt gtgctttccg gccactacct    40740
cctagtagga aagaaactcc ctgtccttca tcaacctctc aaaatgttct cttttttcatc   40800 tcaaatctca accacaacaa caaagtcagg ggcatatctc cgataagtgg taagcagctg    40860
atttggtgat acttcttcat tttttacttt tacttttttt tttttttttt ttgagatgga    40920
gtttcactct tgttgcccag gcaggaatgc aatggcatga tctaggctca ctgcaacctc    40980
tgcctcctgg atccaagcag ttctcctgcc tcagcctcct gagtagctgg gatcacgggt    41040
gcccatcacc atgtctggct actttttttgt attttttagta gagacaggtt tcaccaagtt   41100
ggccaggctg gtcttcaact cctgacctca ggtgatctgc ccacctcacc tcccaaagtg    41160
ctgggattac aggcatgagc caccacaccc ggccttttttc tcttttttaat atgaaagttc   41220 actgcccttg gccaaactga ctttgagacc ttttttgggag ggatagtgct ttggaataaa   41280
cccagcagcc agagttcatt cttagttctg ataaagaata gcccagagac ataggaatca    41340
catacacacc tataattaga ggcatttatt ttattttagt gtcattatat gtgcatttgc    41400 tttatttttta atttgattac atgtagttac tgttgttctt ttaacatgaa ggaaagccct   41460
ggggcagcca tctgttccac agctactttg agaaaaaccg agttgagtgt tacctttgtc    41520
aagggaacta ttacatagat aattttgcct aaaaccatca atgtgtatta taaaagaaac    41580
tgtatacata attttatata aaggtatgtc atgtgacaaa tacgatttct ttttcttgg     41640 agataaaggt cctttgaaaa catgctggag caagttcttc cagatagtat ctctgctttg    41700
acttcaaacc tcattcagaa taaacccaac cccagggccc caagtgtgat ctggtgctca    41760
gccttccact ccgcccgtac cttctgcacc tcagcccacc tccctgggct tctgccactc    41820
tggccccttg atattcttcc tgcacagggc ctttgtccct gctctttttct ctgccagggg   41880 cattccttac ataggtatct atctgctccc ctttcactac aaaggccttt actcagacaa    41940
caccttatta ccctgacctt tcctgactca ttctgtttct gaccacttct ccttcctgga    42000
gatcttcata tctccttacc ttgctttgct ttgattttttg tttgtttgtt tgttgtttgt   42060
ttgttttgtt ttgagacaga gtcttgctct gtttcccagg ctggagtgca gtcgcgcgat    42120
ctcagctcac tgcaacctcc acctgctggg ttcaagtgag tccctgcct cagcctcctt     42180 agtggctgga attacaagta catgccacta tgcctggcta attttttgtat ttttagtaga   42240 gacggggttt caccatgttg gtcaggctgg tcttgaactc ctgacctcat gatccgccca    42300
cctcggcctc ccaaagtgtt ggaattacag gcgtgagcca ccacacctgg ccccctgctt    42360
tgattttctg cagagaactt tcacctctga tagagcctct ctttattaat ttatttgtct    42420
gtctctacta gaaagtaacc tccttaagag aaaggacttt gttttgttta cagacatgtc    42480
ccctgcacct agaatggtat ctggtacata gtaggcactt aggaaatact tacgaaaggg    42540
agagaagtgg ggagagcatc attttttccat ctgttttaact tgttaaggac ttccttggcc   42600
cacctaacaa ttgctggcta tgtaaacagc ttccttataa ctgagatagg taatgtccct    42660
tatagtttta aaattcagat gatccttttta taatatctta ttttggatat tctataacct   42720
tatcataatt tagggatcat gatttggggt atttgccaaa agccttttgc cctgtttgag    42780
agcacagtgg agtctgtacc ctagggtact ctcactccct ctgccctacc acttagggca    42840
aaggtgaaca tggccattcc agtgcccctg ggtgctatgg ggaatggggg aagagtcaag    42900
cttgctgtgt ccactgctct gtctgcagtg ttgctgtgtc ttccattctg ctgggctgtg    42960
```

```
tattctgaac atgggtgcct tggctaaatg tgcccaggag tgagtgggaa atctcactga   43020
gcaattttga gtggaaatta cttgtctaaa atcagcttga ccctgaagcc tgagaatgat   43080
gcatgtggtt aggagaaacc agaggctgag tgcatgggct tgtctccttg tagagggctt   43140
agtttgggct gatataacaa agaccttcg aaatttattg ctcagagttc tggaggctgg   43200
gaagtctcaa atcaaagcat cggcagattc agggtctggc aaaggctcac tttctgcttt   43260
ataggcacag ccggtgcctt ctagctatgt cctcgcatgg cagaagggc aagcaagctc   43320 ctttgagcca cttttaataag ggcactaatc ccattcataa gggtggagcc ctcatgacct   43380
aatgaccttc taaaggcccc acctcaatac tgttgaattg gggattgggt ttcaacatat   43440
gaatttggag ggggattcta acattcagac catagcagta aataagcagc ttgctctcgt   43500
ctgtacaatg agaataaaat ctctactact tgccactcgt atccgagctc tctacgaaaa   43560
ataatcttct gtcttcctag cgtggaagtg attcgtcttg acagagtca cttcatcaac   43620 tgggacctgc aaatgtacta tgctgagaag gacacacccg caaagctag aaccaccaca   43680 ctcaatgaac agctcgggca gatccattat atcttctctg ataagacggg gacactcaca   43740
caaaatatca tgacctttaa aaagtgctgt atcaacgggc agatatatgg taagtggaag   43800
ccgtcactca ttttctgggt gagtggggct gcctgccgtg tgcaggtcat tacttggact   43860
atagcctgtc tcctggcatt gctggtgccc tctcgatgca gagtcctgct gctagggcca   43920
ttctccagct aagcaccaga ggagcaccat ggacagcact ggggacacat gcgtgggaga   43980
ggacagtggc cagaagtggg ctcacagcca ggcgtggtgg ctcaggcctg taatcccagc   44040
actttgggag ggtgaagtgg gcagatccca agaggtcagg gatttgagac cagccttgcc   44100
aacatggcaa accccgtctc tactaataa tacaaaaatt aaccaggtgt ggtggtggcg   44160
cacagctata atcccagcta ctcgggagac tgaggcagga gaattgcttg aacccgggag   44220
gcagaggttg cagtgagctg agatcacacc actgcactcc agcctggtga gagagcaaga   44280
ctctgtctaa aaaaaaaaaa aaaaaaaaa aaaattagaa gtctcattac tatatgatct   44340
agcaattcca cttcaggtta tatactcaaa agaactgaaa cagggctca agagatatt   44400 tgtacaccta tgttcatagc agcattattc acaatagcca aaagatagaa gcaacccaag   44460
cgttcatcaa tggatgaatg gataaataaa atgtggatac gcacaatgaa atattattca   44520
gtctaagaaa ggaaggaaaa tttgacacat gctacaacac agatgaacct gaactcgttt   44580
atgccagagg ttgcaatttt ttgaattttt gcaatcagaa cttggtgatg accttgagca   44640
gtaggatata aataactccc acatgcttag cgttccaata atggaacact aggcataaat   44700
gggttaagga cattatgcta agtgaagtaa gccagtcaca aaaggacaaa tgttgtataa   44760
ttctacttat atgaagtact tagaataatc agatttatag agacaaagca gaatgatggt   44820
taccaggggc tggagtcagg ggaattggga gttactgttt aatgggtaca gagtttcaat   44880
tttgcaagat gaaacagctg cacaacagtg tgaatatact tgatgccact gaactgtatg   44940
cttaaaagtg gttaaaatgg gctgggtgca gtgtctcatg cctataataa caacactttg   45000
ggaggtcaag gtgggaggat tgcttgaggc ccagaattct agaccagctt gggtaacaaa   45060
gcaaaaattt ttaaaaatta gcagagtatg tgctgcatg cctatagttc cagctacttg   45120
ggagactgag gcaggaagat cccttaagcc tgggagttga aggctacagt gagccaagat   45180
cacaccacag cactccagca tggctaacag agcaagaccc tgtctcaaaa tagcaacaac   45240 aaaaaattggt tgactggtgt gcagtggctc acgcctgcaa tcccagcacc ttgggaggct   45300
gagtcaggca catcccttga gcccaggact ttgagaccag cctgggcaac atgacaaaac   45360
```

```
cccatctctg gccgggcaca gtggctcatg cctgtaatcc cagcactctg ggaggcctac    45420
gtgggtggat cacaagctca ggagttcgag accagcctgg ccaatatgat gaaacccat     45480 ctctactaaa agtacaaaaa ttacctgggc gtggtggtgg atgcctctag tcccagctat    45540
tcaggaggct gaggcaggag aatcgcttga acccgggagg tggaggttgc agtgagcaaa    45600
attgtgtgtg cctgtagttc cagttacttg agaggctgag gtaggatcac ctgagcctgg    45660
gtacgtcgag gctgttgtgg gctgggtttg caccactgca ctccagcctg ggtgacagag    45720
tgaaaccctg actcaaaaaa atcaaacaaa aaatcggtta atatggtaaa ttttattatg    45780
tgtatttcac tacaattgtt tgttttcttt gttgttttg ttttgagac agtgtctcac      45840 tctgtcacca ggctggagtg cagtggtgcg atctcagctc actgcaaccc ctccgcctcc    45900
caggttcaca tgattctcct ccctcagctt cctgggtagc tgggattaca ggcacacacc    45960
accatgcctg gctaattttt gttgttgttg ttgttgcttt tttgtagaga tggggtttca    46020
ccatgttgac cagactggta tcgaacccct gacctcaagt gatccatctg cctcagcctc    46080
ccaaagtgct ggggttacag gcgtgagcca ccacacccgg cctacaattg tgttttttggt   46140 tttgttttg ttttttgag acagagtctc actctgtcgc ccaggctgga gtgcagtggc      46200
acgatcttgg ctcactgaaa cctccacctt ccggggttcaa gtgattcttc tgcctcagcc   46260
tcccgagtag ctgggactac aggtatgaac caccattccc agctaatttt gtattttaa     46320 tagagatgga gtttcaccat gctagccaag ctggtcttga actcctgacc tcaggtgatc    46380
agcccatctc agcctcccaa agtgctggga ttacaggtgt gagccaccac acccagccaa    46440 ttgtttttaaa agttgatttc agttctaatt ttctgaaaca tttagaaatt taattttatg   46500
taaatttaga gataatatta aggctaatac tagattcaaa tagagtgcta ttttaaatat    46560
acttaatagc acaattgttt aaaatgatat agggacatgc atatatactt cctacttgta    46620
ggcaccgtga gtgccttttc tcataagaag tatcagtgaa gatggtaggg cactgagggg    46680
ctgaggacgt ggctcacata tgtgagtcct tctgacttgg gagaggtaaa gcatttcaaa    46740
ggatatgatt caggccccta ggagaaggta gtggagaggg acagccactg gtatttgaat    46800
atctagacca ggggtcatct aacgttttct gtaaagtgcc agataataaa tatttttagcc   46860 tgtccaggcc gtatatggtc ttaccaccat cactatataa gcaaagccag gtaaggaggg    46920
gcctctggac ataggtgtag aatcaatttg ttttgtcctg tttgtttctc aggggaccat    46980
cgggatgcct ctcaacacaa ccacaacaaa atagaggtaa gacctttaag ccgaagaatc    47040
gtttgggatg ctggggatgt cagggtccca gcagggccat gcttcctttg aaggtctagg    47100
gaagactctt tcgttgcctc ttccctgctc ctggtggttg cccacagtcc ttggtgttcc    47160
ttggcttgga gacttggaaa cacaactctg tgtctctgcc tttgttgtca cgtggtgtcc    47220
cccgtgtgtc tgtgtgtctc tgtccacatt tccccttcta ataaggatac caatcattgg    47280
attaggacct accctaattg agtatgacct cattttatct tgattacatc tgtaaagacc    47340
ctgtttctaa ataaggtcac attcataggt accagaggtt agaatttcaa catatctttt    47400
gggggaacat agtttagtcc accacaaagt acctttttgac taggcatggt ggctcatgcc    47460
tgtaatccca gcactttggg aggctaagtt tggcagatca attgagtcaa ggagtttgag    47520
accagagaaa ccccatctct acaaaaaaat acaaaaatta gccaggtatg gtggtgcatg    47580
cccgtaggcc catctactca gaaggattgc ttgagcccag gaggtggagg ttgcagagaa    47640
ctgagatcaa gccactgcac tccagcccgg gtgacagagt gagacccata tatggtcata   47700
```

```
tatgtttcca aaaaaaaaaa gggggggagc tttttatttta agacagttgt gagcctcttg   47760
acatttaaga atgtgctaaa atcctaaggt ggttttttgca taattgaaac cttgcctttg   47820
aagaaaagtt catgtcattt gttaagtcaa aatatttta taaaatcata tttgttttt     47880 ctccatttct ttcagcaagt tgattttagc tggaatacat atgctgatgg gaagcttgca   47940
ttttatgacc actatcttat tgagcaaatc cagtcaggga aagagccaga agtacgacag   48000
ttcttcttct tgctcgcagt ttgccacaca gtcatggtgg ataggactga tggtgagtgt   48060
ttctctggca tctcaggcat tagagaccag gttttttgtt tccaggtaac tcctgcttat   48120
ggctcaaatg catgtcaagt agtacacaaa tctgtctcat attagaatgc agtgaatatt   48180
tctcagcact taccactaga tggtttatgg aagagcaaag taggaaacaa gcttcttgtc   48240
cctgaaaatt tacacttatt catagctata gctccaggtg tatttttttc actttgcaaa   48300
tgaaatcttg ttgaaagaaa tgattggtac ttgaactatg atagaagaaa ctaacttttc   48360
ttagcacatt tattactgag cattgactga gagtgaaaag tcaagcttta tctgtatcag   48420
aaatggactt tgaacttgac taatcttttc taccaaataa tttcagatat atgctcttat   48480
ttactagatt ctgttatagt ttgggtttga ataatatga gcctcagcct ggatctcttt     48540
aaggtgcctt tttccatttta aaggagcata attaatgtga atttcatggg aacaagccag   48600
aatggcttgt aggttccttt gcagaatcct tcgatgcagt ttgtgccagc tttgtcacag   48660
caagtttgtc ctgtatcaag gaaagctagt cattttatca caaatggaca taatgataaa   48720
ttatatagac acacatgcac tttatagaaa gagcaaaagg agttcttttg gtgtttctgt   48780
aataaagcgt agtctgcctt cacttcattc cctcacttca tccacttcac tacatcttcc   48840 acttttact tcagtcagtg cggcatacat aagtccctct cttttctcaa ccttaatgtt    48900
tcatatgtag caggtatgaa atttccagag aaggaatatg cataaaaact aaatgtgtag   48960
gccaacgctt ggtggctcac acctgtaatc ccagcatttg gaaggtcgag gtgaatggat   49020
tgcttgagct caagagttca agaccagcct gagcaacatg gcaaaactcc atctcaccaa   49080
aaaatacaaa aaattagcca ggtgtgatgg gacatgcctg tagtcccagc tactcaggtg   49140
gggatcgctt gagcccagga ggtcaaggct gcagtgagcc atagtctcac cattaccctc   49200
cagcttcggt gatggagtga gaccctatct caaaaaaaaa caaaaaacac ctaaatgtat   49260
agaagctgta catgatacct ttcagcaagt ttcaaagaaa cccatttttcc aaggatgaat  49320 ctaatattgc aatgaagcaa ggtaacagag ttcagattag ggtggataca tggaagggtt   49380
tatcagcaga tgatgtgggg aaggatagaa aggggcgata ccaggtcctg aatcatggaa   49440
gcagaggtct aagtctattt gactcaccaa gccaatttta cccaggcaat aagcataaag   49500
tatgatatta caaagtcacc tggttctctt tggttttgac tcataagcac aattattgta   49560
ctcttctctg ggtacgtgat aggattttaa gggctaactg gccaacttag gcaaatgtaa   49620
attcatcctg tggtccctat tctatctttc cccagtggga tattatggga agagccctgg   49680
actacatgct agagatgagt cagcccagtc tgggtccctc tctgagaacc accttcctcg   49740
gtgttgtagt aagaaggttg gatgtacaaa gttccttcca gcagggctgg gcgcggtggc   49800
ttacacctgt aatcccagca ctttgggagg ccgaggcggg cagatcatga ggtcaggagt   49860
tcaaaaccag cctggccaac atggtgaaac cccatctcta ctaaaaatac aaaacattag   49920
ccaagcatgg tggcatgtgc ctataatccc agctacttgg gaggctgaga caggagaatc   49980
gcttgaacct ggcaggcaga ggttgcagtg agccaagatc acgccactgc actacagcct   50040
gggcaacagt gcaagactcc atctcaaaaa aaaaaaaaaa taacacaaag tccctccagc   50100
```

-continued

```
ctgacatacc gcagctcttt gtccactgtc agctgaggtc aagggttgta cgaatagaga   50160
catgttggct tctagtgcag gagcttagag aaagaaattg ctttcggctt ttaaccataa   50220
agtaccagga aaggatccct tgaaagggac cttggggact acaccttcaa gttttgtttt   50280 gtgttttga dacagtcttg ctcttgtcac ccaggctgga gtgcaatggc atgatctcgg   50340
ctcactgcaa cctccacctc ccaggttcaa gcaattctcg tgcctcagcc tcctgagtag   50400
ctgggactac aggggcccac caccacgccc agctaatttt tgtatttta gtagagatgg   50460 ggcttcacca tgttggccag gctggtctcc aactcctgat ttcaggtgat ctgcccacct   50520
caacctccca aagtgctggg attacacgcg tgagccacca caccctgcca catgcatttg   50580
ttttctgcta ctctgtagtg aattagtgta actcagctac tgaaaacacc tgttcattag   50640
cttacggttc tgtagggcag aattctgagc atggcatgac tgggttcacc gctcagcatc   50700
tgactaaaat caagtttggg ccatgttctc atctggagct cagtgtcttt ttccacgttc   50760
acgtgtggtt gcagcaggat tcagttctct gtggttgtag aactgaagtc cccatttctt   50820
tattctttat caactgggtt gccctccact cctagagact gtcctcattc cctgccagct   50880
ggtccacttc accttcaaag ccagcggtgg agaatctccc ttaaattgaa cctttttcat   50940
gctgctccaa gtctctcccc aagaagagtt ctgtcctaag ctcatctaat tcagtcagga   51000
acacctggat aatctatttt aaggtcagct gattaggatc gcacatctgc aaattccctt   51060
cacagcagta cctagattag tgcttgattg agtaaatggg agaaagtgaa tgtacagcac   51120
tgggatggga accttgaggc cattgcagac tcccgcctgc acagaggtca tgtgagagca   51180
gaatgtggaa ggcttggaag ccttcacttc acctggaggt tctgagttaa tgatcagaga   51240
gcttgtttca ggagttttgc gcatcacggg tgtgagagtc tggagcaggt aggcactgga   51300
gattggcaca gaggctgaag gtttgcatta gtatgggtc tttgggaagg ataacaaagc   51360 catgatgtg ggagacactt ggcaaatcat ttaaggggg tgagaggatt gaggagaaaa   51420
agacatctga gagctagggc ttgttttgt gagcgtgtgt ggttttttt ttgttttgtt   51480 ttgttttgtt ttgttttgtt tttgagacca agtttcactc ttattgccca ggctggagtg   51540
caatggcatg atctcggctc actgcaacct ccgtctcccg ggtttaatca attctcctgc   51600
ctcagcctcc gagtagctgg gattacaggc atgcccacc acaccagct aattttgcat   51660 ttttaataga gatgggtttt ctccatgttg gtcaggctgg tcttaaactc ccgacctcaa   51720
gtaatcctcc agccttgacc tcccaaaggt gctgggatta caggtgtgag ccaccacacc   51780
cagtcttttt tttttttttt tttttttttt gagactgagt ctcgctcctg ttgcccaggt   51840
tggagtacag tgccgcaatc ttggctcact gcaacctctg cctcccaggt tcaggtgatt   51900
ctcctgcctc agcctcccga gtagctggga ttacaggcgc ccacaccaaa ccctggctaa   51960 cttttttgtat tttagtaga gatggagttt tgccatgttg gccaggcttg tcttgaactc   52020
ctaacctcag gtgatccacc cgcctcagcc tcccaaagca ctgggattac aggtgtgagc   52080
caccatgcct ggccaggtag tttattgtca cttaattaga gtgagccggg tgcagtgatt   52140
cacgcctgta atcccagcac tttgggagtc tgaggtaggc ggatcacctg aggtcaggag   52200
ttcaagacca gcctgaccaa tattgtgaaa ccccacctct actaaacata caaaaattag   52260
ctgggcgtgg tggcgggcac ctgtagtccc agctacttgg gaggctgaga caggagaatt   52320
gcttgaaccc gcgaggcgga ggttgctgtg agccgagatt tgccactgc gctccagcct   52380 gggcgacaaa gtgagactcc atctcaaaaa gaaattagag tgaatcagct gaggcagttg   52440
```

```
tgaaggagag aagaaaggtg catttagctt tctctgccac cattaccctg aagctaggga    52500
atcaggttga tgagaactga gaggtgggat ttgtggtttg agcatctttc tttgattaca    52560
tcaatttcat gagccacaaa ttagtgtgtg aaagaaaaag aaggtctttc tggttgcctc    52620
taaatgtgcc ataaataaag agttttctta ggaaggttgc tttgtttttg tttgttttt     52680 tagtttgttt ttacaccttc aatttttatt ttaggttcag gggatacatg tgcatgtttg    52740
ttacatgggt atattgcatg atcctgaagt ttggggtaca attgatccca tcatccaggt    52800
agtgaacaca gaacttaata gttagttttt cttttctttt ttattctttt tttttttga    52860 gacagagtct tgctctgttg cccaggctgg agagcagtgg cgcgatctcg gctcactgca    52920
agctctgcct cccgggttca tgcattctcc tgcctcagcc tcccaagtag ctgggactac    52980
aggcacccgc caccatgcct ggctaatttt ttttgtattt ttagtagaga cagggtttca    53040
ccatgttagc caggacgaaa ggtcagcctg ctgcgttggc tgggaattga agtcgggtca    53100
attgcttgga aggcagctat gctcaccact ataccatcaa caccacactc ttttcttttc    53160
tcttcttttt tttttttttt gagatagaat ctcgaactat cgcctgggct ggagtgcaat    53220
ggtgtgatct cggttcactg caacctctgc ctcccgggtt tatgcgattc tcctgcctca    53280
gcctcccaag tagctgggac tacaggcacc cgccaccatg cctggctaat tttttttgta    53340
tttttagtag acagggtt tcaccatgtt agccaggaca aaaggtcagc ctgctgcatt     53400
ggctgggaat cgaagtcggg tcaattgctt ggaaggcagc tatgctcacc actataccat    53460
caacaccaca ctcttttctt ttctcttctt tttttttttt tgagatagaa tctcgaacta    53520
tcgcctgggc tggagtgcaa tggtgtgatc tcggttcact gcaacctctg cctcccgggt    53580
ttatgcgatt ctcctgcctc agcctcccaa gtagctggga ttacaggtgc ataccaccac    53640
acgtggctaa ttttttacat ttttagtaga cgggtttt cactatgttg gccaggccgg      53700
tctcaaactc ctgaccttgt gatccacccg cctcagcctc ccaaagtgct gggattacag    53760
gtgtgagcca ccgtgccctg ccctaatagt aagttttcca cacttgttg ccctccctcc     53820 ctcctttctc ttgaagtccc cactatctat ttttgcagtc tttatgtcca tgagtaccca    53880
atgttaagtg agaacatgtg gtaggtatgt ggtcttctgt tcctgagtta atttgcttag    53940
gataatggcc taatctctat tgtgacaaag gacatgattt tgttccttt tatggctgca     54000 tagtttttta gtccaagtgt cttccagcag tcataaggtt ggaatttgga ccaagtcact    54060
gacgttcttc ccatctctgt tagtctgcaa ttctgtgatt ccattatcag aaggtaatgg    54120
aaaacatttt ttttctttta atgataaaaa tatcaaggtt tttgctctag atatgagtgt    54180
cttacttgtg ggaactttac cactttttat tatttttgttc cttttctctg ctggaaatgc   54240
gtttgctgtc aatattatgc catatatcgc tgtgccaact taagttgccg aagggaaagg    54300
ctttgttctc accgctgctg atttgtctct ggttaaatag tttgccctct agcatttgta    54360
tatgattgct agatggccgg attttaggaag tgcgtttata gcttctagtg aatgactttc    54420
tgagtgaaca aatacagaga gaccctaagt gtcatctta attattaatt aggaagtgat    54480
taatattgac ttaaaagtg aatcctctga gccaattgtg aaggaaggaa ggaaggtgtg     54540
tttagctctc tctgccaccg ttaccccaga gcaccaacca ttccaagtga ggctgctcat    54600
gcatctgtgg ccttcatcct ggtcaaagta ttttggaaaa ctaaatgctc tttctgtcca    54660
aagtcatctg gccacggaaa tgcttttcct tctatttga gacaaaataa ctagagtaga    54720
aaaatagaag atcttgggta ggcagagtat tttttaaact ttttattgaa gtacaacatg    54780
tgtatacaga gatatgtacg tatcataagt atataactca atgaattttc acaaaccaat    54840
```

```
actcttgtaa tgagcaccca gattttaaa aagaacatt atcaatcccc ctagaattcc      54900
ctttacattc ctttccagtg attacaagaa aagtactttc ctgactacga ataacacagg      54960
ttagctctgt cagttttttg cttatttca gtggaatcat gtagcatatg tactcttttg      55020
tgtatctggc tgtgagattt attcctcttc ttattggttt tttctttttt cctaaaagag      55080
actgcatctt gctctgtcag ccaggctgga gtgcagtgga atatcaaagc tcactgtaac      55140
ctcacactcc tgggctcaag tgatcctcct gcctcagcct cctgaatagt tgcaattata      55200
ggcacgtgcc actgaaccta gcttattctt attgttgaaa tgtagttgtg aatagaagac      55260
aattttccat tatttaactt ttaaacatta agatatcgga tagtgatcaa actaaggttg      55320
gttggtttgt ttcaactttt ctttctttct tttttttttt tttttttttt gaaatggagt      55380
ctcggtctgt caccagggtg gagtgcagtg gcgagatctc ggctcactgc aacctccacc      55440
ttctgggttc aagtgattct cctgcctcag cctcccgagt agctggaact ataggcacgt      55500
gccaccatgc ctggctaatt ttctgtgttt ttagtagaga cagagtttca ctgtgttagc      55560
caggatggtc tccatctcct gacctcatga tctacctgcc tcagcctccc aaattgctgg      55620
gattacaggc gtgagccact gcacccagcc tgtgtggttt ttttttcttt tttttttttaa      55680 taaggagaat atagctatgg taaagaaaaa atagcctggg caacatggtg agatcctgtc      55740
tctacaaaaa atacaaacat tagctgggcg tggtgatgtg cgcctatagt cccaactact      55800
caggaagctg aggtgggagg atcacttgcg cctgaagcga tcaaggctgc agtgagctga      55860
gatggtgcca ctgcactcca gccttggtgc cagagtaaga ctgtctcaaa aaacaaaaa      55920 agaaagaaag aaagaaaaca tactttttta gagggaagat aaactggtac aaccttcttg      55980
gaaaacaaat tagtattgta taccaatgag ttttaaaatt atcagtgttc tctggctcag      56040
tattttccta ataggaatct gctcttagaa aataagccag gggcccaggg gcagtggctc      56100
atgcctgtaa tccgaacact ttagggactg aggcaggcga atcacttgag tccaggagtt      56160
tgagaccagc ctgagcaaca tggtgaaacc ccgtctctac aaaaaataca aaaaattagc      56220
caggtgtggt ggcgtgtacc agtaatccca gctacatggg aagatgaggt aggaggatca      56280
ctgagcctgg ggagattgag gcttcagtga gccatgatcg tgccactgca ctgcaacctg      56340
ggcaacacgg tgagaccctg tttcagaaaa acaagaaaga aagagaataa gccaggtgag      56400
gtgacatgag cctgtagccc tagcgactca ttaggctgag gcagaaggat cacttgggcc      56460
ccggagatca agagcagcct ggacaacata gggagacctc tgtctctaaa aagaaaaag      56520 aaacagaaaa atctttacac acatacaaaa gggttattaa agtgtgactt tttgagagta      56580 aaaaatttg gaaattaagt gtctgtaatg ggaaaatgat aacatattta catttgttca      56640
aatgtttata aagaatttaa aaagggatgg caatatgctc agatacagca ttaaaataat      56700
caggatgtaa atgtatattc agcttgatag aaacaatttc agatacagac attttaaaag      56760
gcactggagg gaatgataaa atgtcaacac ctgttgtttc tcctgtggat ggtgggatta      56820
tgggaatttt ccctcattct ccaccaatgt ttctttttta gtttatatta ctgtttataa      56880
gtcaagataa aacaaagaag ttttaatctt ggcataaccc ttccaagtca atgactcgtt      56940
ttcctgggga tgttttgggc tttgcagccc atctgacccc cacaggagcc tcagcagagg      57000
cctcaacaat gagctctgca tttgttttta cagcttttct gggatttctc tcgcttcctt      57060
gttaggtcag ctcaactacc aggcagcctc tcccgatgaa ggtgccctgg taaacgctgc      57120
caggaacttt ggctttgcct tcctcgccag gacccagaac accatcacca tcagtgaact      57180
```

```
gggcactgaa aggacttaca atgttcttgc cattttggac ttcaacagtg accggaagcg   57240
aatgtctatc attggtaagt cccccctcaga gtctgtctat gaatcgctca tttagatgtt   57300
gcttgtgccc attgtattga gtggcatcag gataaagcag ccagtgaaag agctacttgg   57360
ctcctgggag atttctgcag ctttactgaa actggtattg ttggctgggc gtggtggctc   57420
acgcctgtaa tcccagcact tgggaggcc gaggcgggtg gatcacgagg tcaggagatc   57480
gagaccatcc tggctaacac ggtgaaaccc cgtctctact aaaaatacaa aaaaattag   57540
ccgggcgtgg tggctggcac ctgtagtccc agccactcgg gaggctgaga caggagaatg   57600
gcgtgaaccc gggaggcaga gcttgcagtg agccgacatc gcgccactgc attccagcct   57660
gggcgataaa gcaagactcc gtctcaaaaa aaaaaaaaa agaaactggt attgttttct   57720
tcattcttca ctgtgttccc tactcaaagg ggtagccaca gtatctctga atcttgcaaa   57780
tgctgctgac gttctttttt aatccctctc tttttttct tttcttttct tttttttttt   57840
tttttttgaga tggagtcttg ctccgtcacc caggagtgca gtggtgcgat ctcaggtcac   57900
tgcaacctcc gcctcccagg ttcaagcgag tctcctgcct cagcctcctg agtagctggg   57960
attacagctg ctgacattct ttaaccacgt gggctgccag atgctgaatc tggggcagca   58020
ggtggaacat ttctgaagca gcaggtagac atttgtagca gtcttttatt ttaaacaaca   58080
catgctcttt tattttttga gcacctctga gtgctctctt ctgtacttga tggcaggaa   58140
gggaggactc agcaggaaaa gatttctgag aaaagcaaag ctatgcttat gaatcaaaat   58200
catatctgca atgcaggcac ataacagacc accaagtgaa gatgaaaatc acttcctacc   58260
actgaactgc tttaaattcg taatttgaaa taatctcaaa cttatagaaa agttacaaga   58320
atggtttaaa gagccctcat actcttccat atccaccaat tgttaacata atgaaatttc   58380
atttacatat ctctatatat agatctaata tatatctaat tatatatatg taatttcatt   58440
atatatacct atatatatac acacatatat atgtacacac acatacatac aggttattgt   58500
tttctgaacc atttgagagt aaattgcgtt agaaggagca agattacatg ataaaaaaag   58560
aaaataaaaa tataaaaaag agaataaatt gcaggcctaa tgtcccttc ccctaaaатac   58620
tgtactatat accatagtag gtatttccta agaacagaag cactcactta tatatacagt   58680
gcaatgttca gaaccagaaa atttaacaca gtacaatatt atctaatcaa tagactttat   58740
cagattttac cagggaggtt cattctttgt ttttctggtc caggatccaa tctaagatca   58800
caggttatat taggtgatca tgactctgag tcaaggacgg ttcaatctct ttttgatctt   58860
tcatccattg atatttttaa aaagcacagg ctggttattt taggctat ccctccattt   58920
gcgtttgtct gatgttccct catgattaga gctaggttac acattgttgg caggaagagt   58980
ccgtaagtga tgctgtgctt ttctttaagt atcacatcag aaggtgtata cacacacaca   59040
catttatatt tatatatata tacatatatt tatatatgta tatttatata tacatgtatt   59100
tatatatgtg tgtatatatg tagatatatg tatgtatata tgtgtatata catgttatat   59160
atatatatat atatatatat atatatatat atatatatat acttttttt tttttttttt   59220
tgagacagag tttcactctt gctgcccagg ctgaagtgca atggtgctat ctcggctcac   59280
tgcaacctct acctccctgg ttcaagtgat tctcctgcct cagccttctg agtagctggg   59340
attacaggca tgtgccacca tgcctggtta attttgtatt tttagtagaa acaaggtttc   59400
tccatgttgg tcaggctggt ctccaactgc cgacctcagg tgactggccc gccttggcct   59460
cccagagtgc tgggattaca ggcgtgagcc accctgccta gccagaaggt atatattatt   59520
ggtttgtctc attaatgggg atgttaactt tgatcacttg gttaaggtgg tatctacaag   59580
```

```
ccttctccac tatgattgaa ttttttaacca ataaaaatat acaggtttaa ctattacacc    59640
ctccttaggc acacttactg aacgcttttct gtgtcccctta cacagatcta gactgattat    59700
catgcttgcc atctaccttg atttaaaatc tggttaacag tgagggatgt attacaatta    59760
ttgcattaat caaaaaaccc aaaaaaaatg gtcattagga gtggtgttgt ggtcgaagta    59820
ttaaaagcag taagtgttgt gagttcatag gtgagaaact acctgttggt tggatggaga    59880
aaaagtctac aaaagaaagt aactagaaca tggcatagca catggtaggg agtcagtaaa    59940
tatttgttgg aagaataact gaggttataa aaaacagagc tgactgtgaa ggaatctttt    60000
tatatttatt tcactattac attcaatgta gataatgact taccagtttt gttgaaggca    60060 acactttttct agaggaactg atggttttaa gctaacagtg aattatgaga tagtaacatt    60120
tcaaattaac tttataaatg tagttttcta ttaaaaaatc aaacttagct gggtgtggta    60180
actcacatct gtaatcccag catttttggga ggctgaggca ggaggattgc ttgagcccag    60240
gagttcaaga ccagcctggg taacatagtg agacctccaa tgtctataaa aataaaaatt    60300
agccaggcat ggtggcatgc acctgtagtc ccagctactc gggaggctga gatgggagga    60360
ttgcttgagc ctgggggggtc gaggctacag tgagccgata ctgaactgct gcactccagc    60420
ctggacaaca gagcaagacc ctgtctcaaa aaatatatat ataaaaaatc aaactttgtt    60480
gtgtttattt ccttcttttta ctaccagtaa gaacccccaga aggcaatatc aagctttact    60540
gtaaaggtgc tgacactgtt atttatgaac ggttacatcg aatgaatcct actaagcaag    60600
aaacacagga tgccctggat gtaagtttca ctttttattct ttctgcaagg gattctgaac    60660
ttactctctg atgctgtctg ttaagtttgc atgaaagctg tatgttaact gctgaccctc    60720
cctttgcttt gcaatagttg gggtggaaag agcagtaaag taggaataca gccacctggg    60780
tcccagttct gcccctgcca ctgacttcct gggatatcac catggtgccc tctcccagca    60840
tgtgggtctt caaggtctat aggactgagg caggggaatg gcttagctct cttccagtgg    60900
ccttgagcaa gctacataac catactaggt tgtagtctta ctatgtgtgt ggtccccaag    60960
acctccacta acttcaagtt gtagtgcaaa ggaaggaaag cattcatatg tgacaggatg    61020
acagagctga ctataggtca catcttgtct agccaagatg gcagaagcgg ttcaactgat    61080
tgagtatttg gtgtctcatg cctgtagtcc cagcactttg ggaggccaag gcgggtgtat    61140
cacctgaggt caggagttca agaccagcct ggccaacgtg gtgaaacccc gtctccacta    61200
aaaatacaaa aaaattaact gggtgtggtg gtgggcacct gtaatcccag ctacttggga    61260
agctgaggca ggagaatcgc ttgaaccccca gagggagggg gtagagtgag ccgagatcgt    61320
accattgcac tccagcctgg gcgacaagag caaaacttgg tcaaaataaa aaagatgtga    61380
ctataaagta atgagatgtt tactggttca tgttgaaact gtttaaaatg tttaaatcag    61440
gctgggtgca gtagctcacg cctgtaatcc cagtactttg ggaggtgag gtggcagatc    61500 acgaggttaa cagatcgaga ccatcctggc caacatggtg aaaccccgtc tctaccaaaa    61560
atacaaagat tagccagatg cagtggcacc cgcctgtaat cccagctact caggaggctg    61620
aggcaggaga atggcgtgaa ccagggaggc agaggttgca gtgaaccgag atcgcaccac    61680
tgcactcaag cctgggcgat agagtgagac ttcatctcaa aaaaaaaaaa aagaaaaaga    61740 aaagaaaaa aaaagaaaat gtttgaatcg ttcatcatgg gaaaattgcc agatactctt    61800
ttccattaaa agctttgacc tcagctttaa caatggcttg tgtatttag aattggtttg    61860 agggaataat gcttagtgga gagttcatag gtgattggac ttgtatcaca gtttgttgga    61920
```

```
acaagttata aagttgtcag gttcgtgctt atgtcattac accccaaggc agctcccttg   61980
gtctgatatt ttcctagtca tgaagagaaa aagagaaaat gagaaaatga aaaggtaat    62040 agaagattta gaagaaggt aagcttttcc ctttggaaac tggaagtgca gtcctggacc    62100
ctatagaagt ttagaaaagc aaagtctatt ataaagtgat gtttaggctg ggtgcagtgg   62160
ctcatgcctg taatcccagc acgctgggag gctgagttgg gcagatcaca tgagctcgtg   62220
agttcaagac cagcatgatg aaaccccatc tctacaaaaa aaagtacaaa aattaccagg   62280
cgtggtggtg cacacctgta gtcccagcta cttgggaggc tgaggtgaga ggatggcttc   62340
agcctggaag gcagaggttg cagtgagccg ggattgcatc actgcatccc agcctggatg   62400
ataaagccag accttgtctc aaaaaaaaaa aaagtgacat ttaatcccct ctctaaagtg   62460
tatttgtaca gaatctgtca tgtttaatga tctcttttta aattctgtta gtatattact   62520
tcaaagtaaa atttcagact tgatcctgaa ttacataaat taactattct ttgcattggt   62580
ggatttattt ttttaaataa aacagatctt tgcaaatgaa actcttagaa ccctatgcct   62640
ttgctacaag gaaattgaag aaaaagaatt tacagaatgg aataaaaagt ttatggctgc   62700
cagtgtggcc tccaccaacc gggacgaagc tctggataaa gtatatgagg agattgaaaa   62760
agacttaatt gtgagtttta gccttaataa cttttctttt gatattctaa gcagaattga   62820
aatttttatt aagttttatt gaatatttga tctcatgctt aagagataat tgtaacttca   62880
gcatttgaca ctggcacaat ggaagaaggt tatttctttt attcaccaaa ataggagcag   62940
aacagaagtt gccattatga gaaaccaaaa gacaaaatac attaggagaa gttctaatttt  63000 aattccataa tttgtatatc acttattaaa atttattata attttaaac aataacaaac    63060 ctgcatctaa tacttattac attgggggaa ttaccgaaac aattcatatt ctgcaaaatc    63120
ttgaaataag aaaaatatat tgtttctaaa agttttccaa atttaataca tagttttttgt   63180 agggtttaga taagtggaaa atattcaaca aatagctagt attgcaactg gtttacggtt    63240
tatgtcagta taaagccaca aatacacaag aaaagtgtat ttttaacatc cttgattttg    63300
tacttgcatt tttgtcttgg taaattaaat agttcatcct ttagggaaaa agttttttagg  63360 tgtgttggtt tgcagtaatt gtgaaacatg gcagccttcc ctgttaacac tggccattgg    63420
ccccaggaga gcagcaacca ggatgtataa ttagccccttc ttttttacagg ttggcaacct   63480 gtaattacag aaaacttttg gtttgtttgc taattccttt tttttttttt tttaatatac     63540
attctagctc ctgggagcta cagctattga agacaagcta caggatggag ttccagaaac    63600
catttcaaaa cttgcaaaag ctgacattaa gatctgggtg cttactggag acaaaaaggg    63660
taattcattg tgcagggaag catatctgtt aattcacaaa tatttatagc tgccgttttcc    63720 tttgcccaag atgacctcct cagacttttc atcctgtaca aacactgttt ctttggacgg     63780
aagatgcttt ttctgagaaa ccctcctctg tttttccagc acattcttct gcatcctttc      63840
ctgatccccc tcagtagcag tttcttcctt ataatttagc tcctggccat gtcttgctga      63900
ttataattgg tcttatctct ccagccagac gtgggttccc gtcctgaaag ggccatccct     63960
cttgtccctc tgtccttcca gtgctttgac atttggtggg cacagagtag aacaatacaa     64020
agtactgaac aataactttg gttttcttgc caattttatt gcttggcaat aaaattgtat      64080
acctaaggaa agaacgattt taatttttta acttttagaac tcaacaagca cttgtttggt    64140
attgatactt tactttgtaa gccttccaca agaaatcaaa taatgtctct tgcgctgaaa      64200
tcgtcaacgg gttacacact ctgcaaagtt atgggaagca cagccctgac cttaaataaa   64260
tgccaaattg ggtggtaatt taaaaggaaa aaaaatcttc acgtaagggt tggtggaaat     64320
```

```
tattatgctt ccctctgccc ccgcccccg ccaataacag agtaattgaa ccaggaactg    64380
agagtgttta gtaatttaat gaacattggt ttactaaata accagtttat atgtttgata    64440
atatagcaca ttttattatt gaaaacattt caaattagac tttgactttc acttgtttta    64500
ttatggagaa aaggattttt cttctgcatg tgattcctac agattgctat agaaaaatag    64560
tgtgtttgtg tgaatctggt tatgttcatg aactaaaaaa tatcattact aggtaaaatc    64620
aattattcag ttcaacagta agaatgagcc tggcaaacat gacaaaaccc catctctaga    64680
aaaaacacaa attgtttggt ggcttggcag cgagttgcgt agtcccagct acttgggggc    64740
tgcgggtggt gctgagatgg gcagatcact tgaatcctgg aggttgaggc tgtagtgagc    64800
agagattgtg ccactgcact ccagcctagg cagtgggagt gagatgctgt ctcaaaaaac    64860
aaaataaaat aaaataaaaa cagcaggaat gacatttgac ttaattttat tctattgtag    64920
aaactgctga aaatatagga tttgcttgtg aacttctgac tgaagacacc accatctgct    64980
atggggagga tattaagtga gtaaaagcct gcagtatgaa attacgtaat agctcatctt    65040
tgcaaatgca agactgtctg tagaagatag cagatatgaa gaaataggg ttacgatgtg    65100 tcacttgggg cagtttcctc atgtttaaat gaggcaagac aacaacaggc agttccaagt    65160
aatcaaggtg cagcctaaat ttgagcagat tttacttta gggaaacttg ggcccttca    65220 gaggccattt ttctccattc cttctcagct caggccaggc gcagtggctc atgcctgtaa    65280
tcccagccct tgggaggcc gaggcgggtg gatcacctga agtcaggagt tctagagcag    65340
cctggccaac atggtgaaac cccgtctcta ctaaaactac aaaaattagc tgggtgtggt    65400
gcccggtgcc tgttatctca gctactcggg aggctgaggc aggagaatca cttgaaccca    65460
ggaggcagag gttgcagtga gccaagatca cgccactgta ctccagccta ggtgacaaga    65520
gtgaaactct gtctcattaa aaaaaaaaa aaaactcggt tcacctacta aaaattccgt    65580
aaaaagcctg taatatcgct agcaaattaa tatgaattat agtcctattt tgcttttct    65640 aggaactttt acttttgaaa gggaaataga agaaggaaa aaaaaaaccc aaaacttttg    65700
cgggaaggaa atgtgtgggt gggttacatc atgtaggtcc cctgtaatct agtctaggtg    65760
gggcaggcct gataattcaa atgttagcat atgctgaaac gtttgttagc tttgaatcag    65820
agtcgcagca gacctggaaa tgtatgatga aaaagcctg tcttgttctg aagctataaa    65880
tatgctgcac acagttactg tgatgtgttt actgatggcc tgacagttcc tcaagatttt    65940
tccctacaga gcttctctca ggccagcatg aggtcagatt aaactgttaa catacacatt    66000
tgccaggtgt gataaagtga tgagggaatt gatggtcaat attagtctta tttctaatga    66060
tggtgataaa gcattttcta gttgttctag tatattaggt attccgtcaa attagacaaa    66120
atcagtagcc ttatgatcta aatcagttcc atttagaact gatttagttt atgtgcccaa    66180
atagaggtac ataagccatg ccccctttgtg ctttttaggtt ttaaaaaagt agcaacaggc    66240
tgggcacggt ggctcatgct tgtaatacca gcacattggg aggccgaggc gggtggatca    66300
cgaggtcagg attttgagaa cagcctgact gatatgatga acccgtct ctactaaaaa    66360 tacaaaaatt agccaggcat ggtggcatgt gcctggaatc ccagctactc gggagactga    66420
ggcaggagaa ttgcttgaac ctgggaggca gaggttgcag tgagccaaga tagtgccact    66480
acactcctgc ctgggtgaca gagcaagact ccgtctcaaa aaaaaaagt agcaacagac    66540 aaataaatgc ttaatgctta atgagtttac tttagtagtt ttgggcttca agtaatctga    66600
ttaattacta tatggctttg tttattttt gtagatgggg ctgtaaaaaa atttctggtc    66660
```

```
tctcttttga aagtcttaaa aattggtccc gaagctaaag taaaagataa aatgtatgca    66720
agtagcaaat gttgtgacca tgcccttagc tgagtttacc tttatagaga gaggaatcat    66780
cttcccaggt ggctcttaaa ttgatgattc ctataaaatg atttgaatag aaggtatctt    66840 cattttttt ctcttacggc ctttcaatga tttgtcttag tcactcactt ttaacttgaa     66900
aatgagaatt aaattgatgt ggaaaaggga tactagatac ttaatcctct agtgcagtga    66960
ttctccgtgg ggagtgagtt tgccttccag ggacccttg gcactgtcca gagacacttg     67020 cttgttcag ctgcagagaa gtgctcctgg cttctagtgg gtagaggcca gggatgttgc     67080
taaacatcct ccagtgcaag ggatggccac acaaaataaa ggattattag cccaagaca    67140 tcaagagtgc aaaggctgag aagccttctt tggaaggaga agaacaatgg cttttttgtat  67200 gtaatagtaa gagtcctgag ccagaagtta caagataact gagtcctcat tctagttttc    67260
ctatcaacct gcagcaggca aatcacatca ccttcctctg gcttgatttc cttatttgta    67320
acatgaagag attggacaag atatttaagg tcccttccac tccaaaattt catgactcat    67380
ttttctatca catgaaagtg ttacacgtag ccttgtcaca tatatcattt taacacaaac    67440
atttaatttg ttgatataaa gcactgagaa tttctcaaac acagatatag ttttgtttat    67500
atgaaaataa gtttattcct aacaaacaat agccagtatt ctaattcaga tcaagattgc    67560 cttcccttt ttttttttt tttttcctta gaaagactct gtcacccagg ctggagtgca      67620
gtggtgcaat cttggctcat gcaacctcc gcctcctggg ttcaagtgat cctcatgcct      67680
cagcctccca gtaactggg attacaggca ccgccaccac gcctgggtaa ttttttgtatt     67740 tttagtagag acagagtttc actatgttgg ccagtctggc tgcgaactcc tgacctcgac    67800
tgatctgccc gtctcagcct cccaaagtgc tgggattaca ggtgtgagcc acagtgcctg    67860
gcctaagatt gccttttcttc tgttgctgtg tatacatttt caactgtatc ttcctttgac   67920 tgtcttgaa aaatgatgaa ttacatggta ccccatggt ggatgaatcg agacatagta      67980
aaattacatg tcgctcagtt aaaaaaaaa aaaaaaagg gctggccagg cgtggtggct      68040
catgcctgta atcccagcac tgtgggggc tgaggcgggt ggatcatgaa gtcaagagat      68100
tgagaccatc ctggccaaca tggtgaaacc ctgtctctac taaaaataca aaaattagct    68160
gggcatggtg gtgcccgtct gtagtcccag ctacttggga ggctgaggtg gaagaatagc    68220
ttgaacctag gaggtggatg ttgcagtgag ctgagataac accactgcac tccagcctgg    68280
tgacagagcg agactctgcc tcaaaaaaaa aaaaaaaaa aaaaaatggg caaagcactt     68340
tgagtagaca ttttcccaaa gaggacatgc aaatggctga taaacatgtg aaaggaggct    68400
catcatcact aatcattagg ggaagataaa tcaaaaccaa agcaagataa cacctcacac    68460
cctttaggat ggctactatc aaaaacaaaa cacaatagaa ataacaatc attgttgaag    68520 gaacctttgt gtgttgttga tgaaatatat aaaatggtgc agccactatg caaacagta    68580 tggtgatgtt tcaaaaaatt tcaaaaagga ttaccatatg atgcaacaat cccacttctg    68640
ggtatatcca caaataatt gaaagcagga tctcaaagag atacatgcac acccatgttc    68700
acagcaacac tgttcacagc agccaagaga tggacgcaac ccaggtgccc atcagtgagt    68760
gaatggataa acagaatgtg gtgcttccac ataatggaat atattcaact ttaaaaagga    68820
aggaaattat gacatatatt atatagatga accttgaaga cattaagcta agtgaaataa    68880
accagtcaca gaaagacaaa tactgtttga tttcacatat atgaggtatc tagagtgctc    68940
aaattcattc aaacagaaag ttaactggaa gttaccaggg actggagggc gagtgaggtg    69000
aggtgttatt gtttaatagg tatagagttt ccgttttgca agatgaaaaa gttctagaga    69060
```

-continued

```
ttggttggat aacaatgtga ctatagttaa cactactaag ttgtacactt aaaaatggtc    69120
aaagcccggg atatggcaaa accctattgc tacaaaaaat acaaaaatta gccaggcgtg    69180
atagcgtgtg cctatagtcc cagcaactca ggaggctgag gcaggagaat cacttgaggc    69240
tgggaggtca aggctgcagt gatccatgat catgccactg ctctccagcc tgggtgacag    69300
agtgagaccc tctctcaaaa aaattataat gaaaataaaa taaagaaaca aaaataggta    69360
agatggtaaa ctttgttttt ttgtcacaat ttttttttaag tcaaagttat ctcagagtca    69420
agggcctatt tagggtctta cactttaaac actgaaattt ggtttcccct agttctcttc    69480
ttcatgcaag gatggaaaac cagaggaata gaggtggcgt ctacgcaaag tttgcacctc    69540
ctgtgcagga atcttttttt ccacccggtg gaaaccgtgc cttaatcatc actggttctt    69600
ggttggtacg tatcattagt gtatctgtgc ctttaactca aaagaaagaa gttcatttgg    69660
agccactttt agatgctttc acatgttaac tgccaaccta aaagtctctt agcctataca    69720
tgaaagtgtg gttttttccaa gtttgagact taataatata tgatatatga aaggatgtat    69780
accaaagagg taaagtggt tatcttggtt tactaattaa tgggtttttt catttttcttc    69840 tttatagatt gttagatttt ctaaatttttt gttgcatata tattttataa gctggatgtg    69900
gtggcatgcg cctgtagtcc cagctcctct ggaggttgaa gcaggagggt ggtttgagct    69960
taggtgttcg aggctgcagc atgcaatgat cacacttgtg aatgaatagc cactgcactt    70020
caacccaggc tatacagcaa gaccccatct ccattgaaaa atatatatat agctgagcac    70080
agtggctcac gcctgtgctc ccagcacttt gggaggccaa ggcgggcaga tcacaaggtc    70140
aggagatgga gaccatcctg gccaatatgg tgaaaccccg tctctactaa aatacaaaaa    70200
aaataattag ccaggcgtgg tggtgcacac ctgtagtccc ggctactcgg gaggctgagg    70260
cagggaaatt gcttgaacct ggaaggcaga ggttacagtg agccgagatc gtgccactgc    70320
attccagcct ggcaacagag tgagactcca tctcaaaaaa aaaaaaaaaa aaaatatata    70380
tatatatata tgtgtgtgtg tgtgtgtgtg tatatacata cacacataca tatatgtgtg    70440
cgtgtgtata tacatacaca cgcacacata tatatacatg ttttggttat aaaatcaaat    70500
ttatttgtca aatataatca gtgacataat ccaaaaatta tccttcacat aatttaaatc    70560
ttgggaatgg tactcctggg gtaaaactaa agtgaatgta acctttccc tctctgattt    70620 cacagaatga aattcttctc gagaaaaaga ccaagagaaa taagattctg aagctgaagt    70680
tcccaagaac agaagaagaa agacggatgc ggacccaaag taaaggagg ctagaagcta    70740 agaaagagca gcggcagaaa aactttgtgg acctggcctg cgagtgcagc gcagtcatct    70800
gctgccgcgt cacccccaag cagaaggcca tggtggtgga cctggtgaag aggtacaaga    70860
aagccatcac gctggccatc ggagatgggg ccaatgacgt gaacatgatc aaaagtgagt    70920
catgcaccca cggccagtga ggcccaacgt gctagagagg agaaatggct ggaatgtgta    70980
gggggtggat tttctttttt tagatttac agcttaggtt ttcatagagc agatgtttca    71040
taaagtcact taaccatgac aacgcctgtg accctacccc cagaaagccc acagcccatc    71100
aggaggaaag agtatcactg acagggcttc tgaaggatgc gaagaggaaa ataaggtcta    71160 tgggggaaa tttatcctta tattttatt ctttatata gatgttgtgt atttttttct    71220
ctcttactgg ttctcttccc atattttggg tttattaaaa gccctgatat tggctgggca    71280
cagtggctca cgcctataat cccagcattt tgggaagccg aggcaggtgg atcacaaggt    71340
caggagttcg agaccagcct gatcaagatg ctgaaacccc gtctctatta aaaatacaaa    71400
```

```
aattagccag gtgtggtggt gcacacctgt aatcccagct actcgggagg ctgaggcagg    71460
aaaatcactt gaacccagga ggcggaggtt acagtgagct gagatcgtgc cactgcactc    71520
cagcctggac gacagagtga gactccatct caaaaaaaca aaacaaaaca aaaaccctg     71580 atatttaata agttttgtaa gacataaatt attgaactct ggctggtgct tgctttgaca    71640
atatcattct ccttcatcta agcatttctt tctgggactt tcttcctacc tttggtaaat    71700
ctgtgggaac ttcatcattg ggtcacctgg tgtgagttta gagtaacatg tttagcactg    71760
aagaaaagct tccacgtgct ctcatcatcc tcctcacctc cctagaaggc tgcctttttc    71820
tggatgctag aatttaagtc cacacaatta aaatattgag tcctgccatg cagaaataca    71880
gttgtgctgg tattaaagcc tgcagaagca cacccacagc cctcatctct atgtctgaat    71940
tctgttcctt tttcctccct ctgtcactat aagggagtat cttgtattaa aaatactcaa    72000
actaatgacc tggatattca tcctcatcct attgccaaaa tccggtgtca ccttgggctt    72060
atgctcaggt ttcagttttc tcatcggaaa agaaaataat ccctaatgtc acctccagct    72120
ctgtcgtatt attatcactg agctgaagta ttacctgact gtacataggt aattgcatgt    72180
tcctgtgatg ctgggttgct taaatgcatt atatataact agacttttca gtctattttg    72240
tgactcatga gtctgtctct ttcttttctt agtctcctcc tcctccttga tgtatactaa    72300
gaatattcca actttatctt cctcaacagg agtcagctgt atgacgtatg tcatcttgcc    72360
ttctttatca gtgcgtatgt ctgtggtcac tagcagttta attcatccac actgtttttt    72420
tttttttttt tgcatgtgct tgccctacca tgcgaatggt attgcttgct cggagttaga    72480
tctatctctt tcctccatag ccagccagct ctagtttatt ttccattacg tacctttaac    72540
gtaactagcc gtgccaaaag gacaagtcaa acatgatttt tattcagtta taaagtagcc    72600
ttctagataa tgggagggga cgggtttgct ttggagattt atcaactgat tatgtgactt    72660
agacttgaaa cattttgttc ctctgagttc accaatacat aatgagaggg attgcacaaa    72720
gtcaatgtag ataatcttag aggggcttgt ttttcttaag ttgtcttaaa atttttatta    72780
agcactgtta tatgccaggt gcatttaaaa aaaaaacaag gtctccctct gtggcccagg    72840
ctggggtgca gtggcatgac cttggcttac tgcaacctcc acctcctggc tcaaacaat     72900 cctcccacct cagcctccca gtagctggg actacaggca tgagccacca tgcccagcta     72960 attttttgtat ttttttgtaga gttgggaatt tgccatgttg ctcaggctgg tcttgaactc    73020
ctgggctcaa tcagtctgcc tgcctcagtc tcccaaagtg ctaggattac aggcatgagc    73080
cacctcacct ggccccaggt acttttatat ataagttata gagcatccct ttgggataaa    73140
aatataggaa acttagggg tctccttaga agttatacaa gtagtattag tgcctttatg     73200
tactttgtaa aagctgtcat ttcttccaac cacatcaata acaatataca gaaagtttag    73260
ccaagtatgg ggcacacacc ggtagtccca gctacgtggg aggctgagac ggaaggatta    73320
cttgagcctg agaagttgag actacagtga gccatgtttg tgccactgca ctccaccctg    73380
ggtgacagag caagacccct tctccaacaa caaaaaagaa cacacacaca cacacacaca    73440
cacacacaca cacacacaca aagaaattgt tggtcataaa gtagtcgagt gaaattattc    73500
aagtgtcaaa aaataatctg agcatttgct aacattcacg tttagcagtg tagtctggaa    73560
gaagtgaagg aatcatgacc caccatgttt ctgcccctag caaggatcca aggactatca    73620
taggctgcct tctccctcta tcctacctga agatatctca taccagctgg gtggatgttg    73680
tctcttcttg gtcttagacc ctgagaatgt acgtgaagca ggagagagat aaaggcaagg    73740
tggggcatgg tggctcatgc ctgtaatccc agcactttgg gaggccaagg caggcagatc    73800
```

```
acctgaggtt gggagttcga gaccagcctg gccaacatga tgaaacccca tctccactaa   73860
aagtacaaaa attagccggg catggggggtg gcgggcacct gtaatcccag ccactcggga   73920
gcctgaggca ggagagtcac tggaacccag gaggcagagg ttgcattgag ccaagatcgc   73980
accactgcac tccagcctgg gcgacagaaa aagactccat ctcaaaaaaa aaaaggcaag   74040
agggattatt gctgtagcga ggaaatattc tttttgttaa ggaatgataa aagaatgtct   74100
accagtgagg cacctaacac cgcatttgag atttcaggaa actctaaatg cctgtactta   74160
aattttacaa aaaagaccaa tgttacctta tagtgtatct gttcagtgct tttggttgcc   74220
ctgggaacta tgacagtgtt catttcacat ttgtccttgg tctgctcagc gggaaggttg   74280
aggactggat accagggcct ggggcagggc ttcctcttcc tcagccacat aagccaagag   74340
aatctcagca ttttcctcag tggcttgttc aggaaagaaa aggccatggt ttggcaggaa   74400
agagcaagtt tggcaaccat gctggtcata ggaaatattt gtgtgttttc aaagagaaca   74460
taaatattat atgagatgca gtttgttctg ttttttttaga agtgttactg aaaacgtagg   74520
tttggataca tcactacagt tatgttttga atttgccaga ccttgtgttc tgtaactagg   74580
gcaggatttt tgaagcttct ttttagttgg aacgccgcag cattgcagcc acttttcagg   74640
gtctgagcaa tgataggttg tgttctccaa catatctttt ctaaatgatc ttgtctatct   74700
tcacattcgt tacttttaag acccagacaa aactaatcat tctctaattt gaaagtgtta   74760
tttatgacta ttggaagcat aaataaaatt gtgactttaa ttttatatat tctggaaacc   74820
ttcccccgta aagaaaaaaa aaatgtctta aggtcccaga gggccatgaa taagactttg   74880
aaagtttaat agtttcttgg ttaaaactct tttgattaca agtattggag aacaaccaaa   74940
gctagcttaa gaaaaaatta aatttgagga gtgggagacg aggggaggga acctagagga   75000
tgggtcaata ggtgcagcaa accaccatgg cacacgtata cccatgtaac aaacctgcac   75060
gttctgcaca ggtatcctgt aacttaaaag aaaaaaaaga aaaagtaaaa tttatttaaa   75120
cacctcctgt tgtccaagaa gaagccaggc ctcaggaaga tactggaaca aggacataga   75180
tttgcaccag gaacccgtg tctgtctgtc tctctccct tctctctccc tttcctcctt    75240
cttcccctcc ttctctctct cccctcccctc ccttctctcc ccactcttct ctccccactc   75300
ttctctcccc ccattctctc cctccattct ctccctcctc cccacccctc tctccccact    75360
actttatttc tctgccccctt agaaatcttc aggaagaaat atatctattt cggccaggca   75420
cagttgttca tgtgtgtaat cctagcactt tgggaggcca aggcaggtgg atcacctgag   75480
ttcaggagtt caaggcctgc ctggacaaca tggtgaaacc ccgtctctac aaaaattagc   75540
tgggtgtggt ggcgcacatc tgtaatccca gctactcgag aggctgaggc aagagtatcg   75600
cttgaaccca ggaggcagag gttgcagtga gccaagactg cgccattgca ctgcagcctg   75660
ggtgacagag tgagacttca tctcaaaaaa aaaaaaaaaa gagagagaaa gaaatataac   75720
tatttcttac ctcaagaatt tagaccttaa aattctagac acaaaataac tgacttctaa   75780
ttccagaata tcaagagaga gactggctca gcttgggttt tctgtcagtc agggttttagc   75840 acaggaaaca gaccccagtt ggtatttaag caagaaaaga ttcatacagg ggactaggta   75900 cttttcaaaag ctctggatgg tctacagaag cagggtctag gctgggtcac ttaccagaag   75960
agcttctact cttctggtaa gtgataagag gttcctctaa agagcttcca aattaagaag   76020
cctttatagt tgcctgtcaa catccaggta gctggaaagt agatatgagc tctgctgcag   76080
aaatcccaaa agaggaagcg atgctgggct ctgattcact tctgcttcca agtcataagt   76140
```

```
ggatctaaac agtggaacct aattcacaaa gagcctagct gcaagggagt ctgggaaatg    76200
tagggttttt atttcctttc ccacctctct aattagaaca aggatggaat gaagttgggg    76260
gagccgattt gtagtatcta ccacaaatta catatctgcc catgactgac acagctgttg    76320
ccaaagaggc aaggacacag tgtacacatg ggtgcctggg gctcaccctg tggatggaag    76380
ggatggctgt gatcttggca gataatccaa atggaattcg tcacccacat gagatccttt    76440
cccagatatt tatggaggcc ctactgtgtg ctctgtttag caacttgtaa ctcagacttt    76500
gagttgagtt caagagctgg gggtgaggga tggtgagcaa gagcttctgt attattgttc    76560
catcaatgtc tgtctttgtt ttttgtttgc tatggaacca tttttatcaa ctgatgtttt    76620
gcctcacaat cggtttatga tccacagtgt tttctccctc tgcccatag ctgcccacat     76680 tggcgttgga ataagtggac aagaaggaat gcaagctgtc atgtcgagtg actattcctt    76740
tgctcagttc cgatatctgc agaggctact gctggtgcat ggccgatggt cttacataag    76800
gatgtgcaag ttcctacgat acttctttta caaaactttt gcctttactt tggttcattt    76860
ctggtactcc ttcttcaatg gctactctgc gcaggtaatg taatgttgtt attattgtta    76920
tttactaagt agagctctta aatgaataaa aatctagttc tgaaaagaca atttatttct    76980
tctatatttg tagttttggg gctgtgtctc cttacagttg gggcataatt aagaatgatc    77040
atgacttctc taaatgtttc tggtgctgta aaaacatttt accttagaaa ggaggggatt    77100
tggccaggca tggtggctca cgcctgtaat cccagcactt gggaggctg aggcaggtgg     77160 atcgcctgaa gtcgggagtt tgagatcagt ctggccgaca tggtgaaacc tggtctctac    77220
taaaaataca aaaattttcc gggtgtggtg gcaggcacct gtaatcccag ctactcggga    77280
ggctgaggca ggagaatcgc ttgaacctgg gaggcagagg ttgtggtgag ccgagactgc    77340
gctattgcac tccaacctgg gcaagacttt gtctcaaaaa aaaaaaaaa aaggagggga    77400 tttgcttgta tgtttttatc tttatctttg gttattttt catgttgaca ttaagagtag     77460
cgataacagg gctgggtgca gtggctcacg cctataatcc cagcactttg ggaggccgag    77520
gtgggcgggt cacctgaggt caagagttgg agaccaacct ggccaacatg gtgaaacccc    77580
gtctcaacaa aatacacaaa aattagccag acatggtggc gtgtgcctgt aatcccagct    77640
acttgggagg ctgaggcaga agaatcactt gaacctggga ggcagaaggt acagtgagcc    77700
aagatcacgc cactgtactc cagcctgggc gacagagtga gactctgtct cagaagaaaa    77760 aaaaaagaa tattgataac aggccaggtg catagagttt tgcctataat cccaacactt     77820
tgggaggctg agatggggag atcgcttaag gccaggagtt cgaggccagc ctaggcaaca    77880
tagcaagacc cccatctcta ttaaaacaaa caaacaaaca aatgttaaa taaggaagc      77940 agatgagtat gtgctaacta ggctggcatg tgtctttgtt ggtgacatgg agcctctgtc    78000
atcccctcac agactgcata cgaggattgg ttcatcaccc tctacaacgt gctgtacacc    78060
agcctgcccg tgctcctcat ggggctgctc gaccaggtag gagcctcgca caagcaggga    78120
cacttctgga cagatgagaa tgcgttagag aagtcccaag caaacgtttc aatgcattct    78180
tctggtgttt acttctttct gatcaaaccc tattataatt ctgttgtcag gcatcaaggg    78240
tcatggctgt gcttcttgtt ttgtaataag gaaagaggat ttctctgtag tcccagctac    78300
tcgggaggct gatgcaggag tatgacttga gcccaggtgt tcaagtctag cctgggcaat    78360
aaagtgagac cccatctcta agacaaaaaa aaaaaaaaa aaaagagaa aagaggattt      78420 ctgtgactgg gttgaattca ttggcacaca tatttgttat gttccttta gacagtaaga    78480 gcttactatg aagatacctg aaggcagggc atggtggatc atgcctgtaa tcccagcact    78540
```

```
ttaggaggct gaggcaggca aattgcttca ggtcaggagt ttgagaccag ccctggcaac   78600
atagggagac cccatctcta cagaaaaatt taaaaattgt gggcatggta gtgcacacct   78660
gtgaagtccc agctacttgg caggatgagg tgggaggatc gcttgagcct ggaaggttga   78720
agctgcagtg agttgtgttt gtgccactgc actccgggct gggcaacaaa gtgagaccct   78780
gtctccaaaa aaaaaaaaaa aaaagaaaa gaaaaggaaa aaaaggcacc cgagagtcca    78840
atatgtctcc acaataataa tttactcatt ttaaagtcag tttaaatcct ttccaaaatt   78900
tatgtagcta gtgcatattt ttatctaata ccaattctta aaaagaaaga agcactataa   78960
agactaaaaa gtaataattt ataattaact catcaacttg tatgagaaaa ttttttccca   79020
aaggatttgc aacaatatat attcactcag gaggtaaaaa cagtagcctc cctacatatt   79080
tttggacatt actaatttgt tttctttcca taagtagcaa agtaataaac ttatacctag   79140
cccttctctg aattaaatat taagtaatgg tggtctaagc aatgaggttg agctctgcac   79200
accacaaata ttgcaggatt gatcgattat cttgttcagt ttttgccttc ctaaaattta   79260
acagcaggct gcaactttt gtgagatatt aattataaca tatctctgac tgctttgacc     79320
tgatgaataa aataccatca ttttgttttc tccttaagga tgtgagtgac aaactgagcc   79380
tccgattccc tgggttatac atagtgggac aaagagactt actattcaac tataagagat   79440
tctttgtaag cttgttgcat ggggtcctaa catcgatgat cctcttcttc atacctcttg   79500
gagcttatct gcaaaccgta gggcaggatg gagaggcacc ttccgactac cagtcttttg   79560
ccgtcaccat tgcctctgct cttgtaataa cagtcaattt ccaggtacgt ggctttcatt   79620
ggccgtattc agtgtctatt ggtacctact tatatttctg tatatagggt ggcatgcaca   79680
tccacctgac tcccactgca cctgtgccac ttacaaaata taaatgctat tttcatctct   79740
tataccaagc acatttttcta tttcttgcct gagtcaagga tggtttagtt tctggtccag   79800
tattcaagcc acatcatgcc taacttgctg aattctgttt tcaggattgt tagatccttt   79860
atttcttgct aactccccaa aatgagtgct ctgttttttct ctggtttccc aacagattgg   79920
cttggatact tcttattgga cttttgtgaa tgctttttca attttttggaa gcattgcact   79980 ttatttggc atcatgtttg actttcatag tgctggaata catgttctct ttccatctgc     80040
atttcaattt acaggttggt atttccaaat tccaaaaata aatgtacaga caaatgtcat   80100
tagtttagat tttgacataa cttctgttaa gtaataaaat atacaaggtg gaatggctgg   80160
gcacagtggc tcacacctgt aatcccagca ttttgggagg ccgaggcaag tggattgctt   80220
gagcccagca gttcaagacc agcctggaca acatggctaa accccatctc tacaaaaaat   80280
acaaaaaaat tagccaggca tggtggcaca tgcctgtagt tctagctact ggagaggctg   80340
aagtgggagg attgcttgac ctgggacgtt gaggctacag tgagtcgtga tggcactgct   80400
gtactctagc ccaggtgaca gagcgggacc ctgtctcaaa aaaaaacaa aaaaaacaaa    80460 gcacaacaaa acaaatatat acaaattatt attgctagtg aaaattaatg tcttgtctgg   80520
aaattaaatg gtgatggtgg gttgaaaggg cataacatga tgggaggaag acaaattaaa   80580
atagctttac aatagcgctg tacgtgtgtt gaattagata acttaagact taaaaggctg   80640
gataaaagcc tattctttct ttcccataaa acctaatact ggggctagat gtggtagctc   80700
acgcctgtaa tcccagcact ttgggaggcc aatatggggtg gatcacttga gctcaggagt   80760
ttgagaccag cctgggcaac atggtgaaac cccatctcta caaaaatac aaaaattagc     80820 caagcgtggt ggcgcacacc tgtagtccca gctattcagg aggctaaggt aggaggacac   80880
```

```
ctgagcccag gaggttgagg ctgcagtgag ccatgatcac gccactgcac tccaacgtgg    80940
gtaacagagt gagaccctat ctcaaaaaaa agtcagaagt cttgatcacc taactttgca    81000
tttttaatca atgcaatgtc aacaaatgtg cttttttttcc ttatttgctc acttatgtaa    81060
atttgccttg tttcaaataa tttaccttcc caattttgct ttgcttagtc tgatttttaaa   81120 atgtctgttc tttgagccat aatggatatt ttggggaggc caatccagtt gtaaaacttt    81180
accataaatg atctatttat agattatgaa atattaacta tgttcttttt tttatttttat   81240 tttttatttt tgagacagag ttttgcttta tcacccaggc tggagtgcgg tggcacaatt    81300
tcggctcact gcaacttccg ccttccgggt tcaagcaatt ctgctgtctc ctgagtagct    81360
gggactacag gtgcacacca ccatgcccgg ctgatttttt gtattttagt agagacgggg    81420
tttcaccatg ttgcccaggc tggtctcgaa ctcctgagct ctggcaatcc acccaccttg    81480
gcctctcaaa gtgttaggat tacaggcatg agccaccaca cctggcgaaa tattaactat    81540
gttcttagga aaaagaacc acagtgatgc atttgccatg ttctttacag gcacagcttc     81600
aaacgctctg agacagccat acatttggtt aactatcatc ctggctgttg ctgtgtgctt    81660 actaccgtc gttgccattc gattcctgtc aatgaccatc tggccatcag aaagtgataa     81720
ggtataaaga atatagtcct ttcccaactc tgtccctcac agaaaccaaa gcgtttccca    81780
acagcacgtt tcctgcaaaa ttctaagctc atgggaagtt tggtaagaat gattttttcat   81840 gattgcttct ctttaactct atctcacaaa taagtctttt ggaattggga gtttagtgtg    81900
cttgcttttt aatacaaaaa ttaccaaaca taaacaaaaa agggagaaca gaatgagccc    81960
catatatcta tctcctcagt ttaacaatta cagtattaac attttgtcat acaaatcaga    82020
ttgggttttt tttctttatt taagaaaaat gtcaccttct gtagcaggat cctttgagct    82080
acaaggaaca gaaagctgtg actcaaaaca tctctacagt agtgcgtcat cattaatcat    82140
tagtaggctt caggcccagt tgattgagca atttaatgtt gtcaagaaag gattgggctg    82200
gttcttgcca tctcttctct cagaaacctt cattattagc ttcatatgga tgctggaaga    82260
tggccagagc agttctgggt atcacttcct gacctatcag tgtcgggggg agataagagc    82320
ctattctgta gctccttagg ggccgtggaa cttctcaccc aagggcccca gtacagtgcc    82380
ctcaggtctc acgtgccaaa attaggtcac ttgcccattc tggactagtt tagcaaggga    82440
aatcaacctg cccaccgccc atgagaaatg tggctgtgag gggttggggg gggcaatctg    82500
aatacaatca atttccatta gaaagaagga gagagtagag gctactgagg caaccttcag    82560
tatccctcgg gtctcccttt tgcagtgcca acagtatgca gtaacaaccc aggaaagagg    82620
ccctactgaa ttttctcttt gactgtaccc atctggtctg aactagaaaa gggcactagc    82680
ttcagaggag tgggaatctt ggctttgcat tttctagctg tgtgaccttg gaaaagttaa    82740
ataaccttcc cttggcttca atatatatct ccaggtaggt aggtaggtag atcgattgat    82800
caatcaatct atgtatagat atagagagat ggatatagat ttatatcatc atatatatat    82860
gtcgatatag atagatagat agatagatag atagatatag ccaagcactg tggttcatgc    82920
ctgtaatccc agaactttg gaggccgagg caggcagatc acttgaggtc aggaccagcc     82980
tggccaacat ggtgaaattc tgtctccact aaaaatacaa aaattagacg ggtgtggcag    83040
tgcgtgcctg taaccccagt tactcaggag gctgaggcag gaggatcgct tgaacctggg    83100
aggcagaggt tgcagtgagc caagatcgtg ccattgcact caagtctggg tgacagagcg    83160
agactgtctc aaaaacaaaa aaaaagatat agacacacat acacacacac acacacacac    83220
acacacacac acacaagtgg ggacagaact gcctgcatca aaatgggca ggtgtcaggg     83280
```

```
gagttcatca gtgttcattt ctgtcaaccg tctggccagg cctcctccct ggtgtggatc    83340
ttattttcat ccctccccat ctctccccct tgcagatcca gaagcatcgc aagcggttga    83400
aggcggagga gcagtggcag cgacggcagc aggtgttccg ccggggcgtg tcaacgcggc    83460
gctcggccta cgccttctcg caccagcggg gctacgcgga cctcatctcc tccgggcgca    83520
gcatccgcaa gaagcgctcg ccgcttgatg ccatcgtggc ggatggcacc gcggagtaca    83580
ggcgcaccgg ggacagctga tcccttaccc ccaggctggg atgcggccac aaagcacgtc    83640 tatttttta tgaaagactc tcaggacttt gtgtgtgtgt gtgaattgca ttcatcacaa    83700
agatattgaa gacaataaat aatctttata acaaactcct tgggttggac tattaa       83756
```

<210> SEQ ID NO 72
<211> LENGTH: 108687
<212> TYPE: DNA
<213> ORGANISM: Homo sapiens

<400> SEQUENCE: 72

```
tacaggcctg taaaaaataa gggttgggat agcctgaatt ccagggctct tgctgggccc      60
actctgctca atttgcctct cgttccaagg tgaatcagca atttccaagg cctgttgaca     120
ccctcagagg gtttcccaag cacactctgt gtttggggtt attgctctga gtatgtttct     180
cgtatgtcac tgaactgtgc ttgggctgcc cttaggaca ttgatcctta ggcaaataga     240
taatgttctt gaaaaagttt gaattctgtt cagtgcttta gaatgatgaa aaccgaggtt     300
ggaaaaggtt gtgaaacctt ttaactctcc acagtggagt ccattatttc ctctggcttc    360
ctcaaattca tattcacagg taagtaactt atacttgtct ctgcaaatcc attccctctt    420 cccttttaact cttactttgt ggagtggagt gtttctggtt tattaaacat tggtctcttg    480
tccagtgtaa acaacgctac aatacttgga tagaaactta caggatgcat taatgatttc    540
acaacattgt atacaataca gatgactctt ggttgctgtc ttctttatag caatgctatt    600
tcatgtatca atctcttaga gagagagaga gtggtgtaca tgggtgtgtg gtacaaatgg    660
ccgaatagat tgaataatct gctcaaagta aaaataccag tgggcttctt ttttaacttg    720
gctttgtgaa agcacaattc tgtttgctct gataatcaca gattcaatga tcacaaattc    780
tacccttgaa agctggttta atgcagaact acaccgactt tatctttct ccaacaccgt    840 actcatttct tcattgtccc ggttttcaaa aatatagatg caaaaaaaaa tgagctgtgg    900
atgcatgttt agagggggaga aagtttgttt ctaggatcta atttcagttt ttaggtcacc    960
caagccagtg ggagtcacat attgctaatg gcttgagcac agagatcaaa tattattcac   1020
acttcagact gggaataaaa gacagtattt gtcaacattt tgagggggaa tagcttttta   1080
gagatgttag agacaaatta tagtggttat acctaaaact ttttaatatt aggagttagt   1140
agtggttttt attaaacatt tgaagtgata acttatttat gagctgttgt ttaatagaag   1200
ttcttttctg tgggcaacct cgtcccctca ctgctcaccc ccctcacctt ggttcccct    1260 gctgtgctct gtaacactgt gattgtctct ggttgaagcc tccatttccc tgtctaggag   1320
cttctgttta cactccaccc cactctagat tgcaagcccc ttgaataatt tttgtttcct   1380
agtaccaaga ataatggtga caaatattag gggatgactc ctaaaaatgg attaagaagc   1440
tattaggggg gaaaatgccc attttgtggt tttaaaagat gctacaattg ccataaaatg   1500
cccaagtttc attgcagaaa tcaaatactg gagttgtgtt ttgcttggtc aagaggaaag   1560
aactggccgg gcgcggtggc tcacgcctgt aatcccagca ctttgggagg ccgaggcggg   1620
```

```
tggatcatga ggtcaagaga tcgagaccat cctggctaac acggtgaaac cccgtctcta    1680
ctaaaaatac aaaaaattag ccgggcgcgg tggcgggcgc ctgtagtccc agctactcgg    1740
gaggctgagg caggagaatg gcgtgaaccc gggaagcgga gcttgcagtg agccgagatt    1800
gcgccactgc agtccgcagt ccggcctggg cgacagagcg agactcctct caaaaaaaaa    1860
aaaaaaaaaa aaaaaaaaag aggaaagaac tgtacattta gagacaaaga atcgctgtgg    1920
cagttaactt tggtgttaca ttctgttttc ttcctaagca attctttagt cctctacctc    1980
aacggtgcct ctgaagaaag gacttacgtg gccaatggga tcaccgtgta tttatttccc    2040
ttccctatca gccatagccc tcagggctgg aagggcctca ttttagtcta ttcccagact    2100
gggtcaccca cagtgttgac acacagcatc aaccgacagt gagcttatct ggaaaataat    2160 gccttctat tttctttgtt tcttagcata tattaaatgt ttctttcctt ctctaataat     2220
cttttagata aagaaatcat ttgctgagct gataataaca aagtatcct acctacattt     2280 ttaaatgtca gcagtgaaag acgttttaag ggctttaaaa aaaaaaaaa gaagaaaag     2340 aaaactgtag tttagaaagg acatccaaat tgaagaggag caggggcagt tctgttctct    2400
ctgagcagct ctgtgaaggg ggagtttgtg gcgctggggt cttgaaagtc tttacagagg    2460
gcaagacttc acaagagaaa agccgtggag ggaccctcac atgatcagaa tattcacagt    2520
gtgatgtggg gcatggtggg ggcgggtgct ctccactccc gggcctggct tggttcccct    2580
cactgtcctc agctcctcaa tggctttgag gacatttaga ttcttcttac catcttggcc    2640
tgaatgtgga aaaagctctt tttccttaat taagtctaga aaaggtcaac atgtttcaaa    2700
aaatagcatt tgggtggaaa ttaaatggaa agtggaacaa atctctgcag agaaaatgca    2760
aaaccctaga acacagacag agccatctct gcctcttggt ctggtgggat ctctattctt    2820
ctcaaaccca tttcctaacc tctgtgggtg tgggctccaa gtcccaagcc ttatcagggt    2880 aactttttt aagtataaat ttgatcatat ccttttcttgc ctaaaagact tcattagctt    2940
cccatggcct ttaggataag gtcccaagtt ctcagtggta aggatcatga ggccctgaag    3000
gatcaaccag ccacatcctc ccgagttgcc catccgcctc cctgagattc actgggctcc    3060
ttcagccttg gacccggctg ccctgtctct tgcatctggg cctttgcatg tgtccttccc    3120
tgcctggact gctcttccct ctcctcttcc catggaaaac ttgctctcat cttcaacatc    3180
tcatgctaag cacttgctcc agagccttct ccagctctct agacaaggca gctcctctgc    3240
atcagggccc aggagatgcc tgtatttccc ctttcctcac tgccatcctg cttgacgcct    3300
aatttcccag ataatgtctg ccttccctgc cacattgtaa gttccatgag ggtagggctg    3360
gctggagggc tggtgctcca cacaatttt agggtaggta aatcaggtcc tcagagattt     3420
cttcctgggc tcaggctgc cctgaactga tctcacagta cagggattga cattttctgc     3480
aaagagctgt atagtgaata ttttaggtat gggagagaga aagggccata cattctgtca    3540
ctgtagcaca aagcagcca aagataatag aaaatgaaag ggtatgactg tgttcccata     3600
aaactgtatt tataaaatag gatggtaatg gtatctttca gcccagaagg attcagctct    3660
ggagacacct tttctcaacc ctgaccctt ttttttcttc aattcttcta caataccaat     3720
agccaattgc tagtattgat cccagccatt ggtgaagatc agcctgtcca tctgttgctc    3780
caggctgaca tccccaccag ttcacactag cagccttgct gtagtggcaa gtagtgggca    3840
ctgacatttt atgctctcag gatctttgat ttctttctgg catggcttgt agaaccctgt    3900
atctcctcca attttgacag cctcaggacc tttgtggtac tactcattca ggcccatttt    3960
taaggtcagt caaagtacta ggttctctca agtgaccatc tagctgatgg tctctcttcc    4020
```

```
ccatcccctc ctccccagca gtgaggtctt tcagaatgct gttgttagag tgtaagatag    4080
aaacatcttt gatatgtttt taccagtaat tgtcaggaga ctgttctcta atgtgcgtat    4140
ctgtgttgat aagattacac attttatcaa gagaaaactt caaccctgaa tagttaaaca    4200
gaagcgcata tagtgtgcag gttatagacc acatgtcact tagcagagag gaacactgga    4260
gttggtgtgg acaattaaga attcttgggg gattctatga ttaggtgtcc aaagtctgcc    4320
aactagtgct tagacatctc gatttcctgc ttttttactct tagattccct taagtttatt    4380
ggaaaataca tttttctgga atgccttgaa aattctcagt ctgttcctga agagattttg    4440
gggaggttaa ataatttaa tatgttaaag tgcacagtaa aaatgaaata gcattggatg    4500
ttattttcaa ctctgagttt tcttgtgtta gtttaagtaa aattttgtta ttgtaaattt    4560
gttaagaaac cctaattaaa gcctccttca atgtatgaaa ctcaaatcaa gttattaggt    4620
taggtgctaa aaaagtgtta cagctaatgg ccgagacagt agaactaggt gacattatat    4680
ctacttgtaa tcagtgagga aaaataatgt ggcaaaacac catggtactc ttaaatcata    4740
gaaagtgcca aatgaggagg aggtacactc tcaagaacct gcaaaacaaa tatgtttatc    4800
accaaaaact agattcccac tgcatttcca gggtttcaga gactggcagc catgtcctcc    4860
agcatctgat gtatgggttt cccaacatct catctgataa aaaaaataat ttgccagtgg    4920
aagaaaacat ggtctaataa tatatatcag atatatattc tacattcata atgatacatg    4980
gcaattcatc taatattcaa ttctgaaaac ctcttttgtg gcaaatatca caggcaaggc    5040
cttcattctt tctagaaatt tcggtttttc agtgtacttt cccaaactta gtgttataaa    5100
attcccagtg tttttgtggg tacatgcaag taattaagat tttcagcaca atggccttca    5160
aaaatcatca cagccgtttc taagctgccc aaagataaag ggactagctt ccatttctga    5220
ctgaacaacc agtgcatgcc tttagcccta gagagtatac atcttttgaa gtatagctcc    5280
ttggcatgtc aaaaaagaac agtggactac caaagttcag agtgatgcac ttgatgctga    5340
gaaagaaaac aaacaaagaa acaaacaaaa agaacaccct gttccatttc atagctggcc    5400
tggtactcac acctaagcca tgttattctc ttattagaca taaacaatct cacagagtac    5460
caacctcaaa gttactttga gtcaatgcaa ggtcaattta tactttgttc tcagcaaagg    5520
caaaatcaag gtcactgtgc aacccacaaa ataccaaaca ccttgctaaa tgaatggctg    5580
ttatttcttt atctagtcat aacatagtcc cagcttttta acagcatcca atttagaaca    5640
aatacccact acattagatc cttccccaaa tcatctgact aaagcccgag ttctgtaaca    5700
ggttctttct aacaccattt tactgagatg ccccacagcc cctgacagtg tgttcaccct    5760
tggtgcaatg agtagcaaac acgacttgtt tagctacaga tgtattcttg gtgctcactg    5820
actgaggggc attgacaatg ctgtgggcat agagacgcat gatttaatgg attttttgcct    5880 tttagaatgt aacttttaac agtaaaatag aaaccacaaa aactatttgt aggggtattc    5940
ggaaagaagc aaaatgtaag caattgaaac ctaatgtatg gaattgacaa ggggacacag    6000
aaggaaagta aagagaatag gttagtggat tagtattcct gtgcttaatg gaggacagat    6060
tactacaaat gaccctggaa gggcagatgg ggtggaggat caggtaggga ggactcggtc    6120
tttaagcttg aagggcaaag ggaacttcag ctgctatctc cctttgctg gctgctgtag    6180 agatacagtt tcatttcatc ttcacaccag tcctgcaagg tggattttac caccatcacc    6240
accacttcct gacatgaaag atggagaaat caggacgtgg agagagattt taaaataaat    6300
ccaactacgt agagtgaagc aacaggtgta tcaggatctg agagactcca aatttcgtgg    6360
```

```
gcaagacact acaccactgt cctctaaata ctacgaggta tttgcacacc agtggaaaga    6420
aatcttttta aatggagagc taagccaagg gaaaaaataa atggagacta attttttta    6480 atattgtatt ttaaaattag gaaatgcaat aacacatctg tggttaaatg ttgtttatta    6540
ttttctcatt attaaagagt ctctctgttt ttttgaaaaa aaaatttggt taaaacttca    6600
aaaattgtgt aaccggcaaa tgttacagtc tctgaatata atactgctat agtgagcaaa    6660
ttttgttctt gaataaaata actttgaatc tggttccttt agtatatttt aaaccagcct    6720
cataaactac ttaattaaat aatatttctt actctacttc ttaatatgct attaagggac    6780
attctacaaa ataagtgatg agtactcctc aaaactgcca aggtcattaa aaacaaggaa    6840
agtatgagaa attgtcatag ccaagagttg cttaacaaga tatgacaact taatataaca    6900
ttataaactt ggtatcctag atggaatcct ggaacagaaa aggaattagg tgaaaaataa    6960
gggaatttga ataaattatg cactctagct aataataatg tatcaatatt ggttcattaa    7020
tactaatgca agacatttac agtgcacatt ggtacgttaa tactaatgta agacattaat    7080
actaataatg taagacatta ataactgggt gtggggtaca tgggaatttt gtaccatctt    7140
cacaattttt ctataaaatc aaaactgctc taatttgttt aattaaaaga gattcaccag    7200
ggttaagaaa aaaattattt tctgtcatga agtgttttat tttctgcaaa atgattttgt    7260
tttatttagg agtggtatgc tgcttaagat ggaaaaatac atgatgatgg tgcatagtgc    7320
ctccatccca agcttgctaa cattaaccct tttgtggcat tatccagctt ccatatgtt     7380 ctttttaag ttttatttta tttattttta agttctgggg tacacatgcc agatgtgcag    7440
gtttgttaca taggtaaacg tgtgccatgg tggtttgctg cacctatcaa tccatcacct    7500
aggtattaag cccggcatgc gttagctatt tttcctaatg ctctccccac tgccctcccc    7560
caataggccc cagtgtgtgt tgttcccctc cctgtgctcc ctgtatccat atcatgaaat    7620
attttaaagc cacaggaaaa aaaagagaaa aacttaatga acaccaagtt acctccttcc    7680
aactttatcg tatcttaaac cctatgccat acttgctgga acttttttgtt ttaagaaatt    7740 aaaacatgca gatacagttc aggggccctc tgagcccctc cccagtctca ttccacttct    7800
tttcctcaga ggtaaccact atcgttaatt cagtgcttat cagtttcagg taagtcttta    7860
tatttctact gcgtatctat atatctacga acattacaaa tagtgatttg caggtaacac    7920
aatttacata aatggtatca tacagtatca ttctgaaact ttgtcttgtt tgtttaaact    7980
tacgtttgtt gagatttatc catgccaatt cattgatttt aatggctaga taatattcca    8040
ctgtgtgtct attctataga ttattgaatc aatctcttgt tcatttgtat tttctcctag    8100 cttttttgttt ccaaagaagt actgcaataa acaagcttac acatatctct gcatgcattt    8160
tctgagtttc aatctcggct gtatcactta ctaacttgtg ctcttgagct tgtgacttag    8220
tccttcatac tttagtgccc ttatctggaa aacggggata gtcataatac ccatctcagg    8280
aggctgttgg gaggttttat ggcatagcat gtataaagca tttagaacag tgcctgccac    8340
gtattaaatg ccatttcatt gttaattatt ttttaaattg ttgaggaaaa taccagagaa    8400
ggatattctg ggatctgggg tattaacatg tttagccttg ctagatattt ccaaattgct    8460
atccaaagtc attcagtcaa tttatattct cattagctgt gcatgaaagg actctttcct    8520
ccacatctta acaacacttt gtactactgg atatttcatc tttgccaata tttcaatgaa    8580
tagttttagt attcactgct gatcattacc ccaaatttat tcattagggt tgcaaaataa    8640 tgatttttt ttaattttat aggttttcaa aacaggaatg gataatgatt ttactgaat    8700 acttttttgca tttatgaaaa tgattaatta ttttttacct taaataatca ttgcattcct    8760
```

```
gggatcaaca ttgcttcatt tttttcataa actgctgaat tatgtttaac atattttatt    8820
tatcatttta aaatctgttt tcagaagtaa ttataagcct attttatcc ttctttgttt    8880
tgatgtcaaa attatacttg ctttataaaa tgatttgggt agcttttctt attttctt    8940
tcaccaaaac tatttatata agattagaat tatctactgt ttgaagtttt ggtaaaattt    9000
gcctgtaaca ttatctagcc ctgttgtttt ttgaggtggg agactttga atattgaatc    9060
aatatttaa tagccattac ttttaagtt ttctattcct ttataaacaa attttgataa    9120
ctcatatttt tctagaaaat taatcttaac ctggtttca aatttactac catgaaatta    9180
cttagtattt gcttatgatt taaaacttta tttatttac ctttcccatt ttcaattagt    9240
atttgtgatt tatatctctt ttcttcaaca gtcttattga cttgcatgtt tttagttttc    9300
aaaaaacaac ttttgaattg atatatcctt tctactgttt ttcatttat tttgttttct    9360
atcttataaa tcttgcattt tttaggttct tgattagaac ataattcatt cattaatctc    9420
ttaaaagcaa aatgcattta tctttataaa taaatcttga agtatctttt tagctgtagc    9480
ccacaagatt ttacatattt atcaccatat tttaaatatt ttctatttct gtcatgattt    9540
catccttaac ccatatttat ctgcatatgt attttaaagt ttgtaacaca cacaatttta    9600
ctgagtatat gtgtgtgt tttactagtg tttaatttt tagtttttat ttaattgcat    9660
tgtcagaata tacacccta agaataacaa caatatagag aaatacatag ttttcattt    9720
gtagaaattt tttatggctt attaatgggt aagttttata aaaatgccaa atgtaattga    9780
aaaatgtctt ggttgcaggt tccatagtaa tgaaatttgt catgaaaatc tatcgacatt    9840
gtgttacaat tataattaaa tatatatttg attaaatcaa atgaaattgc caacatttaa    9900
tcttttttta cttagaaagt tcaactaata tatgaacaat gttcaaccaa attttaagaa    9960
aaattttatg tagtaaatta cataaaatta cttatttttt atttgaaaag cttttatgtt   10020
ttctaatttt ttgtctgttt atcagtttct aataaagttg tgtttaaatt tttcattaca   10080
gttgcaggct atgttgtgtt aggttgctgg gtatatacaa tccaataatt gatttgtctt   10140
ctagctggat tgtacttta attattatat gtcctttatt atatccatta ttgttttgaa   10200
catggattct attttctga cattaacata acagctttga gacatcagta tttgcatgac   10260
gtatcctttt caccctttaa ttttggacca tttttatgat tttataaatt atttcattta   10320
taataagtat atgtctggat tggctgggtg tggtggctca tgcctgtaat ctcagcactt   10380
tgggaggcta aggcagacag ataatcagag gccaggagtt tgagaccagc ctggccaata   10440
tggtgaaact ccatctctac taaaaataca aaaatgatcc aggcatggtg gctcataccc   10500
gtaatcccag ctactcagga ggctgaggca ggagaatcac atgaacccaa gaggtggagg   10560
ttgcagtgag ccaagattga gccactgtac tccagcctgg gcaacagagc aagacttggt   10620
ctcagaaaaa aaaaaaagt gtatgtcttg actttaaaaa attcaataaa ctgacctgtc   10680
tttttttaaa aaacagcctt ttgagggtat aatttacata tcacagagtt cacctatgta   10740
aagtattcaa tggttttcaa tatattaaca gagttgtgcg accatcacca taatctaact   10800
ttagaacatt ttcttcatcc ccaaaagaaa ccttatatct gttaccagtc actcctcatt   10860
cccctcccac ccctacccct accccagcat taggcaacca cttatttatt ttctgtccct   10920
atagatttgc ctatcttgga catttcatgt aaatggaatc atacagtatg tggtcttttg   10980
agaccgtctt ctttcacgta gcatgatttt gaggttcatc tgtgtagcat gtatcagtac   11040
ttcaatctac atacatttac cgtaattact gaaccgtttg gactattttc aataatattc   11100
```

```
atttatgttt tctgtttgtt atgcttttttt tagtttctttt agttttttttt aacttttgtt    11160
ggattgatga catttttctac atacttagtt tttaatcctt tgcttattta gaaactatag    11220
attttactgg tacttttttca ttgctttttc ttaaaattttt cagatattgg ttgaactttg    11280
ttcagatatt agttgaactt tgtaattaaa aaatggttaa atattggcaa tttcctttgg    11340
tttaatcaaa catatattta attatagttg tataaatatg tatttaatta taattataaa    11400
acaatgtcct cagattgtca taacaatgaa cttaacatac tttatctgca tatcgaacac    11460
cttatcttgt gttcaagtta cactcatatc tacatactgt gtagagtttt aattatgttc    11520
ttttgaaata taaaaggtta tacttggtat caatatttga ttggccgtcc tgacatattt    11580
tgttaactct tgtgctcacc cttgtttctc tctttcatgg ctcccttctg gatactcctt    11640
ctggctaagg cacatcctct agttgttgtt ttatgcaggt ctgtaagtgt aaaccctctg    11700
actttgaatg tctgtaaaga tgctgaataa tttttttggct cagtgtaaaa ttctaagtta    11760
aagattactt ttttttctca tcactttgaa gacattacgc cactgttttc tagcctctat    11820
tgctgatgag aaaacttctg tcagtctgtt ctttatattt gaatatgcat tttccccttt    11880
cacagtgttt aggatggatt ttgtttattc ttgatgcttt actacagttt gattcttgaa    11940
caacacaggt tgcaactgtg gaggtccact tgtatgggga ttgttttcaa ccaatctcag    12000
atgaaaaata tagtattctc aggatgcaaa accagtggat atgtagagcc aattttttcct    12060
atgcacaagt tctgcaagcc aactgtagga cttgtgtata cctggatttt ggtatatgca    12120
aattttggta tacatgggag tgctagaacc aatctcctgc atatactgag ggacatttct    12180
atataatgta tctaagtttt gactgatatc tattccaatc aattcttggt gtctactgtt    12240
aatttgaaga atcaggtaat tgcttctgga aaattcttag caattatctc tttaattatt    12300
acacttctgt cattctccac tctctgcttc tgggattcca attaggtgaa tttagaagat    12360
tttcataact ccccctttct ctcttttatt tgtacatgtg tgtatatatg tatgtaaatac    12420
atatcacggt ctcctcctgt gacctccatg ggtctgcatt tcatcataag gaatagatgc    12480
ttcaatggtg gccagcagtt tcctcagggt cttctcagca gtgcatgggg cccacattag    12540
ctcctctggc tccaagcgaa gagatggtct ctagccccct gtttgatttg gggcacttac    12600
agtcctctcg ccagctaaac tctcacactc gtcagcatcc agacgctgag gggaaaatac    12660
cagctgcttc tgtgctctgc ttactcttcg gtacttctct gccatttctg gttcctgaag    12720
atgtttattt ttatttattt gagtctgact gtatctcttt ttaaaaacat gttatccacc    12780
attgctatat atttgaagca gagaaagtta gtgaagcata aacttcatgc tgaatcgagt    12840
gtctatatcc tggaattctc agcctgtacc ctctataaac taattttttcc actgtgaata    12900
agactaatca tgactctgtc gacatttaca tttttattttag aaaatgtctt ccttctgttc    12960
ctttgatcca agcttgactc accttacctt gaggttgcat ttacaaagga acactgaagg    13020
ttacccaaca gtatgtgggt gtcgttcatc aactacagtg actcaagaat atcaccagtt    13080
ggtttgcctt tctcatggtt ttaatgtttt ctcattaaaa ataaataaag cacagataag    13140
cagaaagaat aaccatccat ccaacaacta gaggaaaatt tatcaatggt tttgctttat    13200
ctttcctata attaagctat aaaaaacaac catccatgta acaactagag aaaacctta    13260
tcaatgactg tggcttatct ttcctgataa ttaggctctt tcagggagtt attaaccgat    13320
tttaaaactt ttgtctgaga ttgattagta aagattattt cttgaaccaa attgttcttt    13380
cgtttggcta ctttgattaa agaagaaaga agagataata attgcaatga ttcttttatt    13440
ttattttata gggtcgttgg ctgtgggttg caattaccat gtctgactca gtaattcttc    13500
```

```
gaagtataaa gaaatttgga gaggagaatg atggttttga gtcagataaa tcatgtgagt    13560
ggcttttttc cctcactgca tcttgtacaa ggagaggtga gaacaaaagt aggacaagct    13620
ggtcaagttt caaggagcag aaaaaaatca gcaacagtag gtagaagtat cattgtgtgt    13680
gattcttata cacaactgtg tggctctccc tagaatccat gtaacgtaat atctgaaagc    13740
actaggtaag aacacaccaa gtgtgtgtaa atgaaagcat ctctcaccaa cacctttcct    13800
agatagagta gggttgttcc agtggtggct gttatgacta cctttagtcc tgtattgtta    13860
ttattaatca taattgagtg agcgctcctc cttaggaaga actgtgccca gactctgcag    13920
accagaatga gatcatgtgg aggggcccta tagcactagc acctgggatg tcctgggctc    13980
agatggttct aagctattgt tttctaaccc tatgatttta catttacag atgcaaaac     14040 tgagacttgg atatgttttt gaaacttggc aaggaactca tgagtaaaat taatggaacc    14100
ataattctaa tccagttgtg tttgattccc aagcccaaga tattgccgtc tgtcaacatt    14160
atcatgcttc tttactttaa taagagtaaa caggcatgat agtgttgaat gacaaagctc    14220
cctagtggct tccttacacc cctggctata atcactgact ttcacctcct gccctgcatc    14280
tattctgacc tacactgggg aaaacagtat gtggtctcaa tcctatggct tctactagtg    14340
tagaagtgtt aatgacatct tgttattaac atcttattgt taatttgtgg tctatatttt    14400
aaacagataa attctgatgc ttttaaagaa ccagacaata aataaatatc aattttattt    14460
tgtagttcaa aaagttgctg tccatttgat attcagatga tgcaaatatt tcatgtcctg    14520
aagaaaagtc cataaatgag taaaggtagc agcactcctg gaccctaaac gagtgtcttc    14580
gtgtgtgtgt gtgtgtgtgt gtgtgtgtgt gtgtgtgtgt gtgtagaaag atagagagag    14640
acaatatgag caggaagaaa gaaaaggcaa atagtcattt gctaatattc catgaataaa    14700
ggtaatttat aggaatattt ttctagagca aatttcttaa tgactgcgtt gcattttgtc    14760
attattatta actgcttttt tgcgttgatt ttttttctg acagataata atgataagaa    14820
atcaaggtaa gtgactgatt tcaacaatgc agcatctttt ctagaataac tccataatat    14880
tcatatcaaa ggcacaaagc agagaatact ttcatgcaca ttgcacttca tataaaataa    14940
tatatacaat ccattctttt tctctttaaa atattactat aatttgattt taaaaacctt    15000
ttggaatatc ccttctaggt taggttcaaa tgtcccctct gtattcagga atggcacaga    15060
actcctgacc taagagggag gaggaaaagt tgaacaacaa gtataatttc atgggcattg    15120
gagaggtctc taaaccccaa attcttgcca caggcaaaga gtagagacct aaagtgtcat    15180
tattgcatat ttctgttcag ctaaagattt tgaattctca tatagaacac atatcagcta    15240
atcacagtct ggtatgaagg cgggattaga tgaggtctaa tttagaagac agaagtgagg    15300
catcaggtaa gttcctgaag tggaggtggt ggaaacggaa gggttaaagg tattttagaa    15360
attttaagta attcacagca gagggaggaa gtggagtgg taagattagc tttgggctgg     15420
gagtggtcag gtcagcctgg gcctctgaga gccacacgtt tcttattgcg tgggaagttt    15480
aaaaaatggg tgtggatgta gatgaatggc aaggagagga tgagtaggaa gttgaatgag    15540
ttgctttgtt tttagaggag gtgagcatgg aatgagaaga tcacagcaaa ttttgccaga    15600
gctgctgaga agaatgggag caatccgcag agaaatgaag tgtgcattgc atgttgagct    15660
ggagagcaca cattcactcc attaattcat tcgttttgca aatattgagt gtctatttgg    15720
tatcagacac tattgtaggt gctgcgggta tagaaaagaa caaaataggc aaaaatgttg    15780
gcccttgagg agtttacatt ttagtgaggg agatataata aacattgtaa ataaatcaaa    15840
```

```
tgtatagcat ggtagctagt gataatctat cactttcttt ctgagaagga aaaataaact   15900
ggaaatggag ctatgaaatg gtgcgtgggg ggtggggttg aaattttaaa gactttggcc   15960
aggcaagact ctgttgagta ggtgatttca aaggaaggtc tagcggaggt gatggagctg   16020
tccctgtggt tacctaaaga aaatgcacct ggggagaagg agtagcaggt gcccgcaccc   16080
agaggtggga acagttgggc atggacaaag gtcagcaaga ggccaggcaa gtgggtgtt    16140
gagaactaga atatagttgg aggaggtgag gtcagagagc caagggccag accgtgggga   16200
gtctcagaaa aaatttagga ttcttttctg ggccagaagg gaagcttagg gcagctgagt   16260
actagactct gcctgtgttg gtatccattc acaaggtggt gaggttgtgt ccagcaggcc   16320
cagcagcctg gcttaaggag aagagggcaa acagctggat ggatgcagga tgaagtttac   16380
aaggatgatg tagagaaaat aattgaggat gatggtgaga gtgtggttca aatgcctggc   16440
agagggacct tggctgcatg gggaaggaag caaaatctta atggggttta gcaatggaag   16500
gaaatgaagg atttaaagga ctgcatggct caagtgaggt tgacaaatag gtgtggaagg   16560
aggaaggaag cgagaaaatg aggtacatgg gcagtcacag agtgccaagg agttaaacat   16620
gtcagacagt agttcctggt gacagcaagg tccaggtgt  attcatggac tgcgtgactc   16680
aggttaagtc aagatccccg aagttgaaga ggtcaaatac aggttaaaca tggccttatg   16740
ggaaatgaaa tgaatgggaa atattaagga aatatgattc tatgaaaagt gtgggcatgt   16800
tcttgaattt ttcatcatta tcaacattat ttaatgtagt tgtaatattt ttaagcatga   16860
ggaagcttta aaattagcta atccaaccac ttcaacttac ccatgaggaa atgcagtcac   16920
aaatagattg agggtcatga ctgagggcaa agagttattt gttggtataa ctgggagtat   16980
agaggacttt ttactttctc tccatacctc tcaggtgttc atctctgtga atcgctagtg   17040
aacctgagat tgagctatac tgaaatctct agaagaggga aatctagaag aataaagctt   17100
gtgtttaaga tactaggttt ggccagaatt ttccagccag tggggatttt ctttcttact   17160
aaagaataac tcataaaatc accacctagg gagaatttcc cattgtattg gaaagggtgg   17220
tctttaaatc cttatgtttt tctcatcagg ttacaagatg agaagaaagg tgatggcgtt   17280
agagttggct tctttcaatt ggtaataaaa ctgtgttgat ttatggcagt gggtgtgcag   17340
ctataaattg tttagatcat gagggagtg  ttaaatcttt agtcatattg gcaggttttt   17400
aacttcagtg atcactttt  cagtcatagg cttttgcctat gtgataacat gctgaataac   17460
tattagaaat atattgctca taaagcatac aaatcctatc caatagatca gaaaaatgtc   17520
ttggaaaatt atcactaagc ccatggttat catatttgta aggaaagtca tcacaacaat   17580
cacatatata tatttattct tatgacaaat ctttagaaat tttaaagtat aggtgtttac   17640
tccaaatttt ctcaggatgg aggcatttct aggcagaaat tggcattctt catagtcact   17700
atcagttcaa caaacaatt  tatagtattt ctcaatgccc cacacagttt atctacttgg   17760
caatggcatc aatgacagtg attattttcc cctaagttgt agatgagtag ctaaaaacga   17820
aagtcagctc ctgaaataaa cagaatgaat tcagagagca ggaaatttat aacatgatct   17880
aacaatgtaa gagtctaatg ttttagataa ttgatgtacc gtgccgttta tttcaatata   17940
attagtatac gaactctgcc actcaattaa ggtgattccc atgaaatttg tgttgagta    18000
ctattcatga gaatctagta actaaattaa gtagtcctcc tacctctcct gctcttcacc   18060
catagatgat ctctgaaccc tttgtttttc aagtttcggt tttcttcatc aactgacatt   18120
tggctgatgt ttgtgggaag tttgtgtgca tttctccatg gaatagccca gccaggcgtg   18180
ctactcattt ttggcacaat gacagatgtt tttattgact acgacgttga gttacaagaa   18240
```

```
ctccagattc caggaaaagc atgtgtgaat aacaccattg tatggactaa cagttccctc   18300
aaccagaaca tgacaaatgg aacacgttgt gggtaggttg ttttttgtttt taattttttta  18360 cttttttgct catatcttaa attgtaattc aaaatgtata gagggatttt tactggctga   18420
gctggagtgg tatctaacac aaagagaata gaaacatgag tttacccata tttctagaaa   18480
ttactctgcc tcaagtttcc ttctatctta ctatgtttta aaatcttaat agaaacagga   18540
ttgaaagtca ctcaccaaat acattgccaa aatgttacca ctttattgag tataggcttg   18600
agcatgacac taccaatact taacgtcact agggaggtga cccatgaatt ttacttgagt   18660
atcatctcca agagttctat ttttccccccc caccaactcc cctctgcccc ttagctttgt   18720
ggctgtggct ggtgatccac ttgatcttaa cccttccatc tgtaatggga atttcatgaa   18780
caggctgcat tactttgagt aaggtacact agtctcaacc agtagttgag tttgtttttt   18840 tctttttttct tttttttttt tttttaagat ggagtctcct tttttgccca ggctggagta   18900
cagtggtgtg atcttggctc actgcagcct ctgcctcttg ggttcaagtg attctcatga   18960
ctcagcctcc tgagtagctg ggattacagg cgcccgccac tatgcccagc taaattttgt   19020 attttttagta gagatggggt ttcaccattt tggacaggct ggtctcaatc tcctcaggtc   19080
atctgcctgc ctcagcctcc caaagtgctg agattacagg cgtgagaaaa ctagggcagt   19140
gctgtgatca gaggcaacca cgcagaagta gccagaactc acacagacac agtcactatg   19200
ctactgtttt ctttgtgata agcctgacag gccaccttgt aatcagtgag tctgtcgtgt   19260
actcagggct gactcactgt catagcatgg cctttgcagt gtgcctcatg ctggctcaag   19320
ttcagaacag cttatttgca cataggaacc cacatattca ggttcaagaa tcaagggtgg   19380
ggcacatctt ggctagaaag acactaggaa tggctccctc agaggaattt atagttttca   19440
ccttcatttt tgaaattttc tataggcttg attccagact atgaatgagt ccttctaaat   19500
cattgacact cttccataat attatctctc ttagggtctt tcattcattt actcattcaa   19560
ccaaattttt tttaaacatc aaatatacca ggaactcatg aaagcatcaa ggacacagtt   19620
gtcttaagag catggtccta gccaggtatg gtggctcatg cctgtaatcg taacactctg   19680
ggagggtgag acaggaggat tgtttgagcc cagaagttcg agacaagcct gggcaacata   19740
gtgagaccct gtctctacaa aaattttttt aaaaaatagc ttggctttgt ggtgtgcccc   19800
tgtcatccca gctacttgag aggctgagat gggaagatca cttgggtctg ggtgtttgtg   19860
gctgcagttg gctgtgatta catgggtgac agaatgagac cccatctcag aaaaaccaaa   19920
agagtcatga tccctatctg tgtgaagctt aagcctagta agccatcatt cagtcaatga   19980
tcatttaaaa acatatgcag tgacagactt ggaggtacct gacagaaaac acaggataat   20040
atacaatgtg aattattctt tataaacaac aagcctactt attctatata agttccctaa   20100
tgtctaaata tgtatgtttc ttttctaaaa ttggaagttt cttttcattt gacaaactca   20160
gagcaatttg tataaaagag agattgagtt caacaaaagt ctttgaaatc cttcatttat   20220
gcgggaggac agaagtgaac tgcttttttac agagggtttt gaccacaaaa cataagatta   20280
atcattctcc ccttggagaa aaaaatgcat tcagacctat gtgtgatgta aattgaccca   20340
agccacggat aacacttatg aggataagtt tttgaggaaa aggtcctcaa gtatatctta   20400
tcatgcctta aaatttggaa ataaatgtga gaggagccaa aatttgaggc atatacatga   20460
tactaggtgc ttatgaatat ttatccaatg aattaaagaa tgaatctact ttcaacattt   20520
gcatcatagc catctattaa aaaggaattc tctgtggcca ctcattactc actgtcttca   20580
```

```
ttgttactgg atcacatacc tgaaggcgag caaagaatac aaactgaggc tttcagaagt    20640
ccactggctt tggctgaatt cacgtaatac caaatgtgaa tggacatttg tccttttctt    20700
tttaaaaaaa ttcatacaga tagctgaaat tgtatagact ataccttttct aggcatttct    20760
ttaccaggaa ctccttgatg agttaaatac tgtcatcgtg agttattgtg atcattgaca    20820
tgaatactat ttgttctatt ctgaataaca tgtttgttta gctgttttat ggtaagatca    20880
ccgcgatctt atgacttggg tgggacagag gagaaaagag aggacatttt tctacctgta    20940
agtagtttat atacctccaa agtcgcccaa actgtttgca ggtttctttc gtggaaaaag    21000
tatatcatta aaagtacagt ttctcctttt attacaatag atgtattagc cttagaatat    21060
acaagacaac ccaataattt tagcaacaaa agcatgtgtg tgtaatgaca ggagctggtt    21120
ttactatttt attatattgg tttccacatg tcaattgtaa tctagtagat ggaatttta    21180
agttaaagcc ttccagatgg ctgtcagtga attcactga taaggattac agagtgtcag    21240
gtctcttgat tagcttatca gaatttctgg tcagaacagt cgaataatag ataaaaaaat    21300
gaaagcagat gaaggaatag gaagttaaaa taccacagtt gcaatttcat tttattttct    21360
tttatccaat taaagtgtaa acactcaaat ggaagccaca aagtctcgtg taacttaatt    21420
gtagaagaga catactgtaa tttctgccat attctatggg tcacagaaac caaccctggt    21480
gtaatttgga aggagtctaa acaagtgtga atattgccag atgagaattt taggggcttt    21540
ttggaggctg attactactg cgggcattgg ggagctcaag tcttcacttc ctctcataca    21600
gataaatcaa tgcagaaatc taggcctgtc ctttcacttg gatttcagtc tatgttctta    21660
gcaatatata ttcagtttgt ataagcaagc actattttgt agctagacag tttaggctat    21720
atacttttgt aatggctttg ttgagataca attcacatac tataaaattc acccactcga    21780
agtgtacaat tagatgtttt ttagtatatt tacagagttg tgcattcact gccacagtca    21840
attttagaac attttctttt ttttcctttt ttttaattat actttaagtt ttagggtaca    21900
tgtgcacaat gtgcaggttt gctacatata tacacatgta ccatgttggt gtgctgcacc    21960
catcaactcg tcatttaaca ttaggtattt ctcctgatgc tatccctccc ccctccccc    22020
accccacaac aggccccagt gtgtgatgtt ccccttcctg tgtccatgtg ttctcattgt    22080
tcaattccca cctatgagtg agaacatgta gtgtttggtt ttttgtcctc gcgatagttt    22140
gctgagaatg atggtttcca gtttcatcca tgtccctaca aaggacatga actcatcatt    22200
ttttatggct gcatagtatt ccatggtgta tatgtgccac atttctttaa tccagtctat    22260
cactgttgga catttgggtt ggttccaagt ctttgctatt gtgaatagtg ccacaataaa    22320
catacgtgtg catgtatcct tatagcagca tgatttataa tcctttgggt atatacccag    22380
taatgggatg gctgggtcaa atggtatttc tagaattta aaacattttc attactagaa    22440
aaagaaaccc cttgcccctc ggccatcact ttctagtacc tcatcctcct ccctatccct    22500
aggcaacact aatctgcttt ctgactgtag atttgcctat tctgaacatg tcatattaat    22560
aatatcatat aatatgtgat cctttgagat tggcttcttt aacttaagca tgtgtttttt    22620
gcagttcatc cacatgtatt tttattgcta aataatattt cgttatatgg atataataca    22680
tgttatgtat ctgttcatca gttgatggac atttggattg ttcccacttt tgagctatta    22740
caaataattc tgctgtgaac atttgtatac agattttgt gtggacatgt cttcatttct    22800
cttgggtaca tgtctaagtg tggaattgct gtatcacatg gtaactctat gtttaactat    22860
tctaggaact gccagactat tttccacagt ggctgcacca tttacatttc tgctaacagt    22920
gtatgagggt tctaatttct ccacatcctc accagcactt gttatttagc atctgtgata    22980
```

```
tctctcatag gtagaataat gaccccccaaa gatatccagg tccttatccc tagaacctgt    23040
gaatgttacc ttgtatggga aaagggtcta tgcagacgtg attcagttaa caatatcgag    23100
atgggggaga ctatcctgga ttatccaggt gggccctaaa tgcagtcatg tgtgttctta    23160
aaagggatgg ttgctaagaa gaaggcagag ggggatttgc ctgtagagag aagagtagag    23220
gcaaggtgac tacagaaaaa aagaatggaa tgacattgcc acagccgagg agtgtcagca    23280
gctatcaaga gctggaagaa gcaggggaa atttctctct tagggcctta ggagggaaca    23340
cagccctgtc agcaccttga tttccaccca gcgaagctga ttttgggcat gtgaggggat    23400
acatctctct tgttttaatt gtggtaattg ttacagcagt cataggaaac caatacaata    23460
gccatcctag ggagcaggaa gtggaatctc attgtggttt tgatttgcat ttctctgagg    23520
accagtgatg tttggcttct ttttaggtgc ttgttggcca tttgcacatc ttcttcagaa    23580
aaatatctat tcagatcttt catttggaaa taaataatat aacaaaatat gtattcagcc    23640 cttttttaaaa ctgggatata tgtctactga ttattgagtt gtaggaattc tttatatatt    23700
ctagatataa gttccttatc agagatacaa tttgcaagca atttctctca ttctttgggt    23760 tgtcttttcta acttcttgat aattatcttt gaagcactga agtgtttaat tttggtgatg    23820
tctagtttgt tcttttgttg cttctgaatt ggtgtcatat ctaagaaacc attgccaaat    23880
ccaaggtctt gataattacc tttgaaccac taaagtgttt aattttggtg atgtctagtt    23940
tattcttttg ttgcttctga attggtgtca tatctaagaa actattgcca aatccaaggt    24000
cgtgaacatt acacttgttt tcttttaatg gctctggcca tgtgaagtgc cagcttcccc    24060
ttcatctttc agtatgagtg taaatttcct aaggccttcc cagaaactta gcagatgctc    24120
taatccttcc tgtacagcct gcagaattgt gacccaacta aacctctttt ctttataagt    24180
tacccagtct caggtatttc tttatagcag tgtgagatga actaatacac tcacggttag    24240
tctacgatcc acttttgagta aattttttgta ggggtgaatt aggggtccaa attgattcct    24300
atctgcatgg atagccagtt gttccagcat catttgtgga acaactattt ttccccatt    24360 gattaatctc agaatcctta tcaaaatcaa tttactgtaa ttaagagggt ttatttgtgg    24420
actctcaatg ctattccatt gacctacaca tctatcttta tgccagtaac acactgtttt    24480
gattaccgta gttttatagt aagttttgaa atcaagaagt gtgattctac tactagggat    24540
tgtctattct gggtctcttg gattttcata taaattgttt aacttctgca agaagtcag    24600 ctagaatgct aggaattgca ttgactctgt agatcagttt aaggaatatt gccgtcttaa    24660
caatattaag tcttctgatt cgtgatccac ttatttgcgt ctgctttaat ttatttcaac    24720
aaggttttat agcttttcaga atattttgca attttttgtt aaattgattg ctacgtatt    24780 tattattttt gatgttatca taaatggaat tgttttcttta attttatttt cagtttgccc    24840
attgctacta tcgcaaaata caactttttt tgtatattga tcttttatcc taaacctagc    24900
tgaactactt atgagttcaa tagttttta gtgggctctt taggattttt tatacaagac    24960
catatcatct gcaaatagaa ataactatac attttccttt ccaatctagc tgccttttt    25020 atttttatttt attttatttt attttatctt attgcctaat tgttttggcc caaacctcca    25080
gtacaatgtt gagtagaagt ggtgagagca cacatccttg tcttattcct atcttagggg    25140
gaaagcattt agtctttcac cattaagtat ggcattagct atgactttt cacaagtgtc    25200 ctttattatg ttgaggaatt cccttctaat cctagtttgt agagtgttct aatcattaag    25260
tcatgaattg agtcatgtgc ttcatctaca tctattaaga tgatcatgca gttttgccca    25320
```

```
ttataatatt gatatggtat attacatcaa tgtatattca tatgttcaat tacctttgca   25380
ctcctggaat aaatcccacc aggtaataat gagtaatcat tttactatgc tgcaggattc   25440
aacttgtttg tatttagtga agattttgt gtctatatta ataagagata taatatataa    25500
gagttttctt ctcttataat gtctttgcct gcttttggta tcggataatt ctggcctgat   25560
agtttggcag tgttcccttc cattctgttt tttgaagagt ttgtgaagaa ttggtattag   25620
ttctttaaat gctttgtaga attcttcagt gaagtcatct catcttagac tctttgttgt   25680
tgaaagtttt tgattgctga ttcaatctct ttagttgtta taggtccact cagattttct   25740
atgtctttaa aaatatttt taatttggca cataaaaatt atatatattt atggtgtgca    25800
gcatgatgtt ttgaaatatg tatacattgt ggaatggcta aattgagcta attaacatat   25860
ttactacctc acacacttat cttttttttgt tgtaagaaca ctaaaaatct actcttggct  25920
tcaggcttcc tgggatgcca aaaaactgtg tgtccgcttg ctttctcaat ggggaggctt   25980
gtggtctggg gcaaattttc agccctggtc actggctgcc tggaaataga ttcagtgctg   26040
ttgttggggg cacggtgggc atgagattaa cctctagtac tgcgggctga gtgggagcag   26100
gttaaggcct gtaactgcca gctttccccc acttccctag tgacctgtat gacttagcag   26160
aggcagccat aatcctcctg ggaacataac tccattggac tgagaaccac accccatcc   26220 cccacagcag ctgcagcaag ccccgcccaa ggagaggctg agctcagagg cgcctatccc   26280
tgcccctaca tggtggtctt tctctacctg ccctggtagc caaagacaaa ggcccaattc   26340
tcttgggaac tctgtggccc tgcccactgc ttgggaaacc tgaatagata accaggtgtc   26400
ctgagggcaa cttttgcattc tccctatagg accatagctg atgcactctt gaaagtgcca   26460
cctcctagct agaggccaac caacataaaa ccaacacact aaataaaaac acaacagagg   26520
accttcacgg agcccacttc actcccctgc tgcctccacc aggtgcaggt gctgttatcc   26580
acagctgcaa gaactgaaga cagatcacat cacaggactc tttgcagact cttgccagta   26640
ccagcccaga gcctggtaac tttgctgggt ggctagaccc agaagagcaa aaacaatcac   26700
tacagtttag cttaccggaa gccccattca taggggaagg gagagaacac cacaccaagg   26760
aagcacacca tgagacaaaa gaatctgaac agcagcctat gaatcccaga tcttccctct   26820
gacatagtct acccaaataa gagagaacca gaaaagcaag gttctttaac accctgaaaa   26880
gatcatacca gctcaccagc aatggatcta aaccaagatg aaatctctga attgccagaa   26940
aaagacttta gaaggttgat tattaagcta atcaaggagg caccagagaa aggttaagtc   27000
caactgaagg aaataaaaaa catgatacag gatatgaaag gaaaattctt cagttaaata   27060
gatagcataa ataaaaaaac aaccacaact tctggaaatc aaggacacac ttagagaaat   27120
gcataatgta ctggaacgtc tcagcaatag aatcaaataa acagaagaaa gaaacttcag   27180
agtttgaaga catgggtttc aaattaatcc atcaaagaca agaaaaaag aatttaaaaa    27240 atgaacaaag cttccaagaa gtctgggact atgttaaatg accaaaccta agaataattg   27300
gtgttctcga ggaagaagag aaatctaaaa gtttggaaaa tatatctgaa ggaataattg   27360
aggaaaactt ccctggcctt gctgaaggaa gatcttttgt ctagggatgt agacatccaa   27420
atacgagaag atcaaagaac acctgggaaa ttcattgcaa aaagatcatc acctaggcac   27480
atagtcatca gattatctaa agtcaagatg aaggaaagaa tcttaagagc tgtgaggcaa   27540
aagcaccagg taacctataa aggaaaacct atcagaataa aaacagactt ctcagcagaa   27600
accctacaag ctagaaggga ttggggtcct atttttagcc tcattaacca aaacaattat   27660
cagccaagaa ttttgtatcc aatggcactt aacttcataa atgaaggaaa gatatagtct   27720
```

```
tttccagaca aacaaatgct gagggaactt gccactacca agcaaatcag ggaaatgcaa   27780
atcaaaacca cagtgtgtta tcatctcact cctgcaagaa tggctataat caaaaaatca   27840
aaaaagaata gatgttggca tgaatgtggt gaaaagggaa cacttttaca ccattggtgg   27900
gaatgtaaac tagtacaacc actatggaaa acagtgtgtg attccttaaa gaagtaaacg   27960
tagatctacc gtttgatcca gtaatcccac tactattaat aggcatgtac ccagaggaaa   28020
ataagtcatt atacaaaaaa gatacttgta tatgtatgtg tatagcagca gaatttgcaa   28080
ttgcaaaaat atggaaccag cccaaaggcc catcaatcaa cgagtggata aggaaaatgt   28140
aatatatata ttacgtatga tacagatatg atatatatgt aatatatatt acattttata   28200
ttactatata ttacatttta atatgttttt gtgtgtgtgc atatatatat atatgcacac   28260
acacacacac acacacacac gcaccatgga atactactca gccataaaaa ggaatgcaat   28320
aatggcattt gcagcaacct ggatggaatt ggagactatt attctaagtg aagtaactca   28380
ggaatggaaa actaaacggt gtatgttctc actcatatgt acgagctaag ctatgaggac   28440
acaaaggcat gagaatgata cattggactt tggggacttg gaggaaaggg tgggtggtga   28500
ggaataaaag actacacact ggatgcagtg tacactgctt ggatgatggg tgcaccattc   28560
taaaatctca gaaatcacca tcaaagaact tattcatgta acccaacacc acctgttccc   28620
caaaaaccta ttgaaataaa aattaaaatt ttttaaaaat aataaaatgt acattataaa   28680
acaaaaaaaa taaaaatcta ctctttcaat aattttcaag catacaaaac attgttacta   28740
actatagtca gcccagtaaa tttcttgaac ttattcctcc taattgaaat tttgtatttt   28800
ttaaccatct ccctaatctc cccacctcta gcccttagta actaccattt tactctctgc   28860
ttctatgaat tcaattttt tagatgtcac atttaagtga gattacactg tatttgtctt   28920
tctgtgcctg gcttatttca cttaacatga tatactcgag gtgcatctgt gttgttgcaa   28980
aggacaggat ttttttaaaa ggctgaataa tattccatta tctatatgta ccacattttc   29040
tttatccatt catttgttga tggacacata ggtggctatt gtgagtaatg ctgcagtgtg   29100
catgggagcg tagatatctt tttgatatat tggtttcatt ttccttggat atatacccag   29160
tataggattg ctaggttata tagcagttct atttctaact ttttgaggaa cctacataca   29220
tatttccata atgactgtac taatttacat tcccaccaac agtgtacaag tgttcccttt   29280
tttccacatt cttgccatca cttgatgtca tccttctttt ttataataac cagactttgc   29340
ttcatgtgtt ttggaggctc ttttttttagg tgcatatatc tccataaatg ttatcacttc   29400
acgatggatt gacccttta tctttacaaa atgattttta tctctagtaa caagttttta   29460
aagtccattt tgtctgatat tagtatagcc actcctgggt tcttacggtt gcttttttgaa  29520 atgattttgt ttttctatct ttttgtttca acctgtttgt atctttggat ctaaagtgtg   29580
tctcctgtag acagtacata gttggatctt gttttattta atgcaatctg acaatctctg   29640
tcttttgatt gtattgttta atccattata tgtaaaacaa acataacatc ctgaaaagtg   29700
gggggaaaaa gtcaactggc tagagccctc aggagccaag taataacatg ttgataagtt   29760
ccctgggtat cttatgcctg atatgtacta gattaagtgt tagaaaagct ggcaaactgg   29820 aaacccaat gagtgcagac caaaaagact caacaaaatc ctgcttttc tagatagtgg   29880 gtcagaaaga gaaagcctag tagaaaactt ctaagcaata attgctctac tctagccaaa   29940
caccacagaa gaaaacggtg acctcactct cacccatgcc agcgaatgtt gatttgggag   30000
catagactct tccacacttg ctaggtggta ataagcccct cttgtgccac cccctcactc   30060
```

```
accccccatgg tgtcaatgga gaatatgtgg gaggcctgac tcatccccac tatagtaagg    30120
cacctctccc cttacctgct gggttggggt gacagagtca aaacattacc accaccgcca    30180
tggaagggga aatcaagaca ttttcagatg aaataaatca agagaatttg ttgccagctg    30240
acttacccca aagaatggc taaggaatgt tctttaagca gaaaggaaat aataaaagaa    30300
gtcctagaca tcaggaaggg agtgcgtagt aacaaaacta tgagtaaatg caatagacct    30360
tccttctctt aagctttctg aattatgttt tatggtagaa actctaacac tgtgatatga    30420
tcctactctg acactgtctg atgtgtgttt aatttggaaa tagataagac acttattaac    30480
gaaggagagt agaggtatgt aatgggaggt aatctttata tatttcactt gaattggtaa    30540
aatgacagca ctagtagact gtgaaaagtg atgtatctat aatgtatttc ctagagcaac    30600
cacttaaaaa gctatacaaa gagagacact taaaaacgct atagataaat caaaattgaa    30660
ttctaaaaaa atgttcaagc agcccatagg aaggtaagag aaagcaaaca cagaaataac    30720
agagagaaca aatagaaaac aagaaagaaa atgacatatt taagccctaa tatatcaaaa    30780
tataagcaag atttttgta gatatagaaa agattaccct aaaatgttta tgaaaatgta    30840
aaaaaactgg aatagctaaa ataatttga aaaagaataa taaagtgaga gaatcaatc    30900 tacccaattt caagacatat tatatagcta atgcagtcaa ggctgtgtgg cattgacaga    30960
ggacagatat atagaccaat ggaacagaat ggagaactca gaaatagacc cacacaaata    31020
tgtccaattg attttgaca aagtggaaa aacaattcag tggggaaag ataagctttt    31080 tatcaaatgc tgtggagca gctggacatc cataggcaa aaaatgaaa ttacacaaaa    31140 attttcttaa atgaatcatg gacttatatg taacaaataa aactaaactt ttagaaaaat    31200
atggaagaga ccattttcat gttctagggc tggacagagc atgtagatga caccaaaagc    31260
acaattcata aagggaaaat ttgataaatt ggacttcaat aaaattaaaa actttgtaaa    31320
agatcctgtt aagagaatga aaagacaagc tactgactgg gagaacatat ttgcaacttg    31380
tatatccaaa aaaggactag atcccgaat atataaaaaa ttctcaaaac tcagtgttaa    31440
aataacaata gcaaatttca gttcaaagat gggaaaaaga catgagtaag gacaaaagat    31500
ggcaaatgag cacatgaaat atgttaaaca acatcaatag agaaatgcaa attaaatcaa    31560
aatgagatat tactatagac ttattggaat ggctaaaatt aaaaatagtg ataaccctaa    31620
atgttgatga agatgtggaa gaattggatc actctaccat cactcatgcc attcaaacca    31680
tgtcatagct atcctggaaa acagtttagt aattaaaaaa attctaaaca ctcaactacc    31740
atatgactca gcatttctac tcttggggat ttattccaga gaaatgaaaa cttatgctca    31800
cataaaaacc tatacacaaa tgttgatagc tgcttaattt gtaatagata aaaattggaa    31860
acagcccaga tatcctccaa aggatgagtg gttaaacaaa ctgtgatcca tctatctata    31920
ttatatggaa tcctccttaa taaataggaa tgaactgtta atgatgaaac ttgaaagaat    31980
tatgctaagt ggaaaaaagc caaccccaaa aggttctaca ctgtgagatc catttatatg    32040
acattcttga aatgacaaaa ttacagcaaa agaaaacaga ctggttgtag ctggggctaa    32100
ggaggatatg gggattggat agaagcatgt ggagatataa aaggacaata tgagggagtc    32160
ttgagatgat gagaatgttc tgatcttgat tatatcactg tcaatatcct gggtgtgata    32220
ttgtactaca gttttgcaag atatttgcaa gatatggctt tagtaaatct gtaagcttga    32280
tgtgtaaatt gaatgacaaa acaaggtaaa atgaaaaaaa aaaggtaaa aagtttccaa    32340 aacaaggtaa aaagaaacaa aaaagcaaaa taagtcctca tgtcataata atttgtaaaa    32400
cgtctcttta tctttttcc tctaatgtca tctctctccc ttctttgcta ttcaacaaat    32460
```

-continued

```
ggggaatctt aattcattca agtagattca ggtctgtttt tgctgttaaa aaaatgccat    32520
tctgtggtcc aaatcacctg cacactttat agaatccttc ctggggtttt atgatgacaa    32580
gtgttcccaa cattcaggca ataaagacct tggtatgcag tcaagggagc aaagccaggc    32640
ctgctctttt ccttcctgtc agttttctg ataggttttt tctgttgttc cagaaatatt     32700
atcaagttct ctaaagcctt aatcacctct tcttcccaga ataaataaa aatgagttaa     32760 ccactcattt cagagacacc gcaggagtga agagagtgat aaactgcata tatctttatc    32820
tgcaccatcc agcagtgata gaattatctt gacctttgtt ccagaaaatc ccagagctgg    32880
gccagtgccc aacacccctta atccacatat gtttgtaaac tggcatttt aatgacagtc    32940 gcttcatcac ttccgcttac agtgcttgta gaataaagac accacaggaa atttaagtta    33000
tttattgtta tcattttaat tgtcacataa gtatacatat ttatgggata tagtgtgatg    33060
ttttgatgca tgtatacaat gtgtaatgat caaatcgaat aattagcatt tccatcacct    33120
aagacattta tcatgtcgtt gtggtgagga cattcaaaat cctctcttct agctctttg    33180 aaatagtcaa tgtattattg ttaactatta tagtcaccta ctatgcaatg tagtaccaga    33240
acttattcct gaacagtaac tttgtacctg ttgaccaacc tctccccatc cctccccctc    33300
cactgctctt cccagcctct gttaactact attctctaag taaaatgttt ggacaaatgc    33360
ttatagtttt ctggtttggg acaccccaaa acaagctgaa aatgaagaga attgactcat    33420 gtataccttta gaaagctttt acttataata atatagtata ctctctgttc agagatattt   33480
agcttttata agagcctctg attgtggata ttcatcgata agtttatgat tttctagttc    33540
ttgttcatct cagggttctt cttagtcatc atgaaagact gggaatgtgg tgagcacaag    33600
agaccttagc tggttttgag gttgtcagaa gggttgacca cagcagttat ttcccttcct    33660
aattagtatt ttgaaagtca aagcaaaatc aggaaacatt tattgatttc aggcagagtg    33720
accaagcagt gtaagcccag ccccttgacct tgagtagctt gcaatctact agcaagacaa    33780
gcataaatgt actcaatata aatatattca ataaagatat tgactaatag tgcagtttat    33840
tctgtattaa atgaattatg ttgcaatgct tgacctgagt tcaatagaga aaaaaaatca    33900
agctcaagcc acaaaagaa ggctgacaga gagcggaaag gatgtaggat gaagaaccca     33960
tgctgaagag gctgcttgct gattctctaa agtagactct ataccattta acttgtccct    34020
gaagatcata actgtcatca accaatatgt taattttcta attatggaat gccttcattc    34080
ataaaagcaa tttcagaatt ttttttttcct ccactccctg gcactgccaa tcccaaaccc   34140
tgtgcagcaa catggtagtg ctgctgggaa aaatgccaaa gtattttct ttgctattt      34200 tcttcttgct atttcccaca agtgtctttg gcttcaacct tagaaattgt cctggtgaat    34260
gaacttaggc tgtagtcagc aaaaagacag ggctaataaa atgcttttct ctcccatggg    34320
aagataacag gcacatttt cagtgtcact ctgagataga gaagttgaaa agctggctag     34380
cattcctaga agaggtaaca gtaagcctcc tgatttacag cacacatcgt tctatcagtt    34440
tcttttcaga cagcctgtct ggcttttgaa aatctttctt gcctgtgatt gctctatcac    34500
tgcatgatga gtatgcatgg aagagactaa agtggaccaa gccctgggct gccatttagg    34560
gtaccctggc ttccaacaac tgctaattaa ttatttcata gtcctagcat ctctgcctat    34620
aaaaatgaag gggatatgca tatttctgt gattggtacc atgaggtctg tttagaaatt     34680
tggttggatt tattataatt ttgcatagat aaaatgtctt actcatgtct aatagaaata    34740
tactatatat agtatattta ttatatatta tatatatatt taaaatatat atattttta    34800
```

```
aatccctcta tatccacaaa tgtaatctct ggtggcttga tcctacttgc aagtctgaac   34860
attcttttcc ctcttttgaa ggttgctgaa catcgagagc gaaatgatca aatttgccag   34920
ttactatgct ggaattgctg tcgcagtact tatcacagga tatattcaag ttagtagctc   34980
ctccgtataa tttatagatc aatatctgac ctcaaagaca ctacaatgag atgcaatgtg   35040
ttgccactct ttaagctaat cagaagccct aagaactaca gtctgtttcc agaggacatg   35100
agagaatgga gagggattct tctctcagat ggaaacttag gaggatacaa gtggctgtcc   35160
agagagatgc ataatagact cgtagttgta atgtcctgtc ctccccctgc ctttccctac   35220
ttcatcctct cttctatatc cagaaatgga catttgcagg tgtgtttgta gggggcagtt   35280
gagtagcttg aagaatgtgg ggcaggggga gatagaggaa agcaaaattt actttctttt   35340
tctcgcattg ctaaagtctc aacaaactgc attccaaccc aaattctgaa aggctgaatc   35400
tagagcatat tttagattta agtgttggaa gggcttggag gtacttaact cttattaaga   35460 aagaaaata tttatctttt tgccttcttt tgtagaaaaa taatgaattc cttcccattc   35520
attcaagaat tccacacagt gctgtttgta aagagaaatg aatcattttt tcccatttag   35580
gcattgggaa tttaatgac aggcttttt ttttttttt ttttttttag ttagggaaaa   35640
tctatcagca gattagattt ttgctgatgt cataattttt gttttacatt tcttgaaaat   35700
tattgcctga aaactatgca tgaatgcttc taggcaggtc tttccgggag gaaattcact   35760
cagaaatggc attaaaaata gttatttaag aacaataatg ccttattttt ggtgctgtga   35820
gccttctttc acacatgggg aaagtgaagc tctgtagggt aaagtccaga agacatgggc   35880
ctgcttaagt gtcagagctg gattcaaacc caaatctcag gctaccctgc tgaaggttct   35940
gtttacctcc acttttagca gcagatgaca gagctcacat cttagttccc aagaagaggc   36000
attttctgaa ttactttccc ccttttctca actgttgtat tgaaagtact tcttctgaa   36060 aaaagaaatt aacaaatatt tcaaacattg caatgctaaa cattcctttg tccatttcca   36120
gatatgcttt tgggtcattg ccgcagctcg tcagatacag aaaatgagaa aattttactt   36180
taggagaata atgagaatgg aaataggggtg gtttgactgc aattcagtgg gggagctgaa   36240
tacaagattc tctgagtaag tagctggtaa aacagtattt tagtgtgtga tttttggata   36300
ataaacccct tgtttctaaa ttaaataaaa atttaaaaat attttcagtt ttcctatgtt   36360
tcatctctta aattgggctt tcatatgtgg catggctttt tcataagtaa tacactgtca   36420
aatatggaca ttaaaattg aaacccaagg tactgcaatt tggtgtgtag accttaatta   36480
aaatattaga aaggaaatat tatagaagac agttaaaaag gttatttagc tgtccaggtg   36540
taactggatt taaatccagt ttacacctag tttaggtcat taacagccac ccaggaattc   36600
taaatgagag gaattagaat tggtcgaacc ctattgaact gaattttgag gtcccctgaa   36660
agacagtcac tctacagtgt agataaagca cactgaaatt caggacccct gacttccggc   36720
acttactctg ctccttactg tgaccttgag cagttatcta accctgctgg aacacaatgg   36780
cctaatacct gggtgatgtc ttaggttctt tcttgctgtt tagttccaag ctctcttcac   36840
tccaactgga caagagatta aggaaatgtt ctcaggaata tgaatttaat ataattatat   36900
tcaataaata ttctggagca attgccttgc acttgtgctc ttgaggaact tacagcctcg   36960 tagggggaaat aagaaatgca agcaaataat cagaactaac acatattgtt tattatatga   37020
taggcgctgt cctataggct ttacatatat tcgctacttt aatcctcatt attacccatt   37080
ggggtaggtt ctattattgt tcttatttta cagacaagaa aattgagcca caaaaaggtt   37140
aagtaacttg cccaacaaga gtctgtattc aaattcctag tctggctcca gaatctgcac   37200
```

```
tcttcaccac tactctatac tgcctatatg cagaatgcaa taattccaca cacatacaaa    37260
tgcacaagga ttaattacag tgttacggaa acacagggag aaaggtgtta cttcttcttg    37320
ggggattata caagattgat gcacgagaag gtatgtgact agaaccttga ggctgaaagg    37380
attcagcagg catgaagaaa gaaaagcttt gcaagacaga gcaaggatat tagctatgta    37440
aaagaaaaag acaaataaga tggtttccaa aagcctttat caacactgag taccagctgg    37500
gaaacctaga ttaagaacaa aattgattgg ctatcaggaa agaggcttga taacatccca    37560
aggtgcagca aattttccaa gatctgagag gctgttaatg ctatccaagg gtgataggga    37620
tagagagatg ggaatgttta aaagggaaag actgagactt tcagcaagat atttgaatga    37680
tcaaattcag ttttagtgac caaaatcttt ctggtttcta gtgatattaa taaaatcaat    37740
gatgccatag ctgaccaaat ggcccttttc attcagcgca tgacctcgac catctgtggt    37800
ttcctgttgg gattttcag gggttggaaa ctgaccttgg ttattatttc tgtcagccct    37860
ctcattggga ttggagcagc caccattggt ctggtaagaa tgtcttttg catctctcca    37920
tgggaagaca tttgccttca taaacagcca aaaatgtgaa gcttgagtcc cttttcctga    37980
gtacagttag caacataatt atcactatct tcatgtagtt tgttagatta ctccccagtg    38040
tcaaatgaca tttcatcgaa tagggattaa tgatgtttta ataggtaaat attgttttat    38100
taacagcaat tacatttatt gagcattcac tgtttctcta ggcactacta ggagcttaat    38160
agtcattatc tctaatcttt acaacaatct tataaagtga gcactaacat cattttaaat    38220
ataagaaact aggctcagaa aggtaagggg atttgtctgg gactgcacag ctggcagagt    38280
aggattcaag tctaagggc tctgactcca aaccccactc actctccaat atgcctattg    38340
ttctccatgt cctcccaagc ttgggcactt ccctgaaaag gcacaacaga caaagagcat    38400
taacaagcac acaagaagga tttctgcaat cacaactgtg ttctccattt catcttatct    38460
ttcagataac ctctttcaga gagaggtgat ctgacccatt ccaagagtta tcccagtcac    38520
tgtctcggtt ccccaggaat tgaggcctgg acaacatata ggaataggaa tttcgggtca    38580
catcagctaa aaacactccc aaggactgag aaattattat tagagcagcc acattagata    38640
gcacgttatg gaatcaggca tactaaaact gtgctataaa tgagaataga atttaactga    38700
aaaactgcat acaccctcac acatcgttga gcaataggta ccaacttcct attgctcaat    38760
agcaaaatat tctcacagtg tctacattat tcaaacattt cccagataaa atagaaaatg    38820
gtttaaagtg acaatagcaa agagctcgct ccatttcatt aggtcaccac ttggctgtac    38880
cgctaacagg ttgtgtgact caggaaaaat ccatttaacc cctgaaaacc tcagtttcct    38940
tgtctttaaa atagggataa tacctcccaa aaacattatg atgattcagg gaataatcca    39000
cgttatgcat ttaagccgtg tcgggcacag aatcaattgc taaagagaga tgtatatgtt    39060
tttcaatcca ctatatcatt caagttttac ggcagtcttt cctactaacc actttccaac    39120
tatactccag agaaccctca acttccacag aagagcttca ggggttttgc aaacattttt    39180
tcatttttt tctgaataca ctaatctctt tcttcaaacc tgtgataaag taatatacac    39240
actcacgtgg atcataggcc acatttcaac atgttggagg ttaacatata gcccagttca    39300
cttggtttta aacagctcta acgcttagtt tctctagtca tctcagtacc catttctagc    39360
ttctcataaa ctcgtcactg atttggaatg ttgtaggtct gcacatgtct tgtcttgctt    39420
tcaagtctgt gtatgcttgt ccttatacaa caaacttcta caagcaacta tacaacaaac    39480
tatacaagca acttcactag gctcaaatgt aaattttaat gttaataaaa acagcttcca    39540
```

```
gtcttggtaa cacagtgaga tcccatctct acaaaaaaaa aaaaaaaaat ttttttaaa   39600 tagccaggca tggtggcatg tgcctatagt ctcggatacc caggaggctg aggccagtga   39660
aatgcttgag tacaggagtt tgagactgca gtgagctagg atcatgccac tgcattccag   39720
cctgggcaac agaacaagaa cccgtctctt taaaaaaaaa aaaaaaagc  ctcactttcc   39780 ttactgttac atgtttaatt cacatgtttt ataaaatgta cactgatgaa attaatatat   39840 tgttttaaa  aactactatg aatacttact taatttacat cttagaattc catctaagat   39900
tttgataaga gttttgctgc taaaagtttg gaaaaactac tggaagataa actcccttaa   39960
tctgggtatt atatatattt ttatatttct gagctagttg atcttccgca atatgtgttt   40020
tttcctcttc ttatttatta atctgtgcca gggttttctt tgggggttca ttttgactag   40080
gactcaatcc aagtcagttt tagaaaaagt aatgtgtcta ctgttaagta cagatgtctt   40140
ttcatttcct tttgtaaaaa tcaaaactac atagttgagc gtctccaact gagtgaaaat   40200
ggactttctt ttctggaatc atctgaaatc gtctttcaac atcatgccta tactttatat   40260
gttatatgtc atatattata cccaatcatg atatctgcat gtgtctctgg cgtttgtcta   40320
taaattatgc aatggccatt ggctaatagc aatgaactat gacatggtct aacttaacac   40380
tttattagta taatgactga aacactttag tcttacagaa tgtcctattt ggaatttatt   40440
ctttgaggag gttcttactt ttagtagggt cattttgata tatcaacaac cagacaaccc   40500
tggatgaagc ttaccataga ccaaatttgg accagatttc ttcctcctgt caatgatgtt   40560
acagtgagaa tctaatattg tattaaaccc atgccacatg ttaaatgaat ctgaatgaca   40620
gactgactta cctaatttct tggacttcac attttctttt cttcttttg  attttagag    40680 tgtgtccaag tttacggact atgagctgaa ggcctatgcc aaagcagggg tggtggctga   40740
tgaagtcatt tcatcaatga aacagtggc  tgcttttggt ggtgagaaaa gagaggttga   40800
aaggttggtt aattggaatc tgattctttc cttaatttca tcaatcagca tagtaccctg   40860
agtctctcag tttgtgcaaa gcggcagacc caccttggtc tgtggcctcc agaggaagta   40920
cttgttcaag agggagctaa gcagagtaat ttaggttggt aatttaggta ctataagaag   40980
tcccaagcct ttagcagtat gttttttaaag atgttgcagt tggcaatttt tagaaagcca   41040
gctcagggta gatatttatt tcaaactctg atggtatgta tgtataaata ttataccctca  41100 tatcagtcta taatgctgtt tgctgtcatt aaagaaaagc ctacatgaga cattacaact   41160
gataccacag aaatacagaa gatcataaga gattactaaa aacaaacgcc aacaaattgg   41220
atgacctaga agaaatggat aaattcctat aaaaatacaa cctgccaagg ttgaatcacg   41280
gagaaataaa gagaaataaa tctgaacata ccaataatga gtaaggagat tgaatcagta   41340
ataaaaagtc tcccatgaaa gaaaagccca ggacctgata gcttcattgc tgaattttac   41400
cagacattta aagaaaaact agtaccagtc ctcctcaaat tcttccacaa aattaaagcg   41460
gagggaatac ttcacactca ttttacaagg ccaatattac cttgataccca aagccagaaa  41520 aggatactac aagaaaatca aaggccaata tccatgataa acatggacgt gaaaatgctc   41580
aacaaaaata ctagtaaacc aaattgaata gcacattaaa agaatcattc accatgatca   41640
agtgagattt atccctagga tgtaaggatg gttcaacata ggcatgtcaa taaatgtaat   41700
ataccacatt aacagaatga aagacaaaaa ccatatggtt atctcaatag atgctgaaaa   41760
agcatttaac aaaattcaat atcctttcct gacagaaact ctcaacaaat taggtataaa   41820
aagaatgtac ctcaatacaa taaaggtaac atatgacaag cccacagcta aatcatactc   41880
aagggtgaga atttgaaagc ttttcccect aagatcagga acaagacaaa aatgcccatt   41940
```

```
cttgccactt cttagcaacc acaaaagacc ttgaatagca aaaatcctga acaagaagaa   42000
caaagctgga ggcatcacgt tacctgatct caaaatctac tacaaagtaa tagatcatta   42060
ttagattatt tgattactat agtaataaaa acagcatggt actggcatag aaacagacac   42120
atagaccagt gaaaaagaat ggagagccca gaaagaagtc catgcattta tagtccattg   42180
attttcaata aagagaccaa caacacacca tgaggaaagg gcagtctctt caataaacga   42240
tgttggggaa actggatatc cacatgcaga agaatgaaat ttgatcctta cctcacacta   42300
tacacaaata tcaactcaaa atggattaaa gttttaaatg taggatataa aactgaaaaa   42360
ctactagaag aaagcatagg gaagaagctc tatgacattg gtctaggcaa tgattttttt   42420
gacacaaccc caaaggaca ggtaacaaaa gcaaaatag acagatggga ttacatcaaa    42480
ctaaaaagct tcaaaaagga agcaatcaac agagtgaaga ggcaatttat agaatgagag   42540
aaaatatttg taaccatac atctgataag gggttaatat ccaatacata taagaaacac    42600
aaacaactca atgacaagaa aacaacctga ttaaaaagtg gtcaaaagac ctgaatagac   42660
atttctcaga agaaaacata caaatagaaa cgtacaaaaa gaaacataca acaggcatgt   42720
gaaaagatgt cacacatcac taatcatcaa ggaaacacaa gtcaaaacca caatgagata   42780
tcatctttata cctgtaagaa tggccattat aaaaagaaga aagatatcaa gtgttggcaa   42840
gcatatgggg aaaatgaaac actgttacac ggatcgcttt tggtgggaaa gtaaatcagt   42900
acagccaaag agtatggaga ttcatcaaaa aatggaaaac agaactacca tatgatccag   42960
catccccact actgggtata tatccaaagg aaatgaaatc actatgtcaa gagaaaactg   43020
tactcttaca ttcactgcaa cattattcac aatagccaag gtatggaatc aacctaagca   43080
cccattaaca gacaagtgaa tgaagaaaat gtgtgtgtaa atttacatgc catattcaat   43140
agaatactat tcagccttta aaagaagaa aatactgtta tttgcagcaa cacgatgaac    43200
ctggaggaca ttatgttaag tgaaataagc caggcacaga aaaatacccc atgatctcac   43260
tgacagagtt gaactcacag aagcagagag cagaacagtg gttaccaggg actttgaggt   43320
gggaggggc aggcgagaac tggggagacg ttggtcaaag gattcaaaat ttcagttaaa    43380
caggggtagt ttgagatatt ttaaaaataa tgacattaat tatctaattg tagttgtttt   43440
aatttagttc atggtgatct aaaagaaacc cttccttatt cacatttaag aggcagttta   43500
taaagtcaag aaatgtgttg ttaacatggt gactatggtt aataacatca cattgcatac   43560
ttgaaaattg ctaagaatag attttttaagt gttctcatca cacacacaca cacaatataa   43620
gtatgtgagg taatgcatgt taattatctt gatttagcca ttccacaatt tatacatact   43680
tcaaaccatc atgttgtata ccataaatat atgtaagttt tgtcaattaa aaaataataa   43740
agaaatgcca gcatgattca aaatgctatt tcacacattt ttattgaaca ccttttaat    43800
taaacacact ttattcaggt actgtgctac atgttcttta taaagtctga taagatttct   43860
atttggtcaa acaggctggg cacagtggct cacacctgta atcccagcac tttggaaggc   43920
caaggcaggt ggattgcttg aggccaggag tttgagacca gcctgggcaa catggcaaaa   43980
cctcatctct acaaaaaaat acagaaatta accagacatg gtggtgtaca cctgtagtcc   44040
cagctacttg ggaggctgag gtgggaggat cacctgattc tggggagttt gaggttacag   44100
cgagctgtga tcatgctact gcactccagc ctgaatgatg gagtgagacc ctgtctcaaa   44160
aaacaaatta gtgttgaaaa gttatagagc attattctag agattaactc ccagtgaaaa   44220
gaaaaaccca aatggccaaa ataatacagt tgtccaaaat gtaattttgt ttattcttta   44280
```

```
atttatctgg tatttattga gtacttacta cgtgccatgc tttgattttt ataaaatagc   44340
taccaactga atagcaactc ttactttatg tgttgtagat ttggtaagat ggtgttattc   44400
tcagttgcta ccaaatccat caagtaaaaa agagaatagg atttacaacc tcttattatc   44460
gtcttttccc cacttctttt ggtttgtgga gtgaggttcc ttatttcttg taaaaaattt   44520
cagtagcata tttcttccac catgaaagac attatctttt attgtcaata aaagagacag   44580
tgtagtgttt taaaaatggt aacaaacata ggatagacct tcagtttgtg tcctgcaaaa   44640
ggttaaaagt tctccatgaa ttcaattcct gagatgtagg aaggcagttt cagaatgcct   44700
gagctatata tgagacaaag cccattgtta atggctagat catggaatta ctgaaaccta   44760
ttccttgcat tggacttcca catagtttca gttatccatg tctcatggct gtgaacctga   44820
ccagtgtgtc acaacacagc gtctcagcca cagggcagat gggtgagtta tagatgagtt   44880
ggtgcaaaca ctagttccaa gcctggggag ctggaaacaa aaagtctggt ctgcttattt   44940
ggagccagtt gcattatttt ctgataagga catgtcatgt gactcaagga aacacttcaa   45000
acataatact agatctctct tgttcatata tttatgttga aaattctttt ctcttggggc   45060
caagcttacc tcactatgca atccaagcag caatcaggca gctctgttaa gtatcgccct   45120
ttcaacatgt ttcattgtca ggttaaaaca aactttaaaa aactacataa aggttattgg   45180
agattttcct ccctgaagct gctctgtgtt tgcgatgatt ttatgatcat tttgtaaaac   45240
cactgcatca cggcctgttt taaacattat aacttgagct gtttctgccg aaattgactc   45300
aagcattttg tcttcacagg tatgagaaaa atcttgtgtt cgcccagcgt tggggaatta   45360
gaaaaggaat agtgatggga ttctttactg gattcgtgtg gtgtctcatc tttttgtgtt   45420
atgcactggc cttctggtac ggctccacac ttgtcctgga tgaaggagaa tatacaccag   45480 gaaccct tgt ccaggtacct tggacttatt gaccgagaca tagcatttcc ttctggtatc   45540
tcagaaaagt ccatggatta gatattttgt ttattacttt ggtgccttca ggaaaaaagc   45600
atcaatgatt ttatggagtc tgtctgtgga aacaagtaat accttaaatt tttttttatt   45660
tccataattt ttttgggaaa caggtggtat ttagttacat gagtaagtcc tttagtggtg   45720
atttgtgaga ttttggtgca cccatcaccc aagcagtata cactgaatcc aagctctggt   45780
cttttatcct tcactgcctt cgtacccttt tccgctgagt ccccaaagtc cattgtatca   45840
ttcttatgcc tttgcatcct catagcttag ctcccactta tgagtgagaa catgcaatat   45900
ttggttttcc attcctgagt tactttactt agaataacag tctccaatcc catccaggtt   45960
gctgtgaatg ccattaattc attccttttta ttgctgagta gtattctgcc atatatatat   46020
gtaattatat gtatctgtgt atatatatac atatatgtta tatatatatc acagtttctt   46080
tatccacttg ttgattgatg ggcatttggg ctagttccac agttttgcaa ttgtaaattg   46140
tgctgctata aacatgcgtg tgcaagtatc tcttttgtat aacgacttct tttcctctgg   46200 gtagatacccc agtagtggga ttgctggatc aaatggtagt tctatgttca gttctttaag   46260
gaatttccat actgttttcc atagttgttg tactagttta cattcccacc aacagtgtag   46320
aagtgttcct tttcactaca tccatgccaa catctattat gttttgattt ttttattata   46380
gccattcttg caagattaag gtggtatcac attgtggttt tgatttgtat ttccctgatc   46440
attagtgatg ttgagcattt ttttcatatg tttgttggcc atttgtgtat cttcttctga   46500
gaattgtcta ttcatgtcct tagctcactt tctgagttta ttgtagattc cggatattag   46560 tccttttgtca gatgtgtaga ttgtgaagat tttctcccat cctgtgggtt gtctgtttac   46620
tcgctgactg ttccttatgc tgtgaaaaac ctctttagtt taattaagtc tcacctatatt   46680
```

```
atctttgttt ttattgcatt tgcttttggg ttcttggtca tgaaatcttt gcctaggcca   46740
aagtctagaa gggcttttcc aatgttatct tctagaaatt ttatagagaa acaaataata   46800
cttatatatt ttatagtaaa gggatgctaa acatttgaat tgataagacc agcaatttaa   46860
taatttcaaa ttaactgaac actttatagc tatgaaatga tgattttctg actgagtcca   46920
aaaagaaaat atgccatgaa aatggaaact cagtgatctc tcagctaaaa attaacagct   46980
cgtataactg agctttatga tagtccaaga tatatactaa taaatgtact tgtgaaacat   47040
aatgagttac taaaatgcca ggtcaataac agccttaact gaacaggtgc tacaaatgta   47100
ctttattgct cacttgtgct aaagtagcta atgcctttaa ttttcattgt ctttacagtt   47160
attcattcaa taagtaatta ttcagcatct actatgtgcc agacacttag aaaatgcagg   47220
ggattcaaca gtgagcaacg gaaatgtggt tttgtttttg ttttttgtttt tttgccttga   47280 tgggatttac actttaatgg agaagacaag caataaataa gtaaccatgt aaatgaatac   47340
agacaaatag agacatgcta tagaggacag agaaccttga cagtgaatag caggataacc   47400
aggtgtggcg ggggtccagg aaggcttctt atcctgctcc ctctcccaag gcctttcctc   47460
cttagcttat ggctctctct tgttgcaact ggactctgat cattgtttga attctcagct   47520 aaaatgccact ttcccagtca ggccttttac actcacccat ttttcattct cttttgtgat   47580
ctgctgtact ttttttttcaa agcacttttg tgatatggaa tatttgcatt tatttacact   47640
tgtgcccacc cgtttctacc ctcagacagt aaaatctacg aggtcaggga aacaaaaaat   47700
gaaatatctg tttcatttgc cctgcaagta aatagggagt cgttttatat caaattctta   47760
agtaaaattt tttagctcca gattccggat agagcaaaca atgaaaaata tcaaaacctt   47820
gtataccaga aatttgctag ctgagagctt aaaattcaaa atctactgct ttaagataaa   47880
tacattgcca gggaaaattg agtaggattt tgatttgcaa atggaagtga ttatcagagg   47940
tcaaaccata atcattccaa accacggact ttatttcatt aagaacatga taatacacaa   48000
agaacaactt tttcaattca gtttatcttg gcagcatgaa cagctgacat cttttgaact   48060
ttgttaaaga aaataaatat gataatacag gttaatgtgt tttgtaaact ttaaagagat   48120
agtatggatg ggaagtgtta ccaatttttat aatttaacca cttcttaaca acttagatac   48180 agttttttaca gattggaaaa gccactgaag tattgcaggt ccagattttta actatagtcc   48240 cttgtctttta ttgatccaat tcctcctaag aactttgaca tttaccaaaa tagggatatc   48300
agtagttggc tttagtccta gctgcttata catacttgct atgcaagaag acaagcattg   48360
agaaaactta ttttttccttt tgttccatgc ctacaaggag aggatagagg tatacaataa   48420
taatggttca gagggaaaag tgaattggta aattgaaaat caaataatac acaataccaa   48480
ctggaagcac ttgaataaaa atcccttttgg taactctctg tagtaggaat ccaattttat   48540
gtctctcatc tttaaatttc ctgcccattg tacagtgagc tactctactt ttgtaaataa   48600
tttattcttt caaccaatat ttcttgagtc cttgctatgt gcagacatgg catactatgg   48660
gtctctaaca ttttaatcaa ctgattatta acctgttact cccaacgtct ttctgtaagc   48720
ctctgcttat atcttaagag aaaatttcct ttgggaagat gaaatgcatc ctttaacact   48780
atattccttg ctctctctct ctcttctctc tctctctctc gctcgctctc tctctcaggt   48840
cttggccaca cttctgagca gcaaactatg aaggctgagt gtgcatgggc tgagttgagt   48900
gttttaatcc acaaaactaa ttaacggttt ggttaatcca gtacgttttg tgatacacaa   48960
aatcgttact ggctgcatgg taattgggca taaatggtaa gtagttcaca taagtgactg   49020
```

```
taattagtat cacttgtgca cagagaaaaa atgcactctg tggtctggta gggaaagatg    49080
aaggggacct gaatggtgca gaaggttgtt cttccatgac cttcctgagt ttcagaattc    49140
attaataaaa ataaacacat aatggagcgt gacattcatt cagtatatac aaagtgtcaa    49200
gcactgagtg acgtattatg taataaaatt actgcatgta atgctctcaa tctcattccg    49260
taattggtgt cattatacta ccacttaaaa atgaaattga agccatgaag tcaagaaata    49320
ttgagaggga tttgaactca ggtctccctg actttgaggc ctaccatta accactgttt    49380 tcctgcctct gactctgtct tcccaggggc catggacccc tttttctcca gcacacccat    49440
agcttaattg ttccacagca gtctcccttc ccatctctct gtctacacta cttctgctgt    49500
tcacagggct aaagaatatg atgttgagtg acaaatgatg gcttattggg atgttgctag    49560
ctactgtgat gatttgggaa tgtgcttttg tcctgtctca ctcactcctc cccatccaga    49620
gagccattca aagagttgga ccccaaactt caatttaggc ctccagtcag ccaggagtca    49680
gcaaactatg gtcgacaggc caaatccagc tcactgcctg tttttataaa taacatttta    49740
ctgggacaga gccacagtca cttatttaca tatgtctatg gctgctttta tactacatgg    49800
cagaactgag taattacttc agagcccata tggcctgaaa agcctaaaat atttatttgg    49860
ccctttttca gaaaatgttt gctggccccg gatctagggc aaatggaagg ttcctttgct    49920
gaggtaggaa gacctctgac gtgtgtggtc ttaaactaaa ttggaccata agaagtgttc    49980
tatctgcttc ctttaccgcc tcctaagtgt gggacctcaa tactttcttc actgtcagca    50040
tcatcatcac caacatcatt actaccattg aagagactag cactggatta atcatcttta    50100
cacacattat ctcatttgat cctgtaataa tcctatgaaa tatatgctat cattatccct    50160
gtgttgcaga tgaagaaatg ggggcttgaa agattacata atctgcctat gggaggaacc    50220
acctgccata attgaggaca aggaaatgaa gagataattt ttgtccctat gcataggctg    50280
ggattctagg gagaaagcgt gagtggacta acccaccacc catgtatggc agccctggcc    50340
ctgttaatca tcctaatgtg tggaatgaag aggttactga agagggagag acatggctga    50400
gaggctctga cactttccat ggttcagaca ctccagccac aaggaagaaa gagaagcagg    50460
agagactcag gcaatttgcc tcaatgtgat acaacaaatg ggaagggtct ggcctataga    50520
aaccatcaca gaccaggatc atttgatcac ctgaaaaaga ctacattcat gcagggccac    50580
tctttggctt ggcaatagac tgtggccaat gaaacatcct ctatgcgagt cacaagagta    50640
ggaccattct ttggttgaca gggtagagag gaggagactg gtattccttc tggaggccaa    50700
cttgaggatt tgcctcattg tctcttcctt accttttataa acagtgctga taataaaaac    50760
agagtgctat ttggtaggaa catctgggca tgatcaggta gccttcccct aaggtaatga    50820
gatgactgca ttggtaagtc aaagaacagc tgccccaagt ctgcacagga acctgaccac    50880
tccacctgca tatagccagc aacaggtgag tctgggagct aggtagaatg gcagtcaaaa    50940
gcctggattc aaattctgct ctactactta tgacatgttg taacctagtg caaattggga    51000
gcctccatac ctgtctgttc actcttctgt tgtaaagata aaatgaaata atacagataa    51060
aacacttaga aacatacctg ttattattgt tattattact gttattcata gtagttgcag    51120
tagttagccc agtgactact ggaatagtag cattagtata gcggtaacaa cagtagcagg    51180
ttggttttgc atgtaccagc ctctagaata gtcaggctga tcttagtgtc tgtattgttt    51240
ttggcaaccc tttaaccaga aaatcactat aaggctgatt atataatgaa ttcaattatc    51300
aaatcactat tcagtccac tttgggtcta caggctacct tgcttagact tcttactcat    51360
ttcaagacag ttctactttg tagaagagta atattcagta aaaaaataaa gtggtatttt    51420
```

```
aaatcataac agtggaaaac ttggagatgc tttacagaac aaaaattatt ttgggtattt    51480
ccaaacagcc aaagagctag cttttgaacc cacagaagag aatttctgat aactctctgc    51540
gttaacatgg aagacccaaa tgatagtaat tactatttac acattaacaa aaacacatga    51600
aaaatctctc tcttttcatt tcagattttc ctcagtgtca tagtaggagc tttaaatctt    51660
ggcaatgcct ctccttgttt ggaagccttt gcaactggac gtgcagcagc caccagcatt    51720
tttgagacaa tagacagggt atgtataagc caaaagtaaa ggccattaac aggtgggggc    51780
tggggggtgg ggcacagaat gaactcctga agaatttacc ttaaagttaa aaatataaga    51840
agctatcgca aggcccttaa ttcagcaaca cttattaaat gctatcatgt gctggtgcca    51900 attcttttt tttttttttt tttttttttt tgagatggag tttcgctctt gttgcccagg    51960
ctggagtgca gtggcacaat ctcggctcac tgcaaccccc tcctcccagg ttcaagcgat    52020
tctcctgcct caagggagtg aatgcaacag ggaactagaa caagtaagac ccctgttctt    52080
tactcatgct gggagaggac aggcagtaaa gaagtatgca cattcaaaga taagacaata    52140
gcagagagtg gtaagtaaat aaaggaaata aaatagggca atgtgacagc gactgggtg    52200 ggagaaagag tctttaaatt gggtggtggt ggcagtatct ctgaggaggt agcatttgag    52260
tggagaactg aagaaaagtc agccatacaa atgaggattg gaggaggtgg ggcgtgggaa    52320
gtaagagcag ggagggcatt catggaagag aggcccccaa gttggaaaag gctgctgatt    52380
taaagaagct gaaacaagcc cagtgcaact gaatagagtg aacaagggc agaggctgga    52440 ggcatgggaa gggcctacca tgcaggactt caagaccatg tccataaaat tcgcttatct    52500
tctaaatatg gcaaaagggg attttactgg ttagtctatg gaagcacact ggaggccaag    52560
ctagggagtc aaaatccaag aacaggccag gcatggtggc tcttgcctgt aatcccaata    52620
ctttgggagg ccaaggtggg cgcgtcacct gagcccagga gttcaagacc agcctgggaa    52680
acatggtgaa aacctgtctc tactaagaac acaaaaatta gccagtcaag atggcatgtg    52740
cctgtagtcc cagctattca agaggctgag gtgggaggat cacctgagcc cagggtggcc    52800
gaggctgcag tgagccatga ttgcgccact gctctccagc ctgggcaaca gagtgagaac    52860
gtgtctcaaa aacaaacaa acagaaaacc aagaacagaa ggggaagttg gcaatctgtt    52920
gttctttctc tttaaaaaaa aaaatgccc tgagctgagt ccaaagcaag ccctggaaat    52980
ccagaggtga tttgcgggct ccctgaacct gtttggttca ctgtccgctg tttgatactc    53040
tttcgccaaa cagtgaagtt gtaacctatt aaggaagtga ctcattgctt tatctgtttt    53100
ataatttggg gtttcatata ttggagtaca gagagattgt taaaaaccac ataaaaatgt    53160
tcattgatgg ccaggcatgg tggctcacac ctgtaatccc agcactttgg gaggccaagt    53220
cgggaggata gcttgagccc aggagtttga dacaagcctg gcaaccctg tctctacaaa    53280 aaatttaaaa agtagccggg tgtggtggca catgcctata gtcccagcta gtcaggaggc    53340
tgatatggga ggatggccta agcccaggag tttgaagatg cagtgagcta tgatcacact    53400
actgcactct ggcctgggtg acagagtgaa accctgtctc tgaaaaaaaa aaaaaaaaaa    53460
aaaaaaaaaa agtcaatta ttcaaattct acctctttct taagattgtt atatgctcaa    53520
ataagatgat gactctaaaa gtgccctgaa actaaaaaat taaggcattt aaaaattatt    53580
tcttaccttt attagcaacc cagtaaggag gtagattaca ttatactcct caatagagct    53640
aaagtgattg atatgttttg gctttatgtc cccacccaaa tcttatcttg aactgtaatc    53700
cccatgtgtc gagggacaga cctggtggga agtcattgga tcacaggagc attttccccc    53760
```

```
atgctgttct tgtgatagtg agggagttct catgagatct gacggtttta aagtggcagt   53820
ttcccctatg cgctctctcc tgccaccatg taagacatgc tttgcttccc ctttgccttc   53880
aaccatggtt gtaagtttcc tgaggcctcc ccagccattt ggaactatga atcaattaaa   53940
actcttttct ttctaaatta cccagtctca ggtattcttt atagcggtgt gaaaatggac   54000
taatacagtg atgaatttcc atcactagtt atggacaagg gaagaagatg atgctggagt   54060
gttctggtag caggaagagg ccctcacttt tctctgatta accagagtgg ttaaattcta   54120
gattgggctt gttgctagca gaagaggtga aattcaggac aacaattgaa agttggtagc   54180
atttgaacac atcatttagg aacactcagt tttaatcatc atctaccatg gatactcaaa   54240
agaataccct cggaccccg attggttgac tagttgcctg gtcttagaaa cttaatcttt    54300
ctgcaattcc tccacttctt caactgaaaa tgggcatatc accagtctag tttggtgacg   54360
gtgacaatta tgtaaataaa agtataaaaa cacctagtac attgtctcct atattatctt   54420
agtaatatat aatatatatt aatattgtta acatatgtta tacatttata atattaatac   54480
aacatatgta ttatatatgt attattatat aatggcacat attatataat atctcagtaa   54540
caacatgata aataataaca attaaataaa ttaattaaat atgtattatg ttaatatata   54600
atatctcagt aatagctcaa gaagtagtga ttattctcac tattattaat aaacgtttaa   54660
tgagtacaca tctttggcgt atctctgcaa tgttttatct ggttgttgtt ctaagtaaat   54720
tcaaattaag atacatgcaa actaagaggc acaataaatg tatacatctt catttgaatt   54780
tactcataaa acagagcaac aaccagataa aacattgcag agatacgcca aagatgttta   54840
tttgaattta caatttgaat tgagttgtgc atcttagttt gagtttacac tgtgtccctt   54900
ttgtatttca ctccagaaac ccatcattga ctgcatgtca gaagatggtt acaagttgga   54960
tcgaatcaag ggtgaaattg aattccataa tgtgaccttc cattatcctt ccagaccaga   55020
ggtgaaggtg agtgctggtc tgttccccag aatagtaaat gttttcttct tcgatgattt   55080
atttgcataa ccacaaattg ctcatttct gaagcctgac tctgtttcca gtaataggga   55140
atggaggtgt ctttctctga agtatcctc gggtgttggc ttatctcagg caacagacca   55200
cattcctttg tgataaccat aatgtgcaaa tcccctggtt gggacacagt ctggcagtac   55260
attcaggcta aatgaactgt atgacgctct gttgaaatga gtggcaggtc ctgtcttttcc   55320
atgcaagtgc tagataaatg acaaggcaat tacaacaatc aggaagcaca ggttcttccc   55380
aaccttcgca gagactgcag aaagtggaag acactgagta tagggtatga agtggcaaag   55440
gaaagctgcc attatgtagg ttttacttc ccatctgtaa attcactagg tcactgcatc   55500
agcccttata ggaaggtatc cttgtgtat tatgctcacg tgtcttgttc agggcacatg   55560
gtgaaaaaa ttattctg cctttaaatt atctttacag gcaatttact ctacaagaaa   55620
attaggatct actaccctg aataaattgg ctttgaaatt agacttattc ctcattttca   55680
acagagtatc tctagccact ctctcttaat atttctgtta tctgcacaga actaaatccc   55740
attttgttag cctaacttaa ttctgacacc acatacctat catatatata tgtgatatat   55800
atgatatata tgtgatatat atatcatata tctgtgatat atatatgata tatatatcat   55860
tctctctttg aatatatgaa tatatacaga gagaaggtaa acatatatat aaaatgcagg   55920
taaatattta tataatataa tatttgtaat atataataca tatatgtga aatatatatt   55980
tatctataaa tatttaaata taaaaatatt tatgtattta tatatttatc tataaatata   56040
aaaatattta tgtattttata tatttatcta taaatataaa aatatttata tatttatcta   56100
taaatataaa aatatttata tatttatata tttatctata aatataaaaa tatttatata   56160
```

```
tttatatatt tatctataaa tataaaaata tttatatatt tatatattta tctataaata    56220
taaaaatatt tatatattta tatatttatc tataaatata aaaatattta tatatttata    56280
tatttatcta taaatattta aatataaaaa tatttaaata ttcatatatt tatctataaa    56340
tatttaaata taaaaatatt taaatattta tatatttatc tataaatatt taaatataaa    56400
aatatttatt atatatttat ctataaataa atataaaaat atttattata tatttatcta    56460
taaatattta aatataaaaa tatttgttta tacatttatc tataaatatt taaatataaa    56520
aatatttata tatttatcta tattttatat ctatatatac atacctacat tatcagtatg    56580
taggtaaata tatctataaa tatatataac aaatgtacaa ataaagtgt atatctctat     56640 ttaccttcat tatatacata aatatataaa acataagtaa atatatattc tgattacata    56700
aagtatattt ttattatcta ttacatatgt acctaaacat caaatgttat aacatatgta    56760
aaggtgcttt gtaagctatg aattacaaag taatacacac tcagtaaata tttttgaatg    56820
gatagctaaa acttatatta caatggtgga gagtaattga ggttttgcc attactttta     56880 atagtgaaat aaaatcttct tacttaaacc tatatgtatt tattcatagt acgagtatgt    56940
ttttaaccct ctgtgtgcca cattgtactg gtgctataat gataaaaaag cacatttgat    57000
gcctgcttgc tctgggagct tacagtccaa tacaggccag taagtgaaaa tgtatttgca    57060
agtttgactc ctagtgtgaa atgaaaggcg tgaggttttg tgacacagag gaccccaaac    57120
cacattttcc ataatcagta caaaaatcac ctcttaattg gtgaaaatat tgacagatag    57180
ttatgaatta gcttctcatt ctttcctcgc aagacctact agccagcatt cagcctctac    57240
gtagcaaaca caccgtgtat atttattaag taagtttatt caaatggtat gttcatacac    57300
catacacatg acggacggct taaaatccgc aaatttcctt actgttaatc catgatcagt    57360
aaattagtac tatatttcta acttaatgga ttttttttct ttaactaatt ggcatagtct    57420
ccttatccta gtatgtcagg agtatttaaa atcagatttt gggacataat tttaaaagtt    57480
aacatgtctt atttacttca cctgtgttaa tgtgcatcat tttacttctt ggtcatggct    57540
ctcagttaaa taattaagta atgtgctaaa tgccaaaacc tcatccttgc caatgtttcc    57600
ttttactggt ttttgatgga tttcagtgga cgttgctttg ggggcataca taaacgcaca    57660
cacagacacc gagtatcaac acaaagcatc tgcacctgta gcctaattgt ttgatttggt    57720
aaacagtgac aatctgaact ttgctgtttt ctttcttctc cagattctaa atgaccctcaa   57780 catggtcatt aaaccagggg aaatgacagc tctggtagga cccagtggag ctggaaaaag   57840
tacagcactg caactcattc agcgattcta tgacccctgt gaaggaatgg tgggtgtctt    57900
ccagaaactc ctcaatacat ggggacagta aagtgcaaat ggcagtatat tgatcaaaca    57960
gaaaggtgta gcatacattg agactgtcct ggcatgcata gttaacttaa tgatttgtta    58020
ctgaattgat gggacacgct tcctacatgg taacagtgtt cagtgaataa ccagtcaatt    58080
ccattcactg tataatgtaa ctgaatgtgc agatacagtc agatgtggca tagcaacatt    58140
tcagtcagtg attgatttca tatatgatgg tggttccata agattataat ggaacatgta    58200
tagaaatctg atatatgtca cttgatgttg gcattgcaga tcaagttaag agaaatgatt    58260
gatatttagt aatggtgcta ggacatttgg aaatatatat ataccatcta aatttgtgta    58320
actacactgt gatgtttgcc agtgatgaaa ccacctaagg acacatttct cagaacgtat    58380
ccccgtcgct tagctatgca taactgtaca tttaaaatgc tattgctgcc tcttcagtga    58440
actgtctatt ccactttttt ctttgtatta taacgaaaat attattgtgt ccttaagttc    58500
```

```
tccagacact aaatatagga ataataacag ggcttgaaat taagagagag cagtcctaag    58560
aaactaagaa aaatgagtat tagtaattgc catttattta tcacatatta tgtgtcagat    58620
actttattaa aatgattact tattgtcaca atgaccccca aaggtacata ggcccatttg    58680
acaaacaagg aagcagagag tcagagagat ggaaacttgt ctagggtcat tcatcaggta    58740
aatgaccaag tcaggattga atccaggtgt gttgggttcc aaagcccatg ctcttttcac    58800
tctgtctcaa aattattctt gtcagcatct ccttgatgcc ttgagatgga atcgtttaac    58860
tatttaatgg cttcaacaaa atgagttctc tatcatgcat atagtattac acaggcatgg    58920
caaacataac agagttttcc tttttcacag acatctcatc tctgattggg tattctttac    58980
tacctaccac cataactgca ctctgaatat atagaaatca tagtttcttg atgtaagatt    59040
tttacatttt tactaatagt gatttttatt tgctcccact gatagtttca cttgcttttt    59100
aacagcaaag tgttatttga tgaatctggc cagaaagtaa gacttactat aaatcatata    59160
tacaagatag ggatcattgt ttatttttat tatatctttt gagtccattt ttgtcaaaag    59220
tcaaaagata taaaaatatt taaaacgtag tgaataactg tctctactct ttactggaat    59280
caaaaatttg tccattcctg ggccaatggt gttaaattaa gtgaacttta tttacatcat    59340
ttatgtttcc acaatgaatt gttctgcagc tatacttgat ttcaattaca tgttatcatc    59400
cttatataaa gaaccacatt tcaagaggaa ttgtttccat tagaatctta ttggcctcta    59460 tttttctgc ccattggtca agtatgacat aatattatga ttcagaaccc tgaaagattc    59520
caaaagttgt gatgttgtgc ccatgctctc taggtgaccg tggatggcca tgacattcgc    59580
tctcttaaca ttcagtggct tagagatcag attgggatag tggagcaaga gccagttctg    59640
ttctctacca ccattgcaga aaatattcgc tatggcagag aagatgcaac aatggaagac    59700
atagtccaag ctgccaagga ggccaatgcc tacaacttca tcatggacct gccacaggta    59760
cccctagcca tacattcctg ggagaaaacta agaggtcata gaaggaaaaa aagttgcaca    59820
attatacaca tttcttctcg tatgattccc aagtcattaa attcttaagc catgttttag    59880
tttcatgcct gaaaaagtac catgagtgtt cctttcatc tgaaaacaca ttgtttatgt    59940
gttcaaatct atcaaaaaag gaggttttct tttgaaaagc tcactttgtt ggtaatatat    60000
taaacatcta ccaaactggg gaactatctt ttttaaaact cctttgacat agatccaatg    60060
tccttattcc ttttattaag catttgtcta agcagatgct aaatgtcatg tggcaataac    60120
ttgcacaata atctcatgac agctactcat aattttcttg tgcttaggca gctaatattg    60180
tgtcaaaaac aattcattgt atatctccat tctaagcaac aacaactaca aaaaccaact    60240
cctcagcatt atacttcaat ggattttgcc accgatggcc tgctaagtca aagaagagtt    60300
attataaagg gttaacacgt atacggttct tactacatac caggcactgt tctaagcact    60360
tcacacctat taactcatta aaccctcaca acaaccctgt tgagcaacta atattattag    60420
ctccatctaa agatagaaaa ctgaggttct gagaggtcaa atagcttgct caagattata    60480
caacaagtaa atggtaaaga caaggttcat actgaggtga tctgccttca gaagagtcag    60540
tgatcttgaa cacttcccct tcagccttct aaattctctt tatgaatagg attgcagctg    60600
tggctatgat atagcctagt agttaaagag tataaagctt tagaatcaga ttgccttgat    60660
acaaatccca gcttctctat ttacaagctt tacaaacttt ctcaagttac tttgggccca    60720
gtgtttcctt attcatcagt tgcaaatagc agcacttgcc tcataaggta tctatgagaa    60780
ctaaaagaga tgttatgtgt aaaaagctca gaaccatgct ttattcatag taggggctca    60840
attcatgttg gttagtaata agcaagataa gtgtctgacc actaacacct aattattaga    60900
```

```
ttccaatgtt gtgctaggcc tgtgagataa tcagtaacca tcttttgtca atgataatcc    60960
ttataaagct agtttgacct tttattcata atgtaaaaac agcctttgca ttatattttg    61020
ctgtgttgtc taacaggagc aaagagacac ggatttgctc tgtgctttaa tcctctgaga    61080
tagatattta ggaccgtgac caatttttat tttggttgaa aaatcttatt tgaagttgag    61140
ctaaagagga atatttacac agcccagtaa accctggaat aaaagcataa atcaattcct    61200
ttatttcaca cataaatatt gattagacaa taacccgtct ggggaaggga tatttctttc    61260
agtggaagtc ggagcagtga aaattcgtgc ttgagaagaa aactatgaca gaaaggacat    61320
tatagtggat cactgtcaga agccatcaaa ttcttttccc ttcatgactg gtgtcacctt    61380
ccatctagca atttgacacc cttgttggag aaggaggagg ccagatgagt ggtggccaga    61440
aacaaagggt agctatcgcc agagccctca tccgaaatcc caagattctg cttttggaca    61500
tggccacctc agctctggac aatgagagtg aagccatggt gcaagaagtg ctgagtaagg    61560
tttgtggaag tcttagtcca ttttacaggt ccatgtggaa atgcttgtgc tgctgcagga    61620
aaggcagctc cttgtggggt gggagggatg ggagtagttg atactacatg ggttcatgca    61680
tctagtctga ttgtttagaa aatattagct gactacaatc ttcctcacag ttgaacagaa    61740
gaaagttgta atttgtttcc aaaagctaca catgtaaaag tttaaatctt gttaagacta    61800
gcttatgata tttttttaagt tacctaaaaa attgttttta gctgttgatt aatggcagca    61860
acagggccag tgtgtgttgg ggtttatggc tgcaagaaaa tgtgctggcc ttttctaatg    61920
tctgcacagc ctatttaaga atattcccag ggaccaagga tctaactttc ctatggattc    61980
tgaaatgatg caaaggtcag tgtcagctct gtctcacagt tttgtttaat ggtgcactgt    62040
acattcttac agattcagca tgggcacaca atcatttcag ttgctcatcg cttgtctacg    62100
gtcagagctg cagataccat cattggtttt gaacatggca ctgcagtgga agagggacc    62160
catgaagaat tactggaaag gaaaggtgtt tacttcactc tagtgacttt gcaaagccag    62220
ggaaatcaag ctcttaatga agaggacata aagggcaagt gcttttttcc tatacttgta    62280
tgttatatta aatagttaat gtctatagtg ctttacggtt ttctatgtat ttcaatactc    62340
actgttctcc caacaactct ggcaggcgtt atatagatgg taaaggaaac aactgaagct    62400
caggaagcta agctatctga tcaagttaca gcactaaaac caaggcttct aactttcaat    62460
tccatccccc ccttttttttt ttttttttaac cctgcgcaaa tagaagaggc ttcctagagt    62520
gtgttccgca cgcagtagaa gcttcatgct tattggctga gtgaattaat caatgacaag    62580
aaagtataat acttattttc aaatgtagat agatacttca ggttctagtg caccttcttt    62640
tttatcagtc tgaattttca gacttggtgg ttacctcaat ctaaattaac caaccactct    62700
aaactttctc caccatttca ctccattagg tgtaactact atatacattt aacataggag    62760
ggttattctg aatagacttt tgaaaagttt agtgtttcta tcattttttt tttgctactt    62820
ctgatggact tctcttaaac tttttatgat ttatgctaaa aaaaaatacc tgtttctgta    62880
gaggtaacaa gctattgtat ggtttaaatg actcagtctt gctgagtatt ttgaaatttt    62940
ttattagaat ctgcaggaca agtcccgagt tttatttatt gcaataaagt taacagaatg    63000
ttttggcatt tgacatagta attatattct aagcaaacat agtaaagaat tctacttgga    63060
tatggttctg tttattgtat atactaaaaa attgctcatg ctgtgttgag tagatgcaac    63120
tgaagatgac atgcttgcga ggaccttttag cagagggagc taccaggata gtttaaggta    63180
agctcaagcc atggggcaga ttacaagctt tccaaatatt ctgaggagtc ctctgtagtc    63240
```

```
ctaatcctca gagaatatct caggtacaac aaggaaactc tgagtagact gccaggtctt    63300
gtcaaatatg aacatgcaag tgatccttgg ttgctatatt gacatttctc tccccaattc    63360
atgggttttt ggttagcttc tcatcttctt ggggataagg gttacaatgg agatgcttta    63420
tggttaaaat tgttgtgtat tgagcttaga aagggggactt cttttaaaaa aaatctgtgt    63480
ttagtgttcc tctgctccaa gctaactgtg gtatgaaaca ctgtcttacg tgaaggtcaa    63540
attcatgcct ttagctccac tctttaatct actgagctgc aactgaatta caaacacttc    63600
tgctcccaga gtaacccatc tgaagtcaaa tcattccata actagatgaa gtaagaaatg    63660 taattttttta gcacttaaaa ataattttcc taaataagag ctatttattt ttccctggat    63720
caatataaag ctgtttactt tcaaaatata ttttttggagt atgctattag tgagactaca    63780
cactttagtc tttcatcctg gtttaagagt ttcaataaaa ctgctcctct gatgttacaa    63840
gtctgtatta agaagaattc tgcccaggag tgtttgtcta tatttataac tgttattcaa    63900 gattttttt tcttaagtca gaagattttt aaaaggcaat gagatggtag caatatctct    63960
atgattgcca tttccatttc taggacattt aatgcaaggc tgtgcaaagt cgcagagata    64020
agacttgctc attcaagatg gataattatt tattgaaaag ttgttaaaga gccttaaaac    64080
attcagctaa caattccaag tagttcaaac gcagatttat tcatttaaat attcaaagaa    64140
tagctcacaa aaagtagtgt atttattttc agatgtagat aaatacttca ggccctagta    64200
tatcttttcc ttatcagttt gaattttcag acttgggttt tcctatctttt cttcttgaga    64260 acaagtttat tcaaacaaat tttaagaaat gctagtttga ctgaatttac tgaatttggc    64320
aaataacaaa gcaatagctt cacattactc tgtcatgtaa aaggtataaa acaatgttat    64380
aggcacctgg tagtaagttt agtcatgctt ttctgattcg atactaaatt taaatcattc    64440
aagtcattag aatcacaacc tgaaaatatc aactaacttc ttaaacccag agaatgacta    64500
ggcatctctt ttggtcacta ggttaaaggt tgcaaagtgg acatgtttct tatgatcagg    64560
ccaacaagaa aataaatatt ttcttaactc ttcagacaaa caaaattcta ctcatgttaa    64620
gtagtttatt tgcagtttat tattagaact agttaaccat tttaatgtga acattaattt    64680
ggctataatt tctcacaaat gttacatttt ggtgattagg atgagaaatc cagaaatacg    64740
atctacacac agaaagtagc tattaacctc ctgcagagaa agatttgtac atttgagtat    64800
gaaagtctgt taaaatatct cattgtacat gctgacggat ttttcttgtt gtcgttaaaa    64860
gatgactaaa tgaagtgtta atatgtatct tgtttctttg gtttcagttt ttctgatggc    64920
taagttcctt ttcagcaata tattttaaat tcaagaacaa tttaatacat aacagccaca    64980
aatttcctaa ataataatgt tgagaaagat agtatttagt cccccaagtt agttgttttt    65040
atttgcagtg agaagtggta cacagcttca gagaaggggga gagacagatg ttgtcagttt    65100
ctgaaaaggg atggtgtttc tagtggatga gagaggtaaa cctgcctagc acatgcactg    65160
cccatggcct catgacagcc taggctagac agctcgaatg atctggagaa tggtgaaaga    65220
gagagactta aaaatataa agtagatatc caaggggcca aggacatagg tcttcccata    65280
ctcagaactg gaaggtagtc agtcatatgt tgatggcctc tcctgctcca caaactccta    65340
ccttggcatc cattgctctg catttgcttt ttaggtcctt gaccttaagt ctcctcctat    65400
caagcacctt gttctcacca gctgacacaa gccattctg cacaccttct ggagaagaca    65460
tcctgacctc tgttacctaa ctgggagaaa tgacttcatt gctgtgtagt ttcaggctag    65520
gtgggaggga gtctctggag gtgtcccaga agtttggtgg cagggagtag cgttgaggag    65580
tggtttaatg cctggtcata atgagtcttg gcaagagtct gaatgtgcaa gagcaaggaa    65640
```

```
gagggagggc ttgaggaaac tgcatggtgt tgaacctggg tgactaagag gatggaagtg   65700
ccattaacag aaaatgggaa caaattggag caactcagtt gatacattac tgccttctct   65760
ggaaggctag atgagcatat agtaggcagg caccaccttg atatttgttt tggtgaaatt   65820
tcacttggat gcaaaatggt agagaaagat atgtgaatgg attcatctag atggcactaa   65880
aacagttgat gcaggtctcc tcatcactca catctctctc tttacaccat ttacttcagg   65940
tgattctttc taaaacacag tcttcagcat tgcctcttaa ccattaagac tgtttacaaa   66000
tgactgaaaa cctaacccaa cttggattta cctttagaga gacagaatca gctcatataa   66060
ctaaatattc caaagatgct ttggcttcag gcaaggctag agcttcagtg atatgtccaa   66120
gctagaaaat agtttctctc tcttcctttc tcagctctac tatttcactg ttggcttcat   66180
ttttcagaaa gcttcttttt ttgaaggtct caacataatt gtcaacagct cccagcacta   66240
aatactttaa gattaaccta gaggagaatg ggggcctcct tcccaggagt ctggggggagg   66300
gaagaggagg gtggagtctg aaccaatcac ttcccatgct tgtcatgtac tcagtatatt   66360
cagcaagcaa ccctgtcctc ccctgtctcc atgcttatgt ttatacattc tctcagtcag   66420
aaatgctctt ttctatagtc tacaaatccc catatcctac cttagccatc tcatccatga   66480
atcttgcctt ggtaacacct gccatacatt tcttttttcct ttgactttcc atactcttta   66540
ttcaaacctg cctaatagca cttaccacat tcttctttac cttagggtgt ggtacaggcc   66600
tcttctataa ggtttaaatt ttttgaagga gaaatctgtt attggctagt ctttgtgtcc   66660
ccaacatcac ctggcattgg tttgtaagtt gtagatgccc aataagcttc tgttgaatta   66720
atgaataaat gaatgaacac attgagctaa attatatttc aacaagatac tcattcatgc   66780
atgtctgaat gcagggtagt atatagcctg gagaaaatct catcagaggc cctatttcct   66840
catatcattt gtaaccatgc taaagtgaac acatcaggta tgagagaaag atatcaagac   66900
cacaatctaa gccagaagga aagtaaagga aatagactgt tgccaaggca gcaattagca   66960
gaaccatgtg ggtttggaaa gtatttgagc cttaggtggt ttttgatga actggtagga   67020
cagctttgct ccctttctct ttctccctcc ctgactacac tctgaatctg ggtccaacac   67080
ttgcaagagt ttagggccca gagcaatcaa cctgattagc tctgccctaa gattagctct   67140
gtcaaaccta acctgcaagc tcccttcct ggttaccatg tgacctacca aacatttcta   67200
tttatttgac atatgaaatg taaacttgga caccagttga tcctgctcca atctggccac   67260
agtctacact gtttcatctt tctgtttatt tacagggctt ccatccggca acgctccaag   67320
tctcagcttt cttacctggt gcacgaacct ccattagctg ttgtagatca taagtctacc   67380
tatgaagaag atagaaaggt caggcaccaa ctgcttatgg gggggaatgg aagaagtctc   67440
tcctggggac tgttgggtac cctttaagcc tgagaatatg agttttctag gtatatatct   67500
agcagtgttt caagtcagac taaaagacag agcattaaga cctaatgaaa actctaagtt   67560
ttacacaata ttttttaatgc agattagtta attgattatt tttaagaata caaggtaatg   67620
aaaactggac ttcggagggt taattgtctt agacaaacta ttctaacaaa cacagaatgt   67680
gtgaattcta gatatttagc agattatttg ctcatatgta gaaatccttt tataaaagtt   67740
gttaagaata cctgaaagct ttttctcaa atttttaaaat ttctttctta aattacaata   67800
attttggcaa aaatccttg atcaacaaaa gtgtttgaat aggctagccc ttattacaag   67860
ttatcaaaat atttgaatta atggaggcca attaggtttc acagacattt gttgatttca   67920
tacaattttt ataatggttt taagatacat ttaaaataat actatcaatt ttaacataat   67980
```

```
tcaaggtagc ataaaattaa agagctagga aagcaaacaa catgtatagc aatacacaat   68040
ttcttcctaa ggatgcaggt gtcctgctgt tgtagacatt gtctaatttt cacataaaca   68100
gaccacccat tctcctccaa gcctttcctc attactgcac gttacatgtc agccctgata   68160
cttttacgtt cattcccta ccacccttcg ttagaaaatt tcatggcaa ttttcttatt   68220 gagccttaat caaagtcatg ttgacttatc cccttctaa attataagcc tctgaaagtt   68280
agtgatacac cttatttgtg tttgaatcaa cttggttacc taacccagtg ccttgcactt   68340
agtaaggcat caggagattt taaaaattag aatgaaaaca tgaatttcta caataaaata   68400
aaaccccaac tgcaagattt atcaaagcaa ataagtcaga gaattttaa attacaagca   68460 catccattat gcatgatata atttcaaatt gtcttaaata aaattccaac acgtgaatcc   68520
actaggcagt aattacaaac attgattcat aatggacaaa tttggaataa agtagagtac   68580
tctttatgac cgtatgaaaa tgacaaggga gtgattgggt tctcttttgt ttttaatgta   68640
ttaatactga ataaacagag gtctcaattt ctaacacagg ctttaaataa attccatgga   68700 agacttttc tcaggagcag caggatgaat cacagtgaga gaaaacacat ttagcaagca   68760
tagtttctta ctgcatcctg ccactaaaga ctcaacctct cttctagttc tagaaatagc   68820
tatttcattg agtccatggt gctgtcccag ataactataa gatgtattat ataagagcag   68880
gagtttaata gagcttcagg ggagaaagaa ccaaacacta cattgacatt tctattgaac   68940
cataacaata ccaatcatat ttaatttttg cattttaatt ttttctagtt tctgggtaga   69000
tatttgacaa taaagtaaa agtaagaaag gatggaaaga agggagggag ggaaggaaaa   69060
tctgactttt tcattgttgt tgttcaagct ggtagaggac ctagcgtagg tgtaggggac   69120
catcagattc cctggacatc tggagatcag attcccatag agttctcttg atgcaggaac   69180
aattcaggag ggaaccattt aactaaaagg aaatctaaat ctaatatacg gtctagtttt   69240
acagagatta aaatgtttca tattatgttc tactagtcag cattatacat ttagaataga   69300
acaattaaac tcagttatat gtaggccagc atacgtttta aaagatgtga ctttacgttc   69360
tctctagtta agggagatag aaaggaagaa gagagaaaaa atgataggag agccaatgtg   69420
attatactaa agctccaagg ggaaaaggtc tcataataat accactggtt tgtacgataa   69480
ttttgttagt cctttaggtt taaaaaatta atgattttg aaaagaaaat aatgaaaaag   69540
ggttaataaa atttgactta tgaaatttct aatctcaagt aacattatat ggtaaaatgt   69600
tgctctgttt tggtatttta aagtatttta atacttaact aaattccaca agcccaagca   69660
ttggtgaaat cctttctttt tctcatgttg atggaaaagg cctaaccta ctttctgtag   69720 attgggaaat actctcttac ggtgctaaag gtcgattcac acaaaggagt tatcgccacc   69780
ttgtggtctt gtggagtatt gactctaaaa cttagaacca tttcctgaga agtctgtgct   69840
ttcacccaag gtctcatggt tagttggtga cagagatgag actataccca tttatccttg   69900
ctctccaagc agtactctta gctcctgtaa acggggtcag atgttagtta caatgttgac   69960
aacattaagt ttaggattag ggaaacccac aggctaaagg ttttagtctc taatatttag   70020
gcaatctctt ttggtgaaac taaaacacaa ggcagaacat gtatgagatc aagtcaggat   70080
caaatattag acacccataa ctgcatcaca gataacttat gtgataggat ttaggcattg   70140
gttaagataa gacagagatg ggacccataa aaatggctat cagtattagt tcatttgaaa   70200
aatctctgct ccttttgtcat agttaccact tttatcatc aaatcttaaa gttattatta   70260
gggcagggaa cctctactga atggaaggca gaaattagtg taacaaagta tagaaagcaa   70320
gacctaagat ttaagtcgga ggttattttt cctctggcct acacagaaga tgtaagaaag   70380
```

```
gaaacagaaa agcccagtgt ctagcattga actatgaatg catcatagta gatgagcaat    70440
tttaaataaa tctcttgttg catgtatgca gcatggacat aaaagtttca ttcattcttt    70500
tatcccataa acatcgattg tacactgtga agtgccaggt atcacactgg ggatgcaaaa    70560
atgaacaaga gctattgtta ctctccctac tatggagctg ctgacaggca tttctttaca    70620
tatgattttt tttaaaagtg ctgtgcaacc tgccagtgct acaatagaag tacaaggaaa    70680
cacatataaa ttttataatt ttacctgtct gtgagatttg ttgttaattt ataatcttct    70740
ctttatgttt aattttgcaa aatcagagag aaaaatattt ctttacagaa tgactttaat    70800
tattttttgt attgttttct tttattcctc tcctgttctt ttagtggaga tatcaaataa    70860
aatgcaataa aaagtccaat atttagggac agattttcta gttttttgcat cattcaagct    70920 ggacagttgc attttttcgg gggggtcaaa ctttaaagtc aaacttttag tatagaggaa    70980
ccaaagaaaa ttattttaat taattcgtat ttcttgttag tgtctcttgg aatgaaaacc    71040
actagacaag aattactttg tatcgctttg aaatgtccta agtgttgttg tttagagtta    71100
aggataactt caggtatcag aaggttggga aaatttctat catgtcaggc tgtgggtgga    71160
ccatcctgtg gggcaatcgt tccagaaaat gctggtattt aatgtcacaa ggaagctggc    71220
agaatttagt gagtgctaat agtcttcaca agttccaaag cctaccettt gatggtacgt    71280 acagcacagc tgacacatct aaaacataca ttatagaatc ctagccattt agtggtgaga    71340
ggagccttgg agttctcaca tactgaactt tggttaccag aattacctga tgagtatttt    71400
ttaagacaga gattcacagt taggcctact aaattgaat tctcgtgaca ggatacagga    71460
atctggtttt ttaatcatca acccacatga atctgagagc atccagatct ggataccaac    71520
cactctctag aacagagaag gggtgaaata ttttgctcta ttgcaagcat tcagttagtc    71580
tcacacaatt tcatgatgct ggcagaatac atgagcatcc tgaatcacag tgttcatatt    71640
cgggtttttt tttttttttt tttttttttg gagatgcagt cttgctctgt cacacgagta    71700
ccctgaacca gagacaaagg actttattat tcatagcaat agcagtagcc agtgttcagc    71760
atttgcactg gctccccaac ccaaccccca gttcccacaa ggcaatgcaa agagggccag    71820
atgataccaa caaatgaagt gggtgtttta aacgagagga aacctgggct tgaggagcct    71880
gactcttcca taatgggcag atgggggcag taaggtttgc acttcacttg ggatgaagac    71940
atcttctttg tcctccaaaa ctgtttgcta tacaaatacc cttgaaaaaa taacccgaat    72000
gaaggtaatc aatgcctctg ttcacaagat gtgcataaac atgggagact cagagagatt    72060
gtttccccag aattacttag tccaagtctc tcgtttttaag gatgaaataa ctgaggtcca    72120
gagagctaga gcacttagta atacacttta cgggtggcca cgttgggctt ttccaagagc    72180 tccattttt ctatgcctat tacactcatg cttttcccagg tacccttatt cctttctggc    72240
ataggttgcc tagagctagt aagctgtcac aggtgaaata attgaacaga aggacctgct    72300
gcatgagtga gcagtaatga caaagtacaa atggtgagag caggccaaga gagaacttga    72360
agtggaggta gtaccaaatt catcaccagt ccaagttgcc ttccctcatt ttatttgact    72420
tgcaactgta atgaaatgga catgacacag actttcattt aaaatgaatg tggtctttga    72480
ctttgtaagc aaagggaaaa ttttgaaga tccttgctgt tgtctatccc tgccatcctg    72540
ctccctaaaa gataaattac tgtgttaatg aaagagagca ctaattaagc tttatagtcg    72600
atttgctgta tatattttg gtaaatgtca atagaaaagc ttttaaaaat caatacaaat    72660
ctatataagc tacctaaaat ccttctcaa agtgggtaat aaatttaaca aattaatgaa    72720
```

```
ttaattacgc ttaagaccaa acttgagtag tatccatagc aaggaaaaac gatggccaaa   72780
aaagacaacg gaggtccatg tataatattt gcctttgaga agataaaaaa ctgctagctc   72840
tgacttaatg gcaactaaag agaaatgctg attaatgtcc actctgtgtg atgaaaatgt   72900
gcaatttaga aatccaaatg cagtactact tacctctggg tactgattaa ggaaaacctt   72960
actgaaaaca tctcaatgat aactgttgac accacttaat gtattttaaa aattattttg   73020
tcttatttca tatatactgg cctaccttac agctttagcc agttactata ttatagaacc   73080
ttgacattta ttttaaaaaa ttgaaaattt caccagtcct caccggtata aatacaaccg   73140
tagcaaaggt tttctttttt taatgggagt tattttctc caagatccaa catatttatt   73200
actctctgag agttaataca catgtaatca tgaaataaga actataagct caccttcaaa   73260
tgcgtattcc ctcagttcag tttttattca agccacagca atagttttgt tcaaaacgat   73320
tcctcaaaaa ataacaaaca accatatccc atagacattt gaggtcactc ataactaatc   73380
aaactatgac tcttaaatct gtgaatgcca aaggatctgc tgcaaaatgt cttgagtaca   73440
tttagatgat taatataacc ctctctctgc tcaaggacaa ggacattcct gtgcaggaag   73500
aagttgaacc tgccccagtt aggaggattc tgaaattcag tgctccagaa tggccctaca   73560
tgctggtagg gtctgtgggt gcagctgtga acgggacagt cacacccttg tatgcctttt   73620
tattcagcca gattcttggg gtaagtacac agctggacta gctttcttct tctcatacct   73680
tttattttat tattttgata agtccgctct ttgttttcat gtatttagct cttttctgtt   73740
agttcatttt tctcatctct aaagaatgaa aaatttccta agcctccatc acacagaggg   73800
taagaaggca agctgagaa ctctcatttg ggctcgcagg gcactcagac agtcattgta   73860
cctataaaaa agaaaatggt actgtcactg aaaattttgt gttagaagtg gcaatttttt   73920
ctagtaatgt atatcaaacc taatcaaaat gcaaagtgga ttcactgaat aatacaaaag   73980
gcttttaggg aaattttgat cttgctgaac agcagaggta caaagtttga cttatatagc   74040
aggtgttagt gtttgatgta taattctcca cggattgcac tattgaaata gtaatgtgga   74100
taggaagcag aaaaagaaag acagaagtaa aataaggcat gattgaaaac taagcttatt   74160 ccaattttc acttcctaga atttcttatg ttctctatct gacttgattg ctgtaatcat   74220
cataataact atgaacatgt atcaggcaat atctaagcat tttatgtaca atagttcatt   74280
taagtttact aacaaccgtc taaggtaggt attcttgtta tttctatttt acaaaggagc   74340
aaaccaaggc acagagagct taggctagca agtggtggag ttgggattca aatccagcca   74400
gtgtaactgt agagccaggt tctagtaaaa tcttgtcatt gcaagattag ttatcaaaat   74460
ttgatcatgg aaacagtact gaaagacagc tgactagatg caggtagtat gtgccttctc   74520
catgaagagg aatcagaata gtaggtagat acttacattt ggaacagatt atctgggcta   74580
gaacattagg attcatcaaa caagggatgg gaagcaccag aaataagaaa ggagaggatc   74640
taaggcagct tacccagttg gggactgcct gagagccaca agaggctttt ggatatgggc   74700
aaacagtaag agagaaacat ccagggctcc aaaatgggct ttcacaatct tggctatggg   74760
gtaaatcctt gacccactag ggccttttcc ctgacatgaa gagctgccta aagattccac   74820
ggagatgtta ctccaaaagg gaaacccaca cagaatcaca caggcatcca atcctggagc   74880
agcctctgtc aggcatcatt ttgagggcct agataccagg aatatacaaa catgcactgc   74940
ctctgcactg cttcaaggag agagagggga gactagataa tcccatcacc cccgggagga   75000
tccctgccat gctgttgtgg tctactgttg agactgagtc atgaacagac tcagagtagt   75060
atcatacaaa gatcacacta ctgcatgaac ccaaaatcaa agccaaagta tttttttaaaa   75120
```

-continued

```
atctccccta caaaagcaaa ttcaaaaatt ggaacaagca actgatacat cagatataca   75180
gatatcaatg gaagaacata ggaaacatga aaaagcatgg aaatatgaca ccaccaaagg   75240
accacaacaa gtgtccagca accaataatg gtgtggcttt gtgtcccac ccaaatctca    75300 tgccaaattg taatccccac atgttgaagg aagaacctgg tgggaggtaa ttggatcatg   75360
ggtgggtgga tttcccccctt gctattcttg tgatagtgag tgagttctca cgagatctgg   75420
ttgtttaaaa cttttgtagtc ttccccttc gctctctctt cctcctggtt tggccatgtg   75480
aagacatgcc ttgcttcccc ttcaccttct gccatgattg taagttttcct gagacctcct   75540 cagccatgtg gaactgtgaa ccaattaaac ctttttctt cataaattac tcaatctcag   75600
catcagtgtg gcctggatgt gagacaaggt gtcaaaaaag attatttttgg agctttaaga   75660 tttaacgact gccatgctgg gttttggacc tgcatgtggc ctggagcacc tttgttttgg   75720
ccaatttctc cctttagaa cagaaggatt tacccaatgc ttgtaccccc attttatctg   75780
ggaagtaaca aacttatttt tgattttaca ggctcatagt tgtaagggac ttgccttgtc   75840
tcatatgaga ctttggactt agactttga gttaatgctt aaatgagtta agacttaggg   75900
gactgttgag aaggcatgac tgtgttttga aatgtaagaa ggacatgagt ttttggaggg   75960
gtcaggggcg gaatgatatg gtttggctct gtgtccccac ccaaatctcg tgtcaaactg   76020
taatccccac atgttgaaga agggaactgg tgaaggtga ctagatcatg ggaggagatt    76080
tcccccttgc tgttctcata atagtgagta agttctcaca aaatctgata aaagtgtgta   76140
gcgcttcccc cttcactctt tcttcctcct gctttggtca tatgaagatc tgcttgcttc   76200
ctctgttctt tccaccgtga ttgtaagttt tttgagatct cctcagccat gtggaactgt   76260
gagtcaatta aacctctttt cttcataaat tacccagtgt caggaatagc agtgtgagaa   76320
cagtttaata gagataccaa tgaaaagaa tttcttgaaa tgccgggtaa ataatttaaa    76380
atattgattt ttaaagatag taaatgcaa gagaaatctg aaaaccaata caagaaaatc    76440
agaaatcaat tcaggatatg aatgagaaat ttaccaagga gataaatagc attttaaaaa   76500
aataagcaga aattctggaa ctcaaaaatt cattgaagga aatacaacat acactttaaa   76560
gcttaaatca tatactagac caagcagaga taagaatttc agaacttgaa cacatgtctt   76620
ttgaaataat ccagtcagac aaaaataagg aaaaagaat aaaagaatg aacaaagcct     76680 ttgagatgtc taggactaag taaagggact gaacatggac taaataaagc aactgaactt   76740
atgaattatc agtatcctga aagggaagag agatcaaaag gtttagaaaa catattttaa   76800
aaaatcatca ataacaacct cccaagtctg tcaagactgt tagacaacca gttcagaagt   76860
ccagtgattc cccaggcaaa cacattacaa aaaggaattc accattatat attatgttca   76920
gaatgtctaa agtcaaagta aagaaagaa tttttaaatt agcaagagta aagcatctac    76980
tcatctataa aggaaacccc atcagactaa tagcagactt ttcagcagaa accttacagg   77040
ccagaagaga aagagatggc attttcaaag tgctgaaagg aaaaaaaaaa ctgtcagcca   77100
agaattttgt gtcctgccag aataagcttc ataagtgaag gagagataaa gttcttccca   77160
gacaaggaaa catttagaaa aattatcacc actagattgg acctacagga aatgctcaaa   77220
ggggtcttaa acatggaaac aaaaggtcat tgctcaccat cacaacaaca cattgaaata   77280
taaaactcac agttcatata aaataatcac acaaggaaga agagaaaaaa ataaaatggc   77340
ataacagaat ttcatcaaac tacaaagaca aaaaaaacag aaaagagggg aaacaattta   77400
taaaataact tgaaaacaat cagcaatatg acaggaacaa agcctcacat atcaatatta   77460
```

```
accttgaatg tgtgactccc aaaaatctga gacaggtccc agttaattta gaaagtttat    77520
tttgccaagg ttgaggatgt gcacccatga cacagcctct ggaagtcctg acaacatgtg    77580
cccaaggcag tcagagcaca gtttggttgt atacatttta gggagacacg agacatcaat    77640
caacatatgt aaggtgaaca ttggtttggt ctggaaaggc aggacaagcc aaagcagaga    77700
ggggtcttcc aggtcatagg tagataagag acaaatggtt acattctttt gagcttctga    77760
ttagcctctc caaaggaggc aatcaggcat ccctttatct cagtgagcaa aggggtgact    77820
ttgaatagaa tgggacgcag gtttgcccta agcagttccc gatttgactt ttctctttag    77880
cttagtgatt ttgggggccc atattttcct ttcacaaatg taaatggatt aaatgtccac    77940
tattaaatac atattggaag aatggattaa aaaaataatc caactaaatg ctgactataa    78000
gaaactcacc ttacctataa agacacatat agactgagag taatggggcg taaaagata     78060 ttccatgcaa atggaaacca agttgagca aaagtagcca cacttatatc agataaaaca     78120
ctttaaatca aaaatagtaa aaaaaaaaaa agacaagata attatgtaat gataaattca    78180
acaaaacgtt ataacaattc taaatatata tgaactcaac atcagagcac ccaaattcac    78240
aaaacaaata taagcaaaac taagaaaaga tagggcaatg caataatagt gggggaattt    78300
aacatgccac tcacacacta gccagatcat catgtcagaa aatcagcaaa caaacattgg    78360
acataaactg gattttatat caaacttaac agacatttac agaacattct acccaacaac    78420
tacagaatgt acagtctttt cctcaggata tggaacattt tgcaagatag atcagatatt    78480 aggcccacaaa acaagtctta atgaattttt taaaaactga agccatatca agtatcttct    78540
caggccacag tgaaataaaa ctagaaatca atactaagaa gaagtttgga aactatacaa    78600
atacatggaa attaaacagc atactcttga ataatcactg ggtcaatgaa gaaattaaga    78660
tggaaattag aaaattttt gaaatgaatg aaaatgaaaa cacaacatac caaaacctgt      78720
gagatacagc aaaagcagtg ctaagaggga agttgatagc attaaatgcc tacataaaaa    78780
agtagaaaga tcacaaatta acaatctatc attgcacttc aagaaactag aaaaagaaca    78840
aaccaaaccc aaagttagca aaagaaaaga aataacaaag accagagcag aactatacaa    78900
aatagaaaca aacaaaaaaa aaaaaacaaa ggagcaatga aacaaaaaat tgtttctttg    78960
aaaagataaa attgataaac tgctagctaa tcaaaaagag agaaaatcca aataaactca    79020
atcaaaaatg aaaagaaga tattataaca gataccacag aaatacaaaa gattatcaca      79080
gactattatg aaaacctaca ctggaaaact tagaggaaat agataaaattc ctggaagcgt    79140 gcaacctacc aagattaaat caggaagaaa tagaaaacct gaacagacta ataatgagta    79200
gcaagactga gtcagtaata aaaaattttcc taacaaaaaa aataaaaagc ccaggaccag    79260
aaggattcat agctgaattc taccaaacag gcagagagct aataccaatc ctcctgaaac    79320
tattttagaa atcagaggag ggaattctcc ctaactcatt ctacaaggcc aatatccacct   79380 gataccaaaa ccagactagg acatcacaaa acagaaaac tacagaccaa tatctctgat      79440
gaacatagat gtaaaaatcc ttaacaaaat aactgaatcc aagagcacat caaaaagata    79500
acacaccatg atcaggtggg atttatacaa ggcatgcaag gatggttcaa catatgcaaa    79560
gcaataaaca tgatatatca cataaacaat attaagggaa aaaattatca tttcaataga    79620
tgcagaaaaa acattcaaca aaattcatca tcccttcttg ataaatattc tcaataaact    79680
aggcatagaa ggaacatact tcgacataat aaaagccata caaccaaca gcaaatatca     79740 tacttaatgg ggaaaagttg aaagaattct aagaactggg acaagataag gatgccaatt    79800
ttcaccactc ttatttaaca tagtactgga agtccttgcc agagcaatca ggcaagagaa    79860
```

```
aaaaaataaa aggcatgcaa attagaaaag aggaagccaa attatccctg tttactgatg    79920
aaatcatatt atttatagaa taccctaaag acttcaccaa aaactcttaa atttagtaag    79980
tgaattcagt aaactttcag gatacaaaat taatttacag aaatcaatag tgtttctata    80040
caccaatatt gatctagttg agggccaaat catgaagtta atcccattta caatagctac    80100
aaaaaaaata cttaggaata tatttaagca aagaggtgaa agatctccct aaggaggacc    80160
acaaaacact gataaaagaa atcatagatg ccacaaacaa aaggaaaaac atcccatgct    80220
catggattgg aagaattaat aacattaaaa tgaccatact tcccaaacca atccactgat    80280
tcaatgcaat cactatcaaa ttaccaatgt catttttcac agaattagaa aaaacaatt     80340 ttaaaattca catggaacta aaaaaaagag ccctaatagc caaagcaatc ctaagcaaaa    80400
ggaacaaagc taaggtatc atattatttg gctgactaaa ttattctacc aaggtataca    80460
aatagacaca tagatcaatg gaacagaata gagaacccag aaacaaagcc atatacctaa    80520
aaccaagtta tctttgaaaa agtcaacaaa aatattcatt gaagaagtga caccctactc    80580
aataaaaggt gctggaaaaa ttggatagca gtatgcagaa gaaagaaatt agacccatac    80640
ctctcaccac ttacaaaatt aacacaagat agatagaaca cctaaacata gacctgaaac    80700
tataaaaata ctagaagaaa acctaggaaa aactcttctg gacatttgct taggcaaaga    80760
atttaattca aagtcctcaa aagcaaacac aaccaaaaca aaaatagaca aatgggaata    80820
aattaagcta aaaagctttt gcacagcaaa agaagcagtc aacagagtaa acaaacaact    80880
tacacaattg gagaaaatat ttacaaacat tacatccaac aaagggctaa tattcagaat    80940
ctatagggaa ctcaactcaa gcaacaacca ataatttca ttaaaaggta ggtgaaggac    81000
atgagcagat attttcaaa agaagacata caagcagcca acaaacatta aaaaatgct    81060 caacatcact aatcatcata gacatgtaaa ttaaaaccac aaagagatac cattttacaa    81120
cagtcagaac agctatcttt aaaaagtata aaaacaacag atgttagcaa agatgtggag    81180
aaaaaagaat gcttatatac tgctggtgag aatgtaaatt agtacaacct ttatggaaaa    81240
cagaatggag atttctcaaa gaactaaata tggaactacc atttcatcca gtaatcccac    81300
tactgggctg tattagggac agcgttctct agagggacag aactaatagg atatatatcc    81360
atatatgtat acacacacac atatacacat atatatacat atttataggc gtttatagga    81420
tatatatcct atttttgtgtg tgtgtgtgtg tgtgtgtgtg tgtatatata tatatgggag    81480
taataggata tatatcattt tatatatata taggagttta ttaagtatta acttacacat    81540
gatcacaagg tcccacaata ggctgtctgc aagcttgagg ggcaaggaag gccagtctga    81600
gtctaaaaac tgaagaactt tgagtttgat gtttgagggc aggaagaata cagcaggaga    81660
gaaagatgta ggctgggagg ctaggccagt cttgctcgtt tacattttt tcttcttgct     81720 ttatattcac tgagagctga ttaaattgtg cccaccagat taagggtggg tctgccttcc    81780
ccatactgct gattcaaatg ttaatctcct ttgtcgacac cctcacagac tcacccaggg    81840
gatcaatact ttgtattctt caatcaagtt gtcactcagt attagccatc atatgggcat    81900
atacaaaggg aaagaagtca ttatgtcaaa aagatacctg cactcatatg tttattgtca    81960
cactattcac aatagcaaag acacagaatc aatctaaatt tttatcaaca gaggattgga    82020
taaagaaaat acgatatacc atggaatact actcagccat aaaaaggatg aaatcatgtc    82080
ttttgcagca acatggacag aactggagga cattaccccta agtgaaaaaa ttcagaaaca    82140
aaaaatcaga tgccacatgt tctcacttaa aagtgagagc taaacaatgg gtaaacatag    82200
```

```
acatacaggg tggaataata gacactaaag actccaaaag ttgggaggat gggagggaga    82260
tgaaggttga aaaattgcct attgggtaca atgttcacta ttcaggtgat gggtgcacta    82320
aaagcccaga cttcaatatg catgtaagaa atctgtgctt gtaccccta aatatacaaa     82380 aattttaaaa agttaatttt aaaaaagcag tttaaaaaaa tgtgatcatg ttttcttggc    82440
tgaaattcac acacacatat atacacataa atcctttgag gtccacaagg aaggaaacct    82500
agaactgtca acttgtacaa ggtgatgggg ccaggactag ggcccaggtt taccgaatcc    82560
tagtctatag aatttgccaa catatcacat tgtcagagct tattaaatga taaaagctta    82620
cattttagtt ccctactcca tttctttctc tcacatcacc tctcctgacc gtaaaaatga    82680
ccccacaagc atgagttgta cagaaaaacc tggataatcc acaaacaaaa tcaagtccat    82740
cgtgtaagga gggccccagc caccactgta gttttcgcat tgcccccttg tggtaagtga    82800
agaaatcaca ttaatttcag aaaggtagag aatcggaaac actcaacttt gattaactga    82860
atttctagtt atatggtgcc ataaactttt atgctgaaaa tctttgaaat aatttatatt    82920
tcttgatttc ctagtaggta caatatccaa atataaaatg aatcatcttt tattccctcg    82980
acagatctgt attgattgtc ttccccagac atggtgctgt ggactgggga atgcatatcg    83040
gttatgatgc tttccctagt ggagttttca gtctgtgagg aagataacat caacaaaaaa    83100
aaacccactc atcattcaac agatatttac cacctatagt tttccaggca ttgtaactaa    83160
tgttgggcat agagtggagg acaagaaaat cattgtgtgt ttgtgtgttg cttgcacaaa    83220
gctgacattc tagtagggag aagctgggga agtgcatttc actgggcaat gatgttagtg    83280
tagaaggtgt agggaatagg gttggatcag aaagaatcca agcctgtgtc ctggatgttt    83340 gcttttttaaa agaaatccaa aatgtcagct tctttgctga ttatttcttt acctcttata   83400
aaagcagagt aaagaatatc ctcacccatc tccacctaaa ctgtgcatat gagctgctgt    83460
ggagagttct gactttcctg tcaggagatc tttcttctga aactggctct tctagttact    83520
taccacatcc tgtgtgccct gggatcatgt catacctctt ctcccggtct ccatttccta    83580
caaaatgcag gatttaaaag atgatctcta agatatcttc cagctctagt ggtccatgaa    83640
atggctaagt taaaaaaaaa aagagattca actataattg ctgtccttct tgagcacctg    83700
cttggtcatt ggtggtgaca atattctctg tgtttcttct ggtgacaacc agaaacctta    83760
agatggactt agagacttaa gggctgcagg accagagtag gcagcatcta ggtgatgaaa    83820
tccaaagtct actcgtcgtt cttgttctca cagggttata tttgctaaga gaatgatgcc    83880
gaacaaacca ctattttttcc tctctggtag agtaggttgc ctctttgcat aattatcatg    83940
tgttcattag taaactcatg atgctttctt ctcacagggt ataattgtga gtctatttat    84000
agttgctcta ttttccttct gacataccta aagggcacaa tatgcacatt tgttgtattg    84060
agaccacact gtgggaatgg acccagcaaa tgattgggcc ttattaggag cccagttgcc    84120
aatctagcta agcctcaata tacatgtaag gcgtaatttg tctgcttcac tttccctgtg    84180
tccatttgac ttggaaaatg tgccaatgtt ccaagcacag cacttgggat gtagcatgct    84240
ggggaaaaaa aaaaatggat gtgagagtcg ccagctctgg atttgtagta ggtctctact    84300
ctgtactatc tgtatatatt taggtgagtg atttatcctt gataaatttc ctcatctgta    84360
taaggagcaa gaaaatctac ctcactgggt tgttttgaga atcataattc ctaatttaag    84420
ttacagcagg ttaatctacg catttgacat gtggcacata gcaaaaggtt aatgaatgtt    84480
agttttctcc ttcaacaaac ttaccattac aaaaatagca aagatgtgtg ccaaaactac    84540
aactagtaaa ggaacagagg aatctatgga tggatagccc ttggagttgc atttcaacaa    84600
```

```
taagaatata caaagaactc gtggagcaga attttgtgaa aaaagattat ggatagagag    84660
atgcccaacc ttgaattgga cagttgtatg aattttaaca ttagctaaat gctcttcctt    84720 ttttaacac tgagaaggta agtaatacaa aaagctaaaa gagcataccc aatagaaaac    84780
cactgcacca gaagccaaaa aacaggcatt tcttatcta gtaataacca ctagcttaat    84840
gaacttgaac aaacaacttg atgtttgggg ctttatttc catctataag agttaaatgg    84900
gaaaatctgc tgttctatag accatcatta taaaaggtga ccttaaggag gaatgggaat    84960
tgtggcatcg cagtttgggg tttcagggta tttgcacagt aattttaaaa atatttatct    85020 ttaaatttt gaattttag actctgtaaa cttacgagtt atgctatgct gggaagaatt    85080
actgtgctac ttctgaacc cacttttacc agtattgagc accatgaagg ccctagaaac    85140
ttcatcctac aaacagtaaa atctcattaa tttagaaccc ctcctactca ctttgtaatt    85200
tgccataatt tgaacgggtt acttttgctt tacaaaaaaa aggatttgtt aatggagtag    85260
cacatattgt ttccaaggag atttatttgg caaataatag ctacttagta aatattttg    85320 aataaatggt ctccttttgaa caactatttg ttgacactgt tttaatgact caaattaatt    85380
caggaaaatg aataaagatg tattgtatag ctctctaatg catacttctg accttcccag    85440
ttccctcacc tggcctaaat tacaaaggtt ctgttatgca caaatccat ttcaccacaa    85500 ggcaatgtca ttggagtatg ttcttttcatt tttcttattg taacaagatc ctcagttact    85560
tgaacagatg tctgtaaatt cagaatacgt ttgagtgtag tttactaagc attatacact    85620
aaaaactccc actcacaatg gccgtagttt tttaggggt gggggaatgt ttcagcttct    85680
ggtgagttag aggcaacaac ctcaatatca gatgaatgaa attttttct ctcctaaggc    85740 aattccagtc aatgctttga tagtttctt tttaatgctg tatagtctat aaaactaatt    85800
aaccggcaaa ttacctgagt gaaagtcata ttttcttta tttagtaata gagaaagata    85860
tcggtcaaaa tattaataca actttgagtt ttgtcccaga caacatttcc agatctcgat    85920
tccctccctc cctcccttcc ttccctttt ccttcataac tccctctctc cttccctccc    85980
tctttgcttc ctttcttcct tcttcccttc cgtcctctct tccttcttct gtccctcctt    86040
cctttccttc cttcctttct tccttcttc tcagttttat tacttaaatg ttttaatcat    86100
tttatcatcc ttttcatctg tgttgatgaa aaaccaacac aattgcctaa aaaggcaaaa    86160
taacaagaca aaaattctgt aagtcatcac cattggtttt cattcaccag gttttccgcc    86220
ccacagagga ctgtagtaca tcgtcatcat attcttagct aactttcgtt taattactag    86280
catgtttaaa gtggaaccat tatttaaaag actttatttt ttagagcact tttaggttta    86340
cagcaaaatt agaggaaggt acagagattt cccatatacc ccctaccacc ctacacgcat    86400
aacctccccc attatcaaca tctcccacca gaatgataca tttcctacaa ttaatgaaca    86460
tacattgaca catcattatc acagatccac agcttacatt agggttcact cttggtgttg    86520 tatatttat gaatttggac agatatataa tgacatggta agaaaaattc attttaaaca    86580
tgtaaataga tttatttttc tatttataat aaagttactt tcttgtttac tatctttcca    86640
agactttttc aattcctgat aaagaggaac aaaggtcaca gatcaatggt gtgtgcctac    86700
tttttgtagc aatgggctgt gtatctcttt tcacccaatt tctacaggta agaaatgtta    86760
tttttcagta agtgatttag ttattttcc tttttctca ttaaaatttc tctaacatct    86820
ccctcttcat gttttaggga tatgcctttg ctaaatctgg ggagctccta acaaaaaggc    86880
tacgtaaatt tggtttcagg gcaatgctgg ggcaagatat tgcctggttt gatgacctca    86940
```

```
gaaatagccc tggagcattg acaacaagac ttgctacaga tgcttcccaa gttcaagggg    87000
tgagctatgg gagggaaat agaagtatat taactgcatt ggcattcttt cattagagca    87060
ttctgacaat cacctgcatg ttttctatgg aataggacc agtgggattg ggatatccta    87120
aagccacatt ttccactgct tctaacactg acaaacagca gctaaagcac agtgtctccc    87180
aggcagtgcc cagaatcaat atatggcatg caccaaaatc tgtcagggtt ttggatttcc    87240
tctgagtcta acttaggaac atttctgagt ctgttttcag gcccagagac tcagcttcaa    87300
caagattcaa tactgccccc caggggtgg gtgaacaggg caaggaagtc tccttactca    87360
cacaggaccc cagagtgtgg tttagcctta tgaacagaga agctgtcctg ggcagcctct    87420
ggaggagccc agtcaggaaa ctgagggaaa gaaataaacg atttttatct agaatcttga    87480
aggcgtcgaa gagctgactt tctgattaag gtagacagag ctgtggtgtg taaacccaa    87540 aacctacagc cttgttcaag gggcttacac atatgatgag gctagacttt tacaaaacca    87600
ggtgtttgga ttaaagtgaa gagagccaaa ttgcccttcc aacatctcta cccactttct    87660
gtgaaaattt tttaaaaaac cctaatttaa aattatttt aaaagaaat aatatgttaa    87720 taaattcttt aaaaaacaaa accaaaggaa aaaattttta agtacaattt taaaactgaa    87780
ctatggtctg tgaggctctt agaagaaaaa actcactgga ctgatagtgc tgtactgtag    87840
tctcaactcc tagacagttt aaccaaaaat accaaaaatg atatggcaga atttcaacgg    87900
atcatggaat cctttcactt aggggaaat ccctataaat aggccacttt caattcatct    87960 aggcttttc tggaagcaca tgtgtttccc atagacttag ggttacactc tacatatgtg    88020
ttgcagtctt tcttgtttcc cctgaaataa tctaaggtga acatatttc ataattatgt    88080 attcttctac agtagatttt taatgagtgc acaatacttc attctcatct actgtcatgt    88140
cttaaaggat tctctagtta cgttttccc ctaggttttt ctcctcctta taagcaattt    88200
atatcatttt atatcgagct tgccacatcc ttgattattt tcttagttct caaaatgtaa    88260
tcactcaatc agtgtataat cattttggaa gattttgata tgcattgcat aactgcttaa    88320
agaaactttg ttccaatttc actctcatca ttggagtact gtagtctact ccctttactc    88380
ttgaatttag gctaaataaa taagtcataa tcttatctct tctattttg tggccttcaa    88440 tctgcaagga gcttttgaag gttatttgct atcactagaa ttcagagagt agcatctaat    88500
tatcttaaaa acacttatct tttaaaaag aggattttct cagaatttt ctaatacttt    88560 tgttgttttt taaaaaataa gattgctagc ccaggtcaaa cttatcttaa gattagtgtg    88620
aggtagattt ggctttgttt tcttgaagtt ggatagaaaa tatttcaaaa atatttttta    88680
aatatagatt acattttcta ctggtttgaa atgtttcctc ccattgtgaa tattaacttc    88740
ccatatatac ttagaactaa ctttggagat tctctagtct gaattgatca atttgactta    88800
ttctatttaa aaccttattg ttttagttga taattttttt taattttgt agatagatac    88860 caagtaggtg tatatattta tggggtacat gagaggtttt gatacaagca tgcaatgtga    88920
agtaagtgca ttatgaagaa tgaggtatcc attccctcaa gcacttatcc tttgtgttac    88980
aaacaatcca attacactct tagttattt taagtgtaca attaaattat ttattatagt    89040
cattctattg tgctatcaaa tagtatgtct tattaattct ttctattttt ttttttgcac    89100
cctttgtttt aattcttata acttgataca ttttagtatc tggtaaggca aatccctgca    89160
cactaatttt tcctcttcga aattctctta tctatttctg gatgttaatt attttaatac    89220
attttacact cattttaact tcttctaaaa atttattttt attctggtga aattcatatg    89280
cacacataca tacacagtag gattgctatt gtggggatac taaatttttcc tgagagacat    89340
```

```
acaaacaaga ctctagtttt tagcaagatt catagttata tgtcccacta tcttgctcac    89400
tttttctcat gtattttttc cactattttg aatgagatct ttttctcaat tatatctgta    89460
aatgagttga gatgaaagct gttagttttt gtatacttat cttaaggact ttccaagctc    89520
tcttataagt tataatttta gaaatttaat agtctactgg gttttctagg tatataataa    89580
aataccagat atagttctga aatattacag gtttggtttc agaccaccgc aataaagaga    89640
atattgcaat aaagcatgtc acactaattt tttcacttcc tagtgcatat aaaagttgtg    89700
tttacactat actgtattct actaactatg caatagcttt atgtctaaaa ataaacaatg    89760
tacatatctt aatttattaa tagcaactga ctgaccacgg tggtggttgc tgaaggttag    89820
actggcaata tcttataaga caactgtgaa gtttgcctca tcaattgact cttcctctca    89880
tgaaagattt atttgtagca tgtaatgctg attgatagta ttttacccac agtagaatgt    89940
ctttcaaaat tggattgagt tctcttaaac cctgctgcta cttttattaa catagcattt    90000
tcaccaggag tggatttcat ctcaagaaac cagtttgctt atccataaga agcaactgct    90060
tatccattca agtttatca tgagattgca gcaatttaat gcagcacatc ttcagactcc    90120
acttctaatt ctagttatct tgctattttc atgacatctg cagttactcc ctctgaagtc    90180
ttgaactctc aaagtcatct gtgagggttg gaatcaactt cttttcaagca cctatttatg    90240 tggatattct gacctcctcc catgaatcac aaatgttctt tcataaatat atatatacat    90300
ataaagtgta tatctatata tacactgtaa gttctagggt acatgttctt aatggcatct    90360
agaatggtga atccttttcca gagggttttc aatttacttt gcccagttcc ctcagaggaa    90420
taactatggc agatgtagcc ttgtaaaatg ttacttctta aataaaaaga cttcaaagtg    90480
aaaattactc cctgacccat gggcagcaga attcatgttg ggttaacaag cacaacaaca    90540
ttcatctcct tgtacatctc cgtcagagca cctgggtgac taggtgcgtt gtcaatgagc    90600
actaatattt ttgaaagctg tatttttttcc tgaacagtag gtgtcaacag tggcttaaaa    90660
tattcaaaaa actgtgtttt caacagatgt gctgtcatcc agcctttatt attctattta    90720
tagaacatag gcagaggaga tttagcatgc ctcttagggg cctagaattt ttggaatggt    90780
aagcttcaac ttaaagtcat cagctgcatt atccctaac aagagagtca gcctattttt    90840
cgtaagtttg aagtcaggca ttgacttctc ctctctagat atgaaagtcc tagatggcat    90900
cttcctccaa tagaaagctg tttggtcaac acggaaaata tgttatttgg tgtagccacc    90960
tttatcaatg accttagcta gatcttctgg agaacttgtg gcagcttcta cattagcact    91020
gctgcttcac cttgcacttt tacattgtgg agatgctttt ttccttaaac ctcataaagc    91080
aacttttctc ccaaagcttc ctcacttctc tcagccttac tagaattgaa gagagttagg    91140
gccttgttct gaattaggtt tggcttaagg caatgttgta gcaggtttga tcttgtctcc    91200
agaccattca aactttcttc atatcatcaa taaagctggt tcacttcact ttcttattat    91260
ttgtgtgttc actagaatag cacttttaat ttccttcaag aacttttttt ttctgcattc    91320
acagcttgac tatttattta gtcctatctc aggactaaat gaggctaaaa tgaggcctaa    91380
cttttagcct atctcagcct tcaacacacc ttcctcactg agcttagtca tttctagctt    91440
ttgatttaaa gtgagagatg tgtgacttta tttcacttga acacttagag gccaaggtag    91500
cgttattagt tggcctaatt tcaatattat tgtgtctcag gtaatagga ggtctgagga    91560 tagaaagaga gagagacaga atgaccagtc agtggagcag tcagaacaaa cacatttatt    91620
gaataagttt tcagtcttat attggcgtgg ttcgtggtgc tctaaaacga tggcaataat    91680
```

```
aatgccaaag atcactgatc acagatcacc ataacagata taataatgaa aaagtttgaa    91740
tattttgaga attactaaaa tgtgatgcag aaacataaaa tgaacacata ccattggaaa    91800
aatggcacca atagaattgc tctgcatata cagggttgcc acaaaccttc cattagtaaa    91860
aatcacaata tctgctaagc aaaaaatgca aaaaagatca ttttgtcttt tcttttcttt    91920
ttttatattt atactcattt tattttctta ttatattagc tagagctcat tgagaaataa    91980
gagtggtagt agaggtgatt ctctcaagca agacaaaaac tcaaaactac aaagtagaca    92040
tgttggactt cataaattca aaacttttat ataaacaaat gataaactag aaaagcattt    92100
ataataaata ttaatatccc taatataacc atattatgtg tagtgttcct aaaaccatca    92160
tgaacgatat tcatgaggat ggggaataac tgacactttc atacaatgta caaagttttt    92220
caatgttttt tggagagtaa tagtaaataa tagtaagcaa atgttttgga gagtaatagt    92280
aaataatgat atccccccaa aaactttaga gttgcttttc aagtattgtg taatgcctga    92340
cagtccttgc caaccagaaa ttcttttttct ttttaatta tatactcttt gaacagaatt    92400
ctgatgagtg aattccctcc tattgtgtaa gaatgtgtgt tcaaggatat ttatcatttt    92460
ttatattaac caaaaaatta ataaaattcc ctggaaacta cccaaatatc catcaacaga    92520 aaagagttg aatcaattat gatacattta tactaaggaa tattgcacag ctattttta    92580 aagtgttcct atatattgat ctggaaggat agttatgtac cattgataag tgaaaaaaag    92640
tcaaagtaca aagtaatatg tagagtatga gccctttttg taaagaaaaa aattaaaata    92700
tatgtatata ttgttaaata tgtatctatg ttttgtttgt gtcttaggtt gtattatttt    92760 caattttaa aaaaatacca attgaataaa atgtaaaagg aaacaaaata acgacatccc    92820
aaagagctgc aaagttgctt ttcaagtcct ctgtaatgcc tgacagtcct tgccaaccaa    92880
aaattctttt ttaaaaaaaa ttgtggtaaa atatttgtaa cacaaaattt actactttaa    92940 ccatcttttaa gtgtacagct gaatggcatt aagtacattt acattgttat gtaaccatca    93000
ccactattca tctctagaaa tgttttaccg ttccaaagag aaattctgta cccttgaaac    93060
ggcaactccc catcctgctc tccctcccct cagccccagc aaccaccatt ttactttctg    93120
tgtctatgaa cctgactact ctatgtacct catctaagtg gaatcatatg aatttatcct    93180
tttatgtctg gcttatttca cataacatga tgttttgaa gtttctctat gctatagtat    93240
gtgtcagagc tacatttta tggatgttta ttttatggat atatcatgtt ttctttattc    93300
attcatctgt ctgtggacat tcaggttgtt tggctgttgt gattaattct gctctgaacg    93360
tgggtgtaca aatgagaaat tcttgattta gcctgttagt ctccaaggaa gtcagcacta    93420
acacatggga atgctttggg acacaatttt atattccatt tgtgtcttca attcagtata    93480
aagatgcaaa ttattcctga ataacagtgc cttagcatcg aatggttact aacaggttac    93540
cttttgtcgt tttacatttt tttgtcttaa ataaaaatgt gtttctacaa ttttaaaaag    93600
aagtgatgta attgtcctca cccaagtatt ttctacagag tgtgccaagc tttggtcgta    93660
cctgcctagc tgcaactgaa acgacgattt ggaaccattg gatactctga ttagtataga    93720
tataattacc acagtggtcc attctccatc tatattggga ctgaatccat tttgtccatc    93780
tgcattgact aaatagctgt gtattacagc agcatgtaac tttgtaccaa cgagcaggct    93840
aacttcaatg agaatcaaag tggtatctta taatagtctt gtatcaactt caaaatata    93900 attatagagc aagcattaat cttcattgaa taagtaatat tacctcaagc ccaatggctg    93960
gatatcttca aacaagccaa atgcatcagt acttgacaca tgtgtagccc atgtttaggg    94020
ctgcattaat ctcagacaga ctgctctagc actgacactc ttaaaatgag attagtcaat    94080
```

```
aaatgaactt cggataagct atgaataaag aacctttta ttaattcagc cttcagatac   94140
gttatgtgag ctcatcattt aaaagaactt aatcatttaa aagaacttaa cttttttgaac  94200
agggactac catatgaccc agcaattcca ctcctaggtc tatatccaaa agaattgaaa   94260
gcagggactt gaaaggtgct tatacaccag tgttcatagc agcattattc acaatagcca   94320
aaagttggaa ataaccccag tgtccatcaa tggatgaatg gatatacaaa atgtgatata   94380
cacatacaat ggaatattca gttttaaaag ggaatgaagc taggtgtgat ggctcgtgcc   94440
tgcaatccca gcactatggg aggccaaggt gggaggatca cttgagctta ggagtttaag   94500
accagcctgg gcaacatagt gagacctcat ttctactaag attaaaaaat tagcaggtgt   94560
agtggcatgc atctgtggtc ccagctactt agcatgctgg ggcaggaggg ctgcttgagt   94620
ccaggaggtc aaggctacag tgagccataa ttatgccact gccctccagc ctgggtgaca   94680
gagtgagacc ttgtctcaaa ataaaataaa ataaacaaaa aataaaaata aaaaggaatg   94740
aaatttgtat acctgctaca acatgcctga agcttgaaaa cattatgctt agcaaaataa   94800
gccagacaca gaaggaaaaa tattgtatga ttctacttct agagatacct agggtaggca   94860
aatttataca gacagagagt tagaatagaa gtcaccaaga gcttggggga gagagaagaa   94920
agggaggtta ttgtttaatg gatacagagt ttttgttgga catgatttta aaagctttag   94980
gtatagatgt gtgatggtta caaaacattg tgaaatgcca ctgaattgta cacttaagaa   95040
tggttaaaat gatatatatt gttatgtata ttttatcaca actttataaa aggtctgacc   95100
tttttgtgta atggtaattg gtaaaagcga ctgtgtgtct gagacgggtt gattgctttt   95160
tggtttgcag gctgccggct tcagatcgg gatgatagtc aattccttca ctaacgtcac   95220
tgtggccatg atcattgcct tctcctttag ctggaagctg agcctggtca tcttgtgctt   95280
cttccccttc ttggctttat caggagccac acagaccagg atgttgacag gatttgcctc   95340
tcgagataag caggccctgg agatggtggg acaggtaatc ttgcagatct aattttccca   95400
ttcctcatgg ctgagtggct atcagacaaa ctgttaaaaa cgagtagtac gaagagactg   95460
aaggaagctg tcagcccaca agacaggcac acttaagaac cttccaccac cctttctatg   95520
cgtgcttggc gcaaaggctg aggcaataaa gctccgagac tctgagtatg agccagtgtg   95580
gagaaatagc ggagtgaaca caggattgcc tgttcaattt cctctcgcat agtgattcat   95640
tccacattcc aatttggtgt actctcattt gcagggtgg atagttcagt tttctggccg   95700
tgaagctttt gcaatttaat ggttcccctg agccatgctt tccacacaca caggagctat   95760
gatggtttta atggcacatg cctttgctct tcatacttta gagtccccca ggcttggggc   95820
aagtgtcttt cccaaccaga attatgaact acagtttagg ttttggatac acttaggttt   95880
tagctacaca ttttaaagtg tgttctaatt aatatcttgt ccttgggggg taaatgaggg   95940
atggtagcat aaacacttct caagtataag aattaaggga aacttgaatt taactgaaaa   96000
attgtctcgt ggtccagttg ggttgatctc cagccacgtc tttgtattcc cagatgatgc   96060
attctctgat ttgtaccaca ttctgccatt tgcaccatct aatccaggca gccactgaaa   96120
tgtcacgaaa ggagttattt ctgcccttgt attcctaaga ctctttttca atcttcagat   96180
tacaaatgaa gccctcagta acatccgcac tgttgctgga attggaaagg agaggcggtt   96240
cattgaagca cttgagactg agctggagaa gcccttcaag acagccattc agaaagccaa   96300
tatttacgga ttctgctttg cctttgccca gtgcatcatg tttattgcga attctgcttc   96360
ctacagatat ggaggttact taatctccaa tgaggggctc catttcagct atgtgttcag   96420
```

-continued

```
gtgaggaata tctagccaag gtgagaaaag atcaacacac aaggaaggaa tagcctggtt   96480
ctgtcagtta gcttttgct gcttagcaaa ccatcccaag cttggtgtct tacaatagct    96540
gggattaatt atttctcaag attcgtggg tcatcagggc ggttcttctg acctgggctg    96600
actcagtcag gcttctgtgt attcttctgt ctccacatgg cctgtctagc agatgagctt   96660
cttttcttca tattatggcc tcagagttcc aagtgccaca aaagagggca agccccactg   96720
tgcaagtact tttcaagtct ctccacgcaa agaaactttc taattttctg tttggccaaa   96780
gaaagtcata ccatcaagcc caggtttaag gaatagaaaa aaatagaatc cacttttttga  96840
tgagaggagt aaaaaagcca tgttgcaaag ggatgcatga aagtgtgaat taatatgatc   96900
gttgtttata acaatctgc cacacatgtt aatgctgaga aaatctagag gtcttggcta    96960
agatggttca tagagaactg ttttgtttga actcctctct tgcaaagagg gctgactcct   97020
cccaactgac tcctcctagg cagagacagc atgggccata caggtgaagg atgttccatt   97080
cgtatagcca aagcctgctt ttctaataag attagctttt agtccaattt ctcacatttc   97140
cagaggtgaa agcctaaggg tgtcagggta ctggggaacg aggtacacat gtatatgggc   97200
gagtcggggg gtaagggtgg agatggtctg agaaaggttt ggagggcatt aggaaaagtg   97260
gtcctatagg aatcggttct tgggtttcct tctctagcca tgagtcccgc cttctcacct   97320
ggtatctctt tcagcacttc tctcccactc cactacaccc acccagctag gaaagtgtct   97380
cttttctaaa tctttgcata tttaaagcta ctagtctaaa ttagaaaaca caaaccattg   97440
gcttattttt atttagttta tattaaggtt ttagaataat tttagaataa tttagaataa   97500
ttttagaata atttagaata ttttttttgcc aacatgtaaa aatctggggc tacaggctgg   97560
gtgcggtggc tcatgcctgt aatctcagca cctcaggccg aggcgggtgg atcacttgag   97620
gtcaggagtt caagaccagc ctggccaaca tggcgaaacc tcatctctac aaaaaaatac   97680
aaaaattagc caggtatggt gatgtgtgcc tgtaatccca gctacttggg aggctgaggc   97740
aggagaaagg agaatcgctt gaacccagga ggcagaggct acagtgagct gagatcatgc   97800
cactacactc cagcctgggt gacagagtga gactccatct caaaacaaaa caaaagtgg   97860
aactacagaa aacttccaat ttctggcttc actttaaaaa ttggaacgtc atcttccacc   97920
attttccatt tcatttcaag tgcttttcat tcccttaggc tttaaactgg gctcccgggg   97980
atgttcagat ttgcaattct ggcctaaaac aattcctgct tatgaactga gcagtgtgac   98040
acacaaagac acatccctta tccctatccc catcccaggc agaccctctg tgcatgacag   98100
tgcaggtgag cagctttggg ggctactact cacatcataa tctctacagc aacaaagtta   98160
tctctcatta tatttatcat tcatttattc attcactctt tcgttaatta agtacatgtt   98220
gactatagtt agaggctaag acaagtagaa ggagacaggc aattgcatct gtcttgctct   98280
ctgaagcata aattatatac atgcctggtg caaaatgat gcttatatca tcaatcatta    98340
tcttttatat acctattata gattcaataa ctgttagaat tctagaaaaa tcaactcaat   98400
ctggtgatct ttcaagcctg cttttctttt taaaaaaatt ttttcagaag tcttttccc    98460
cctcaaacaa ttttctttc ttttttttttt ttttgagac ggagtcttgc tctgtcaccc    98520
aggctggagt gcagtggcgc gatcttggct cactgcaagc tctgcctccc aggttcatac   98580
cattctcctg cctcagcctc ccgagtagct gggaccacag gcgaccacca ccacgcccag   98640
ctaatttttt gtatttttag tagagacggg gtttcaccgt gttagccagg atggtctcga   98700
tcttctgacc tcgtgatccg cccgcctcgg cctcccaagg tgctgggatt acaggagtga   98760
gccaccgcgc ctggccaaca attttcttaa aggaagctat tgtggtcaaa taaaggtttg   98820
```

```
gaggtctgag ctctcccccc ttcatgcttg ttcagtcctc ttcttactcc tttttcatag   98880
aacacagttt gaaaactgcc agtcccttaa acaccaccct ctccatttcc agacaagtct   98940
gaagtgactt gctcaaggat atttggtcct ttcctggcag aaccagggct agatccccaa   99000
acttctgcct tcaggtcatc acaccaacca cgccaccctg ctctcttcct gtgtgtctgt   99060
ctggttacag ggtgatctct gcagttgtac tgagtgcaac agctcttgga agagccttct   99120
cttacacccc aagttatgca aaagctaaaa tatcagctgc acgcttttt caactgctgg    99180 accgacaacc cccaatcagt gtatacaata ctgcaggtga aaaatgggta agtgttggaa   99240
tactatgcag ccataaaaaa ggatgagttc atgtcctttg cagggacagg gatgaagctg   99300
gaaaccatca ttctcagcaa actaacacaa gaacagaaaa ccaaacacca catgttctca   99360
ctcataagtg ggagttgaac aaacagaaca catggacaca gggtgggaa catcacacac    99420 cggggcctgt caggggatgg tgtggggtag gggagggata gcattaggag aaatacctaa   99480
tgtagatgac aggttgatgg gtgcagcaaa ccaccatgac acgtgtatac ctatataaca   99540
agcctgcaca ttctcacacat ctaccccaga acttaaagtc taataaaata aataaataaa  99600
taaaatgtgt aagtattgat gaggggtaag gttgtgcgta tgtgtgtgca ggacagccat   99660
tagggatggc catacaatac cacttggctt ctaaattcct gctgtatatg ggttcattca   99720
tacatacttg gagaagacaa acagtagatt tataaataca aaggaataaa gtaaattagc   99780
atcaaaaatt attcctaaag ctggcatttg aacaaggtga tgacattcag tgaatgctaa   99840
attctgtgta atataaaata cacttagttc ccaaatgaat gaagccagtt gtcctctgag   99900
atctacctaa ccactgtgtt ttctattgat gttctgatac agaatgtaga aaatcactt    99960 cttcctgtcc aataacattg atttaattca tgttcatctt gattcaagtt ttagcttatg  100020
tggatgtcct gaaaattaat tcaatctcaa caaaatatct gttcttctaa ttgatagata  100080
ggtatttgta aatcttctct acctattttt gaaaatttta gtatgttcca gaaagcaaag  100140
caaacctaaa cactagtaaa gctaagctaa attctgtaat cttctaaat tggtaaaatt    100200 tctccttcag ttcagtaaat gtaaagtttc tgtgtggtct attaaatgtc tatccatttc  100260
tagattttat aagttagagt tttaagcaca ccaaagtaca atagaaagta ttcacctttg  100320
cagtacagac ctcaggtaac tttctttcta ggtcgtttta agtgtaacat tatttttagt  100380
ctttaggaga acaaagctat agggtttgga cagttactgg cttctgtgat gtcatatctt  100440
ccagctattc tcttctattc agaatgtcag gaatagatgg caagaaaatc cccttatgtt  100500
agactgggaa tagggggagt caaatgtctt taatttcgtt gcccaagcct tcctttatac  100560
tacatctttc agaacacaaa atggaatgtc ctttttattaa gttgctgtct ttatactttg  100620
cactttggca gcatggtttg aaggtatctc aagcagggat tttaaactca agatttaggt  100680
gtgttttcaa tattctaggc ttcagtaaga gcatctctaa ttttgatcct cccatccaca  100740
ggacaacttc caggggaaga ttgattttgt tgattgtaaa tttacatatc cttctcgacc  100800
tgactcgcaa gttctgaatg gtctctcagt gtcgattagt ccagggcaga cactggcgtt  100860
tgttgggagc agtggatgtg gcaaaagcac tagcattcag ctgttggaac gtttctatga  100920
tcctgatcaa gggaaggtgg taagccacgc aaccttttg agaattttgc cttctgcaga   100980
gtatttccaa cccctaaaag tgggcttcaa gttttgtctt tgccagactc actttaaaat  101040
gcttgcctaa ggcacttacc ccatgcatat tttccagtcc cagtcatttg ctgcttcacc  101100
tgattctacc tcacaatttc taatgtcaga ttttccccag ttccagatgg cctgctgacc  101160
```

```
agttaggcaa agaaaactgg gcacactgca aagctggaga tgagtgtatt taatagaagc    101220
actcacttac ccgtaaatgg agcagaaagt gcagactaat caggaaacta atgaccagga    101280
atggaaaaag tagagtgata agggaaataa tgataaatga gcaagaaagg agagttagca    101340
tgaaaagatc taagacaatc cttgttcaag aagctgaaat ctaaataacg caaggaactc    101400
agattgagag ccatgtacca taaatcttta gcaaggatat ttgaaatttt ggtgaatagc    101460
tttggtattt attttcata acatttcttt ctcttttctg tccttttttt ctttctttaa    101520
aagtaatata tgcagaaggt cacaaaatca aataataaat atttataata aaaagccacc    101580
cccctgcttt atgcttacac tcccactcca catttctctg ctcaaaggca actattttg    101640 accacttgat gttttttgat ctcccaatgg tgacttttat gtctttaaat aatatgctca    101700
tgctatttca tgatttaaca aatttagact ctctgtgatt tattctcaag agataaaaat    101760
ctacttactc tcaccactcc ctccttttgc ctacctcctc ccaatatagt tatatcattt    101820
tttaggcctt ctatttataa atttgtaaac ttctgatctg cttccgttgc tcttccacca    101880
cctgtagata gttcctcttg aattctcact ttctaaaaga aaaatgttag caatcctacc    101940
tttattttca cctcttactc ttttcacctc ttacttcttt tacctcttaa gttctaactg    102000
cacttttatc aagaattcag agcacattct gtttataaca ttatcttttcc tgccttcact    102060 ctaagttgat tctaaaagtt gaaaatcaat tgacagcttt tttaatgatt atgtaaatat    102120
tgttcatcct tcagtcaaat agtgagttac atttacatta tattttttg attgttttc     102180 tgaaaggttt cttttttttct tgcattcttt gtcttcatga aaacctttgt gttcttccaa    102240
tgtctctgtc aggccatctc ttccctcatt tctgtcactc gcaacgtttg cctgttgaac    102300
agtcatcatc ctgtgagttc cctgtgatat ttccttggat tagatccatt atttcgtagt    102360
tcccatacat tccttttct agtttttacc cccttttgtt ggagctcatc caaaagcaaa    102420
tttctaagaa atagttcata gatatgggtc tgaaaatgtt ttgttttgct tcatacttga    102480
ttaattgttt aatccctata ttttgaaagt ggcctttctg acttccctga atagtataat    102540
ctttaatgta atatactatt atgaagagta taacattatg aagagaaatg ctaagaaaat    102600
tttgaaaaag gcaactaaag atttccttgt ataaagcaaa gcaaggaaac aagcaaacag    102660
aaattgacag aatccaggaa gttataaaaa taaggactaa gtattgattg cctataattt    102720 ataatcccctt ctgttattaa gttgaggtat aaagattgta aatttgtttg aaagtatttg    102780
gtaaccaata aacctagaaa gcccattgta accagaggta taattctgat aagtcagagg    102840
gttcaatttt ccaaaatgtc acttctggca tgcctgcagc aacatagat tgtgaactat      102900 gcaaggtaca ggaaactgaa tccctcatat ttacttttcc aacattaaca tgtacattaa    102960
gtatattcct ctgaatatgc ccagtgaatg ttctggtcac aggtcaaaag caaggccaat    103020
aaggaaatca ttatgacttc ttgcatttca taggcacagt atattttgtt acaacatcgt    103080
aaaacatttc tacaaacatt ttaagcagaa aacctaccac tttttatgtt ttttttcaa    103140 agtcctcttt gctcttaatc taccaaatgt aggcgttcaa tattttcaac atttatttgg    103200
atacctatga tgtgcctgtt actgcatgag tccctgtggg agagtctaag gaccatgaag    103260
catgtcttct gccttctagg agcttacaat gtagcacatt tagaagaatg agcaaacagc    103320
ctgagtgttt aattattaaa ttgtgttttg cagacttaag tgctatggaa aatgagtaga    103380
gcaagataag ccagggctaa ttgttattga gaaatgcttt atattttttc taatagtgtt    103440 tgcttttttcc attacttaga aattatctta aatataatct gttcataccaa tttatcacaa    103500 tttttttctg aaataatagg gccaaatact ttatagtagc acgttaggca tctgtgcctt    103560
```

```
taatattcta ggactctttg gtgaatcagc tcatgtggta gatattcaag tacctggact  103620
taactgccta actagactgt gagttcctag gaaacagaga ttatattttc tttacgtagc  103680
agacatagat ggcttaggat ggtgctttgt ggcaggtgat tcaaatatat gtttgttgat  103740
tgactaagtg aataaatgta ttccttttt acttggtttt attatctcag ttatgcagag  103800
aatggtgtta gtaaaatcaa gaaaacaggt ttgacccta tattgcccaa aagcttcaca  103860
gagaaaaatc ctttccataa ctcatgagtc tcaaaataga gcaaccctgt atatttgtag  103920
agagtgtgct gcaccaaagt aaggggacgt tgtttcttac ctgaataccta gagcgtcttt  103980
ctcgtttgcc ccacctgtag agccagagtt caggaaataa ataggaccat agtctgatta  104040
gtgttaacat ggatgccact cctgatagac attacatcca gaggtcaaag gcaacataat  104100
ttattccata attttagcct tgggattgtt agtctgttaa gcaaaccaaa tgtcctgcat  104160
aacacctaat gctagaatat gaactttcct cactgctgga attctaaaaa cctaatgacc  104220
tgtcatctcc tctattggca gatgatagat ggtcatgaca gcaaaaaagt aaatgtccag  104280
ttcctccgct caaacattgg aattgttcc caggaaccag tgttgtttgc ctgtagcata  104340
atggacaata tcaagtatgg agacaacacc aaagaaattc ccatggaaag agtcatagca  104400
gctgcaaaac aggctcagct gcatgatttt gtcatgtcac tcccagaggt gagtacgaag  104460
tcagagccat tccctatgag agacaaggat ggggagaagt agaatgacca gagtgtacag  104520
gttgagcatc cctaatctga aaatcccaaa tccaaaatgt tccaaaattc aaaaattttt  104580
gaatgccaac atgattccac aggtggaaaa tttcacactt gacctcatgt gatgggtcac  104640
agtcaaaatg cagtcaaaac tttgtttcat gtacaaaatt attaaaaata ttataggaat  104700
ttacttctgg gctatgtgta taagtagat aagaaacagg aattttgtgg ttagacttga  104760
gtcctatccc cagggtatct cattatatgc agatattcca aaatctgaaa aaatccagaa  104820
tctgaaacgt ttctggtccc aagcatttct gataagaaat attcaatctg tattatgatt  104880
gtggctctag aaggtcaaag gatatgcaat ttatttcaca gtgcccctgg actgtcttag  104940
ttttttaagc aaaagaaata tccttcatca acatactctt taattttgga aagtattgta  105000
ttgcccaatg caatggatgc tatttttgtt gaatttttt gtacattgag ctttagttta  105060
gcatagtggg gaaacacctg agatttggag ctgacctggg cttgcatcca agctttgcca  105120
cttagtagct tcatagcttt gggacaatta tcctttctga gattgtctat ttcatctgca  105180
aaatgcaaga aaataacgtt aaaatgaaga aaacacactt aatagccaca caatgaaagc  105240
ggccactggt attactgcca tcatcattat ttcattactt ggcaatgtgt accgtgggtg  105300
gtgggtaagt tacacctgcc ttactgtctc ttactttgcc aaaccaagt ccagatttcg  105360
cgcaatattg actctgcatt tttccatcca ccaaaagtcc ctcttagttt tgatcacaag  105420
aaaaattaca acatggaaac caaattgtag ggccaaattt tacctttaac cttctctact  105480
tacttttaa aaatatccct gggaaaattg ttttttcttta taagtgatta tgtttataaa  105540
ttttgtgggt ttgtggaagg cttttgtttt gctctttca caaagtctcc taagttttag  105600
gctcttggcc cagttcttac ctgttagccc aatctataag cacatggaaa ttactatttg  105660
ctgaatccag agatcaaaag caaagattgt gtgtctcctg gaagattcat ttatcccaca  105720
aacccttatt gaatagctac tcatgttggg caaggcactg tcatggagct ggtttactgc  105780
attgtcctca tacagacttg cccgtggcac ccttctctga gcactttgtc tccacaaaga  105840
caaagcaggt tttcatgggt ctcacctggc ttaaaggagc attcctcagg aggcaaggga  105900
```

```
agcagggaaa ggaaacagct cgtgttgtgg aaggcaagga agagaagtag tcaaggcaag  105960
gacttagagg agagcaagat tcactttcat ctggattcag atttcacttt cactgcttgt  106020
tacttgtcct cgcaccattt tcttacctcc ctgtgcctaa gttttgtaat ctaaaaaata  106080
gtgtgggtat ggtttctgtg aatattaaat gatacccctag ctagaatagt tagcacaata 106140
cctctatggt aaacactcta tgaatgttaa ctaattttta tgtagccatg ccaggcatga  106200
gtgattttt cttcctaatt ttctctaaaa ctcacaataa atatgtgaag taagtgttaa  106260
tactgcacct cagatgccta gccagctcaa aaaaatttaa ataatttgtt catgaacaca  106320
agctagtaag cagcagagtg gagcttctaa ccaaagcctg tgttccagaa tgctgcctcc  106380
ctaatacagc aatggaccag aagatctcgc aaaagacatt tccattcttg ggattagtcc  106440
atattggaag gattttttcca gataagaatc tagaatcaga gagtctcaaa tcaaggagga  106500
tctcatatat gggctcttat gtggacacag ggagaaggag attgaaaata taaacctaaa  106560
agaaatgcag aaatgaggaa taatgtcccc ttgcttccca catcaaatgt cacaaattcc  106620
atattttct tatattccta agtggatttg acatcctcca tcctatagga ggactcactc  106680
actgttccct agttcaacaa acaaataatt taaattacag aggagacctt gacatgagtt  106740
cagtacagca caggagcaat aactgtttct atttctcaaa cttatcatac ttttttttcag 106800
aaatatgaaa ctaacgttgg gtcccagggg tctcaactct ctagagggga gaaacaacgc  106860
attgctattg ctcgggccat tgtacgagat cctaaaatct tgctactaga tgaagccact  106920
tctgccttag acacagaaag tgaaaaggta agtgttgaat ttctaaagtc ttagatcatt  106980
acaaataagt cttttgctgt aaaatttgtc cttaataaaa tggcactatt ttcaattttc  107040
tgattcgtta acagtagaaa ttggcaatac tttgtggaac caaaagacaa ttatctagag  107100
caagtgattt aatataagat tgcttcaaaa aaaatatttt accttttaaaa taagaattgt 107160
ttttaagatt ctttaggcta agtgacattt ttttccaaag gcaaataatc acctttcttg  107220
aataaagtaa aataatctag attatctgtt atattttata gttctaaagt tatgtgacag 107280
agaaggtagg ccacatgcaa cacaaagaaa gaggtgatat ctgatgtgtg gtttgcatga  107340
aagaagatgc aattgagcaa aacacaatta tgaaatttaa aatgtataat taatgccata  107400
acaatcggga ttccattttg gagagagcta aaatgtcttc aatgaagagc agtatccagga 107460
atggccactt aactgctacc ctccgttgtt ttcttcattt catttcagga aactagacca  107520
tcaaatattg taaaattatg tagggacttc atagtttgct tccttcttgc tccactgaaa  107580
tttctcagcc agtgcactgc cattgaaatc actgatgcat tgcattcagg gaatacttgc  107640
ttaatcctct cttatgttga gcctttgggt ttgccgtcaa gtataggatt gttattcagg  107700
tcgtgttaac tgaactctca tgatggtggg ctggggagca atcatgcatc tttgcatcaa  107760
ctttccatct tctctttgca gacggtgcag gttgctctag acaaagccag agagggtcgg  107820
acctgcattg tcattgccca tcgcttgtcc accatccaga acgcggatat cattgctgtc  107880
atggcacagg gggtggtgat tgaaaagggg acccatgaag aactgatggc caaaaagga   107940
gcctactaca aactagtcac cactggatcc cccatcagtt gacccaatgc aagaatctca  108000
gacacacatg acgcaccagt tacaggggtt gttttttaaag aaaaaaacaa tcccagcagg 108060
agggattgct gggattgttt tttctttaaa gaagaatgtt aatattttac ttttacagtc  108120
attttcctac atcggaatcc aagctaattt ctaatggcct tccataataa ttctgcttta  108180
gatgtgtata cagaaaatga aagaaactag ggtccatatg agggaaaacc caatgtcaag  108240
tggcagctca gccaccactc agtgcttctc tgtgcaggag ccagtcctga ttaatatgtg  108300
```

```
ggaattagtg agacatcagg gagtaagtga cactttgaac tcctcaaggg cagagaactg    108360
tctttcattt ttgaaccctc ggtgtacaca gaggcgggtc tataacaggc aatcaacaaa    108420
cgtttcttga gctagaccaa ggtcagattt gaaaagaaca gaaggactga agaccagctg    108480
tgtttcttaa ctaaatttgt ctttcaagtg aaaccagctt ccttcatctc taaggctaag    108540
gatagggaaa gggtggatgc tctcaggctg agggaggcag aaagggaaag tattagcatg    108600
agctttccag ttagggctgt tgatttatgc tttaacttca gagtgagtgt aggggtggtg    108660
atgctaccat tactgtgagg acctacc                                       108687

<210> SEQ ID NO 73
<211> LENGTH: 77349
<212> TYPE: DNA
<213> ORGANISM: Homo sapiens

<400> SEQUENCE: 73
agcataataa attctttaat gatatagtat actagaaggt gataaatgct gtggaaaaga      60
aaatcaaagt aggataagag gaactgagag tcctgagggt acaagatcca acttctaatt     120
gagaagagat ttttaggagg tgagagtgtc ctccatgtca gtattttggg gaggataatt     180
ttggacaggg ggaacaacta gtacaaacac cctgaggtgg agtgctgcct ctcttgtctg     240
agtaatatcc aagaggccag tgtggctgga gtggagttag gcaaagacaa aataaataaa     300
aatgagatca gagaggtcac ggagagggca cagcattgta ggccatgact gagtgaattg     360
ggggctacca cagaaatgtg aagagaagag tgatgtgatg tgactcacat ttcaaaagaa     420
tcatccaggc catgcttttg acaatggaca aaggcggaag aggaggaaag gacagaggca     480
gagagacaat taacaagcta ttatagaaaa tcaggtggag atgatagtgg cttgcatgat     540
ggtggtagag ctggaggtgc agggcaaagg tcagattctg aatatatttt gaaagtaaag     600
gcaacaagat ttcctgacag attgattatg gtgtgtcaaa gaaagagagg aatgcaggat     660
gattccagtg ttttttgttga caactataag tctggagctg ccaactggat gcagaagttc     720
actggagggc ccagcctggg gaaaggatca ggagcaggtt aggcatgtta agcttgagat     780
gtctgttaaa catccagata ggaatgtcaa agatgcactt gtgtttaaga gtcaggaatg     840
caagagggaa ttttaggcta gaaacaaaaa gttagaaatt attcgataca gatggtatttt    900 aaagctgtgt gactgactga catgacagaa gtggcgagaa tagactgaga agtccaagga     960
atgagccttg gaccactcca gtgttaggta agtagttgaa aaaagagag agagagaagg     1020 catcaaagga gactgaggaa gagtgatcag gaaagcatag gaaaatccga gaaacatatg    1080
gtgtcctgga atctatatga aaaagatata ttcagaaaga cagagtgata aatctgtcaa    1140
attattgaat ttgtcaggta aaataagaac agagaattga tctttggact tagcaaagca    1200
gagattatca gtgacttttta taaaaatagt ttccggtagtg tggaaagatc aaacttctgt    1260
ttagagtggg tttcagagag aacaacagga attgaagaaa gtaataaact tgccaaccca    1320
gtttagctcc aaaggaaaag agggaaatat gatggtagct ggcaggggaa gtgtggtcaa    1380
gagaggtttt ttgtttgttt ttcaagatgg aagaaataac agtatgtatg taagctcaca    1440
ggagggatcc agcaggcatg gggaaattga tgatatagga cagaaaggga agaatggctc    1500
cttgtgaaag tgaaggggga tgggatctac aggatgaaca tgcaaacaaa gactggctgc    1560
aaagagaggc atgaatagtt catttacaga aacagcaaag gcagagtgtt ggtacagatg    1620
ctggtaagtg gaaaaatatc atggtaggag gttatggagt tccattctaa acacttcaac    1680
```

```
ttcatcagtg aaataagcac ggtaatttag cagaatgtga agatgtaaaa gaacagaatt    1740
tgagaaaaca gacgatatga aataattatt agaaaagcag gtgagtgaat gaactaagaa    1800
aattatcaaa ttctcttta ttagagactg aagaaactgt catctcctta tgtgctaatg     1860
agtttaataa tgtcctccag tcaccacaag ccttctttca aactacacaa ttccaactgc    1920
ttccgtctca gagtatcttg aaataatgat ctgaccgcct gttagaccag tgaagggaag    1980
gaatttgggt tgatttaaga agagaatcct catggtcatg gtagactgat atggagagaa    2040
aacattttga ggaaaaatac tcaactaaat tcatttctac tccagcatgc agtttcaagt    2100
caagttccac cttagctcca ggtggcaggc agagcaggat gcagaggcac agcacaagta    2160
aggggtgagt gccgaagctg ctggctcctg ttccagtctt tcttccttgg cctcgcctga    2220
acttttacta taataatagt caccatttat taggtgtctc ctacgtgcag acactttac    2280 acacagtatc cctaatccta ataacaccct tattttatag atccaatgac tgagtcaaga    2340
attacataac ctggccagac agctggtaca tgggaaaggt gagattcaca ccagggtcca    2400
cccagcatct ctacttatac catgctctgc tttaaggttc tctgagaact cagacaagcc    2460
ttgggctaac aattgtgtta acaggacata gcaggtgcaa ggacccactg gtcatcctgc    2520
tacctgatca gaaggaagga aagttgtatt tgttgctcac ctactatgtt ttaggcatag    2580
tactaggtgc ttttacctag tacttaattc ccttatcctc aactcattta ttcctcgcaa    2640
taacctgata agggagatgt ttttatcctc attttacata taaggaaaca ggcctagaga    2700
aatgagcaca gtgtccaaag tcacatagtt aataagatgt gaagctctga gtttgaaagt    2760
ctccggtttc aaagccatga aacttatggc tccccgtttt agacacttcc ttttgggaag    2820
agtgtggagg aattaatcag aaagaagaaa gtcatactca aataggtggt aggagcagag    2880
acaattcaat acagacagaa gtcttagatg agagcagtga gccagggcac tggactggga    2940
ctcaggaggc ttcccctaga ctctggttcc accgatgcag cctcaggcag gacttcacct    3000
ctctgggcat ccgtttcttc atatgttaaa catacggggt tttaattaga tgatcgctga    3060
agacccctct agccctaaaa ctctgtgtct cttaagtgct aagagggcac caacagcgtt    3120
cctcctcccc aaggagcata atgtgatggt tcctgccggc cctggctgac tctcgccgtc    3180
cttggagata attgggttca gtgccacctg gaccagaact ggggatgcgg aagcaagagg    3240
cgagtctatt gctctctctc ggtcctgggc cgccctgtga ttgttgggcg tccggaaact    3300
gtctccccta tgggtttaaa acaaaactg agcgcccatg gggtgtgaca gtcatctgca    3360
ggggcttggg tggcccatca ggcgaggctt tctcggcacc cgaggctcca gcctgatctc    3420
ggtcttatcc tgcgaccggg ctggttctgg cgggtcgcca gggtgggcgg cggcccagc     3480 cgggcgcccc ggcggcaaga gcggcaggct gcgcccctgg cccgcgccta gcctggggag    3540
agagctgggc gggcggcggg agctgctctc gcgggccgcg ccctcgccc tggctgcaac     3600 ggtaggcgtt tccgggccg gacgcgcgtg ggggcgggg gcggggcgg gggcgaggcc       3660 gcggcgagca aagtccaggc ccctctgctg cagcgcccgc gcgtccagag gccctgccag    3720
acacgcgcga ggttcgaggt gagagaggtc cgggcgcgtc tggcctcgaa gggagacccg    3780
ggacgtgggg cgcggggcgg gagtggccgg acctccaccc agtgccccg ggccccgcga     3840 ctcgtgcgcc gggccgccgg agagggtgta cttggttctg aggctgtggt ttctcctcag    3900
gctgagatgg atcttgaggc ggcaaagaac ggaacagcct ggcgccccac gagcgcggag    3960
ggcgactttg aactgggcat cagcaggtac atccccagca gccactggct tttccgttac    4020
acgccaatca gcaggactaa gttcacccct ggaaagaagt tgtaaaaatc ggttgatgcc    4080
```

```
tttgaagacc tttgttttgg aggcttcttt gaagggtctt gcatccggtt ctgaccttgg   4140
agcaaacgtg ttgtgtggcc tcaaagaatg tcactgaggc tccttttgga acagattcag   4200
gaagaaaagg ctgtcttgaa aagtgctccc ttcccttttgt gcaggggga ttcaatgaat    4260 atctgcattg tataacattc attgtattac gtaactcttg aaacttttac aaatgacttt   4320
catatacatc atctgattgt tcagacttaa agggtgtcag acatctgctg ttgatggctg   4380 tgcttttttga acaagggcag tgaagcaaaa actccctccc ctcctgccca tccctgtta   4440 tgtctcttcc tccttgtctt accctcccc ctcctctcat cgccaggctt atttgtattt    4500
ctcctttctg ggaggatagg tggggagggg gaacttctgt acatccgaat cagttttgtt   4560
caagtggtag ggggaagcag cgcttccttt gccttcatgt ctttctcggt tcccctggcc   4620
cttgttaaac tcacttcaca ggctttatga gcggggcaga agttcccagt caatggcgtg   4680
tgtctttgtt tcctctttca ctgtgggaat agtgaatcat tttcgccttt agcctgaaat   4740
agtttatgag gctattacgg tctctgagtt cataccaggc tacccagaaa aaattgacct   4800
gtgtcaagtg atcacccaga gggacaaatt tatcagtctc tgtagtttgt cctcaagctg   4860
ctagggcttt gattagctaa ctgaaaacat gcctacctga tgcttaaact gaagcattat   4920
tttagcctgt taatgtggtt gtgcagtaac cttgctgtat ttcttctaag caccattgta   4980 tttttttcata gaaaatttag ttttgccatg tagaattgaa aaagtgatag atggtgttac   5040
ttccaatgga agtacttaca cacgcaatag aaaaatatgg ttttcatcag ctggctgttt   5100
aggcagggat tgactgtgag tctattaata gatggcattt tcatgaagaa gtctatttat   5160
gtattgcact ggcttaacat ttgatgcgtg tgcaaaggag ctattcctac aaaaggtgta   5220
gtaacacttc agaacccagg aaagtcctca gaggggaagc ccacagcttc tgctggaaag   5280
aagaaagcag ctcaaaagag aaatacagaa agttaacaat aagttaagac cacatgatta   5340
tgaaatcaaa tgtagtgaaa ctaattttta taaaagcaga ccaaagataa tatatttaaa   5400
ggaagttaag cctgcttcaa tcaaattagt tatattcttg ttctaattat gttgctattg   5460
cccatggcac attcttttga acatatttag tggcagatgt ttgtccagtg attttagtca   5520
atactttaca taatttggaa tcatcttatg agtaaaactt tatcatttac ctggataaat   5580
gcatcatatt tatgtaaaaa tcatcatata tatataaatc atcatacaca cacacacaca   5640
cacactccct catagagttt atattatagt acggaggaca gacataaata atgtacatac   5700
taaataagta aaccacagcc aatgttagaa ggtaattaac gccatggaaa aaagcattaa   5760
tccaggttaa ggggatcagg agtacaaaag gggagtactt tgtaatttta agtagggtgg   5820
ttagggtaga tcttatttta aaggtaatat ttgagcaaag acttgaaaga aatgagagga   5880
gacagctgtg tgggtatcta aggggagagc attcccggaa aagtaactg gcaatgcaaa    5940 gaccctgagt caggtacatg tttggtgagt tcatggaaca gcagagagtc caggctggtt   6000
ggagcagagt aagcaggttt gggagtaggg atgtggtcag agaggaaata agcaaacaga   6060
tcgtgtagga cctcagaggt taatgcaagg attttggctt ttattgtaag aaaaaggaaa   6120
gccattgtag gttttttgagc aaagaagtag tgtatggctt ggcattttga ataattact    6180 ctgactgcta gttgaagata gactgaagcg gcataggtgg aagtggagag actaggcagg   6240
aggctgccct actggtgaca gcaatgaaac tggtgataag tggttaaatt ctagatgtac   6300
tttgaatgta tcaccaacaa gattgcctga caccactctc cacaatcctt cagaagaata   6360
gacattccta atttaaatc atgattttt ttaatttag aaaacaaata acttaattga     6420
```

```
cttagcgaca ctgttagcat acttatctttt cctgtgtatg tgagctctgt aaggcaggcg    6480
accatttctt atgtatccat gtatctttgt agtaccttcg acagttactt ttgtgcttgc    6540
tatgtttgtt gaactgaata attttgacat tttgtgaaca tcactcttat atttgaaaat    6600
ataatagttg aatattgtaa ctaaacatat ttatgttcaa ttgattgtaa aacattttgt    6660
aacagtttta aattgaagca attctatttt ttacagcaaa caaaaaagga aaaaaacgaa    6720
gacagtgaaa atgattggag tattaacatt ggtaagctgt gaaatgttaa atgtgaataa    6780 tcctacctttt tattcaaatt tgaggtattg aatcaattac ctttaaagca aatactttaa    6840
gattgtctag ctaggcgagc tgactcatac ttgtaatccc agcactttgg gagactgagg    6900
tgggagggtt gcttgagcac aagagtttga accagcctg gacaacatag tgagatctca    6960
tctctacaaa ataataaaaa taaaaatctt aaaaatagc atatgtcatg gcatgaacct    7020
gtagtcccag ctacttggga ggctgaggca ggagggtctt aggagtctga ggctgcagtg    7080
agttatgatc acaccactgc actccagcct gggtggcaga gcaagaccct gtctcaaaaa    7140
caacgacaac aaaaaactgt ctgcagacag caataaattg tccttgctgc acctgtgctg    7200
tataagtttg gcttattata gtcaatgacc cacattctta agatggatga tttttttaaaa    7260 agtagagaca ggctggcgat gacaccggac agagctaact ggtgtgcaag gaaagtgaaa    7320
atgggaattg tgttagtagc acaatgcaaa ctcaacaatt tcaagaaaat gcatttctgc    7380
atttgcttca cagaccccca ccccaaattt agcttaaaat aagcttgcat ttcaagaaag    7440
taattgttaa gtacataaat tttaatttaa ggaatctaca ttcacatttg gtttccaaaa    7500
aattggctaa ataggggta actattagga attctgatta tgcttaaaac agttttcggt    7560
gcttttctgt tggtacaaga caagacaata ttttggaag aagtctcctc atctggtttt    7620
catttgaaat atgtcttaca gaggcagctc aagaaagcat ttgcccattt ttggtaaata    7680
tgacgtgttt caaactgtga cagccattat ttggtagcaa agaagttaga attaagtgtc    7740
atgtcagctg aaatccaact tagtaattaa atggataaaa agacaccaaa acatccacac    7800
tctcaaacac tgctgcatac ttctcatgta accaaaagcc cctattcatt gtcttctctc    7860 ctctttttt atttgtttaa aaagcctcag taagggcaat ttaaaaaaaa attagcactt    7920
tggagaataa attgttttatc aaatgaaagc tggttttatt tattttttta gaagtttttt    7980
tttctttatt ttttaaatt tgtttaaatt atactttaag ttctagggta catgtgcata    8040
acgtgcaggt ttgttacata tgtatacatg tgccatgttg gtgtgctgca cccattaact    8100
tgtcatttac attaggtata tctcctaatg ctatccctcc cccatccccc caccccacaa    8160
taggccccgg tgtgtgatgt tcccttcct gtgtccaagt gttctcattg ttcagttccc    8220
acctgtgagt gagaacatga ggtgtttggt ttttgtcct tgcgatagtt tgctgaggat    8280
ggtttccagc ttcatccatg tccctacaaa ggacatgaac tcatcatttt ttatggctgc    8340
atagtattcc atggtgtata tgtgccacat tttcttaatc cagtctatca ttgttggaca    8400
tttgggttgg ttccaagtct tgctattgt gaatagtgct gcaataaaca tacttgtgca    8460
tgtgtctgta tagcagcatg atttatattc ctttgggtat atacctagta atgggatggc    8520
tgggtcaaat gatatttcta gttctagatc cttgaggaat caccacactg tcttccacaa    8580
tggttgaact agtttacagt cccaccaata gtgtaaaagt gttcctatttt ctccacatcc    8640 tctccagcac ctgttgtttc ctgactttt aatgattgcc attctaactg gtgtgagatg    8700
gtatctcatt gtggttttga tttgcatttc tctgatggcc agtgatcatg agcatttttt    8760
catgtgtcta ttggctgcat aaatgtcttc ttttgaggag tgtctgttca tatccttcac    8820
```

```
ccacttgttg gtgggttgt ttttttcttg taaatttgtt tgagttctt gtagattctg    8880
gatactagcc ctttgtcaga tgagtagatt gcaaaaattt tctcccattc tgtaggttgc    8940
cagttcactc taatgatagt ttcttttgct gtgcagaagc tctttagttt aattagatcc    9000
cattttgtc aatttttggct tttgttgcct ttgcttttgg tgttttagac atgaactcct    9060
tgaccatgcc tatgtcctga atggtattgc ctaggttttc ttctagggtt tttatggttt    9120
taggtctaac atgtaagtct ttaatccatc ttgaattaat gtttgtataa ggtgtaagga    9180
agggatccag tttcagcttt ctacatatgg ctagccagtt tcccagcac catttgttaa    9240
atagggaatc cttttcccat ttcttgtttt tgtcaggttt gtcaaagatc agatagttgt    9300
agatgtatgg tattatttct gagggctctg ttctgttcca ttggtctata tctctgtttt    9360
ggtaccagta ccatgctgtt ttggttactg tagccttgta gtatagtttg aagtcaggta    9420
gcatgatgcc tccagctttg ttcttttagc ttaggattga cttgccaatg caggctcttt    9480
tttggttcca tattaacttt aaagtagttt tttccaattc tatgaagaaa gtcattggta    9540
gcttgatggg gatggcattg aatctataaa ttaccttggg cagtatggcc attttcacga    9600
tattgattct tcctatccat gagcatggaa tgttcttcca tttgtttgtg tcctcttta    9660
tttcgttgag cagtggtttg tagttctcct tgaagaggtc cttcacatcc cttgtaagtt    9720
ggattcctag gtattttatt ctcttgaag caattgtgaa tgggagttca ctcatgattt    9780
ggctctctgt ctgttattga tgtataagaa tgcttgtgat ttttgcacat tgattttgta    9840
tcctgagact ttgctgaagt tgcttatcag cttaaggagg ctttgggctg agacaatggg    9900
gttttctaga tatacagtca tgtcatctgc aaacagggac agttttactt cctcttttcc    9960
taattgaata ccctttcttt cttcttctg cctgattgcc ctggccagaa cttccaacac   10020
tatgttgaat aggagtggtg agagagggca tcctgtcttg tgccaatttt caaagggaat   10080
gcttccagtt tttcccattc agtatgatat tggctatggg tttgtcataa atagctctta   10140
ttatgtttag atacctccca tcaatacctg atttattgag agtttttagc atgaatggct   10200
gttgaattt gtcaaaggcc ttttctgcat ctattgagat aataatgtgg ttttttctt   10260
tggttctgtt tatatgctgt attacgttta ttgatttgtg tatgttgaac cagccttgca   10320
tcccagggggt gaagcccact tgatcatggt ggataagctt tttgatgtgc tgctggattc   10380
ggtttgccag tattttattt tattttattt tattttattt tattttattt attttatttt   10440
tgagacggag ttgcgctgtt tcgcccaggc cggactgtag tggcgctatc tgggctcact   10500
gcaagctgcg cctcccgggt tcacgccatt ctcctgcctc agcctctcga gtagctgaga   10560
ctacaggtcc ccaccaccac gcctggctag ttttttgtatt tttagtagag acagggtttc   10620
accatgttag ccaggatggt cttgatctct tgaccttgtg atccgcccgc ctcagcctcc   10680
caaagtgctg cgattatagg cgtgagccac cgcgcccacg gttgccagt atttattga   10740
ggatttttgc attgatgttc gtcagggata ttggtctaaa attctctttt tttgttgtga   10800
ctctgccagg cttggtatc aggatgatgc tggcctcata aaatgagtta gggaggattc   10860
cctctttttc tattgattgg aatagtttca gaaggaatgg taccagttcc tccttgtacc   10920
tctggtagaa ttcggctgtg attctgtctg gtcctggact ttttttggtt ggtaagctat   10980
taatttcaga gcccgttatt ggtctattca gagattcaac ttcttcctgg tttagtcttg   11040
ggagggtgta tgtgttgagg aatttatcca tttcttctag attttctagt ttatttatgt   11100
aggggtgttt acagtattct ctgatggtag tttgtatttc tgtgatatca gtggtgatat   11160
```

```
cccctttatc attttttatt gcgtctattt gattcttctc tctttctttc tttattggtc   11220
ttgctagcag tcaatcaatt ttgttgatct tttcaaaaaa ccagctcctg gattcattga   11280
cttttttgaag ggttttttat gtctctatct ccttcagttc tgctctgatc ttagttattt   11340
cttgccttct gctagctttt gaatgtgttt gctcatgctt ctctagttct tttaattgtg   11400
atgttagggt gtcaattta cacctttcct gctttctctt gtgggcattt agtgctatta    11460
atttccctct acccactgct ttaaatgtgt cccagagatt ctggtatgtt gtgtctttgt   11520
tctcattggt ttcaaagaac atctttattt ctgccttcat ttcgttatgt gcccagtagt   11580
cgttcaggag caggttgttc agtttccatg tagttgagcg ttttgagtg agtttcttaa    11640
tcctgagttc tagtttgatt gcactgtggt ctgagacaca gtttgttata atttctgttc   11700
ttttacattt gctgaggagt gctttacttc caactacgtg gtcaattttg gagtaagtgc   11760
agtgtggtgc tgagaagaat gtatattctg ttgatttggg gtggagagtt ctgtagatgt   11820
ctattaggtc cacttggtgc agagctgagt tcaattcctg gatatccttg ttaacttctg   11880
tctcgttgat ctgtctaatg ctgatagtgg ggtcttaaag tctcccatta ttattgtgtg   11940
ggagtctctt tgtaggtatc taaggacttg ctttatgaat cttggtgctc ctgtattggg   12000
tgaatatata tatttaggat agttagttct tcttgttgaa ttgatccgtt taccattatg   12060
taatggcctt ctttgtctct tttgatcttt gttggtttaa attctgtttt atcagagact   12120
aggattgcaa tccctgcctt tttttgtttt ccatttgctt ggtagatctt cctccatccc   12180
tttcttttga gcctatgtgt gtctctgcac gtgagatggg tttcctgaat acagcacact   12240
gatgggtctt gactctttat ccagtttgcc agtctgtgtc ttttaattgg agcatttagc   12300
ccatttaaat ttaaggttaa tatagttatg tgtggatttg atcctgtcat tatgatttta   12360
gctggttatt ttgctcatta gttgatgcag tttcttccta gccttgatgg tctttacaat   12420
ttggtatgtt tttgcagtga ctggtactgg ctgttccttt ccacgtttag tgcttccttc   12480
aggacctctt ttagggcagg cctggtggta acaaaatctc tcagcatttg cttgtctgta   12540
aagtatttta tttctccttc gcttatgaag cttagtttgg ctggatgtga aattctgggt   12600
tgaaaattct tttctttaag aatgttgaat attggccccc tctctcttct ggcttgtaga   12660
gtttctgccg agagatcagc tgttagtctg atgggcttcc ctttgtgggt aacctgacct   12720
ttctctctgc atgctcttaa cattttttcc ttcatttcaa cttttggcgaa tctgacaatt   12780
atgtttcttg gagttgctgt tctcgaggag tatctttgtg gtgttctctg tatttcctga   12840
atttgaatgt tggcctgcct tgctagattg gggaagttct cctggataat atcctgcaga   12900
gtgtttccca acttggttcc attaatcctg tcactttcag gtacaccaat cacacataga   12960
tttggtcttt tcacatagtc ccatatttct tggaggcttt gcttgtttct ttttattctt   13020
ttttctctaa actcctcttc ttgtttcatt tcattcattt gatcttcaat cactgatacc   13080
cttcttcca cttgatcgaa ttggctactg aagcttgtgc tttcgtcaca tagttcttgt    13140
gccatggttt tcagctccat caggtccttt aaggacttct ctgcatcggt tattctagtt   13200
agccattcat ctattctttt ttctaggttt ttaacttctt tgccatgggt tcgaacttcc   13260
gtctttagct cagagaagtt tgatcatctg tagccttctt ctctcaactc atcaaagtca   13320
ttctccgtcc tgctttgttc cattgctggt gaggagctgc attcctttgg aggaggagag   13380
gcgctctgat ttttagaatt ttcagttttt ctgttctgtt ttttccccat ctttgtggtt   13440
ttatctacct ttggttttttg atgatggtga cgtacagatg ggttttggcg tggatgtcct   13500
ttctgtttgt tagttttcct tctaacagtc aggaccctca gccgcaggtc tgttggagtt   13560
```

```
tgctggaggt ccactccaga ccctgttttc ctgggtatca gcagcggagg ctgcagaaca    13620
gcgaatattg atgaacagcg aatgttgctg cctgattgtt cctctggaag tttcgtctca    13680
gagggctgcc cggccatgtg aggtgtcagt ctgcccctac tgggtggtgc ctcccagtta    13740
ggctactcgg gggtcaggga cccacttgag aaggcagtct gtccattctc agatctcaaa    13800
tgctgtgctg ggagaaccac tactctcttg aaacctgtca gacagggaca tttaagtctg    13860
cagaggtttc tgctgccttt tgttcagcta tgccctaccc ctagaggcag agtctacaga    13920
ggcaggcagg tctctttgag ctgtggtggg ctccacccag ttcctggccg ctttgtttac    13980
ctactcaaga gcttcctggc cgctttgttt acctactcaa gtctcagcta tggagggcac    14040
ccttccccca gcctcgctgc caccttgcag attgatttca gactgctgtg ctagcaatga    14100
gcgaggcttc gtgggtgtgg gaccctctga gccaggcgtg ggatgtaatc tcctgatgtg    14160
ccgtttgcta agaccattgg aaaagcgcag tattagggtg agagtgaccc gattttccag    14220
gtgccgtctg tcacagcttt gcttggctag gaaagggaat tccctgacct cttgtgcttc    14280
tcgggtgagg ggatgcttcc ccctgctttg gctcatgctc ggtgcgctgc acctactgtc    14340
ctgcacccac tgtccgacaa gccgcagtga gatgaacctg gggcctcagt aggaaatgca    14400
gaaatcacct gttatctgtg tcacttgcac tgggagctgt tgactggagc tgttcctaat    14460
cagctatctt ggaaccgcct ctgaaagctg gttttaatgc ataggtttta aatctgcctc    14520
ctacagaaaa tacaatccta caaaccttaa tgtaggaaca gaattttca tttgaattta    14580 gaagttttag cttaagttaa acttaaattt aatatttatt ttcacctctt actagatatc    14640
ttaatagata tttttttgtcc tgaaagaggt tgaggataaa actgtgctct aacaggagtt    14700
agaaatatat tattttctgg aaaatcactg aaaacaaacc taggtttact taggatgttg    14760
ctgtgaaatt cacctcgttt taaatttatg cttagaggct gtaaaattgt attcaattaa    14820
tatgaaaaca tttaaaatgc tttttaatgt taacaacctg accctgtgct tttaactata    14880
gctgacagac tcaagtgttc tgttttcctt ttcccagaac cactaaaaat gaacctttgg    14940
gacactggtc cctttgtgac aattttaggg acccagctcc attggctctt gactttacct    15000
gctcccattg ttttatccaa gctctgcctg gtttctgacc cttttgtctct ttcggttctc    15060 ttgcttgccc tgtgtgtttg atgatggagt ttgtccctgt ccctgaaacc ttgcctgaac    15120
tcctggaaat ctttgagaat ggtgtacaca catatccact ttccaccatg tgcctctaac    15180
ctcagcctca cccggggttat tgacccagtc tgacctagct tcagccctca aaggctccac    15240
tgtgccaagc ctggctcatc accctctctc ccaataactg ttctttgtcc ccaaaagggg    15300
ctgaggtggg gggaatgggc agagtaaagc attttaaaag agaggagaga aaaaaaagat    15360
aggaagctat agaaatggaa atgtaagatg aggaaaatgt agtctagaag gcagaggagg    15420
aaagaagaac aaagagaaag agagccataa atgggtcaat caaaaacaga agaaaaggt    15480 gagaaatgga agaggactaa taagacagta acaaagtcct ttgaagtgtt agaacactga    15540
actgctggtt agttcttgag ggttgtgcac ttcactgtga caactggtat caccctttcc    15600
ctctgtaggt agtactgtgt ccaagattct tggtgtggcc caccagcgca ggccttctat    15660
ctctctccaa catcctctcc cacactttgt actgtgccct tcaggaattc cactgccagg    15720
ggttacttaa gcattccatg tagtttctag ttaccttctt attctaagcc taaattcttc    15780
ctacttcttt tacactcgcc gattcttctc cagcgaactc cctcttaccc ttcaaggttc    15840
tgcatacttg gcaggtgaca ctggtgaaaa ctaaattttt aaaaaggtt ctgcataagg    15900
```

```
atctccatag gcaagacttc cctaaggtgc atatatagac acactgtaat gtttattgtg   15960
cttcactact gagttgcctt tttaaagcta acttaaacct tctaaaggga tcttatctca   16020
aaactcagag catctatttt cctctatttt aaattctccc tctgaaatat tctgaatgct   16080
tttttaaagg atgtggtgtg tgtgtgtgtg tgtgtgtgtg tgtgtttaaa cttaatgtct   16140
ttccctagcc gttctttatt accacaggag ctctgggata tcaaataata tttcttaaac   16200
ctttatccct tttgattgta tagtaattat ttattcaaat cagataccaa ttaaacataa   16260
ttagattgat ttcttcacag aatacaaaat aaacagaatc atgaaattaa gttgttaatg   16320
atttgaaggc ctccttttct aagacattca tttacaactc ttaaaaaagt actgacttta   16380
aataaaaatc caaagaatat ataattatgg aagaggagaa attccattcc acagctaagt   16440
attattttat ttcctttttt tagtttcgat actccgattg gcaggataaa ttgtttatgt   16500
cgctgggtac catcatggcc atagctcacg gatcaggtct cccctcatg atgatagtat   16560 ttggagagat gactgacaaa tttgttgata ctgcaggaaa cttctccttt ccaggtaagc   16620
atttctttac cttttaaaaa aatccatagc atttctttaa ctgggtaaaa atttgggagt   16680
tgattttgct attcattacc atcttattta atgatttgga tatctggttg actccagata   16740
tcatagaagg agttgtaaaa ttctcagaaa attgttcaaa tactcgttta aatttaaaga   16800
aatatgtgta ttgttgtttg acttttaata caggtgaagg aaatacacag gaagcttcta   16860
aataaagtaa ggaagtcact ctacttgaga acagtggaaa tgtaatgaga gtatctctat   16920
gcagtatcca tcccattagt aattgctgat gagtttcaaa gcacatcagt taaacatggc   16980
agtacttctt agctgtgttt agcttgtaga tctgtttctg ggttttcttt tcttctctcc   17040
ccttcacctt aaaaaaaatt atcccatttt tctgtctcta attttggatc aaccagattg   17100
actgaacttt gagatggcat ttcactaaag agtgaatgga ttcaatacgt cccttggaac   17160
tcacccaaag gactatgatt actgaagagc caagtgtccc ataagttaat gttatcaata   17220
cgagaggccc tgacaatagc attacagtgg ggctccaata gacatggtta ttttcatagt   17280
aacgaaattc aacatagaaa ggaaaatttt catgctttct accaagcctg aagcctcttt   17340
tctctaagag accttgtggg cactgggctg gagaagactg agtgaagctt tactgttgca   17400
cagatggtag aatattttca aaacactggt aaaggaaagg cagctttctt agcaaagata   17460
tgtaagaaaa attactctat catttagaca gcattgaata agaatttaca gtgttcactg   17520
actgagaact acatatttag ttactattgt aggccttacg tgtaatttcc taagagaata   17580
ggattgttta attaatacag cagaatatgt ttacataaat attgataaat attaatgcct   17640
tttaaaaatc cagtaaaagc atcctttgaa tatttaaagc aaactcctat aaaagtttat   17700
ttatttattc tcaagtaata tagtttctga aaaaaacctc tttataataa aataacaat   17760 aatggtgatt tttcattgtg cttactatgt gctaggtcct atgctgagca ctttacatac   17820
attattccac tttaccctca caagaacaat actacacagt aggtaatgtt atcttctgtg   17880
atagatggca aaaccaaggc ttggagaggg caaataactt ttccatagtt acactgctgg   17940
tctttctgcc atccaaacca tgcttattat catatatagt atagtgtcaa tatagatgat   18000
tcggaaaaaa aagtgcttgg gaaagtttta aatggattgc ttatttgtga ctagtgacca   18060
aaactttaac ataaacattg tgaagttgtg gtaggacaga tagtttaaaa agtctttaaa   18120
gaggctgggt gttggtggtt cacacctgta atcccagcac tttgggaggc caaggtggtg   18180
gcaattaagt tttgagtttg ggagttcgag accagcctga ccattgtgga gaaacccccat   18240 ctctactaaa aatacaaaat tagccaggca tggtggctca tgcctgtaat cccagctact   18300
```

```
ctggaggctg aggcagagga atcgcttgaa cccaggggc ggaggttgcc attgcactac    18360
agcctgggca acaagagcaa aactccgtct caagaaaaaa aaagtcttta agaaatggg    18420 agaggtagga attttctatt gtgtatttgt tttcctagaa aatctacaga tctacaacat   18480
attaattttg tatacatata gagcaggatg atgcccatat aagacacct cagttaaaaa    18540 tctatttctt atggaatact acacacctat aaaaaatacg aaatcaccag ctacttggga   18600
agctgaggct ggagagttgc ttgaacccag gaggtggagg ttgtagtgag ccgagatggt   18660
gccactgcac tccagcctgg gcgacagtgc aagaccttgt ctcaaaataa ataaataat    18720 aaataaataa ataaatataat aaataaatac aaaattgtgt cctttccagc aacatggata   18780
cagctggagg caattatcct aagcaaatta acacaagaat agaaaccaa atactgcata    18840 ttctcactta aagtgggag ctaagcattg ggtaacacat tgacataaag atgagaacaa    18900
tagacactga gatctactag agaggggagg gagggcagca agtgttgaaa aaccaaatac   18960
taggtattat gctcactacc tgggtgacag gatcattcat atcccaaacc tcagcatcac   19020
acagtatccc catgtaacag aactgcacat ataccccctg aatctaaaat aaaaattgaa   19080
attattttaa aagaaaaga aaaagaaat gcagactccc aggccacatc tggacccact    19140
gaattagcaa tggtatttta gcaagacatt tccttcccca cagtgaatca gagatgcatt   19200
tatgcacatt aatactcaag ggtctattaa atggtctgac cttccagatg cggagctggg   19260
tttctcaccc atcccttag tagcaggaca atgactgtat aggaacttac accagctgcc    19320
tttgattccc atcttatttc atctggaaaa aaaaaatcaa agaaactaca aagacgttc    19380 tccaactcct gaattgtcag caccatatct ccactgcccc tactttgaaa ttatctttgg   19440
gtttcacatt tcctgatctt caaaccataa agcaccattt attagagcac caatggaata   19500
tttttgtgga ataagaccca actttatctg ttcatgtatg gtctagcacc tcttttcaag   19560
tgtcgcagat attatctctt ggtgactcac attagccttc cagcgaagca cttatatgtc   19620
cataaaatat ctgtgaaata atgtagagaa actgatgatt acttctaggg agagaaagtg   19680
agtggctttg aaaatgggtg ggtgtgatgt ctccctgtat tctcgcttgt aactgttgac   19740
gtatacacct ttaccaagaa aaataaatt taaagtaaaa aaaaaatttt aaatggcttc    19800
tacacagggt taaaaaaatc agattaacag atgaatggaa aaataagata tggtagatac   19860
atacaatgga atattattca gccttttgaa gggaaataac ttctgacata tgctatgtca   19920
tagatgaacc ttgaggacat gacgctaaat gaaatgagcc actcaaaaaa agataaatac   19980
tgttcgattc tactttatg aggtatctag agtaaaattc ataagaacgc aagtggaatg    20040
gtggttaata ggggttgtgg ggaggagcag tggggagctg ttgtttaatg ggtatagaat   20100
ttcaattttg caagttgaaa aagttctgga ggttggctgg acaacagtgt gaatatactt   20160
aacagtactg aactgtacac ttaaaaatag ttaacatggt aaactttatg taaggtattt   20220
tatcacaatt aaaattttta aagtcagatt aaagcaatgc aattcactta tcacacatca   20280
tttctctttt ggaccaattt tattagttct gttttgttt ttactaatac cagaataatt    20340
cccaactttc ttatttggag cagtttgctt tttttttttt ttttaacttg tgcctaatta   20400
tgaaactgaa tggctttaag ctggacatgg cagagaggtg ccaaattcaa ggtctctctg   20460
gggaatggca caagcaagtc acttacagaa ctgtggttga cacagagata aactcgcgag   20520
agttgccaac tttgttttgg tagcctccga attataaaca ctcctgttat gatgcttggt   20580
accctgtagc catgtttctc attaggctta ctggatgcta tggagtattt agatggaaag   20640
```

```
ttcctcaaat gttatgaatt tccagcatcc actctttggt cgtttgtaaa aataatattc    20700
tcatacctct tagaagacaa tgaaatcttt aaaggatact cactctaaat ccagactgct    20760
tattgatgtg ttgagagttg tagagtttaa caaaaatcat gggggttggg aacagataga    20820
gtgaggtact tagctgaggt tccagcttat ctcttagaga tgtttactta gtctattctt    20880
tagaattgtt ggatgcttgg acaaccagac ttaataggag ccaaatgaga aaggcatgtt    20940
agaagaaaaa aaggttcata ttacaagagg gtctgacaat gacttattgt gagcaaagct    21000
cgtccttgtc aacagaataa agccactcca tgacagggtt gttccctcac aatgagtcag    21060
ttgtgcagaa agtatgcaca caacattctg catccaaaac attaaggacg gagttggaga    21120
aaacagtttt tctgcagagt gtcaaggact tgatatcttt tatgctgtct ctgtgactat    21180
aatagtctag aaaattctgc gggaaaatag ctgcaccctg attgtccttg cattgcctct    21240
tgtttgaggg gaaaaatgcc attttgagcc cccaagatat cttcataact gtccatagtg    21300
cctagggtgc ctgaacaaac accagctctt tattttataa tgaatagttc tatgtgttaa    21360
aagaagtcct aggcaacatt taaaaataac taaaagtaca taattggatt gtttgtaaca    21420
caaagaaagg agagatgctt gaggtgatgg atacctctct ttcttcccct ttgaaaaaaa    21480
aagaagtctt gggcagaatc cgggaaggca gacattgatt tactttgaga ctcaaaagtg    21540
aaaatgaaga ctatgtttcc ctatctaatc cttaatgtat acactgctta ttcagaccct    21600
tcacccataa gctgtgtgac catgagcaag tctcttaacc tctataatcc ttactgttct    21660
catctttgag aggtaagcat caatttactg atagaattaa gtgagatgat ttgtgtaaag    21720
tgtctggaac atagtaaatg atcaataaat attgggacaa actagctata agaacttgga    21780
aatgaaacaa cccactctgt ctcttcatct gtaaaatgga taggttatat aggtactctc    21840
taaaatgaac aggcagcttc aggagttccc cagttcctta ctacgggagg cattcaggtg    21900
gactgggtg taagttctcc atcctggcat attagaatca accagggtac ttttctttt    21960
ttgagacagg gtcttgctct gttgcccagg ctagagtgca gtgaagtgat catagctcac    22020
tccagccttg agctcctggg ctcaagtaat cctcctgctt cagtctcctg tgtagctggg    22080
actacaggca cctgccacca tgcccggcca acttttgta aaggtggatt tcaccacgtt    22140
gcccaggctg gtctcaaact cctggcctca agtgatcctc ccgcctcagc ctcccaaagt    22200
gctgtaatta taggtgtgag ccaccgggcc tggcgggggg cactttataa aaatgtgatg    22260
ctctggactc aaccagagat tctggctgca ttgggcttga gtggagcctg aacatctgta    22320
attcttaagc tccccatgta attctaatgc acagacagcg ttaagtacca ccaagccaaa    22380
tgaccatgta gatatcgttt atgagactga agcagaatag gtagcatctg acaagaccag    22440
gagtaggctc ttttcagatc tagcaggcca tgacttttca ggcaacacac caacatatgt    22500
ttagttcacc tttgtcccag gcagcagaaa ctctgagttt ccccggggac tctggagctc    22560
ctcaggttac taacccagca ctagatttcc attcttgaga ctctgagaaa ggagcgggtc    22620
caatctggaa cgctcataga ttcttttccta ggagggagag tcaatttgag ttggtatctg    22680
tgttagtcca ttttgtgttg ctaggaagga atacctgaga ctgggtaatt tatgaagaaa    22740
atatgtttat ttggctcatg gttcagcagg ctgtaaaagt atggtaccca catctgtttg    22800
gggcttctgg caaagcctca ggaagctttt actcagtgag ggaaggtgaa tggggagcag    22860
atgtgtcaca tggagagaga gggagcagga gggagaggcc aggctctctt taacaaccag    22920
ctgtcacatg aactgagtga gaactcgctc attatctcag ggagggcacc aagccattca    22980
tgtgggatct gtcccttga cccaaacacc tcccatcagg ccccacctcc aacactgagg    23040
```

```
atcacatttc aacgtgagat ttggagggaa caaatatcca aaccatatca gtatccttat    23100
tgagagaatt taaaagtttg aggtaggtgt tgaaagagag gaaaaactta tttaagattt    23160
cacccaattt ttcagttcag ggaaataaaa aaaccacaat gatttttaca aatgccacag    23220
ctttagaata gcttgcctgc ctctagttcc aaatactctt ccaatttgcc ctatttaaaa    23280
cttcaggatg gaaatgaaca cacagaaagg aactgataag atgaaaagta aaatagggta    23340
tgaatcttca aggttctgat agcttataaa gagctagatt aataatcgga aatttcactg    23400
tgaacatcag tagaaattat aatcctgggg gaaagatgag gctgcagttg gggccagatg    23460
cctggtaatt gatcctgaca gtagtttgag ttttaaataa gtttcaacct tatctttctt    23520
tggaaaaaga taaggaggat acacagcacc acgaaaacac gaaaacacga cccctgggct    23580
atttacacat ggcaaaggaa caaagagacc aatttctctc ctaggaccat ggaaaatgag    23640
aaatatgtac cctgatgtgt tttctcaaca atgctgtggt gatattttat cctattattt    23700
tgtgaatgca gtagatgtag gctgtttctt attttttcat ttgtctttc taaaaaataa    23760 aaataagtca ttgtcacatg aataaatcag tatagtatag tgttacgagc ataggccaaa    23820
ttgcctgggc tgactttcag ctctgccact tactagctgt atgacattga gtaagttact    23880
ttatttatct gtgcctccat ttcctattct ataaaatggg gtttgtgaaa tagtctcacc    23940
tcataagata attaaatgaa ttaacacacc taaagtattc agagcagtgc ctggtattta    24000
ataaatgctc aataaacatt agctattatt aaaacatgga aatcaggaaa gatacattga    24060
cattttatca aattagctca aattaataga caatagattt ctttccaatt aatactgctt    24120
caaaaaatac tagaatacag cagtgctggt aaacaagagg tggaatgcag gatgttcact    24180
aattgccagt gatcactgac atgcctttga gcaactaagt tatcttccct gtctagtttt    24240
tcctcctttg cgatggatgt aacttagcct ttcccttact tatgtcatat gagacatgta    24300
aagaaaaaac acacagatat aaaaataaaa tttattgaag ttctataaag tgctttgagc    24360
caccaaaaaa aaaaaatgcc tcttaaatcc tgtgttttct attttaaata tttcttattc    24420
cctcctctgt cttctgtgtg ttttgtggct tccttgtctc ttcagtggct cctctgtgcc    24480
tccttagaag gctgctttgc taaaggctga gaccgccagg atgggggaaa gacctgggag    24540
ggcttatctt ccccttctt ggcccttaat gtccagtacc taaacccttg gctctttac    24600 ttgagtaaag tgaaaagaat gcacttaagt gtgcaaagaa aagtgttttt taaagagaaa    24660
cttaacaata gcatcttcta gctttcatac atttaaatta ttaacagatt tttaaaaacc    24720
tggcaatgcc tattaatagt ttgatctttt aacatgtttt attttatttt ttaatttagt    24780 gaactttcc ttgtcgctgc taaatccagg caaaattctg gaagaagaaa tgactaggta    24840
actcatatat atggtctact ttttaaagt ttcatttgaa gataatttcc aattacagag    24900
ttataagaat atacaaataa cgtgtactct ttacccagat tcacctatta ttatcatttt    24960
tgctcccaaa tcccaattta aagtaagatg cacacatcat ggcccttac tgcagtatga    25020 ctcctaagaa taaggatatt ttcttacata atcacagtac agctattagc ttcagtaaat    25080
ttcagtactt ttatctaata taacatctat attccaattt tgtcatttga tccaataatg    25140
tcatttatgg cattttctcc tccttctagt ttctcaatag aaatctctaa agcctgtaag    25200
catgatgttt gtatgtctgc atagcagtgt tgctgattgt aacgagtgct gtctgtatgc    25260
taaaaggcct gaaaggtgtc tatctggaag cagtttataa aattagataa taaaaatttg    25320
aaagtattga tatgtactta ttatttttta aaatactaac tttctactaa tttggtaaaa    25380
```

```
cattccaaat tcgtttgaat tcatgacatt ttatcatatc tttttttaaa atatttcaaa    25440
ttctgacaaa taggaacaaa gttttttggt tctttttata aagaatgtgg aaaaatcaat    25500
atggaaaggg cgatttcaca tgttcaatct gcttattact atatttgcaa tatgtaaata    25560
gtagtgaact tttcagtaca ataagatata caagtctaga atataattat taaagaggag    25620
ttaaattgta tccacaagtt atcaatatca gttaaaaaca aatcattaac tttttttgcag   25680 ttaacaacaa aaatttatcc attttctttg gctaacagtt caagtaaata gatttgccat    25740
catggagctc atcactttat aatttaaaaa aagaaaaatg taatgtctgt ttgttataat    25800
gtcctataca gttttttgttt taagtttagt aaattgatta atttccagtt ctgaaaattt   25860
ctcctgaaag agatgaataa aggatggtag ggtgggggtg gtggctcatg ctataatccc    25920
agcactttgg gaggcggagg tgagcagatc acttgaggtc aggagttcga gaccagcctg    25980
gccaacatgg tgaaacccca tctccactaa aaatacaaaa attagccagg tatggtggtg    26040
catgcctgta atcccagcta ctcgggaggc tgaggcagga gaatcacttg aatccaggag    26100
gcggaggttg cagtgagctg agatggtgcc actgcactcc agcctgggtg acagagtgag    26160
actcagtttc agaaaagaaa agaaaagaaa aagaaaaga gaaggtattt aatagagcct     26220
ttctcttttt tttcagatat gcatattact actcaggatt gggtgctgga gttcttgttg    26280
ctgcctatat acaagtttca ttttggactt tggcagctgg tcgacagatc aggaaaatta    26340
ggcagaagtt ttttcatgct attctacgac aggaaatagg atggtttgac atcaacgaca    26400
ccactgaact caatacgcgg ctaacagagt aggtacattg ttaatgtcac actttcatat    26460
agaaattaat tactgtgtga aaatatgtca aggaaagatt ttaaatgaaa aatgttacta    26520
gattgagcat ctgatctata ttagaaatcg atcatctggc agccatgtct agcagcatct    26580
atagcctatg ccattgcatg ttggcttttcc cccaaggtgc atagtaggtt tatttgagga   26640
ctgaattcac atcttatacc tgtttatttc tcatggaact ttctactgca ggacgtgaca    26700
ggtgctagac tgtcagtaaa gatggttgaa tcaatgaata gatgattgaa ttaatttaca    26760
aagagacttg ctttagtaat tgtcaactct tcacttattc aacaaatatt tgagggtgtt    26820
tcatgtgcga agtaccattc tgtgtgttcg taatatatca gtgaacaaag cacagatctc    26880
tgtccttttg gtgcttacat tccagtagag ggagatagat gataaacttt cctgactggg    26940
agtcctggca aaggcatcct gagcaaataa gtcaaaaaaa aaaaaaaaaa aaagggaaaa    27000
gcaagacatt tagggccttg taaacctcca caaagacttc aagacttcag ctttcaccca    27060
gtgaaatggc agccgctgga agtttctgag ctgaggagta gcatggtcag acttgcattt    27120
tcaaagcatc ccactggctg ctgtgttgag aatagacttg gttgggaata gggacaagag    27180
tagaagcaaa gatctcttcc ctattacttc cctataagaa gaaatgcagt aatacttccc    27240
tactactgtt gcttattatt gttgcaatgt tcttcttaat tcttgctttt aaacagatac    27300
atttttatgc tcaaaatgtt aatgcttctc tcataggatt gactcattta atagtatcaa    27360
cttaatgata ctaacttatt agaagcattg atcaatcctg aatttcttcc tttgtgcggt    27420
gtttaggtgg ggaagatgtt attcaagagg ctaagactct gaaagaggct tgcagtcagt    27480
gaacaaattt tacttgtcta tgtgtttgtt ggatgtctac ttcatctttc taactgaaac    27540
ctcctgcctg taaccactta ggtgtgatct tttttagtga catctccaaa atcagtgaag    27600
gaattggtga caaggttgga atgttctttc aagcagtagc cacgtttttt gcaggattca    27660
tagtgggatt catcagagga tggaagctca cccttgtgat aatggccatc agccctattc    27720
taggactctc tgcagccgtt tgggcaaagg tatgtgaaag ctgggccttt ttatgtgtgt    27780
```

```
taacccctgc acacagtaat ctttaatatg cagaagtctc gtacttgtac ctgttcaggt    27840
ctacattaaa tgtcagttga aactacatcc agtaacatgg tgttaatatg atgctttcat    27900
aaggaaatta attttttaaca taattcaaaa tgtcacaggc tgggtgtggt gactcattcc    27960
tgtatcccag cactttggga ggccaaggta cataaatcac ttgaggtcag gagttccaga    28020
ccagcctgga caacatggca aaactctgtc tctactaaaa atatgaaaaa ctagccttgc    28080
gtggtggtgc atgactgtaa tcccagctac ttgggaggct gagacaggag aatcgctgaa    28140
ctcaggaggt ggaggtcgca gtgagcccag atcatgccac ttcactccag cttgggtgac    28200
agagtaagac ttcatctcaa aaaaaaaaaa aattcacagt tcttacttcg attaccctta    28260
gttaaggaag tgcaaccttta aaatataaca tttccctcaa attattgcat gaacataaaa    28320
attttaaata gagtttgtat ttgttctatt tgttttaatc attacctgtg atggttaagt    28380
ggcactctgc cagttttgcc tgcaataaaa atacacaaaa tgtattctac tttagccaac    28440
acttcagagt tgagaaattt tactggcaat ttttgctcat cctgacgttg atgatttaca    28500
cagtgaacta cctgtatctc ttttgttttg attcttcctt tgcttttctc ctgaaacatc    28560
ttgtttggct atcttattat tcagcagaat gcccatgagg aggtctggaa gtattgtttt    28620
tatagtaatt aaaaattgtg acacaagtcc aaagtgggtg gatcacgagg tcaggagatt    28680
gagaccatcc tggctaacac agtgaaaccc tgtctctact aaaaatacaa ataattagcc    28740
aggcgtggtg gtgtgcactt gtagtcccag ctactcggga ggctgaggca gaagaatcac    28800
ttgaaactgg gaggcagagg ttacagtgag ccgagatcgt gccactgcac tccagtctgg    28860
gcaacagagt gagaccccgt ctcaaaaaaa aaaaaaaaaa aaattgtgac acaataaagt    28920
taagaatggt aaattctttc aaagcagtaa agttttattt tattttaccct tacaactaac    28980 aaagaaaaac agtagatgtg gaacttgaca gtgttcccaa gagtgctatt tagagaatta    29040
tgtgtggatt ttcttttttc ctgagtactc ttggggagcc tatcaccagg gtgggtcaga    29100
tatagccttt gagggatgtg gacgcagcca ttggatccag aacactggca tttgctacat    29160
gactttaata tttgttaaag gagagggttt gggaagaaaa agtaggttaa agggttgacc    29220 agagtgccttt taaacttttc tccctataca aaagtgatca ctgtttctttt tctgtccaga    29280 tactctcggc atttagtgac aaagaactag ctgcttatgc aaaagcaggc gccgtggcag    29340
aagaggctct gggggccatc aggactgtga tagctttcgg gggccagaac aaagagctgg    29400
aaaggtcagg aaggttcttt agccactggt ttaaggaatg tgttttttaca ttttgttgct    29460 tcttctttgt ggtatgtgtt ttttaccttc cctttcctaa tattaaccct tctcgcataa    29520
attataagca ccctttactg atggctatag ttgaatgtca gactctaaag caagattctt    29580
aatcatttat gttccatgga ctcttttggc tatgtgataa tacaaatgga ctcccttgtt    29640
tttaaatgca taaccaaaaa tatgctagcc ctttgggaag ccaaggcagg agggtagctg    29700
gaatccagga gctcaagacc agcctgggca atgtagtaag accctggctc tacaattttt    29760
ttttttttta ataagctgag tgtggtggtg tgcacctgtg gtcccagcta ctcaggaggc    29820
tgaggcagga gaatcccttg agcccagaat gtcaagggtg cagtgagctg aactccagcc    29880
tggatgatag agtgagcctc tatcacaaaa aaagagtaaa aatttttaa aaaccaaaaa    29940 ataaataaat aaaagcccca aaaaacaaaa taagtagggt tacaaaggaa ataattata    30000 ttaaaaatac ttatcaaaat atttttatt ttattttact ccttaatgac tatgaactgg    30060
aatatagaag agaaaaacct gagaaaacat cgacttccta gttatagccc agaattcttt    30120
```

```
gtagggcctt gtgggtcctc cataacaatg aggcagggct tcccacccag gcctctggca   30180 ttcaactta  atgatccagg ataagcctgg aaaattgacc agtatctgga ggcatgttgc   30240
aaactcttct ctgaaaaaat tatcaaggca tgattgacat atgaaaagct gtgtatacat   30300
ctttagtgtg tatatctcaa tgagtttggg gataagaata cacctatgaa aaaggctatt   30360
ctgctctact taaatgaaaa taattactta gggttttatt taaataacaa tatcccctac   30420
tgtagttgaa gtatgattcc atataaagta ttttctttgg ctattctatg ggactcttga   30480
tactcacaac tcttggatat aaaaattctc tggaaattct ctagcattaa aaacaaagtt   30540
tcccttattc cccccattta attttctact tttctattcc ttaatccctc ttcaaagcca   30600
acatgtttct gatcctctaa cctcttcctt ttttctctct cactgctgct tcctgtacat   30660
aatagtccac acagaccaca ctaaccctca gttggacctc aggatgtcag tgtaatctgt   30720
gccgctccat tagccccggt aagcgagcca cctaagcaaa ggtaattaca gtgtgtccgc   30780
tgctgtcact ggagctgtgt gtcacactgg gcagatgcaa gtcttcctgc cacgccttga   30840
ggctcagcca cacaggagaa atcacagcgc tagctgtggc ctgctggcta cccccagaga   30900
tgcagctgtg ctctatgaat gcagccccca accagaggaa agcaccctga agacctgggt   30960
gctttacgca ataaaaaga  caaaccttct gatggcagaa tatgtttttt aaaagactaa   31020
tgaattctca tgttttattt ggttcaacac taaaactggt gttgctgtgt tttgtttttt   31080
gttttttttt gtcacaaaga aaaatatcct agtttgtgtg atattttccc ctcgaagtgt   31140
cattgcatac ccattggatt tttctttaaa tttcagggag cccaaattaa attttacata   31200
ccctctgggt ctagtatgaa aaagtagatt tgatttaact tgatgaaaaa aaattgtaat   31260
ttaacagaat cattctagat attttaaact ttatatcaaa tgccagcagc cagtaataat   31320
gcatttgaat tatgattcaa agatatgata gtaatagaat gagcaaaact caggaagaga   31380
taaaagttga acacaatgat actaatataa tagtaagaga aatgatcagg cttgctaact   31440
atgaaccagc tactgtacta cttttctacaa ttatctacca acctcacaat tatcttgcaa   31500
attaggcatt attaaatcca ttttcatat  atgaaactaa agtctggaaa aattgaataa   31560
gaactcatat tccataagta gtgactacct tataacctgt atctagcttg acagatgaag   31620
gtcagcctga tttttaaaaa agtcaaagag agaagcctat gtttatgtac aacaacatgt   31680
aaaattttca tccctcaccc agtggacaat agagggacga ttttctttc  tccagagaag   31740 agacattgac cagagttaag aatctaactg tttatgagtt ccagtgacat ttacaatcaa   31800
ttctggtttg gcttggtttc tctcattccc tcttaaccct gacttgtgat attgccgtga   31860
aggtgatgga gaagctcttc catatcccag ggtgagccct caattctgga ataaccacag   31920
gaatgttggt tggcttggaa tggatgaagg gaaatggaac cgggccagta aagagaaggc   31980
ttggatctgt tctaggcctg gctgatcctg aattagttca attcccaaag atctgggtct   32040
caccatgggt tcattacctt gactgacttt gttacttaaa cctccaacta taggagcc    32100 gagtgtgact cggactatgg attgttattc ttaattataa tgttttccct ctcatttttc   32160
tggtaggtat cagaaacatt tagaaaatgc caaagagatt ggaattaaaa aagctatttc   32220
agcaaacatt tccatgggta ttgccttcct gttaatatat gcatcatatg cactggcctt   32280
ctggtatgga tccactctag tcatatcaaa agaatatact attggaaatg caatgacagt   32340
aagtagttct cctaacattt atgaagaata tgaaaatctt atttctccat ctaccttctc   32400 tttttctttga tatcgctcct ttttgaaaga tgaacatgat tataggtttt tgtttttggt   32460
gaatctttcc actgtccagt gggcagagct gactttctag tatatacaag tcataattat   32520
```

```
gagtgtggat aagaaaatag catgtggtta gaccatttgt gaaacatata caatgtataa    32580
aaggaaataa aaatgggatg aatttaggaa taaacaaata tggatgggag ccatcctccc    32640
tctgccgttg agttttattg tataagaaag taagcatcat tattacagaa taggtcattg    32700
cacaagaaaa tgttacattt atatcactta aaacaatcag ctctctgaaa tacaagaaga    32760
gatgttatgt tagtttgttt ttatttatca aaatgaagat agcttcattt tatgattgtt    32820
aaaataatat atactaattt tacaaaggat taggatacag aattttttaaa attaaaatta    32880 cttacaatct aataatttat attctcttga tgataatttt tggcatatat cttccaggtc    32940
attttctata tatatacaca ttgttttctt tcaaaactgg gatcatacta tgtatatctt    33000
tttgtaacca catttatgaa ctaccaatat tttgtgacca tcttttcatg tcagagactc    33060
agaacaatat gtaactattt aaatagaaat cttttaacat ctgtacttcc ctatcttgct    33120
aaaatgagga tactgagcat aatttggccc tttgatgatg acttgggtc attatgaaag    33180 tgaatatttt cagaatgctt tatgcagtgg tatcttcaga cttcattgag aggttgtggg    33240
tgttcgactt ggtgagccct cattaatgct gagtctaatt tttctcactt ccatcttctc    33300
tctggcagtc ggtttggaag cttgctaccc tttcttcact tcctcattta ctattgatgt    33360
tttatgaaga agggaggttg aatcctgaca accgttcacc tttggtgatg agtttgtcct    33420
ctatggcctt aatttcctca tttgtagtat gtggataatg acacctatcc ggtagggctg    33480
agattgctat ccccagaggg agcccaagca aagccctctg catagagggc agggactcta    33540
ttgcattaac cttatggcaa ctattttggt caacattatt tttctttctt actggtcctt    33600
atctgtattg cagatggggg atagatattt aactgatatt tgagttatgg gtaacatgaa    33660
gtgttgctgt gttttgagaa aagccaaatt atatgtagaa gttttaccat gccctgagag    33720
aaaaaaataa tttatcttca cttatgtttt tctcagttaa gttatgctaa taatctggat    33780
tcctgaagct gtattctgag cttctttata tcaattcatt ttcctagtga aaaaatactg    33840
tgaagggaaa tgtgttaagt gttgtatgct acagtacaga ataactgtgt aaaggaattg    33900
ctaaccagtg cacactggag tgattttatg ttttatgatg tgcaaactgt tacttttttat    33960 gttaaaaatc tttaaaaata tatgtgacat ggtgcttttt aggagcatta catagggcca    34020
aaatctgcca tgtttatat tgaaccgtct atgtaattcc atgcatagtt agagaaaatc    34080
atataggatg gaataataat actgactgaa aatgtttctt tctggtggca tttgtgagtg    34140
agtcaatgaa ataggtttga aaaatctttt taactctgta tgtattcagg agaacaatag    34200
gtagtttgag aaaatagacc cactcaggca ataaaatgct atattagcct tgcaaatgtt    34260
gctcttccac aaaaaaaaaa ggaaaggata aacctaaact taatccttta tgtactatgt    34320
tacatataca tcacatttta gataataatg aatgccagaa tgtgacttaa acttttcctc    34380
atgttatttt gctcaggttt ttttttcaat cctaattgga gctttcagtg ttggccaggc    34440
tgccccatgt attgatgctt ttgccaatgc aagaggagca gcatatgtga tctttgatat    34500
tattgataat gtaagtcatt tattattttta gtgccaaaag aagtctttga gcttgtataa    34560
ttaaatctgg ctttagtttg catatttttg aatcaactac attgaataag ttgtactgac    34620
taaagtgaca tttaattata tgaaatgaat gacctgttag taataaatga agaaaaatac    34680
ctcttattaa tatttttaa atgtatcttt agataatata ataatactga tctcatttg    34740 gaaaggaca tctgcactag tgcagagcaa agacgtttct cttcctagtt tttatctttt    34800
tcactttcat gttgtagcca gactgagaat cttatgattt ctatatggga tgggggtag    34860
```

```
ataaattatc ggtgggacca aaattgacag tatattttgc tgtgggttcc ccctctccaa    34920
aaaattatca ctgcatgttt ggtatgattt taaataaact acattaaata aactgactac    34980
agtgaaaaag aaaaagtttt gacgtaaaaa agtaagtcac tgcattcaaa tattgcaagg    35040
tagctaagtg aaatttgatc atttaatcta agcaatttcc tttttcattg atccaagtcg    35100
tgagaaaagt gctcagtttc tgattgtatt aaaagtttac attatttcta ataactgct     35160 ataatcaacc attcaatctt ctcaattcaa tctattacat ttattattta ggaatgagct    35220
aattttcact aaatgctgaa atacttggct ataatatata tcaattatag catattttg     35280 ttattgcact tgtataaata tgcatatctg accatttaga aaatttatga ggatatgcca    35340
aaaacttaaa gggaaatatt atatgaaatg agatgaatat ctcttacgta cttttcagga    35400
aaacactatt ttctgaaaag gagtatttct ttaaacagca cacatacata tacacacaat    35460
cttcatcttg ggttttttctt atgtaaaggg gattgtgaca ttccaggtcc tattttttgga   35520 atttgctgaa tcatattcct taaaaatgca acttgtttgt gctatgatgg aatagtcatt    35580
acatttgttt ttatttagaa tcctaaaatt gacagttttt cagagagagg acacaaacca    35640
gacagcatca aagggaattt ggagttcaat gatgttcact tttcttaccc ttctcgagct    35700
aacgtcaagg tactgtaagt aatatttata ggaattccta actgaggttg attgttgaat    35760 catttttaaag aataaagtct ctattatttt gatacttatg tgccttttcc tttgggggtt   35820
atattccctt atttgatact ttttttttcaa atttcaaact gaatcgaatt attcccattt   35880
tagggctttg ttgtgaagtg tgttcttttt tctcattttc cttacagatc ttgaagggcc    35940
tcaacctgaa ggtgcagagt gggcagacgg tggccctggt tggaagtagt ggctgtggga   36000
agagcacaac ggtccagctg atacagaggc tctatgaccc tgatgagggc acagtaagtg    36060
ggaagaacca agctttccag agtgggaagc tggatacaaa ttggccctttt gaaattggtt   36120 tttcagtaac aaatttgcgt gtgaatccag ttttggtaaa aagcctacaa aatggcaatg    36180
ccgatggata atgccttcac acccttgggc tggtttcaca aatgcattaa ataaaagtca    36240
taaaagctgt ggaagctgga caaagctctc ctctgttctg actaagcttt cataacacat    36300
taaattactg caaagcagtc tacaaaccac tgagaggatt actttcaatg agttagagtt    36360
tggtcaaaca tactccatat agcaattgtt gggaacaatt gatgacaatt agggtcacca    36420 gatatttag acagcaatt aaattcatcc aagacagttg agttttctta aacttaggaa      36480
tatctaaggg ggaaagtggg atggtctctt aagaaactag tctcttgaga aaattctaga    36540
aacacagaga cagtaatagc ctagggtatg ttttttttgcc atttaaaagt tttgctataa    36600 atttgaatttt acagaaaatt gtaactagag aactcacaga tccttcaccc agatttagat   36660
tgtttatatt ttgacccact tgctttatca tcttctcttt ctccgtgtgt gtgtgtatgt    36720
gtgtgtttat gtgtgtgtgt gtgtattatg tatacccctta tacttcagaa tacattccta   36780
aaaaggacat tctcttagat taccacaaaa caatgattaa aaatcagtaa atttaacatt    36840
aatgcaatat acaagtccac gagctatatt cagaatttcc tcagttgtcc caattttaga    36900
gcattgagtt tatctgatat taaaatggat tataattcaa taattgtgaa aacagaagat    36960
tataaggtaa aaagtaaaaa taatggcatg ccaaaaccaa aaatcataaa aaggcattgg    37020
gacagaacag agatctccag aattaataca taattttcta caatacatgg aactatttat    37080
ttaatttaat aaaattaata ttattggaaa aatctgatat tactatgggg gaacataggc    37140
ccattctcat ttactaaagt aaactctggg ttggttcaag tgtaaatatt ttctttattt    37200
tttaaaaaga acctggtaaa ataccaacca ttgagaatta aattattatt gaaacaactg    37260
```

```
acatttttaa agaaagcata tgttaacaga aaaaaagat cttcagaaat tctataactc    37320
agagatattc actgttaaca tcatgattta acaattttct taccactgaa ataatagaaa    37380
aaaatgccca gtggcataat tgattaattc agttgttcct taagcctctt tccaataaaa    37440
accaataaaa ctatgatgaa agaaagcaat aaaggcctga catggtggct aatgcttgtg    37500
atctcagcac tttgggagat tgaggtggga ggttcacttg aggccaggag tttgagatca    37560
tcctgggcaa ctaatgagaa tctgtctcta caaaatattt tttaaaatag ccaggcctgg    37620
tggtgtgcac ccatagtcct agctacttgg gaggctgagg caggaggatc acttgagccc    37680
aggagttcaa ggctgcagtg agctattgtt gcaccaatgg ttgcaccact atgctcctcc    37740
aaagcctgag tgacagaatg aaactctgtc tctaaattta aaaaaaaaaa aggacaaaaa    37800
taatgaattg gaacaaaaga tttattatat atggaaaaag tattatattt attattagag    37860
aagttaatat gaatatatga aggtaaccct gctcattatg aacatgcgac tctctggaat    37920
atataaagat ttgtaaaaag tttcaagaaa tggtcaactt tataaatgta tacaaatgaa    37980
aacagatata agctatcacc tcatacctat taattggaag aaaacagatt aaaatgataa    38040
aacccagtgc tagtaaatta caatgaaaca gatatattta tatattcctg ttgacaatgt    38100
aagttattaa aatgttttaa gataattatt tagccttttta ttaacaagca acaaatgccc    38160
agcaaatcca gtcattgtac atgtaagcaa ttgttgtcaa gggagaaaaa ataaatcata    38220
atcttcaact tagtaattct ctactcttgc aataaatatt gaagtaagtc aaatatttaa    38280
gaagaaagga agtaaattaa agcatgtaaa aaatagcaaa acatgggcca ggcgcagtgg    38340
ctcatgcctg taatcctgta atcccagcac tttgggaggc caaggcgggc ggtcacgagg    38400
tcaggagatc aagatcatcc tggctaacat ggtgaaacac cgtctctact aaaaatacag    38460
aaaattagcc gggcatggtg gtgggtgcct gtagtcccag ctactctcga ggctgaggca    38520
ggagaacagt gtgaacccgg gaggtggagc ttgcagtgag tggagatggg ccactgcact    38580
ccagcctggg cgacagagcg agactccatt tcaaaaaaaa agcagaacac cataagctat    38640
caaaattata tgtagaccag gaaggtaagt gtgcatttttt atttaaattt aatattggaa    38700
cataaaaata atggtatgcc aaaaacataa acccaaaat tgtttatggc aaataatcct    38760
tccacgaaaa aactgtatat atgaaaataa atatcaggag agagcataag ctttttattt    38820
ttgttcttgc atattgctgt ttatttctaa ttattatttc taaacactga accaagttaa    38880
atattaggta ggatgttttt catgaatggt cctgatactt cagctattaa atggttaaat    38940
acttaatagg aaatatttct ttctttcaga ttaacattga tgggcaggat attaggaact    39000
ttaatgtaaa ctatctgagg gaaatcattg gtgtggtgag tcaggagccg gtgctgtttt    39060
ccaccacaat tgctgaaaat atttgttatg gccgtggaaa tgtaaccatg gatgagataa    39120
agaaagctgt caaagaggcc aacgcctatg agtttatcat gaaattacca caggtaaagc    39180
ctctgataaa gtagttgtcc ttgaaattag aatttcacct cataggactg agtttattct    39240
tcaaaggttt agctaataat gtttgagatg caagattgtc aactttgct agataagtcc    39300 cctgaatgac tcagttaggg gttaaaggat tatagcatgg tagatgatta atataaaatt    39360
ttatacagca tgtgtcagtt ttttataatt cagaattcat ttatcttatc atactttatg    39420
atacattaaa atagttaaga caaagctcca tgttgtcttt atgtagttct atagaattcc    39480
tagccttttt aaatttaagt tacttcaaga gctgatccat gttttctgtg ttagaaattt    39540
gacaccctgg ttggagagag aggggcccag ctgagtggtg ggcagaagca gaggatcgcc    39600
```

```
attgcacgtg ccctggttcg caaccccaag atccttctgc tggatgaggc cacgtcagca   39660
ttggacacag aaagtgaagc tgaggtacag gcagctctgg ataaggtcag tagactctaa   39720
aaagctgaag gaccaccaca ttgaaaccta ttgaagattc ttgccagtgc ttccggagtc   39780
tgggctgaga aacagaaaca tagcaaatgg agctacctca tggagctgta ttgatttctc   39840
ctttctgtca ggttacattg tcttcagaga caggtgaagg gtactgactt gttttgacca   39900
tggtgcagtg agcccagatc caggtcttta taacaagcca tttagctttg tttatttctt   39960
gcacatgggc tattgcaaga ctactttga ccaaaagtag tcatgttaaa atatatat     40020 ttttaaatcc ggttacccag acactggtcc agctgaaaac taattcagaa tactcaccct   40080
attttgtagg cagtgacatc atctttatct attcatgtag gtgaccaggt gcttttctgg   40140
aaataaagtt caactctgta cttgtctaag catataaata aacaattcat ttaagggtg   40200 ctgagttcat ctgtccagct cagatatttc taagtctctc attagcattt ttactaagct   40260
gaagtgtcac aggaaagacc ttatcttggt acacttttgg gggtaatgct gatgtcatct   40320
gtattaacaa cacaatgtaa ataccagagt cagatgacac catagaaatt agtttcaaac   40380
acataaatat cataaatata tttgatttaa gacagttcag taataatatg tgcaagttcc   40440
ttaaggaatt ctatctgaac cacctcttac aatttaagag acaagctgca cgaaccttat   40500
tttctcagga aaatttatat ctgaatccta agttaaccta attccttttt atgctgtaaa   40560
ctgtagttaa ttaatgcctc atggtttatc agcttaatat cttgactctt tttgttgttt   40620
tttaagacag ggtcttgctc tgtcacccag cgtggagtgc agtcgtgtga ttatggctcc   40680
ctgcagcctc cacctcctgg gctcaagcca tccttccacc tcagcctcct gagtagctgg   40740
gactgcaggt gtgcgccacc acacctagct aatttttgta ttttttggtag agatgggttt   40800 ttgccatgtt gcccaggctg gtctcaaact cctgagttca agtgatcatc ctgcctcaac   40860
ctcccaaagt gctaggattt atagatgtga gccactgcac ctaaccaata tcttgactta   40920
ttttatataa tttaataatg attaataaca caataataat tattccttac aaattcttgc   40980
actgaattat actgcttttg tgtatattaa atcatgatat taaggagtca aaatataatg   41040
catatgagac tggtatatgg ttggttattc tgaagttact taaagcagta catcataaag   41100
taatacatgc ataagttatt ctaacttaaa aatataatta gacattcatg tattggcata   41160
gactttttag agtaaagtcg ggtagaatga gagatatatt taccaaaaaa tcaaaaacaa   41220
aaaagagtcc tattcagccc tggagtctag gttccaatca tttccaggat acagatattc   41280
aatatacaat atagttcttg ctgtgctaaa agaatagaat tattggagat gaccagtatg   41340
tattgttttt cataatatga cctctgccag aaaaactgtg atcttgcaag ttttagtacg   41400
tatttggaca agtcaattca ttcaattta gctgtttctt cgtgttctat aggatcatag    41460
cacactcctc agttgataac cttttttata tttactttaa aaatagctga tgaactactc   41520
ataatttttt aaagtctcca ggaaaagcca ttagcagctt agggtgatgg ttaagagcac   41580
aggctttgat gctaggctgg gattggagtc ctggctctgt tcttttctag ctgtgtcctt    41640
gggcacgtta actaacctct ctaagcctga gacatctctg aagtaatagg ggaagagggg   41700
acagaaatag tatcatagga ttatttaaag aataaccaag atactgcatg taaagttatt   41760
agcacatgcc tagcacatat gaaacacttg atattgttgg ctgctgctat tattatggtg   41820
attagcatta ccaggattat tattattatt atttttggt tgctaaattg gttacctatt     41880
gctatgtaag aaactatctt gagtccacgc ttaaaacaat tcagtgtatt ggctgagtag   41940
atcctctgtt ctttccacct gagcacatgg ctgcatttac ctggagggct ggcttcatta    42000
```

```
aaatggtcca tggtggcctc actcacacgc tggctgttgg ctggccatct caattctcca    42060
tgtgacttct cacactcata caataggcta acctggcttc cttatatgaa agtttcaggg    42120
cagtgtaccc agagagcaaa gactaatgtg tgaagtgtcc agaggattag actccagaac    42180
tcatcttgtt ggtcacagca agtcataggc tagcccagat ttgaggagat aacagactgt    42240
gcctcttaat gggtgagcag taaaaaatct gtgaccatat tgaatcttct aaagcatgcc    42300
ctctgtcaca attatttaca tttcttccac atgcaaaaga aggtcacctc ttcctcagac    42360
cctcaaaatg ttcatacagt gatagcatct ggctcaaaga ccagtatctg aagatctgca    42420
tgtggtctaa tacagatgag ggtcttcatt ttcagctcat cttgacccac agacctatga    42480
aaaagacaag ttatcatcaa cacatactct caacatagag tggcggtgca gggacaggat    42540
aatcatagca gatactcatt caaaaaggat gagaacagaa agctcatagc agtccttggc    42600
catagcaatt ctgacatgca gccaattacc ccactactcc agggaaatgg gatgtttctt    42660
gattaaggcc tgattctgct ccccaggagt gggttcccta gtccattgtt ctctttagtt    42720
ccagggtctt ttaccttccc tctaagaggg cttttccttt tcataagaaa tgatctgtat    42780
ctgcagctga gtggatttct ttgcatgttt ctgcccatag aaatttgggg ccttttcat    42840
tttgtatttt tttcagtctc ttttagacta agctgaagga ctgtcttaaa gactttgtga    42900
gtttacttag aatctagctg tcatttactc aagcccagaa agttatgcct atatatttta    42960
ttttgagaca ggctcctctc ttctttgggc tgcaagtgaa cctgccatca gaaaactctt    43020
aaatagtttt taaggctttt tttttttttg tagctgaaag tgtccactag gctctgccta    43080
aaatctttca gagattttg ctaaaaatct tacacctaca cactctgatt tttgccctaa    43140
ttttattgga tgactaacaa cttcatttc caactgagta ctggggtctg ctttattgtc    43200
ttaaattctc cttgtaacca agtagctcat tctttagctg atcattctct tcccaaacct    43260
cattgtacac agctagggga atccacttgt ctctcctata gtctgtctag agatgtctga    43320
aatctcctca gccagatgta caggttcatt aagtaaaatg tctttcttcc aagtcactgc    43380
aggaaatatt tttgtcaaat tttccaaggt tacataatga aggtactcct tttctatcct    43440
ctaatagcaa tttctttact cttgtttcag tctccactaa caatattatc accttccttt    43500
caaccaccac ctaccactca atcccaaagc caatgtcaca tgttttaggt ttttggttac    43560
agcagcatac caatctaatt actaatttct gtatcagttg ttttaagcca agaatttagt    43620
gacttaaaat acaacttta ttgcccacaa atttgtgggt tggtaaagtg gttttttctgt    43680
tggttttgcc tagtcttatt tcagctcagg gtcacctggg ctggaatatt caaagtggcc    43740
tcactcatgt gcctggcagt tggggatggc tgttgcctaa ggcaggttgc ttttcctccc    43800
tgaagccagt tatccttcag gaggctagag aaacttcctt tcactgcggt tccagggtaa    43860
catccgaaga tggcaaacag acgagctgtg tgagatccct tgaggcctgg gctcagaaa    43920
ttgtagaaat caatttcttt acatttcttt tgtcaaaaca agttacaggg cctgcccaga    43980
tatgaggagg cagagaaatt ggctccactt ctgtatagga gaagctgcaa agtgtttgtg    44040
gccatattaa tctgccatag ttgctatgaa aacagtttat aatctgcact aattggctcc    44100
acactgcaag gtaattatgc taatattttt acagacaata aaccatacct ttaaagataa    44160
acccttatt actatgtccc caaagaagat accaatcaat cagttagcca gtcactctaa    44220
cttacaatcc aactctcttt ttaatgatga aaagttgaat ttcataaatt gtagtcttgc    44280
ctctgaggac cataaggatg tatcactatt atatctactg ttatttctac tcaattaccc    44340
```

```
atcctggaag aataatattt ttattttgtg gatcctttat acattgatca ggccttcctt    44400
gtgtggcaac agcttactgt agttacctac ttatttttat gccttctctt tcctaggaag    44460
aataaaccac cccaggaggc agaattaata aaaagattca tatttgaatc tcttcaacag    44520
cccagtgcct tgcacatagt agaggctaaa taaatattta ctaaattgac tatgatggcc    44580
cagctcattg agaaaatatg tctacattaa aataattttt tttttgagac ggagtctcgc    44640
tctgtctcca ggctggagtg cagtggtgtg atcttggctc actgcaacct ccgcttcccg    44700
ggttcaggca attctcctgc ctcagcctcc tgagtatctg gactacagt cacatgcaac    44760 cacgcccagc taatttctgt attttagta gagatggggt ttccccatgt tggccaggat    44820
ggtctcaatg tcttgatctc gtgattcgcc tgcctcggcc tcccaaagtt ctgggattac    44880
aggtgtgagc caccgcgccc ggccctaaaa taaattttaa tagtgatgac catattagct    44940
tttgactcta cagatagcaa ctatttgtca aaataaataa aatgctatta aatataagat    45000
cttgaagaaa gatataacag cagattttgt attttgactc ttttaaagaa aggcaataca    45060
gtttcatacc tacatgcaca ctcctgatca tggtgttatc atagaagaac aggaaaagaa    45120
acaaaatggt ggccaggtgt ggtggctcac gcctgtaatc ccacaacttt gggatgctga    45180
ggctggcgga tcacgaggtc aggagattga gaccatcctg gccaacatgg tgaaaccctg    45240
tctctattaa aatccaaaaa aaaaaaaaaa aaaaaattag ccaggtgtgg tggtgggcac    45300
ttgtagtccc agctactggg gaagctgagg cagggtaatc gcttgatccc aggaggtgga    45360
ggttgcataa gccaagatca tgccactgca ttccagcctg gcaacagagc aagactccat    45420
ctcaaaaaaa aaaagaatg aaaacggtga tttatggtg attttataa aaagattcca    45480 aaaggtttca ttctgatgct gtttaccaa agttccagaa aggctagtag attagtcctc    45540
cctttgttta ggcccacctt tcatccctga acatcccaaa ttagtcaaag gtctaaattt    45600
cataatagct ggtgtcccta aatctaggat atttatttat caatgtcctg tcatcatcag    45660
ggtgtctggg agctctgaaa aaaaaaaaaa aaaaacaac aacaattttt tgtgtcaaag    45720
ctctactttg gccaacttct cttggtcaaa ggtgacagtt gcttacttct aaattgatga    45780
acacgtactt tatttctttt acatagcaat cattcactca tacatctgat tccaattcct    45840
ttgtgtatat atgttgacat atcatcaacc tattatcatc atcatgataa tatagtcatt    45900
gttagcaatt tattcatcac tgttagcatc atgaatataa ttacagtaat caaattattt    45960
tgtatatgcc ttattatata tggactaaac ccagcttcca tataagtaaa tatttgtgag    46020
tgcttctttg gggcttatat actaaaaatc aaataatagt cttaaatgtt gtccaagaga    46080
gctgtgttct agcctctctc tctttccagt gatgtttctc ttttatattt acttaaaaac    46140
aattgattca tctggattta ttttaatgta aggactaaag tagaaatacc acattacttt    46200
attaaatggc tgcacaattg tcccaatacc atttattgta taattcacct tttctttacc    46260
aataggtagt accatatttta ttgtaattaa attcttagat ggtttatgtc tatttctgga    46320
ctctccattt ggttctattg atcaaattac ccattcacgt gctggttttt cctaggtttt    46380
actattttaa ttgctgtagc tttttatatg ctaatatctg ttagagatat ttccttctca    46440
ttactcctct cattaacttc ttttttcagaa ttttcatggc tattttaaa aaattgagat    46500 acaaacacat gccataaaat tcacccttta aaaatataca attccgggt ttttagaata    46560 ttcacaaggt tgtacaacca tcactgctat cgaattccag aacattttca ccacctcatt    46620
aagaaaccag tcactctgca ttccaccctc actctagccc ttggcaacca tgaatctacc    46680
ttctgtctct atgaatttgc ctactcttag atatctcata taaataaaat cataccatgt    46740
```

```
gtcatcttttt gtgactggct tctttcactt agcacaatgt tttcaaagtt catctatgtt    46800
gtgatgtgaa tcaaaatgca ttctatttta tggcctaaca atattccatt atatggatat    46860
accacatttt aaatctgttt gccaattgat gaatatttgg attgtttcca cttttttgcct   46920 attatgaatc tagcctctca ttttttaattt atatgttaac cacttaggtg aattagacta   46980
ttctctaata accatcctaa tgatgtggtt tgattgtctc agagtaggag tgatcttaag    47040
ctattgggta aaagggctaa tgagtgtcag aaagagtagc cattattaat gacataatat    47100
caatactttt attggcatta tccagggttt aaatgcccat ttataaatcc acccagcaaa    47160
catatgaggc cactaaacta gttagacagg tgatttgtag attttagcat gcataaaaat    47220
cacctagggc acttgttaaa gagcagattt acttgcctta ctctagagat tatgctttgg    47280
atggcttttg aaccataatt ttaatagtcc tgatcccaag gtacattttc acctaaactg    47340
cctgctttca gttcatcaga attagttaag atcaggctct taaaaagaga tcctacagca    47400
gtgctctgga aaaggctgtc acttggcaac aacttcccta aaatatttct ggtgatgtct    47460
ctagcattcc atataactta gagctagggc ttctcagaca agtgtgaaaa cactgaagaa    47520
ggatcaaacc cttattttc ttaagtaaac actgacacta ccataggttt ctggagaaat     47580
cacccatcct cctactgaag gggttagcca cttgtctggt cccaaactcg tctgactttta  47640 atttttcata aagagtgatg cctttgccat aatcacgcag agatctggag tataaactac    47700
tctctaatca tctacaaaca gcattcatcc aagtgcttaa ctgtgcatgt taattgacag    47760
tgtgccaata ctgtaaccct gatgcaccac attttgttc ttttaggcca gagaaggccg    47820
gaccaccatt gtgatagcac accgactgtc tacggtccga aatgcagatg tcatcgctgg    47880
gtttgaggat ggagtaattg tggagcaagg aagccacagc gaactgatga agaaggaagg    47940
ggtgtacttc aaacttgtca acatgcaggt acttgctttt caggaatttt ttctgctatt    48000
tgctcctcaa tatagtgttc tttaaatatt aaaatatgat ccagtgaatg ctatactgag    48060
caagaagaaa cttcaacaag atgcctaaaa gtgtatatct gagactttaa atcagaatct    48120
gtaaagaggt agcaggtgag aaaataggggg aaagtgccaa aaacatcatg gatatattcc   48180
ttaggacaga ttcctaattg cctggggaat gtggtcaaac taaaaggtcc tttctaccat    48240
aatgggatgg tcagagtttt gggagtcaga ggacgagaaa agtgtttcga cttgtccgag    48300
gagccccggc tctgagttat atggaatgcc agagacttta ccagaaacat tttagggaag    48360
tcattgacaa gtgaccgcct tttccagagc actgctgtag ggttccttt gaccagccag     48420 gatctctagt ggttgaggga ggtctcatgt gatctaaaat tgtttcccag atgatcctaa    48480
taagaccatc atcaagattt gtggctctag gaagtgaata gtttgtcttt taaaaggaaa    48540
aagcaggcca ggtgcagtgg ctcatgcctg taatcccagc actttgggag gctgaggtgg    48600
gcagatcacc tgaggtcagg agttcgagac gagcctggcc aacattgtga accccccatc    48660
tctactaaaa atacaaaaaa ttagctgggc atggtggtgc acgcctgtag tcccagctac    48720 tttgaggct gaggcaggag aatcgcttga atccgggagg tggagattgc aatgacctga     48780
gactacacca ctgcactcca gcctgagtga cagagcgaga ctctgtctca gagaaaaaag    48840
aaagaaaaga gcactcattc attctagttc ctaaaacagg ttatattgat aatgattggt    48900
ttttcatatt attaagacat gttattatac tcagtcactt gagcaacatt gcagaataaa    48960
taacctaaga atattttatt ctatgaacga ttctatttgt gaaagtatat acatttgctt    49020
tgatacaact gtaattagca tgtacacaca tattttgtt cttttttctt aacatttcag     49080
```

```
atatacgtca tccacatact attattttaa tgggtgctca gaagttcatt ttattaatgt    49140
gtgaaattag tcattttcct aaagttagat atttggtctg tttccagtat ttctctattc    49200
taaatattgc cactgtgagc acaagtagat caaaaaaggt tgtcaaaatt ttgccttgct    49260
ttctgacaag taactcttct gagccttcgt ttctacattt ggaataccaa acctaccatg    49320
agaggttgct ataagtttag aaaaataaac atctgaatac ttgtgtacta aaaacaacct    49380
actgaaatgt ttaaagggt ggattttgtg atatgttaat tatattttta aaaagctgtt     49440
tttctttttt tttttttaaa aaaaaaaga cctgacacaa attagatgat gataaatggt     49500
ggttactaaa atttgcaaat tcccccaaat gaaaatacca aatgaaatga cgaaaagttt    49560
tataactcag gcttgcatgt gccagagggt gttctacagt ggagggaatc aatgatagtg    49620
tctctgccga atgctaccat atggcctagc caccataaag ggtctttgtc atttcactag    49680
ttaggaatgc ataaaatgtt actttaaatc cattttagtt ttaatttcat gagtggttac    49740
caagggtctg tgattttgcc cataatgaca tgttgaatcc tcaagtgaaa taaccacttg    49800
gctgtcctat tgccataagc tcttgtaaga atgacctctg cttccatcag gacttggatt    49860
gggagactgc taaagagatg cagacagctc tgacctttct atatcaaatt cccaagctta    49920
cttcttagg aaaagttgta catttgaaga ctgaacagtc agtggtctgg catgatagaa      49980
atctgtcacc aactaggcaa tagctttgag caagtcattt aaccaaattg ggttttgtta    50040
tcctcacttg ctaaatgagc aggggcttca ggtaagatga cctctgatat ttctaccagc    50100
tctggcattc tgtgattctc agccccttg aatagttcca cctgggtacc cccacatttc      50160
ccatttctga tttgagtttt gccctcccac ttacttggtg aggctggaga gatgagggaa    50220
agacccactg tgagcctgag agtcagcaga tgctcaagct aatgcagtac tcttttctca    50280
agtttcaaag accaacctgg ttttcattca cccttgtttt ggtattgttt ctaacaagta    50340
tcactgcttt tccattaggt agactgttgg ctcttagttg tttctttttaa atgtatctta    50400
attttttttct gattataaag gtaatgcatt cttttttaaaa atcaagcatt tttttaaaaa    50460
atccaaacat tacattctag aaacttgaaa gtcatcataa gccaaatccc tacaaacagc    50520
cactgatagc tatttcgtat ttatttttca tctttgccag cctaaagagt taaacagtat    50580
cttcaaattt aactatttat aagattgagc ttatttctac attttttattg gccatttata    50640
ttttcttcc tctgtgaaag tatttgttcc tgtattagga tattttttctg ttgtgttgtt     50700
catgatattc tcattgattt gtgagaactc tttacataaa aagaaaatac actcttctct    50760
tgcgtgtatt ggagagattt ttttttcctg ctttgttcct ttcaatttca ctttgttgta    50820
tttggctgcc ataaagaagc tttaaaatgt atgtaattag gttgtcagtt ttttcctcca    50880
tgtcttcagg atttgaggtt gttctccgaa aggatattta ccccatttcc tttcagcatt    50940
ttttgttctg cttttttaca attaaatctt tgagacaact gaagtatacc tgggtggaag    51000
aaatgagggc tattggtttt aaatagatac ttttaacac ctggtggaaa agtggctatc      51060
ttggcttgga gctcaatgac ctttcagctg aagcacccaa caccaactga gtgttttagg    51120
taaggcacag aaaaaatatt atgaaagaga caggtaatgt tcatttggtc atagaaggaa    51180
gctaaaatct gaatgggctt attggaagaa ctgtccattg agatggacct cttgatagca    51240
tggatgagat taccaaaaga ggaaaagttc tggggaggta ttcatgagag gtggtctggt    51300
ttgacttgcc atgagctaga ttttttggga tccaggcttg ggcaggtagt gggaagctgg    51360
ggatgatttt gagctgccct ttaggaaaat aaatctggta gcagtgtggg aacagatggc    51420
agtgagaatg caagggatca attacaaagt ctgcagccta ggttggtttt tgttgagaga    51480
```

```
tggtataaaa ctgattcagt aatgagcaaa taaggaaatc caccaagcag aacatatcac    51540
tgcaatgtgg ttcaaggcaa tatataagca catgggcagt gttctgtcag atgttgaatg    51600
agcaactgga aaactaagag atcatgattg gctattgtat gtacagtaag gcactagcca    51660
aaggattggg ttcagggcag gtcttgaagg gaggagcaag aacaagacac tactacaagg    51720
actaagaccc tgaacaaact attaagatgt gtagttggac acatcttaat agtggaggaa    51780
gcaaataggg aaccagtcca aagtccaact ccagcagggc ttgatgttcc ctcaccctta    51840
ctaggcagtg aactagaagt ccttagatca gcacccccac ccccattccc attaaaaaga    51900
gaactgatct cacagccagc aatgaggctg agcctgcatg ttgggtctcg ttgtgtgcat    51960
gagagcagga ctgtgaggaa ggaagatgac catactcagc cagtcgagga agacagtttt    52020
acctcccgtg ggtagtgacc aggcccttg attcagcttt tcttgtttgt agctttaaaa    52080
acaagccctt gttagtgttt ccatgtagtc ttcttccctt tcttggtggc catgacttgt    52140
tccctggatt attgcatatt aagtaaattc ctatatacct tctggattac gaaaaatgtg    52200 tcttaaatt tttagaaaat attcttatac tccgattttc ttattgttca aattgaattt    52260 aaccttcta tactttatag ttttctagct atccttgatt gagaagcagt taggaaatct    52320
gaaaatcttg atacatgtaa tattccaaat tgctttatga ttctaaactt ggaggttaca    52380
tccatttgga gacacacaca cacacacaca cacacacaca cacacacttt aatgtcttga    52440
tattctttca gacatcagga agccagatcc agtcagaaga atttgaacta atgatgaaa    52500 aggctgccac tagaatggcc ccaaatggct ggaaatctcg cctatttagg cattctactc    52560
agaaaaacct taaaaattca caaatgtgtc agaagagcct tgatgtggaa accgatggac    52620
ttgtaagttg ttttttcactt aaattaagtc ttttactttg tagttttgct acaattattg    52680
aaattcttag ccttgcaaat atttttcagg cacagatgac tgctactatg agccatactc    52740
tttgtaaaga aaaaaatttt caaattttaa atgtatttga caatgaattg aaatcagttc    52800
caattataaa tgggttttca agggaaaaaa aatccagaaa tgtagtcttt acgctgagat    52860
gcttaatatt aaaattaaat ttgacattca tctttgaggt ccagaggtaa taagactggt    52920
ccaaaacgag aggccctgat atttgcatac tctattgggt aggattacat tgattatct    52980 atattaggaa acccagaata gcatccgttt aagcaaatta agagttttta tttctgtttc    53040
acatgccaaa atcttagagg tgaaaaaccc agggctagaa cagtagctcc acagtcccca    53100
tagacacaag ctcccttcat ctttatctgc actaccctgg catcaggttt ccatcctcag    53160
ggtcacttat gatctaaggt ggctcctgaa gccctaccta tcacatctgt ggtccaagca    53220
acaggaagaa acaagaggt tttccagaat tcccacacaa tactattact tataagtcat    53280
tggtcataat tcgatcacat ggccatactt agcaatgagt atggaaaatt caatttttt    53340 tttttgctgt atgcattgac attctaaatt agattgaat tctcttactt agaaaaagag    53400
gagaatggtg agaaatagca acgttggatt taggagatta ttaactccag ttaacaaata    53460 attttatta tttatttatt tttaatttta tttttgaga cagggtcttg ctgtgttgcc    53520
caggctgaag tgcagtggtg caatcttggc tcactgcaac ctccacttcc cgggctcaac    53580
tgattgtccc acttcagcct ccttagtagc cgggactaca ggtgtgtgcc accacacctg    53640
gctaattttt ctgtgctttt tgtagagacg aggttttacc atgttgccca ggctggaaca    53700
aataatttta ttatacagag ggaatccatt ccaaaaaaag atttccttat ttcaagatat    53760
agttttgata tattttgatg ttatttgtta atgaagactg agtttatttt tactcttgtg    53820
```

```
ttggcctgag aaaactaatt ctaccaataa tttattgcat ctgtttttat ctgtgcatgc    53880
tattactgca gaaattacaa ggactctctt agaggtctta atcttggtat atttatagaa    53940
agaagaataa caattgtacc attttggagc gtcattatta taagtcagat aagcaatttc    54000
ccctcttttg gctatgaaat tatccacttt tcatttcctc atttattttg agagttattt    54060
tgctatctct ttaaactcca gtattttata ggagcacgtc tcttgaagaa atgcacagag    54120
aagaggggga ggcaggaaat gctgcaatca acaagattgt cccaagtacc atcataggga    54180 gaaacaaca tgccaaagga gagggagaga ttaagtctga ttagagggac ctgtttgtgt    54240
gctgaagagc agtaaccaaa gaaaagatt cattcattat gctggagata gggacttaaa    54300
gataatgtta actagggagg aaaaaaaaaa accctgaaat acagaaaaaa tgggtaattt    54360
gaaagaaggc tcagtagaac ctacttctat attctctgtt ttatagagat ataaatataa    54420
cctttctcag tgacctcaag ttttttgggat tccatagtca cctctgtctc aagtttaatg    54480
ttaaactgct tctatcatca aaacattctt tatgagacct aaatcctgca tgcttggcca    54540
gacatttaat taaacatttg ctgagaatct tatatgtgcc aggaattgga ctactttcta    54600
ggaatataaa gacataatct ttaccttaaa aaaagttaca tactagaaat ggaaatatgt    54660
aaacaaaaaa atcacagaca agctaagcta tgaaataaga gaagtctgca cagggaaaag    54720
tgtggtaaga gaaaaggaat gtaattaatt tggttttgtg agttgaaat atggtacaga    54780 aaaggcaagg ttttggggtg aggaggccaa gcccatgttc tccagttagt aatggtttcc    54840
tacatttgca aagatgttta tccatctact caggtgtatt gtctcatttg acccagatat    54900
catccctgtt agagaggcag gactgtatca taatatatga gaaaactgca gctcggctta    54960
tgtggtccag ccatgactgt cacaccaata cagtgttgtg taactccaga gctggatgcc    55020
aaggtatttg tgcccagatc ctgctacctc gcagtctgct gaggccagaa tagggacggg    55080
ctaagcatcc catgaaggtt atttcttggc cgaacaaccc atactcagct tatgatgtgt    55140
aatcagtaaa cattgttaac atgttataat atactgtcct actctctagt agtttgcttg    55200
tcattctctg cacctagttt gcgagtccct tgagggcaat ggccatgcct tttctatgtc    55260
tacagactct ggtaactgtt gtgtcatcac cagtttgccc tgatgtttat atgttctagg    55320
aagcaaatgt gccaccagtg tccttttctga aggtcctgaa actgaataaa acagaatggc    55380
cctactttgt cgtgggaaca gtatgtgcca ttgccaatgg ggggcttcag ccggcattt    55440 cagtcatatt ctcagagatc atagcggtaa gtttgcaaac accacataac agcctgaatt    55500
agatcaattc atcagctgct gcttctccca acctcactga ctggctccat tctgggatta    55560
agcagcctta aattaaacta agccaaagtc cttaaatccc ttttgagaaa agctgtgagg    55620
gaaaagataa gtagccttg aatcactcta agttatgata ttaatgaaat tataaaatgt    55680
aaaatcaatg aagaaggcat tctaatgagc tctcttcatt tggtgaaact ggtgtcagac    55740
aatgatcccc aatctgtttg tgtagaaaag ctggtacaag tcgcacagtg aggtggagag    55800
agagtggagc agggaggggt taaagtcata gagtttaata agagtccagg cactgggtat    55860
agactggcct caccactcaa tagctctcgg tacctcagtt tcttcatcta tacaataaat    55920
ctacctcata acatggctga ggattaagag attatatagg taactatctg gaaagcattt    55980
aagagtgtgt gccttgtagt aagtattcaa aaagcgatag ccacccatt ttagcaatcc    56040 ttccaaggct tggggagtcc aagactaaga aagaaaacat actagccaat cattcaatta    56100 attggggat atttaaagga agttatcaca aatataaagc ctccatcaat tccatgaaat    56160
ccagaattca tattctacaa tttcagtcaa gctctaatgt tattggagag actttgttgt    56220
```

```
tgaggataaa taattctcca tcatgttacg agtttattat ttttgtgatg ttggacatcg   56280
atccacaatt aagaccacaa gccaaaaaat aaataaatta gaaaagatcc tcctccaaat   56340
cttttaaagt ttcaaaacaa agcaagctct ggctctcttg caattcaagg caatgtggac   56400
tatatatttt ggggcatctg tctgcctagt gctgctccag gcactggaga tacagtggta   56460
cacaaataaa ccaagttgtg ccctcaaaca gcggtttctg tcggggaaga catgcaatgg   56520
acaaacaaaa aaataacccc acaaacatgt aacatgttga gggataacaa gagttttaaa   56580
agatgggtag ggtaatagag aggtgttagc tgggggtgct gtttcagata ggatgctcag   56640
gaaaggcccc tctgggtgga agcctgatgg aatgagaagt ggagggctgg gacagggagg   56700
agtcacaggg agcaagggac atataggaag aggaacaaat gctaaaatgt gcaaccactc   56760
acagtccata tgcagtatgt caacctatgt taacaaccat gcagtcagaa agtagaatag   56820
agattaccag gagctgggag gaggagggaa tggggagtca gtgtaatggt atcaagtttg   56880
ggaagtttgg gaaggcgaaa agttctgtag atggatactg gtgaaggttg cacaacaatg   56940
tgactgtact taacgccact gaattataca cttaaaaatg gttaaaatgg taaattttgt   57000
gttatgtata ttttaccaca attaccaaaa ccctacatat ttgaagccta gttttaaaca   57060
tgtgacactc aagccactat ttatgagagg aatgaagaag gatcagttat gtaatccaag   57120
tgggcgtttt aaatattctt ttgtagattt ttggaccagg cgatgatgca gtgaagcagc   57180
agaagtgcaa catattctct ttgatttct tatttctggg aattattct ttttttactt   57240 tcttccttca ggtaggtacc catgatttgc ctttctcatc aagtttataa tttaattaga   57300
gaaattaaat taaacctaat ggagcttcca aattcttaca gtgaaataaa ttgcaaacat   57360
gattggcata aggctctgct ggagggtaga ctccttatca gggggaagtg tgacttccct   57420
gtgtcctaac ttatattaca ttacaagttt gccctcagca gacattcatt accaaggaca   57480
agagacctca gtttactgca gaacataaga gtaacttaaa ttcaacaggt tgggaactgg   57540
gaaagtacag tccaatagca ttctcttttc tgttgttact ctttatagaa tatcaagtaa   57600
cttctctgat cttttcctac ttaattgatg aactatttga aagaacataa tattttgcat   57660
tctaacgttg tagacctggc caaaataaac tagtcaaact ctctaattgt acttttctac   57720
ccagttagac ttctctgtaa tttcttttgt ctctttaacc cagtgggcac cacataggcc   57780
tttcgaatat aatacaatcc atcaagtcag caaaatagtg tttcctagtc atgccagcat   57840
gcttctcttt tattattgtt gaaccaatgg caaagtaaac caagttttt atttagaaat   57900 cattgcccta ctagacacaa ctcaatgatt tgatccagcc ccagtccctg gcatgctagg   57960
gagtgcagct agaaaatgtg tttcaggggc cgcaggaaca gtgggctgat gcatagaacc   58020
tgtagcaatc caccagcaaa tggagggga gggcagtctg gtcctggaca aggaacacct   58080
ggggccgatt cactgggtgc actgatcatc tatcccctg gcttagtaaa cagttctgat   58140
gtgcactccc ccgtgtgccc tcggcacggc tacccaaca ctcacactgt ggctggagac   58200
tcacacgtcc cagaagtaag cccacttctg gatatctgga ctcctctcca gtttggatgt   58260
ggtaattaga aagtaggaaa ttgtcccaaa gaggctgggg aaggaagagt accctgattg   58320
ttccccaatc tgagtgcagg tggagctgtg accaggaacc agcatactca tttgatcttt   58380
gtttctaagg tcatccttcc tttacactgc atgagccaaa atgaattcgt gtgtaggact   58440
ttgttacttc tgtatttaac tggtttattg gaagtagtag gaacacactg aattttgtag   58500
ttaaacacag tatctttgtc actgagatgt tgtccttcaa agttttgaaa aataaaccta   58560
```

```
tttagaatgg tttagaagcc agaactggac acctttaagg ttttttggcct ttgattgtaa    58620
tgcatactga tgattttgca gtacatgaat ttgacgtggg ggctttgaat tcgtatttgg    58680
tcctggactt ttgttatttta aatagttaac atacaaataa tgtaaaatca atgtgaatat    58740
aggcacctgt gtcagaatac tagcaactgt tacccacaca acgggcaggt ttggtcactt    58800
ggtgggtttc aacccaatga ccacatcaag gaggatttag caaaggaatt ttataacttg    58860
tcacaagtga gaagctcaca gagcttagtt cccaaagcag tatctcccca agctggaggc    58920
tgggtcaggt tttataagcg tatggtaatg aagtgtgatc tgattggatc ttgcaatgaa    58980
gtgatgccgg gaagcaccat ctgactggat cctgccatgg ggtggtgtca gagctcaatc    59040
tgattgaatc ctgcatcctg ccatgtggtg tctgcttctt aattcagtcc ctgattcttg    59100
tttcggagca cttaggttcc tgctatggtt gcatgcttga ttcatctggg gctgctcagg    59160
ttattaacat gacttgagga tccgtggcaa ctgtaaaaca actcataact ttgctacata    59220
aaagttgaac atgattggtc tggtgcaatt acatacataa agatcaaaag agaccatagc    59280
cttttttctc aaccagggtt tcacgtttgg gaaagctggc gagatcctca ccagaagact    59340
gcggtcaatg gcttttaaag caatgctaag acaggtagga gtgtgcgctg gagaatgcct    59400
tctgatcttt cacatttctt ccatattaag cttcttactg ttcttattgt tatgtcgata    59460
tgcatgtttt ccccccaggg tattcacgca aggatgggc agagtcctgc aaattgtcct    59520
ggtccttcaa gagctaaaga cttctcatgt tttttttgtt tttttttgt ttttgttttt    59580
tttcatagaa ataggcttta tttgggtagc tttggcttat tctgtaaata tctctctcca    59640
tgtagacact atcatttcga agacctgtat ctcttttctg gatcctgtgc aggccctggt    59700
gagtccattg agactccagg atgtctttaa accaagaaaa acctagttga tagcattttaa   59760
tctcatgtac cacaatctac catactaact gtaggtatcc tcaaatgtta ataattgagt    59820
tttgtttatt tcttatttga ggtctatttt cacattaatt cacttgtttg tttattcaaa    59880
cattacttat catgtaccag acactgtgct ggtggctggt actgtataat ccattatttg    59940
ctctcctcgt aagttcacat tctagtgcct gacataggaa aatatgcaaa catgaattat    60000
ctatttttat agaaaatgcc taagagaggg ccagaatatt atccattcaa ttgacaggaa    60060
ctgattacat ttctgttcac aaatgggcac atagtaggta gtatattctg attaaatctg    60120
tctacaaatc ctatttcagt atctcctaaa ctcttgctat gcaggaaaaa ttattttatg    60180
tgaaggtaaa agatgccatg gatgagtagc ttacaattaa aattaagtct cagacatgct    60240
tctttttttta tccctgtggc taactggaga tcagacacac tttcaatcag tgtttaacaa    60300
aaaatcaaac aaaagcttgg tgagaaacca gtgcttattt tctcctgcct agaatctatc    60360
agaacaacat gtccaagaca gctccaccac cctttatgag agacaacacc atatcagggc    60420
agaagtgtcc atagtgaaag acctgatgat tgggtgaatg gaatgcctac cagcctccca    60480
gccttgggag gagctggcaa ggagcatggc agccatctgg gtgagccctg cccccctaga    60540
ccagagatgc cctccctgct accacagagc agtcaggaag ctgggttctg ctagattctg    60600
ggggtgtgtg ctcagagcaa ggccaggagc tctacactgc atatgaggtc tcccctaaat    60660
ttcctcagca ttggagcttt gggaggcttt gtctggtttt ctttgcttgt tttaattttg    60720
aactaacata aacgtgtatt ttatgccata ggacatgagc tggtttgatg accataaaaa    60780
cagtactggt gcactttcta caagacttgc cacagatgct gcccaagtcc aaggagtagg    60840
tagactgcac tctacttgta gttttttaca taacatggtt ttagataagc atgtagcata    60900
cccacacttg ttaagatgct tccagctaga aatagcagaa agctcaaatc aaaactgctg    60960
```

```
taaacaataa gcagaagatt aaacttcaag gttgattgac ccactgcccc ctccagattt    61020
aatccagaat ccaggttccc tcattggctt tggctttatc ccaaggctga ttccctgcag    61080
tcacaggatg gctgctaata gtaattagaa ctacaggctt ccttatttcc catccagtga    61140
aagagagcac acacctctac ctcaaccacc aaacaaaaac cctttgctga aatctaattt    61200
gggctaattt gggtcacatg ccccaccctg aaccactgtc tccaggggat ggtggtgttc    61260
tgagtggcct acgtccccca cccctttagc tgaggtgggt tactttgcag ctcactgctt    61320
ccacacaaca ggagaaggag gaatggatgc agagagctga ctgcaatgtt gctacagcca    61380
cctttgtttt ctgagtggta caacactaat tcatccttat atgtgctttg tggtggatgt    61440
ctcttaggac acgtacccct tgtaacaaca gatggtctct ttccctttta cacttttgaa    61500
ttaaatggtc tttaaaatta cccaggtaca ttggagttag tttcctcttt gaacattgca    61560
tctatgaaaa aatacatgca cccccagtgc ccatccacaa agcagagaag ttgattactt    61620
ggttctagaa tgttggttca ggtgggcagg agaggaatga gagtgtaaag gcacaatgaa    61680
gaaatgtctg cagagcctca tgagttaagc acaggtgttg tgggtttatt gtaatgaaag    61740
taagccaatg tagctcaggc atagaaccca ctcatcattc tgaccaagag gctaaggctg    61800
gagcgcatgc atttggagct taaaactaca gttgctttgt gcttttttctc tcccaggcca    61860 caggaaccag gttggcttta attgcacaga atatagctaa ccttggaact ggtattatca    61920
tatcatttat ctacggttgg cagttaaccc tattgctatt agcagttgtt ccaattattg    61980
ctgtgtcagg aattgttgaa atgaaattgt tggctgaaaa tgccaaaaga gataaaaaag    62040
aactggaagc tgctggaaag gtaggtcaaa taagatttca attggtgtta agtgttgttt    62100
ttagacatgt gtttttatttg aattattttat catgatatgc aggctttaat aattaaatgt    62160
ttgtgcccac tacaactaat aattgtcaat tgtgtatgaa atatttttact gtattaatgt    62220 ctagaactta aatataaggt gattaacata aaacgttgag cctatagaaa gcacttaaca    62280
tagttatgat aaagaacttc tgaatattca aagtgcattt cattttactt catgtccaaa    62340
tgctactgtt tggacaaatg tcatccctgt ttcacaaacc ttcatgcaga agactgtaag    62400
tgaattgttc agggtcggac atgtgctggc atttaagaga tcctcttctt tttggctgtg    62460
atttctataa ttaagatggc agccaccaga tggcagtaat gcctcaattt tgtgttctc    62520 actataatgg caattgggct taacatttac ttgagcctta ctacgtgcca gttattgtgc    62580
tacatattta tatgcaccaa tttattacat cttcacaata atcctataag gcaggcacta    62640
ttgttatccc aatttcagaa atacagaacc tgagattcaa acagaagtta gagatttggc    62700
tgggatttaa gttcaggtct agtttcaaag ctcttacctc tactatatgg tctctttata    62760
tgtgtttaag tgtctaaatc tacacataaa cattttattt acaagtacat gcactgaaat    62820
gttcacatgt agattataac catgaacatt cttagtctta tttatgtaat tattatcctt    62880
tattgaaaca tgaggaagtg aagcagataa taaatataaa ttgtgatata ggttttatag    62940
cattgcactt tacaaagccc ttttacaagc attactgcaa ctgaccttaa ctagttatga    63000
gaagtggaac agacagtatc tctataggga agaaggcgtc agagactggg tgagtgacta    63060
gcttcagagg caccatatta agagggaaga ttaacattcg gactaaccat gtttccacta    63120
aaccaattat gtctggtgaa atcctttctt gtcctcttgt aatcagcatc agctgccgct    63180
gcatgcagcg ttaggtataa tagtatctcc aggtttccat cagaattcac tctcctcatt    63240
ttcacgctgc atcctctcca agacttggag cttgctagga caatatgtgg ttcccaggac    63300
```

```
ttgggaaccc ctgggtgtct agagttcttg aagattctct tggctgctgg ctgtgggtac    63360
tttagggcat catttccttg acttctgagt gtctcaacta actgctgaag aaacactgtg    63420
tagctctgtt tcctcccctg cccctcaatc ctgcttcttt ccacatttca tatgggagaa    63480
tggtcagttg gatggaatga aaataaactt ttcttagaca agttacatga tagaaaacat    63540
cttgaatcta gttaatagtc ttagctccat taattgttag aattttgtca gagtagagca    63600
ggtagaattg agcagtattg aaacaaaaca aaatcttggg ttattagctt tggtcttgct    63660
attcacagtg tgtgaggctg gagaagatcc ccaacttctc tagtcctcat gtcctacctt    63720
agtaaaatga gaaattgtac cagatactgc cccaagttcc ttccagctaa acccctgtta    63780
ttctaagcat cagagattga ataactcaga ctggccagtt taaatttttt tagtagctac    63840
tttaacctaa tagggttatg aaatatgaaa gattaaatat gaaatatgaa agattttaaa    63900
tatgaaagat taaaaatgtt ttaaatgtta atatcagcag ttcaatcata gtttaatatt    63960
gtttactcag tcagcacttg cttaagagtc ggaaagaagg ttctagaaaa accccaaatc    64020
actatttaaa aagaaacact ctcatttacc tgggtacagt ttcatcatca ttaaagtaca    64080
acagggtttg aggtattccc atcccaattt tccaaaaagg gcttggtagt gagggtgttg    64140
gttactgggc agggagtggg gagggaagac tgcctcataa ccatcttgac ccagggcttg    64200
tctggtcact gagattaagg gccctctgtg ccacagctaa cccgtaaggg agttgatcca    64260
tgactagaat gtcaagagga gtgtcaagtc attactggtt tctccttgtg taaattacac    64320
agcaggggta gcagaatagc attatggctt aggaacatgg actccacatc agatagtctc    64380
agttggaatt cttgctttgc tacttattaa ctttagaact taaggcaatt cagttaactt    64440
ctctgtgcct cggttctctc atctgtgtaa ataggaatac tatttccctt tcaaggttgt    64500
gaggctaaat gagatcatat tggtgaatga ggtaatactt ggacatagta aaagctcagt    64560 aattttctc tattcttgta attgctatct gttatatctt tattacaaat gaaaaatcta    64620
tggttattca gtctcaagca tcacatatct tcctttcagc tcattgcaga agctaagaac    64680
tgaggtaaaa aaaaagtct taagctgtt aaaaacctaa aattaagatc ttatgctcca    64740
tgtgctgttg gtttagatga ctcaactaca gaactaagat ttagactaaa tagctaagtc    64800
acagacaatc aacatttgtc aagggtggtt tggctgtaag aatcagagaa ctgctctggc    64860
tggtttgggt aaaagcgatt tgatataagg acactccaaa gtgcaagaaa tacaggcagt    64920
ttgtgtgtaa ctggctctta cagccacagg ctctaatatc tgagtcttcc tatacatcta    64980
ttccattcct cggatgctgt atattcagac cagcttctta cacatacccca atgtgacatc    65040 agcctctgaa gccccagggc ctcacggttc aaacttgtgt ccagggccag gaaaccaaat    65100
ctgattgacc cagattagtc agatgtctga ctctgattta atcacggatt taaagcatgc    65160
tcatgttgtt gacaattggg atctccttcc cattgtgggt ggacagcttt tataagaagt    65220
tatactcagg gaggaaataa ttggcagctc caataggccc ttagaaatca cagcctaatc    65280
ctttctttta ggactctgcc ttgtgaagaa agccaggcca caagggggtt gtgactaagg    65340
ccagtcatgt aactgcctgg tggcaggctg ggaatagaac caggcccttg gttcccaggc    65400
cacagttctt gcccttagct gatcagcctt cctgagcata caaagacttg cctaccatac    65460
ttagcacagc cagaagtacc agttttgtca taaagctagt cttgaacaga ttatgccttt    65520 ggttttttaat ttaaaggaaa ttaaagccta tcaacgtaac cttcaggata cttttgacag    65580
agccctaggg cttattttc attatttcag aagtgaaaac accacttcta atgaaggtct    65640
attctgtgtt acagattgca acagaggcaa tagaaaatat taggacagtt gtgtctttga    65700
```

```
cccaggaaag aaaatttgaa tcaatgtatg ttgaaaaatt gtatggacct tacaggtaat   65760
gaaccatatg attcctgcta agaacctagt gctttcctaa ggctgaatta ttgtcccaaa   65820
aagataataa aagctctgct gctccaaaca atgatatgac tataagggtg gcctttttc    65880
aacaattctg tcactgaaaa taagtagctt tttgatgtga ctaggacaca gaattatatt   65940
ttttacatct tatgcaaaca acaagaatag gtctccaaga cgtaaaagat atagagaatt   66000
gcacagtctt tggttatcag tgcaggcaac ataaataacc tatctgggtg acttaagaca   66060
aacattcctt taaggaattg ctcaaacctt tctttgcagt gtgtagactg aaccaaaagt   66120
gagacttgct attgggtatg ttccagagga aagtatttca tttgttctct gaatgaggac   66180
cagatccaac ctactctgaa gataaagaaa cacagactat ttcagtggtt tatagttgag   66240
caattcaaga aactcctaat ggcaccattt gccactcatt tccactgcag cctgatttta   66300
taaatgagta tgtttaaca caaagttgaa cacaacttag attacaattt tgcagactgg   66360
aacagtagtt ttgaacactt gcaaatttga acagatatct ttgaaagtct caatttatgc   66420
catctcctca gttatgcaca cttcatatga tactaaataa catgcagcta cacctttgtg   66480
tccatttgtt gtttgacata aacatgtat gcaccattaa tgatgacctg ttttaactt     66540
caaggagggt taaggaagaa tagaaaggtg aagctaatta tgaacttggt tataatttaa   66600
agattcaata gcttcacaga atgctcaagt tttgtaacac catgttcaca gcacataagt   66660
taaaccatcc aaattagtaa tactttgaat ttttccttt gccaaaaaca ccctcatatt    66720
tgagagtaac tcaattatag ttcttttgga ggattcagaa gccaataaag tatagcatga   66780
agtcaaatta gaaactgtac aaaataaatt atatacaggg gcggctggca ggatctagct   66840
tgggaaagga cttctggtgt atatctatgt aaacttcagg gactcaactt ttgtgaatct   66900
gaaacatgaa ttttaaccta acagagtaca attagttaca ggaaacaaca taatagtagt   66960
aaatcacatt cagataattc aaacttaaat tcagatcctg acatttagg tattttgaa     67020
acaacaacta tgcttaatag gagttgaaca ttggagtcat cagatattaa tatgtaataa   67080
tatcagttat catttgagga accactatga actaggcact gtgctagaca tttatatggt   67140
ttttgtcaaa acaattctgc attacagtga ttatttccat ggtataaatg tttagagaag   67200
ttatcattta cccaaactaa tataactgga ggtggaactt aaacccactc ggccagactt   67260
agaagccgtg ctcttttccac tacacagcgc taaaggaggc tgaagagatg gttacaagta   67320
tactgatttg cttttcagga attctgtgca gaaggcacac atctatggaa ttacttttag   67380
tatctcacaa gcatttatgt attttttccta tgccggttgt tttcgatttg gtgcatatct   67440
cattgtgaat ggacatatgc gcttcagaga tgttattctg taagtagctt tagaaatatt   67500
aagattattc tataataagg ttttagtagg tttatgcaaa agtttagagt aggaaaaaaa   67560
tgactcctgt gtccaaagat gaggtcaggg atttaaattt accacagttt ccatcctggc   67620
aggcacagag atctgatctt gttaatactc caagtgcagt ttcattttgc gggctacaat   67680
taagcttatg aaaatgatca gaaagcacag ttttagttgt acatatgatc ctggtcagga   67740
tgatgcaaat tttctcatta tagaatatag gcagaaaaaa tcataattag aaagttgctg   67800
gtgaccatgg actcaaaaca gggttatata gcttactatt atctacaacc aaaacatggc   67860
ctggaaaaca agatgggaat acttgttgga agtctggcaa aggcactctc tccctaacca   67920
ggcctgagat gagacagccc tgccaacatt tgcctctcag cctctccttt ttccttggtt   67980
tccaaggcaa actactggtc tttctgtttg atgccttctt tcataatgtg ctcagcacat   68040
```

-continued

```
tccattaggt tgcaatctgg gcttgaaaga gggaagcaac tcttttttaag atcatttggt    68100 atgtttctgc tctggtggga tgattttaaa gcagtggtga acagccattt ttgaaacagg    68160
gtcaagacaa aaaagcgaaa gtgtgttaag agctgggttt tttttttcat ccaaaattaa    68220
aattaccatg aaaaaatgta tctatataat ctttgtatca ggatcccagc aggaaacaaa    68280
tggcacagca aatgggttaa ttgatgagtt tgctaaaggg tctatttaca aaggcctgga    68340
aagtgttaag gtaagcagta cccaagaagg aagttaacac cccagcaata cccagctgga    68400
aactgctacc accctaagcc taaaggcaag agaagggaaa gatagccaga actcagcata    68460
ggtgctttct gtggtctttg atggagggac agcaactgca caagcaatct gacaagaaag    68520
aagccaaaga aacaaatacc ttggcctcac tcccttccag cctccctatc ctctgctgtg    68580
ccttccattg gccaaatcct atgaaaccag aggacaagaa aacctttga ttcagttcat     68640 gatagttgga atccccagac atggagtagg gggatagaag gtagagatgg gtaaaaagtg    68700
aggagtgatt tgggggaca aatggaacta gcagctgggg attacaactt agagtacaac     68760
tatttattgt ataaaaaata ttgagaacat ttctgaaagt gaaaaccgtt ggaaagtcac    68820
attattcctg cttcctttct ttttttaaaat cattgaaatg ttaaattatg gaaacctaga   68880
agacagcttt aggcagtaca gggaagctat gcagccacat gtgggttgtt catcactatt    68940
ttaaaactta gttttttggca actcaccttt tcgtcaagca tttaaaggaa agttttacta   69000
tacctctcat cccagccct aggtattaaa acccatttt aatatcttag ctttagaaat      69060
ttgaaggtga aaacttaaag ttctccatta ttagtagaga actcccactc ctttctctgg    69120
ggtagtgctg gtatcagaag taaattgctt tgtgaagttg tagatctcag gatctttagc    69180
ccttcctaaa agttgtcata atcaatatcc atctttaaag agcatataat tagaaaatag    69240
aactttagtt taaggtgact ttttttttcca gagtgctgtc aatagttatt ttaactttta   69300
ttttaggttc aggggtacat atgcatgttc gttaatacag gcaaactcat gtcatggggg    69360
tttggtgtac agaccatgtc atcacccaga tactaagcat aataactgat agcatagtta    69420
ttttaattgt aaataaaaag ctatttctag taaaagctta ttttccctaa taaaaattat    69480
ttacagtgat gatgattatc atttgtgtgg tagtacagaa gaaaccacaa actggaagtc    69540
agggccagag ctttatcaga aaaagcttac ttggaactga tcaaggccct tacacacttt    69600
gtgcttcaat tccctcaact ctaaaaagag tataaccagc aactaaaatt agctgagctc    69660
acagatcaga ttcagttata agcctcttct tgaaagtaaa aaccctttggg aagtcacagt   69720 agtcctaaga aattagggc tactatgcaa agggaagtca gaaagcaagt cgagaaaagg     69780
taaaccctca ggaagtggat cttgcccctc tcctagattt ctcttgttac tagaattta    69840 tgaaaatgta tgtcggggag aaaggggatg attaaggagt aaagggaaaa aatactggta    69900
agcactatac ctttagactt tcaaacatca tggagttaat tataaaagct aattttttgaa  69960 ttcctctact tctgtctagg gtgttttctg caattgtatt tggtgcagtg gctctaggac    70020
atgccagttc atttgctcca gactatgcta aagctaagct gtctgcagcc cacttattca    70080
tgctgtttga aagacaacct ctgattgaca gctacagtga agagggctg aagcctgtaa     70140 gttctctgat gcctgatgat gcttgatcaa ttttttccta aggtttgctg tctgctagat    70200
tatagctaca ggataagttt gtgatgatta caccaacatg tgtttcattt aatttgtaat    70260
atttatatag ctaatatttg ggcaacttga ctgacattta aaatttat aggtggtttc      70320 aaggatcctg aagtttagca catcaaaata aaaaaaaaag ggaaaccag atatattaga     70380 actgaatagt ttccacaaaa atttagtcat ttctacataa aggtataatt ctgccatgtt    70440
```

```
aatgcaatta gtaatttgac tttaatcact ttttataata gttaagatgt aattggtaag    70500
aagggcagtt cgttcacaat gagagtaata atcctgtgct ttattatcta taaaggtaac    70560
ttaaactcac atctgagtgt tctttgtatg acacaagatg ctacacgttg taatatacaa    70620
gcagctgtgt aggtaaagag gctaggactt aacacagtct ttccaggact ttcccaggta    70680
tttcatgttc tgataaaatt gctgtgccca gtgagtgaga taaagaaagt gaacttaaga    70740
aactgccagg gtttgccatc agggctgccc actgaaactt gggtagaaa ctgttgctaa     70800 atttccaagc ctttagagtc ttttggacac tggcttgatt ccagcttcag aataagcagt    70860
tgggaaagct aaatgaatat cttaaagaaa tcagaaacta agttagataa caactcatgg    70920
taatgacttt ttgtctaatc tcacctatac ccctatctct caccttcatt tcacaccata    70980
ataacttgct atcaatatta actggcacca gaactatacc aaatatgaat tttatgtttc    71040
tctactacag tctttggtaa agtttccttg aaataatatt tcttattcca ataattatca    71100
ggccaattat aatagcaaca tttaaacatt tattcaggat aaatttgaag gaaatataac    71160
atttaatgaa gtcgtgttca actatcccac ccgagcaaac gtgccagtgc ttcaggggct    71220
gagcctggag gtgaagaaag gccagacact agccctggtg ggcagcagtg gctgtgggaa    71280
gagcacggtg gtccagctcc tggagcggtt ctacgacccc ttggcgggga cagtggtgag    71340
cacatttcct tataacttga ttgaaggcta tattttaatt ggcccaacca atattgtcat    71400
aatggaaaat attggacaaa tgtagaccta gaatcctgtt tgatacaatg accacattct    71460
ataaacccca actggcacca tatctgggaa atatatgggg acaataggac agaatgtctg    71520
gaattcagtc tagctcagaa aatactgaat ataagtttaa ttttacccct gtcatgggcc    71580
tttccagtca gtctgattgt tctaagcaaa tactgactta ctggcttata aaggtgaact    71640
acagactcct gcccaaattc aaagctgact tccaaaacag ggtgctacct gcttattgcc    71700
tccccaccgc tttcagtttt gctgccttct cttaccttga attctcggct ctcgaacttt    71760
gactttgatc ctcaacctcc agcccttttca tatttggctt ttgtcattga ttttctagca   71820
tgtagccccg tggctctctt ccttgagtga agaccaactc ttactgataa tgcttgtatc    71880
tgccataacc ttgggacagc acccatgaca gagccctggg agcctgtccc cattagacag    71940
tcaccaaagt gttaagcctt gtttctttta ttaatagttg ttaagcctaa atcagccttg    72000
ttaagcctaa tttagttgtt tctctctgga aatcttctgc tttgctatta tagctattct    72060
gcaggtaaca taggcaaacc agctcaccaa aactctgtaa atatggtgtg ctgatacgat    72120
ggtgggaatt ttttttctttta ttgagatcaa gactagctgg acttgtgtct attcctttgc   72180
ctgtaagctt taccttacac gaggctgtat tttcaagtac atattacaac acttccctag    72240
gagcaccatg cctcctgcct atagcaagta aaacaaaaac aaaaccatca ctgccagcaa    72300
aaataatcct cccaaagaca ctgccctttg taacttgttc cttttccatg ggattcttgt    72360
ccttagtgct atcagagagg tgagggaaag ttaaggctag tagttttcag ggaaaagaga    72420
ggtagaggta ggaccagagt caaccagctt ttggggccct gcttctgatc agcttttca    72480 ctgctgtgca tgggggaagg ggaaatcaag tcaaggtgaa gggttaggat tattctgggg    72540
acagcagacc tgagtgggac accttgatgc aggcttcttt aacgcagagt aggacacaga    72600
tggctggagg agggcagaca aggacaaaga gaagtgtgaa aaaagagggt caaatgtgct    72660
accattttgc cagttagacc aagataggga tggcttaatc accataaaaa tcatcatgtt    72720
ggccatgctg gcctcaatgg tataagtctt ggagggttgt tgttttgaag ctgctgacac    72780
```

```
cctcatgcaa cgatcctcca aatggacaat ctagtaactt tttagttttt ttttcttttt    72840
tatacccttc ttatagtttg tggactttgg ttttcagctt ctcgatggtc aagaagcaaa    72900
gaaactcaat gtccagtggc tcagagctca actcggaatc gtgtctcagg agcctatcct    72960
atttgactgc agcattgccg agaatattgc ctatggagac aacagccggg ttgtatcaca    73020
ggatgaaatt gtgagtgcag ccaaagctgc caacatacat cctttcatcg agacgttacc    73080
ccacgtaagt taaagagtag ctgaaatcag aagagactac ttttatccc ccaaacaatt    73140 accaaagtta tgccaacaaa atcttgtaac aaaatatgtt gatttactaa cattaacaac    73200
ttggacaagg cacttcagga taccaagctt ccttatttgt aaatgggaat acattatgcc    73260
tacctcatac aaatgtagtg agaagctcaa aaccaccata cttcaggtta cagactggtg    73320
gttgagggct gcatttagac tgcagtcatg tttggtttag ccctatggta cttttaaaac    73380
aattatagtt tttattttga gataattatg gatttacatg taattgtaag gaatacagag    73440
atcttatgta ccctttacct agtttctgcc aatgacaata tcttgcaaaa ctagtataca    73500
gtatcacaag caggatactg atattgatac actccactca tcttattcag acttcccttg    73560
ttttacttgc attcatttgc atatggattt agttctgtgc agctgtattg cagatgggga    73620
ttcatagatc cactaattaa gaacactggc caggcacggt ggctcacacc tgtaatctca    73680
gcactttggg aggccaaggt gggtggatta cgaggtcagg agattgagac catcctggcc    73740
aacatggtga acccctgtct ctactaaaaa cacaaaaatc aaccaggcgt cgtggtgggc    73800
acctgtagtt gcagctactc aggaggctga ggcgggagaa tcgcctgaac ctgagaaacg    73860
gaggttaaag tgatccaaga tcacaccatt gcactccagc ctgggcgaca gagtgagact    73920
ccgtctcaaa aaaaaaaaaa aaaagataca gaacattctc atctccataa agatccctca    73980
tattgccctt ttagagccat gcatatatcc cttcctccca ccctcattcc tctcaaactc    74040
tggcaaacat gaatctgttc tccgtttgta aatttttata ttttaaaaat gttttataaa    74100
aatatataca gtatgtaaac ttttgggatt aacttttgtc tttcagctaa ttccctgaag    74160
ttgtgtgtat tcataggcat tgcttttttat tactgagtga tattccacag tgtggatgta    74220
ccacagttta accattcacc tgttgaagga tagctgggtt atttcctgtt tctggctatt    74280
gcaaataaag ctgctgtaaa tacttgtata caggtttctg tatgaattca agttttatt    74340 tctttgggat aaacacccag gagtagaatt gtggagcagt atggcaattt catgtttagt    74400
ttataagcca ctgctaaact gttttccaga gtggccatcc catttttacat tcctaccagc    74460 aatgtgtaag tgatgtagtt tctctgaatc tttgccagca tttactgttg tcattagttt    74520
ttatttttac cactctgata agagtgtagt gatacatcac tgtggcttta atatgcattt    74580
cccaatggca aatgatgttg aacatagttt tttatatgct tatttaccat ctatatatcc    74640
tcttggtgaa atgtctccat gttgtttgcc catattctaa ttggatttt atctttact    74700 gctgagtttt cagaagtttt ttttgtttgt ttgtttaaca tattgtaatt actgttggat    74760
atgtagtttg taaatgtttt ctcccagtct gtagcttgtt tattcatcct ataagaaggt    74820
ctttgcagag caaaagtttt actttgatg aggtccaatt taccaattct tcctttatg    74880 gattatgctt tcagtgtcaa gtcaagaac tcgttgccta gccctaggcc caaaatattt    74940
tctccatgtt ttttttctaaa agtttatag ctttacattt taaatttcag tccatgatcc    75000 attttttagtt cactttaaac atgtgtagcc ctggaaggat ggcttgaggt ccctaaaagt    75060
gatggtaggg acaattcatt ttatggcatt cttccagcat tcggggttcc actgggttac    75120
actgacgtag agcttaatta ttttttgcttt tattttctgc tatagttaga aatcactcac    75180
```

```
acccacaaat aaaattttaa aacccttttca ttttggttag ccttaccaac ctttaatgca   75240
cattgacctg aatcaaatat tggatttgac tgtgaataga aaaatttaca gcttcagctc   75300
ttaatataag tgaccactgg accttaggaa attaattcac atgatataca tcactgcata   75360
agccctgcaa actgaactga ctcaatttac atctctattc atatgctctt tctcagccta   75420
gaatgctctc tcaaaatcta gctccccaaa cttctctaaa aagatttctt tcatttattt   75480 ccccttttt ctccttctac cctgtctcca taacaacttc tatctccttc ttctgatctt   75540
tcatagtgtg ctgtgtatac tactacagtc ctgtgttaca taacaacatt ttggtcaatg   75600
acagactgcg tataccacag tggttcccat aagattataa tggaactgaa aaattcctat   75660
tgcctagtga catagctgtc ataatatcat agtgcaacac aaaattcaag tatttgtggt   75720
gatgctggca taacaaagcg actgcactgc cagttgtata agagtatagc acatactact   75780
atgtacagtg cataatactt gataatgaca acaaatgact tattgattca tatatccgtt   75840
atagcatttg ttatttagga gtatcctcct cctattttaa agaaagttaa ttataagata   75900
gcctattgta gaataccatt gagaattaaa gtcactagtt ttctagtttg attttgaaaa   75960
taaacactct gttaagttga aacaacgtta tagaaactgt tattgactct aaatgttttt   76020
cttgtaaata gaactgtcaa ctgttaagca acagttcatt caacatattt ataatttggt   76080
taacttgcag aaatatgaaa caagagtggg agataagggg actcagctct caggaggtca   76140
aaaacagagg attgctattg cccgagcct catcagacaa cctcaaatcc tcctgttgga   76200
tgaagctaca tcagctctgg atactgaaag tgaaaaggtg tgtgtggcct cccaacttat   76260
gtcttattta atttatgaaa tagaagggat tttgctgtca accatgaaaa aaacacacac   76320
aagcacaggg ggaaaaacac agaacgttag atagtggttt ttatttttat ttttttgaga   76380 cgggggtctcg ttgttgccta ggctgtagtg cagtggcgca atccagctca ctgcaacctc   76440
tgcctccagg gttcaagcga ttctcttgcc tcaacctcct gagtagctgg gactacaggt   76500
gcctgccact atgcccagct aattttttgta tttttagtag agacagggtt tcattatgtt   76560
ggccaggctg gtctcgaatc ctgaccttgt gatccgcctg cctcggcctc ccaaagtgct   76620
gggattacag gcgtgagcca ccttgcccgg ctgatagtgg ttattttgaa gtaatggaat   76680
attttattct aaattttcta aaatgattat atatttata aagtaaagca ttcaaaagaa   76740 aaagctgca caaattacat ttttagcaca ttaggaatga aaaactggaa aatactcaaa   76800
agggaactag ttaaacagaa gattagaaaa tttaaatact tatgaatttt tttacagcat   76860
gggaacccat ttgtgttata tttaaaaagc agaacataac tatgtagatt aaatgttgat   76920
tatacaaaat acacatgcat aaagttcaaa gattctaaga tactagaaat taaaagttga   76980
ttagaaaggt aacattttca aatttacttg aatgttaaaa ctaatttata caattttgg   77040 gataaggtgt ctgtctgatt tatcaatagg ttgtccaaga agccctggac aaagccagag   77100
aaggccgcac ctgcattgtg attgctcacc gcctgtccac catccagaat gcagacttaa   77160
tagtggtgtt tcagaatggg agagtcaagg agcatggcac gcatcagcag ctgctggcac   77220
agaaaggcat ctattttca atggtcagtg tccaggctgg gacacagaac ttatgaactt   77280
ttgctacagt atattttaaa aataaattca aattattcta ccattttatc tgacttgtaa   77340
aataagttt                                                          77349
```

<210> SEQ ID NO 74
<211> LENGTH: 36779
<212> TYPE: DNA

<213> ORGANISM: Homo sapiens

<400> SEQUENCE: 74

```
ccgcagctga cgcaggcggt tcggaaggcg gaagctgccc cgctccgacc gctcagtcag      60
cgccgcggcg cctacacctg ggccccgac gcgcgggcaa aggcgcacgg cccggggcgc     120
ccgaggggc ggtccccgct gggggcctcc aggcgtccct gagcaacgat cccttccaag     180
tacctccccg cactctccct tccctcctgg cccgaagctc ccgagggcgg gggttggtgt     240
ggggccctgg ttcttctacg ccgccctgag catcccgctg cccccaaccc cttccaagtt     300
cctcctcgca ctaccccctc cccagcaacg tgaaggggag gggcgtgccc agggtgagca     360
cgccctctca tgaatattaa taagcgcgca tgcgccctgc ccggcgtgct gggtagaggt     420
ggccagcccc ggccgctgct gccagacggg ctctccgggt ccttctccga gagccgggcg     480
ggcacgcgtc attgtgttac ctgcggccgg cccgcgagct aggctggttt ttttttttct     540
cccctccctc cccccttttt ccatgcagct gatctaaaag gaataaaag gctgcgcata     600
atcataataa taaaagaagg ggagcgcgag agaaggaaag aaagccggga ggtggaagag     660
gaggggagc gtctcaaaga agcgatcaga ataataaag gaggccgggc tctttgcctt     720
ctggaacggg ccgctcttga aagggctttt gaaaagtggt gttgttttcc agtcgtgcat     780
gctccaatcg gcggagtata ttagagccgg acgcgcgg ccgcaggggc agcggcgacg     840
gcagcaccgg cggcagcacc agcgcgaaca gcagcggcgg cgtcccgagt gcccgcggcg     900
cgcggcgcag cgatgcgttc cccacggacg cgcggccggt ccgggcgccc cctaagcctc     960
ctgctcgccc tgctctgtgc cctgcgagcc aaggtaggag ccttctccg ggcctccctc    1020
ccagccgtcc tctccctccc ctcgcggcgc cctgggcggt tgagccccgc gagcaggctc    1080
ggcagccctc gagcgcccga ctcctcgccc ctgcgcccga gcggctgcac ctgggctgag    1140
cgcgccaact cccccacggg agccctgcc tcctgagggt gacccctcca ggccggacag    1200
gggcgcgttc gctccgctgt tgcccccgg gaagtcgtcg gatttcttcc gcactcgtgc    1260
attttttttt tttttttgccc cggaatcatg ttgagtcctt gaacgtagtt tcgcaaaatt    1320
attttcactc ggcgaggagg gctcgtcggg gcggggagtg ggagggagtc gccacctcta    1380
tactcgaaga aaacagcttt ctcccgcgct gacctacctc cttccctcgc cggcaggtgt    1440
gtggggcctc gggtcagttc gagttggaga tcctgtccat gcagaacgtg aacggggagc    1500
tgcagaacgg gaactgctgc ggcggcgccc ggaacccggg agaccgcaag tgcaccccgcg    1560
acgagtgtga cacatacttc aaagtgtgcc tcaaggagta tcagtcccgc gtcacggccg    1620
ggggggccctg cagcttcggc tcagggtcca cgcctgtcat cggggcaac accttcaacc    1680
tcaaggccag ccgcggcaac gaccgcaacc gcatcgtgct gcctttcagt ttcgcctggc    1740
cggtgagtga ctactcggga aggaggccgg gcggagcctc acaccgcgc ctggccgagc    1800
cctgttatcc cttgcgagag ggatttaaag gctttggct tgaaactagg cgctaactgg    1860
ggaaatctct aggggtggcg ggtgagggag ccgggacact atagttagat ctcggctggg    1920
gtagtcgagg tgggtcccat tcctgctgct atttgcttag tgcacaaaag tggggatccc    1980
agagggttta tggaccagg ctcctaggaa ggccggtgta aacttgcaac ttgaagttcc    2040
cagagtaact ctcccggccc caagccaaga gatcgttgta gctgatctct ttgcttaact    2100
aattaaacct ggtgcgccgt ggaaggcgac tcggcgcagt tctggcctgc gaacgccgtc    2160
caaattggca acctccccctt tcccgtgaac ggccgggagg gcgggtgtgt ccttcctgga    2220
gggtgtgggg gagtccgttt cccgctgctc cccgggagat tttagtgtgt gcgggggcgc    2280
```

```
tctccaggtt cggcttaagg gccgggggcg gccgccgcag gaggaggttc ttggggccct    2340
cacaggagct gtagacctgg gaaccccagc ccgctgctgg ccccttcctg ccccgcccc    2400 cgagtggtgt agctcttgtg gcctcacttc cagcggttcc cgggctctgg aacagctgtg    2460
tttgcagact tccccgggaa gggcgggtgc acggcccccg caagccttcg ggggccgtgc    2520
caaggcttgg aagggtggt cttctggagg tagtgcctga gggtgtaagt gataggccct    2580
catccccccg ccccattccg cccccaaagg agctcgaggc ccgggcccag ctggcagatc    2640
ctgcagcgag gcccttgcaa catcccaaaa tgggtggaag gaagatgggt gcgattgcag    2700
aaggggagga aagggaaatg ttggggggtgt gccctctgcc tggctcctgc tgtccaggag    2760
gcatgactca ttgccaagac tggggcttgg cctagcctgt gctgggaggg tgggtggtga    2820 gaggggagc tcggtgcccc agagcattgc tttccaccac gtgctctaat ggggtgcact    2880
ctgctgcctc ctgtccgccg gcttaggttg tgattctggg aggagacaga ggggagacta    2940
tctggctgtg tctgtgtatg aagcttgggg tggctcttaa aatccacgat tacaggagct    3000
ggcattataa agtgccctct gctgtgggtg agataagaca gttatcaaaa actgccatga    3060
aaaggggttt ataaaagaa aaattaaaac caacgctgtc tgtgaagctc tcttgaggtc    3120
caagggctgt ttctgttgtg ggatttcatt tttaccaaga gtatttatct tgtttgttaa    3180
tcccctatta gggagaactt taagctaaag agtctggctg cgtttaaatc tggctggccc    3240
aagctgactg tgaatactca aactgccctt gaacgtgtgt ttggagttta ggggaaggg    3300 gcctgcaggt ggttccaccc tcctgccgga ggatctgtct ggagccctc gcttttcaca    3360 agaccataaa aggaatctta ttagtgatgt ggaaaagcag cagcctggct gaggctcatt    3420
ttggagagta gggtcagagg gatggctaac atgaaaacaa ggaggcttgc tccctcgctg    3480
gccaaggaaa agtgacctag aaaagtgcgt ctgtccgctt ttgacacttg gtcagagtcc    3540
tcaatggaaa acgagcggaa atagtgtggg agggtaggag aggcgattga tttgcatttg    3600
ctggtgctct tctgtggttt caggccccac gggtcaccaa ccatgaaata gactctcggc    3660
ttttctcgaa tgggggaaga ccgatggggc accactgaaa atgtggttct tttgaagttg    3720
ggacaaacgc atgtatcact cataaacaag tctccaccct gatgccccag aaaggcctgc    3780
tgtgaaacat aagatttaat tctcaagaga aattggagtt taggtgtatt tgttttttctg    3840 tatgtggttg gagaaacggc acagtccgta actttcaaga atgattccag gctgagtaga    3900
aacgtaactg aaaacacttaa gtagctgagc gagtatttaa ctagagggca cagcttcatt    3960
tagtttggca attaactatg tcttttaaaa ctgatttcct tgaatgggaa ataaatgaac    4020
ttagtacaga attcaagaga tagcaagaaa aggatatatg gttaaaaaca aaacaaaact    4080
ccaaaccacc ttgggctccc aaccctagc aggcacaatt accatttgca tgagtcctcc    4140
caaatttgct gacgctgggt atcagcaaag ggtgcagggg taggtcagtg tagaaggtca    4200
tgtagttcat gcttttttgtt tggaattatg accctatcc aagcaactgt tcatgttcta    4260
gagaggacga ggaggaaacg atttggtcag atatgaaata cagtccatgt tctggtgtgc    4320
atgtgaaagg ctttgtagag gtggcccttc ctgtcatata tcatatctga gtatgtccca    4380
cgtggtgtcc cctgccccgg ctctggtctt ggggtagttt ttcaccactg gcttctaatt    4440
ctcatactgt tgctgctcta aggggcttaa cttgcagcaa ctatctggat taatgattct    4500
caaattgggg gaccaagtga taagaaccat tattgtggga agtaattggg cttaacagga    4560
aataatttag gaattaccac ttataaatca ctgaaacggt taatctgtac ctcccaaaat    4620
```

```
tagtgctaaa tcccagtagt gcctgcttat taaaaataca ttagtgtaat taccactact    4680
catctccaaa agcttttggg gaacttcaga accccagtta gctgtattgc tgcatcggtg    4740
gccccagagt gaaatgaatc tagagaaacg ttaggggaag aaattggggt atctggctta    4800
ttagcctcat atttaaattc cattgatcct attaaaagac ttgctgagat caacttttt    4860 tttttttttt tttttttttt tttttttttt ttttggaaa atccaatgaa acgtgattct    4920
tctgtgtgag ggatgccagc tttggcccc ttcatgcttc aggcctgaat gaccaattgc    4980
cacgatgcta atcacagaat gtaattgaca ggcccttact tttatgcctt ttgctgtctt    5040
ttccagtccc tgagcttctg tagatatggt gtgggcacat ggagggctta aggatggggt    5100
tctgatttga cctgcctcct ttctgcagcc aggatttgca tcctgcccgt gtagtcagca    5160
tgtatacaaa gaaagagcat gtgtgtacgt atgtgctcag agcaagggac tttctgcatg    5220
tggagaaaac gccttttgcc ctaagaagtc tacctcaaac caaagggatg aagtgatgta    5280
tctgtgttgc aacactgggc ttgggggaaa gtgaagctgt gcttgctttg aaagagctgt    5340
gctaagtatc tgcagaatag ctgctccaaa aatggaatct ttattccagg tacttggttt    5400 ctaattttt tttctcttgc aggtgtaacc ttctgtgttt tctttctcct tgttgtcttg    5460
tttcttagca acttattcaa acctccagta cttataggaa tttgcaaccc accagttcca    5520
cacccgtaat tctacaggga cttaagatgt ttttagaaaa cggtgaaact ttggcgtgga    5580
ggctcttggg ggagttcagt gggttaaaag gagagtcagc agcaacttac aggcatgcaa    5640
cctcccagaa aatcagcaat ctaagtgctg ctcaaaatct tcacaccaaa tagtggtgcc    5700
tttggggacc ttttagatag aagacgtgga aagtttagca tggagaaaaa agttacttaa    5760 aaaaaaaaa acagtgtcaa ggtaacaagg agccttcaca gttcctgatc tgaaaacagg    5820
aatgtgaacc agaggccttg gctggattca tatcacccac tggccccatt gtagaagggc    5880
cagaagttgg tcccaatgtc cggctttcaa ggttagtgac aatgtaagaa tgcatgatct    5940
ctggatgtgc atacaattag cgttgtaatc cataaatgca aatactcctg caaattcttc    6000
catggtaaac ttctgtaagg catgttgctc ttccacctac ccccatcctt caagcctagg    6060
atctaggctg ctgagagaag tgactcttgg cttcagcttt taaatatata tatatctctc    6120
aaaacttaat ctttttcttcc aactgttgga agatacattg ggatgaatgg aaagtggtga    6180
ttctaaaatg gtggtggaaa tggaggaggg tcctgggttc agaaaaatcc caccttact    6240 ttggtgcatg gcactgggtg gctgtgttgt gacttctttg ctgatttctg attaccgcat    6300
ggaccacagc agccctgtga ctgctgttt tttttttttt tttttttttt atggtgccag    6360
tgacatctac cattggtgca gtgcgtgtgc tgggaagaaa ttccgcaagg tggctcccag    6420
tagttaaagg agtacataaa tagtcaaaca tgcagagtcc tctaccagct caacccagtt    6480
tttatgcact tttggtaaat aaacagaaag gcttcttgtt caggcttgct ctgtgtgaac    6540
cagaccgttg tgcttggctg gcttcttggt attctatcta ttaacctcgc cacccttttg    6600
taactggtgc atttaattat cagtgggatg ctttttcaaac aggtaagggt aatgatggga    6660 aaggggtgg ggatgtctca ttgagagtca caaatctgga tatgagcttt ggggcccctt    6720
ggtgagcctt tgagtgggct ttgatgagaa aatcacccctt tgtaaccaga tcggactcta    6780
ttgacatgtc aagccctaca gacttgattg ctttctgtgc ctgaagtctt agcctagatg    6840
ctataggata gttgtccttt cttatctcac tttcccaaaa cccactcgca ttgtgtgcat    6900
gagtacgtgt gcatgcgcca cacatggact cccctgcaacc ttttctgctt aatatgtttt    6960
gtgactggaa tatttttatac tctggccacc cagacacagg caggacaata gagttggccg    7020
```

```
aattgactga aatgaggatt atggagaata atagggcctc tccaaaaata atgctaacac   7080
aggacaagcg acaggaagca acagttgagt cagcagagct cagggcccct gacgaaccct   7140
gggagccgac tgactgtgca caatggccgc gttggcacgt cgggcattcc caggatgtgc   7200
gtgccgccgg cgggcctgcc tgtcgcagca gcctggggtt ttggacgccg cacgcgtgcc   7260
gtttggatgg cggtttattt gtgtccgtca gcttggcagg aggggaggca gccgcttctc   7320
agggcttggt ttggctgtca ctgttgccag gaaaaggaag ctcccggctg ccaacacaat   7380
tacctttgtt tcttacatcc cccctctta atgtggcaat taagtgctta ccgctctgcc   7440
cagtgccaag gtaaccgcca tggagtggga cagggcagag aacacaacct tggcacagca   7500
gcctaagtgt ggagggcggg aggaggtgca ggggcccag ccttgctggg aacctggtgg   7560
cccttggatg ccttggggct ttgatgccag gactctcctc taggtagaat tccacagaaa   7620
tcttccaaaa agcaattccg aaggctgacc attcctcttt gatgccacac cagaatggga   7680
accagctgcc aggtttccag atttccttgg gcttggagct gggaaggggc tgaagtgact   7740
cactttgcaa atccagacta aagatctgtt tgctaccct ccttcctgtg tggccttcac   7800
agtactgttc tggaaaacat aaggaaagat gaaagccagg tgactcttcg gcagagtctt   7860
agttctgtag tctgaaatca agaaaaaccc aggtatttgc ttttgttgtt gttgttttgc   7920
tgtataaact taagtttgaa cacttgcctt tccaagccct cctgggatgg aggactccgc   7980
ctctactggg ggtcagagtt gcagtggctg cttgtatgtg acttcggcat agtggatttg   8040
ctgctctgtg gcctggtccc tgctttgatg tggggtgcat gatctgggat ctcagtgcct   8100
gggtgtatgt tcagggatgt acagaggtca agtgtgggcc tgggaaaaat taaagttctc   8160
tagcaactaa taatcattgt taaattatct tgattgctga tctatagtgt ggggatggag   8220
tgggaggttg agtgcctcct aataggaacc ttggagggaa tccttttct ctgtagggct   8280 gggcaggagg aatcctcctg ccccaggaga ccctaatccc ctccctgaaa cagacaggaa   8340
aaaaagtcca ggctttgttg ccgtcactgt agctccctgc cctcaccctg tctctgcctc   8400
tgagaaagaa gggcagttca tggaaaatca cagagccagg cacgtagggc tgtgtgcaat   8460
tcttttctct ccaggtgggg tgatgtcggt cagcaacttc tgaggttttc ccagttctgg   8520
cgaggatgag cctggtagac tgcttggtcg tccaagttct tgtgcaagac ctaaggatgc   8580
tttcctcttt gagtattaaa ctgagttagt actgccatgc cagctcagtc ccggcacctt   8640
cccttgcagt ggggttgtg ggtattatgt gtttagcgct tgtgcaagtc tgtcaaaact   8700
cctggtatca atgcatttaa tcagaggatt aattacaaca atactgttga agtggaggac   8760
gtgggcctca acgtgaccag caaatgaagg gcttaattat acagaatcag ccacacatct   8820
ggcctcattt tgactgtgct cttacctcaa atcagtagag aaatataatt tcttgctgct   8880
cttagggaag agtcctgtaa tttgcaggaa gtcctaagaa acttaaagag gcagtaaata   8940
aggtataact ttcgctaata aaatagtaac aacagcaatg aatttggacc tgtggccact   9000
aacaggagag ggctgggtat gtgccctggc ttgcccggtt ttgcttgctt ttctgagcat   9060
tttcccacag ttatcagtga acgaaatgga atcctactct gctttgagta tgaaacatat   9120
ttcggctgaa ttcaaggca gggtctatca caagatattt ttatattcag agatgacctg   9180
ctgtgtcact ctgagagcgc taagctggcc ttgagttatg aatgaaactc ccttttaccc   9240
tccctttttc tcttttttcct ttatcttata ggtgctttct cttctcttgg cagcagtgtg   9300
cttctggtgg cacagcacgg tattatttaa tctatacacg cttctatttc ctatggcttg   9360
```

```
gtttctgaca cagcaaagca gggattcata acctagttca tgttccttgt ctacccacc   9420
tgccttgagt acatttcttc agtgccaaga tagcagaagc ttcatttaaa cgctggtgtt   9480
ttgtgagact gaccttactg taaattacga aggaaaattt tagaaaagga gggaatttgc   9540
taatagctta ggtttggctg ggggtgggga ggtggaattc tgagataagc ttggaagata   9600
aaaggtgcct tcagtttaac agctggcatc ttgccagtat ccagggaatt tgtttagtta   9660
gtagactctg attattcttg gaatgttaga tcttattaac agataagttc atcaataaat   9720
ataacccatg ggtgtgcggt tgtttctccc tttgtacttt cttccctggg atctgccccc   9780
aactccaccg cccaagtgag gttgacttct ttgtcttgca gagtcacttt gcatctaccc   9840
cctcctgttt cctagagtta cccgatactt gtgggagcca ggatggtctc acatagacag   9900
agttttcaaa ggggttctaa aaaggaaaag ggggcctccc tagagactgc ctcaccaggg   9960
cccaaagtgt aaccttagca ataccccctc ggtacaaata cctggttagg ttagcttaga  10020
ataaattctt tgtgtgtgtg tgtgtgtgtg tgtgtgtgtg tgtgtgtgtt tcctcatgca  10080
ctagggtcag ggtctggaaa gttttgggaa actatatgct aaatactctc atatcatata  10140
gtgaggtggc atttcctgat ctcaactttg agctgcctgc atgcatgttg actccagtgc  10200
gtccctgcca ggtgaaagga gtcatttgtc aacctgggaa gagtgctgac aaaggaaggg  10260
gagttggttt ggatttaaac atccaggaac tcaatgcaac aaccaacaga attttattt   10320
tggcattatg gttttgtttg gtggggtatt ctgggaggcc aagaatgtac gagattttgg  10380
aaagtcgacc ctgtttctga attgctaaat tgtttgtttg tcttgcagag gtcctatacg  10440
ttgcttgtgg aggcgtggga ttccagtaat gacaccgttc gtaagtatcg cttctgtgga  10500
cttttctcta aacacacgtg gaagtgtggg gcttggccaa ccagttggag ctggatctgt  10560
ctccttagta cttagcattt ctgccacctc ttgccttctg ttctccctg taccccaggg  10620
tgaaccttca gtggaatgta ttccttaact tttctaggat ttttgcttgg aatattaagt  10680
ggccagaaca gaatcccagt taactcattc cctgattatg aaacctagat tatcttcggg  10740
atagagatct taatggtttt acaactttaa aaccttgtag tctgctaaag gatcaaagta  10800
gtgactttt aaaagtccat ttaaactta agtgagtgtt taatctctca tcagaaagat  10860
aaagccataa aggtggtgct gggctctaga gaccgacctt gaatttcact tggtgggcag  10920
gtgagcttct agtctctccg ggtttcccac actgctccac aaacctttca ttgaagcgca  10980
attccagagc ttcacagcca ttacctgcct tgtcccttc tgaaagatgg ctctgttttc  11040
agtgcaggtt gcctttcagg actgaggggt tggttttggt ggataagcca tggaggatgt  11100
gattgaaatg acatagtctg gcttacaaag tagtcttgct cttaattgt aactttacag  11160
tgttttcgct cacgagccga aacttcaagt tccctttttg ccagcagagt ttgggttgcg  11220
gtcgctggaa aacttgatgc tcactgaaat ctcttggtct gtgcatgagg aagagtggat  11280
ccagcttctt gtcttggctc tctgttctct gaatgccttg acttttttgc ttttctatct  11340
taccatttt ttttgtttgc tttcactgtg aataatatat tttcatcttt ccttgccttg  11400
ctttttttg ctgacagaaa atggtgaatg cacaccgtgg gtgcagtgag gcttggtgc  11460
ctgctacgtg ggcagcttcc acctgtggct ggcttattgg gctacttgga gccacagaat  11520
cattgctgag ctccgatgtg ccagagagtc ccaggccatt tgggtcactc ttctagcttg  11580
ggaatcttaa gtccagcttt ttggatgtca tcctccctgg agggggagct catgaaagtc  11640
caaggttcga gtcttcctcc ccagagggct accctgtaat gccgtggggg ggtgtgtgtg  11700
ggggtggcag ggaagctctg tcagccttgg ctatggctga tgccagtcag ggtcatagac  11760
```

```
acctgtttgt tctccctcc ctgccacaaa cgttgaggac tgtgaacatt atgtcactgt    11820
gacctgctta caatggtaac taagcgttag gcagaagggg ttgaggaggg gggagacata    11880
ggctcttctg taatagtatg gtgtcgacat ggtgttcttt cccctccctt ttagctattg    11940
aaacaatcca cccggtagag tgaacagctt gaggttgatc ctggcctgtg ataagagcca    12000
ggtcagtata cttgttaggg acatgtgaga gacctccccg ccacactgca gcattcacag    12060
cacctttcct ggacctcctg tcacctcgca ggtcagggag ttatgtcccc tgggaaccca    12120
gggcttgtcc agagctaccc acagttgtct gcatttccag gtagcccgat tttgggggttc    12180
taggatgttt catctcctgg ggggtaatc aaatccctgg aagaggacaa gaaagactga    12240
ggtaggaata aagttctttt aaacctcaag ggtgcccatt gcaggttatc aaaactcact    12300
tggtgaaccc tgaagaggga gatgggtttg gtggaaatgg tttctccact tgcctatttg    12360
gcctctttta tgatgcttcc aaggaatctt gaattcagca cagtcaaaac caaactcagg    12420
atcttctctt gccaaaagca gtcccttccc agggccccctt ctgggtgtct ggcaccgata    12480
tttgaacact cattgccata agccagaaat atagaaggcg atctgtgtac cccctctctg    12540
ttagcatcca tacctagtcc acctccaagt tctgaaaaat ctctccagct cttcacttga    12600
atctgcctgc cttctgccac tgccctggtc caagtcacca tctgctcatg actgaactta    12660
gagtagcctt cgtctggtcc acctttatct gctctgactc acctctagtg ctttctccat    12720
tcttctgcca tcctggtctt ttcagagcca taacatttgc ttgtcaccct tattatgaaa    12780
aaccaaccac ttggtggcct tctgttgctc ttgggacaga tcttcatgtg gcccacaagg    12840
ctctgtgcag cccagctttg tctccctgcc agccttgtct tacacaccgt gttgtccatc    12900
gtatctgtag cctggccata ccctagcagt tgccttccta tcctcaacta catcacatgc    12960
tttctggcct caggaccttt gcacatgctg tttatgctac ttggagtgtt ttgttccttt    13020
cttcaccctc agccactccc tctggactgc actccacagg gcagaagctg aggatgttca    13080
gaagcccaaa cggagttggc tgccctgtgg gacccaagcg agttgtaaac attctggctt    13140
cagatgtaaa tcaaaggcag agccctgagt tttagggcag agaattcctt ctatcagctc    13200
tgcagtgagc cctcacaggc agactcgggc ccaaatatag cctaggtgct gtttatgtat    13260
ttgaaagtat ttaaggctgg tccttctgtc atcggtcctc caaagtcttt tattacattt    13320
tgggactgtg gtatatagag ttccaaattt cttttctcccc tagagcaaat ggtttcagtt    13380
tactgtaatg cataataaac atgtaaacat aaataggcac acttcagacc aggttttccc    13440
tgtagcttag cttttctcggc taaggccccc ttccaggttt ttgggtcggt gtggtcccag    13500
gttatgctca gactcgccct tcatcacctc tccttggcc tgcgaggcgg tcatggcttc    13560
ttcgtgactc atcttcgtgg cactggggat tgcagggagg catggtgatg tccttttcca    13620
gtcacaaggc tggactgcca aacgaactgc cacagattcc tttccagtgc cccaagctga    13680
aggaaagcgt gatcaggaag caggcagcag acgtatttga acccagacat gctcgacccc    13740
ctccctgagc aggtgtgaaa ttatgtatgc agctccatag ctccactgag gattctgaag    13800
tgatcctctg cacgacactt cccggaaata agtggaaagc ttactgcatg actgaaaagt    13860
acatatcagt cctgcacccc taggattgcc ctggactctt gtctaaactg tttgttgttg    13920
ataccagcct cagaagctgg atgcctttaa gccatggcta gtgtgtttaa ccgatcccctt    13980
ttatgaagat cttgtaagcg cgtggtaata gcccactatg cttttttaact gaaccagcag    14040
agcaaacata gttaatggag agacattttt gtcattcctg ggcctctgtt tatttgcaaa    14100
```

```
aacgagtaaa gtgttacctg cctgcaagtg gttcagtgcg tgccggggtg tcaggctgca    14160
ggtatgtgag cttgttcaag gcttgtcttg cccacgcagc agtttgagag ccctagaggg    14220
cgaacgctgg ggccctgttg gaagcggtgt gtggatgaag ccacccagga gtcccttctc    14280
tcctggtcac ttatagggct tgcatcactt tttaaaggag cactgcccg  aggcctagaa    14340 aaacagccat gtgggtgggt aagaatcaca aagacattgc aagtcagtcc taactgtctc    14400
tccaagatgg tcttgaattt gacaaggtga tgaagagttg gtgctggcag gtttaagaaa    14460
acaaacacaa aaccaggttg gggtgctgat ttagtgcctt gctgcctttt cagatccctc    14520
ccctgaactg ctggcacctg atgtttgagc tattttgta  cctgtctctt ctcaaactag    14580
atgataagtg gcctcagggc agggactaca tactcctgag agctgcttga gctcgaggtg    14640
tttattatcc tcagtaagca ttttttttca ggagcatgac ttggctcaaa aaacaaaaa     14700 gaaaaagaa  accctcccct caatttacct gtgtctaaac tttggtgaat tattctccca    14760
tctgccttct gggcagagga gaaaggtgga atgcatcaag ttcaaggtct tggtatttaa    14820
gagctggctt taaaggttgc catgttaaca attgtaaaaa aaaaaaaaa  aaaaaaaaa     14880 aaagtaactt aatcgtctcc ttggcttcca gttaagagtt ttgaaatgga caaaaagctt    14940
ttctgagcaa gacataaaac cctaaaacca gaaatgattg ctgacccttta tctggaataa   15000 tgaaatttct tcaagagcaa cattccatag ggagctactg tctctcatat gtaaagagca    15060
cttgcaagtc agtatggcaa tgtaatagaa aagttggcag agaagagaag ctgttgctgt    15120
tcacaggaac aaatataaat ggttttgtaa ctaccagaaa gggctcttgc catcacttag    15180
ttaaatgcta attaaatgag atacctcttt acctatcagg catagattag aaggtttgat    15240
aatgtacaac gttggcagtg ttattgggaa acacagcttc ctgggtggtg ggaggacaga    15300
ctggtagttt gagactgtgg acagaggttg atttgttgtg cacggactct gattcagcac    15360
ttccatttct agagtatctc attgtgggaa ccatacacag gcagatacgt tcaaggaatg    15420
ctcactgtgg ctttgtttaa tagtaagaag cccaaacgac tcacatgcac acatgtcagg    15480
gactaggtaa attatttatt ggtgtttcca gacaatgaaa tactgtgtac ccattaaaga    15540
aggtaaacaa gtggtaacag gttgtctctg ggtaggggca taaacttttc atttctttgc    15600 ctttttttaca acagatagaa ttttgtagca ggtgcatatg ttttttatttt aaaaagccaa   15660 aatggtcagg gaagaaggct gcaatgtgaa tattaacatg attcatcact tgtctctag     15720 aacctgacag tattattgaa aaggcttctc actcgggcat gatcaaccc  agccggcagt    15780 ggcagacgct gaagcagaac acgggcgttg cccactttga gtatcagatc cgcgtgacct    15840
gtgatgacta ctactatggc tttggctgca ataagttctg ccgccccaga gatgacttct    15900
ttggacacta tgcctgtgac cagaatggca acaaacttg  catggaaggc tggatgggcc    15960
ccgaatgtaa cagaggtatg tgtgtgtgtg tgcatgtgca cgtgtgcctg ttgcttttag    16020
tgtccattta tcaccccacc agcaggcagg tggcatgcgg ctatctcagg tggggtggga    16080
ttttggctgt tattctgggc ctgcagtatg aagatgcgga gtgtagaaga tgctgttggt    16140
gccccatcca gatcccctttt actggcatcc ccatccccca ggtgctgtgt tggctgccaa   16200
cagctcacag ctgctccttc tcaggagact cgtccttggc caaaccagtg catgccccat    16260
tcctccagct cacagtcagt gattgacaga catagggcta caaagcccag cttcctttgc    16320
cttaaaacag tagtacaatt tgcactctag agcttaccct gggattaggc tgaaatcaga    16380
ctccagttga gaccatgttc ttgctcagct ctttcccctta ccccatctgc ttccctcaat   16440
tccttctacc tatgtccaga tccccttctc agactctgct tctaaggaac ttgacccaaa    16500
```

-continued

```
atagatccag acaggactag gtcagcccag ttgttgtctg aacaggctat cctataggaa    16560
atgatagccc ctgcattcag ggtagccttg cagcaagttt tcactaggtg tctttggggg    16620
catggctttg atggggagag gtatgtggtt agctcaagct ttcctattgg tgtaggagtg    16680
ggcccacttt tagtctctgt gctgtctact gtcccagtcc ctttatagaa ttcagtgatt    16740
ccaattcata gcaacttgat gggtaattct gttaactgta taatatcccc tcatgagcaa    16800
taatgtactc tgcttatttt acatgataat taggtaaatt gttttgatag actcaatttc    16860
aaagtgagtt tttcaaccat gagagagggg tgggtcatgg gggaaggaat ttacagctct    16920
cccgggtagt actactgctt tcttaaataa ttggagagaa gagtttaaaa aggatggcat    16980
ttctggaatt caaatgaaaa ggggaattca ttaacatatt ttagtgtgtt ttaaaaatta    17040
aacgacctaa cacttagtgt gggttttttg tttggtgttt ttttttttttt ttaagataag    17100
gtgctcactt tgtcacccat gatggcacaa tcatggctca ctggagcctt gaactcctgg    17160
gttcaagtga tcctcctgcc tcagcctccc aagtagctgg gactataggc acatgccacc    17220
acacccagct tttttatttt gtgtagacat agtcttgcta tgttgttgag ctggtctcg    17280
aactcctggc ctcaagctat ccttctgcct caatctccca aagtgttggg attataggca    17340
tgggccactg ttgcctggtc ttagaaactg acattttta gaagttactt ttttcttttt    17400
tttaaacgaa gtagagaatt gctctgcaag gatactttat aaaagtctca ccagatctgg    17460
ccaccagatt agcctgccca atgagtccag cctggctggc tctgttagtc ccatggaatt    17520
ttcaaaccag gcatttggta tgggttgttt tttttttttt tttttttttt aaaggctgag    17580
gctcatctga atgtgtcctg gtgggatggg aaggattat ctataccttt ttttcttcta    17640
atgaaagg tgtgggcaga atggaaactg accaagctct gctcaaggag ccagggtagc    17700
tgtggtttag agaggctgga cgaaggtccc ccttccctcg tcaacttgtc tgcattttgt    17760
cccccaaacaa tatcatgttt tcagaatctg ctaacaaggc cttgaagttt aaagctggtt    17820
ttgttatttg ggcccctccc atcttcctct ccttacaagg gacttgatat gagacctgtt    17880
aaaatcgtgg aatttgcaga ctttaatgca atgggccatt tcatgaccg gggcgatgca    17940
aggaacaggc agtgtgctga cacgcccttc tctgtttttt acagctattt gccgacaagg    18000
ctgcagtcct aagcatgggt cttgcaaact cccaggtgac tgcaggtaaa tcaactggtc    18060
ttttgtgaga tttcttttaa ttttccttta tgtaagagag gaactgactt tattgtgact    18120
atgcctcttt tttccttgga gaacaagaaa gcttttttaa aaaaaaaatt cagatagaca    18180
catccgaagc ttattaaatt ataccagctg tctggtggaa tgcacacacc acttctctct    18240
tggaataaaa agaaactctt tgggcatagc cagtgacttc atgtattaac tgttctgtaa    18300
attgataaca cattttata atcttccctt atagtgctga tgggctagat ggagggatgt    18360
gggcttgttt ctttgcgtct ctctcctctt ccaccaaggc tttcttctcc cagcccctc    18420
cccgactttt cccatcaata ggcgaaagtc cagcattctt tagaatggga ttagtccaat    18480
ctcctggccc ctttgcaggc gggagctggg ttggtgctga gaggttaatg gctgccctgg    18540
aatcttgtca gttgagcctg atgaatgtag acttttgctg cagtcctttg aagtctgttc    18600
ctttatggtc caggaacaat gcggaagcca aaggaggcc tgccctgacc acttcacgat    18660
ggcgggtttt ggaacttctt gaaatttata ttacgcccgt ttggaaaagg cttatttttgg    18720
gaaatattgt tggtgtctgt ggtgtttttt gcagtcttaa tgctttgctc tccctcctcc    18780
caaattttaa ggagtaacgc taaatggatc ctttgagcct gtcactttg cccccaaagc    18840
```

```
tactctgaca tgagtaaagg gaatcttatg aaacatagtc taaaccagta tgtcccaaac    18900
taatgttatt tggggctctt attaaaacgc aggtcctgat tctataggtc tgggctgagc    18960
ccaggtttct gcatttctaa caagctccca agcgatgctg ctgatggaac catcagcaat    19020
cactgccccc agacctcagt actcaaagtg taacttccag aattaacaag ggagctgtta    19080
aaatgcaggt tcgtgggctc cgtcccacat ccatagaatc ctagtccttg gtttggccca    19140
ggagtctgca tttgacaagc tggccacatg actttgctgc ttagtaaatt ttgaggctac    19200
tcctttaaag agaactatct gtggcccttta cctttatgat ccaccgctc cgtctgttcc    19260 cctcccatgc aaggggggaac atggaactaa attaagaact ggttgtcccg aattgtctct    19320
tcctacactt cagaaagata gtttatttcc tggaaggctg aggggcttct cctgctgtct    19380
cccattggtg gcgatggact gtagtattta acagcattgc tgtccaatgc ggagcaggaa    19440
tccacctacc ttaactcttc ctaattaagg gtgttctgga gaaagtccca atggcagtgc    19500
tattagtgat tccaagcctg ctgcctgctc agatggatat cagcggaggc cgactgtgat    19560
ttgtgctgct gtcatcagaa cacacataca gctatacagg ggagggccct cccagccaga    19620
acaacaggct ttgtttccag aatttagccc tttctctttc gaagtcccac ctccctctcc    19680
ctgcccagac acgcactgat ggccttattt acttaaggtg cgactttccc acacatcatt    19740
tgcatagtct cccagcccag ttttccctcc ctaccttgaa agaaagtcaa aacagaacct    19800
tcacgctgag gaagttcagg ttgtgtcctg ctgcagaaat agttgaatgg caagttacct    19860
gcaagttgtc ttttggatta tgtattcac aggttatttt ttttttcacc cccacatgag    19920
aaaatttact ggttttttgtt gttcccaagt agactgagtc cctttccctg ggtatacatg    19980
cttgcttatt gcaagcctgc caataatatc aaacttaatt atgaatcatc atctgaggaa    20040
agtcacttca atttctcatg agaatcttaa tcatatatta ttaaactggg ataacttggt    20100
tggtgcctct tttagggtca gtattttttat ttgttttctt ttgaagtcat ccatggcctc    20160
ttgtggttgc ttttttatgc ttggggattg aggtctcttt aattaggtga ggttgggtcc    20220
tcagctgcct ctccttgcct ttatgaggca acttgaagag ggctagtgat cctgaatttg    20280
gaagagaata agggaagacg gtgagaatat tgccatttcg taatcagttc cctcttacta    20340
tctttcaggc taagaatatc agccttgaca gaatggctac accccttacct cccactaacg    20400 tgggtgtccg cttttgagaa attatttaga ttgtaatttt gttcttatct tactcctta    20460 gtcacttgtc acgttgacat tccattttac ataaaccaga atccagtgtc taactttaaa    20520
ccacacattc tagtgatttc tttgcatgtg ggtgtgcata gcttggtttc agaagttagg    20580
aagtggttag tcagtattct caggggttaa gttgactctc agccgtgggt gattagctat    20640
tagctagatc cctataattt tcccatgaca aggatttgct agcctgcctc ccgctcttgg    20700
gaaaccgaaa gccttttcctt ctggggagct agaggggggcg ggggttgttt tccagagtta    20760
cagctgagca gcttaggggg ttggcgctga tcgtggctttt tcccaggtcc cgttctggaa    20820
acatgttgcc catcccaccc gcaccccacc ctccacccctc caccctccac gctccaccgg    20880
gaggctagtt gatgtttctc cctgccttcc cccacccttg ttaaagcttg gctcttgaga    20940
aggcaattaa agtttcagag ggcttgaaaa ttcaagggag agtggtttga gacgctgccc    21000
cctctcccac cccagatgaa agttgttgta tttgttttttg tttttgcttg gggatcagag    21060
gcactatttg gccccaaaag agtatgatta atcaaggtgc ttatataaaa gaacctcaac    21120
tccgccaata ctagataaat taagcagact gcttttcttt tttttttcttt tcttggcaaa    21180 gcaagaaatc actataaatt agcacacagt aatgggacac aaattatgga gttggttcca    21240
```

```
agtgttgtca tttccttctc cttccctata gaagtgggtt tagagagcct actctggctt   21300
tggccaaggg agggtgcccc tttctctcct tgttttttta aataaagcgt catcgtgagg   21360
cagtttcctg ctgcacttgg tggcttgttg catttctgtg cactgggtc atgactttct    21420
gtgcagacaa agagcagagt ggcaagtgca gcgtctgcag agactttggc atagctctct   21480
tgtcaccgag agagtccttt cctctatagt ctgtcgcaac taggtgcacg ggttgattta   21540
ttccatgcct tcacctttgg ctcactcgtg tgagcctgag aagagagtgg ctttgtgaag   21600
ggcatcccca tgctggcctc ttcccaaaca gccctccttt tgtcaggagt cggctgggag   21660
gggacctcag ctcaactgtg aaaatgtttg tttatacgga gccctgatg agccttggga    21720
gtctaccttc ctgtccccag aaacaaaaca gaaaaagcct ggactttgca gtcttccatt   21780
tgaattgtac aggtgtctct taacgttcaa aaggctaacc tggaggtgtg ctgtgtgtct   21840
ccaggtgcca gtacggctgg caaggcctgt actgtgataa gtgcatccca cacccgggat   21900
gcgtccacgg catctgtaat gagccctggc agtgcctctg tgagaccaac tggggcggcc   21960
agctctgtga caaaggtatg gcccttaggg atgagaccca gggtgggatc tgggggtggg   22020
atggcactaa tttggtttct aattttattg gcaggggctt ttattctgaa ttctccttga   22080
atgctgtgtg ggttttctgg tttttctttt taaaagacga ctgggggctag aaacatggtg   22140
ggttcgccat cttcacaggc gtctcttagt gactccagga tcttttggc agatctcaat    22200
tactgtggga ctcatcagcc gtgtctcaac ggggaactt gtagcaacac aggccctgac    22260
aaatatcagt gttcctgccc tgaggggtat tcaggaccca actgtgaaat tggtaagtgg   22320
tccaagatga atgagagccc tttgtctaat ttttctgtac tcagctttta aaaatatac    22380
ttaaggactt gtttaaggaa aaaaagtga aaatagcttc caaagatagg ccttatccca    22440
accattctat aagcctttgt aactttcaag tctctaaagt tttttgggtg atgctgattc   22500
gtataggagg cagcgggaga tgaaatgacc ccagctctga gatgtcttgg aatgtggtta   22560
gagacagctc agcgagaaag atgacttcct ttctttccta gacacagcag ggttctatca   22620
cacgcttgct tttggttttt gaaatatgct tgcactagtg gctgtggtgt gggattcggt   22680
tggaggggg tgtgggagg taacggtgtg caggcatccc tctctgactg ccatcctggt     22740
ttttgcagct gagcacgcct gcctctctga tccctgtcac aacagaggca gctgtaagga   22800
gacctccctg ggctttgagt gtgagtgttc cccaggctgg accggcccca catgctctac   22860
aagtaagtcc aattttcagc ctgtgtccat tctaaggatc cttgtgccaa gataccacgc   22920
tggggagagg tacctaggct tgtccagtgt gaatgtctcg gtgagagagg ggcgggtgca   22980
ggcctaagtc tggtaagcag tctggtggct tgtgtgtttg gaagtctccc agcaccccca   23040
tcctgtccca ctaaggtagc gcatgtatct gttcttggaa ggaacgtcct cgtggaatcg   23100
cttgttcctt tgcatctgct tcctggagct ggccaccttc caattgtggt tattcttctt   23160
gcagccatgg agaggctgcc ttcaggggag gttgtcactt actactggat tctgtcatag   23220
ggccaggggg cccagagaa gaacctggcc tgcagagttc ctttggctgt gagacagggc    23280
tgtatatcag aatcacctgg gctgctttac agtgtaaatc tctgggtccc ccagattccc   23340
tccagaatcg gggagtccat ggtctttgat aaacttctgg aattctgcag tgcagccagg   23400
tctgagaacc gctgtcatca gcaccccagg tgtggttatg gatgtggatt tctggggtca   23460
gattgcctgt gctggtccta ggcccccacc tgtcacttgc ggaactccag caggccacag   23520
aagctccccg ggccctcttt aaatggcaca gtagcaattc ccatctccga ggttgtcata   23580
```

```
aagacacaaa agtgaatact tcataaattg ttaggagttg tctctggtca gagcagaagt    23640
ggagaatgca gcctctaggt gtgctatttt gggcaaactc tgtaagcaaa tgagaggaat    23700
aaggttttcc acctgtaaag aactattttt cctgacttct tagctacttc tgagccatga    23760
tgaaactttt ctttaaaaat aaagattagg cagatagaga tgtcctgtgt tcctcctggg    23820
cggatgctcc gtcagtatcc agctgtcttt ctcccccact gcttaggttg gggattacat    23880
gaactggggc agtgggggat ttaaagctaa atcaaggct tcggccttat cgtcaccgtc    23940
ccacttgtcc tgctgtagct ttccttgtag caggtgtctg gctcttcaat gacagcccct    24000
catgtaagag gtgatgttaa aggatctaat tgtcagatgg attgaattaa attgtcaacc    24060
ccctcctttt cttgttgacc agacattgat gactgttctc ctaataactg ttcccacggg    24120
ggcacctgcc aggacctggt taacggattt aagtgtgtgt gccccccaca gtggactggg    24180
aaaacgtgcc agttaggtaa gaacatccct gtgactgtaa tttttatacc aaggttggct    24240
ttgattgtca aagccattac agaagacgag cgtgtggccg gcagtgtgag ttcacactcc    24300
atcatgctaa gaagtaattt attatcaaga gtctagcagg cctgggagaa ataacttgaa    24360
tgcaaatgga ctagctcttt taggccctgt gggaaagtcg tgggattcct tgaaccatgt    24420
caatcgtctg tccgaggagt gttcagctgg gttccaaaag gggatgatct catgaggaat    24480
gagctgtctg cattcttttt gccacattta aatcccagca actaggctgc ctgggttttg    24540
cacagaaatg cctggtggct ttctgctgtt ttgttggggg ctggttaact agcagctgga    24600
aagttatcaa ttagggttct tattggataa tagctaggga gagggatcag atgcttaaaa    24660
tagagggaac ctctagtatc ttttatttag ctagcttatt aaaatgtctc atgtctcaga    24720
caaactctgg cctgttcttt ttttttccaa ggtgggggag atgggggttg aacttcattt    24780
ctcatgctca tccccatctc ctttcagatg caaatgaatg tgaggccaaa ccttgtgtaa    24840
acgccaaatc ctgtaagaat ctcattgcca gctactactg cgactgtctt cccggctgga    24900
tgggtcagaa ttgtgacata agtgagtgac tttgtttcca ttttgatttt catgaaactt    24960
gggtagccga cttgctggtc cgtactgggg ctccagtcct aggacttgag cagtagaagg    25020
aaaaccttag agtgggaatg gttttttgag agggagtggt cagggcagca gtgaaaacat    25080
acactttatc aggctcatta gctgcgaaaa ccagccatat tctgataatg tggctgaaac    25140
aatgatgtga agtttcactc cctcattctg gaagaattag ggagggtccc cacccagcgt    25200
aataacctta tctcacggaa agcacacagg aaatctgatt tgaaacttat ctatcctgag    25260
ctgagaaggc ttttcaatta agcccaattt cactgtaaat tacctctttta aaatgatgac    25320 ttatttattt tttagatatt aatgactgcc ttggccagtg tcagaatgac gcctcctgtc    25380
gggtatgtaa atctttgctt aaatcaaaac tttgacaatt gacaacaaat ctttagattt    25440
gtgcgacact aggagagctc tgtccctgtg agatttaaaa atttgggtga aaaagagtc    25500 tcttggaagt ttcgctaggg cttatgttac cccagcctcg tgggagtcat tttgaaggca    25560
tgcacataga aattcctcta accactttca gaggtttagc atttggctat tcagtgaac    25620 cagctaaacc gcaacagtca tgctaaaccg ctgaagccct gtgtttgtgg aatacataga    25680 aaaaagcat gtgtctctct ctccccttct cctcttctag gatttggtta atggttatcg    25740
ctgtatctgt ccacctggct atgcaggcga tcactgtgag agagacatcg atgaatgtgc    25800
cagcaacccc tgtttgaatg ggggtcactg tcagaatgaa atcaacagat tccagtgtct    25860
gtgtcccact ggtttctctg gaaacctctg tcaggtgagt ggtggcaaaa cctcagatgg    25920
ccaagttttt agagcagagc cgctgcctcc tccgcttccc tttactttc cctcagctct    25980
```

-continued

```
tgtgtctgga atttcctaac atctattaac atcctattga tgagagagtc tctgctagac    26040
aaatgctggt ggaaggagat actgacgaat tattttcttc ttagtgtctt cgtctttgtg    26100
ttcttttttgg ttccctccac cccctcttgt gctccctctc ccactctgcc ccgttgtttc   26160
aaatactgga cattggcagt ccctacagca tagagatgta tcttacaggg tgtctcctaa    26220
tagaaaccga aggaactgtc agattccagt gcctgctgcc ccagagaagt tatcgtgaca    26280
cctttgtttt actctgatcc ctcccccttt tcgctgttcc tgatatttgc agctggacat    26340
cgattattgt gagcctaatc cctgccagaa cggtgcccag tgctacaacc gtgccagtga    26400
ctatttctgc aagtgccccg aggactatga gggcaagaac tgctcacacc tgaaagacca    26460
ctgccgcacg acccccttgtg aaggtacctc ccttctcccg ggacctggct gtctccagac   26520
ttgctccttt tgtccccact tactaccact gccccttgtt acacttgaga agtaatgtat    26580
tggtgaggag gacctctata gtgaaatgat cctgcctgtg tagcgggccg caacacgtgg    26640
aaacaatcta ttccggcctg ccagtgggag agccgtgtct acaagtagcc caggggagag    26700
aatgtgaaat ccatttagca ttcctgttct ggggtgggct gatgtgcaac gctgaggcaa    26760
atgcctgaga acaacactgt caacagaact tcctgcaacg gcagacagag ggggatgttc    26820
tgtatctgca cggtcaggta tgggagcccc aggccatgtg gactgtgact agtgtaacta    26880
gaaactgatt ttatttcatt ttagttcatt taaatgtaaa tagccacatg tggccggtgg    26940
ctgctgtatt aggcagcaca acatttaaag cttctataag attgtccttg agccttgctt    27000
aagatcaaaa aggaagtaaa taaagcaggt ccttttgcct tagcaagtgt ttaccaaatt    27060
gggtagatgt caaaggtagg atgaaggggga tccacaagca tgtgggtttt cctggttgtg    27120
tggagggaga aaatgcttta aaactctttg cctggagtct caacttttgcc tgtcataatg   27180
tgatgtggca cgttgccagt atcttggctt ccctggggtg tgtctcatta gccagagggt    27240
ccctgtctcc aggaaagtgg gcttggccca ggcccttggc ttaggaatgc cgcatctgtg    27300
ggtgcatggc tgtgatctga tcccaagcct atcttctagt gattgacagc tgcacagtgg    27360
ccatggcttc caacgacaca cctgaagggg tgcggtatat ttcctccaac gtctgtggtc    27420
ctcacgggaa gtgcaagagt cagtcgggag gcaaattcac ctgtgactgt aacaaaggct    27480
tcacgggaac atactgccat gaaagtaaga ctccctcatc cgggaatgga ccagtgctcc    27540
ccagcctgcc cctgccctg cctctgcccc tggcccaccc tgggatcatt ggtgttgaaa     27600
gttttttttt tttttttgag accgaatttc gctgttgttg cccaggctag agtgcagtgg    27660
cacgatctcg gctcaccaca acctcggcct cccaggttca agcgattctc ctgcctgcct    27720
cagccttcct gagtagctgg gattacaggc atgcgcacca cgcccaccac gcccagctaa    27780
ttttgtatttt ttagtagaga tggggtttcc ccatgttggt caggctggtc tcgaactccc   27840
agcctcagat gatccacccc ccgaccccca acttggcctc ccaaagtgct gggattacag    27900
gtgtgagcca ccatgcccag cagtgttgaa attgttttaa tcagaaacag taaggctggg    27960
gagactggtt gagacttatc cttacatctg ggatctaaga ctgaggtcgt gttcaattta    28020
ccagatcact ctgcctcgga gcctccatat ctatgttgga acattctgga atgttgctag    28080
gttgggtgat tcctctttttc tgtaggagtt tcttccccac tttcacctag taccggtgac   28140
taaatgccca tgtgagggca ttaagtgggt aaggcactct ctggaagctt ctgcttgata    28200
agccgcctgt ctaatttgag aaacagccct gatggagggt agcaggtgga ggtgccaggt    28260
gcattgtgtc aggagggagc catgaaaact gctgaacagt gcttgtctat ggcttcacaa    28320
```

```
gtccttcagt tcttttttg ctttactttg tttcatagat attaatgact gtgagagcaa    28380
cccttgtaga aacggtggca cttgcatcga tggtgtcaac tcctacaagt gcatctgtag    28440
tgacggctgg gaggggcct actgtgaaac cagtgagtct gccactcttt ggggagctct     28500
gggatgtatg ggtcatgttg gagggatccc acttcaacgt gggaaaactt tctttgtact    28560
ggaaatctct ggaagcaaga ccgcagtgat ttctgcactg gacagtatc acttgtgtct     28620
catttgcatt tatgagtcct gatgatagct tatggggagg agcttctgct gaggacctat    28680
agaattagac tgtgtaataa atattcctgc ttgcaaggaa agtcatattt ctactttcat    28740
ttccatggga cttccagagg cccacccac atcttgccta acttgtggca ttcaaagtaa     28800
cccagttggg agctccttta ttcctggaaa agcctgattg tgttaaagta ctacgactgt    28860
ggctgttctc agaataggat gttggatgta agcagtagga aaggcttggc tctcgcctgt    28920
cgtgaatggt cctggatctc gtcttcagcc gattgtctcc cctttgattc tagatattaa    28980
tgactgcagc cagaacccct gccacaatgg gggcacgtgt cgcgacctgg tcaatgactt    29040
ctactgtgac tgtaaaaatg ggtggaaagg aaagacctgc cactcacgta agtggtagtt    29100
ggccttggat gctatctctg ggacccttcc ctctgtcttc tgtgggaggg ggccactggg    29160
actcacactg aaatattttc ctccaggtga cagtcagtgt gatgaggcca cgtgcaacaa    29220
cggtggcacc tgctatgatg aggggatgc ttttaagtgc atgtgtcctg gcggctggga     29280
aggaacaacc tgtaacatag gtaactttat gccccacgtg ggatctgcag tgggcatggc    29340
cacctgggcg tgtctgctgg ttggcccctg gagcttatga tatttctctg ggcctggttc    29400
ttgcccctcc agactgtttc tggatactca gggagggtgg tcgtgtctgc tcttctttta    29460
tagcccgaaa cagtagctgc ctgcccaacc cctgccataa tgggggcaca tgtgtggtca    29520
acggcgagtc ctttacgtgc gtctgcaagg aaggctggga ggggcccatc tgtgctcaga    29580
gtgagtgtcc tccccccttg aactctccca gggctgtcgg agcagatcct gacacccttg    29640
gggacttgca atggaaacca gaagcagagc tgtttgatgt ctgcttttgt atcacctggg    29700
tctgcattaa tgacttgatg ggatacagcc ctgacctggg catgagaaag tcgccaataa    29760
gataagtgga gacagatggc gtctcagttc ccagctctgg gtctgaccag cagcctgtct    29820
ccttccattc tcaccccac ccctatcccc taccagggcc tcttcctgtg tacatgtgtc      29880
ccacagcaaa tgaaactaag tgtggtgcgg gcctggttcc aatttagcaa aggtattttg    29940
ctggtgttaa ctacgacttt atcatttggg tattaggaaa ataagtggtg gttttactta    30000
gggctaagac cgctttccct gttgaagtcc tcactattaa gttgtctttt ctttgcagat    30060
accaatgact gcagccctca tccctggtaa gtgtgacatc ctttaagcc agcactcatc      30120
cactatcgtg tgtgtgtgtg tgtgtgtgtg tgtgtgtgtg tgtgtgagaa tcacccaggg    30180
attgtgttta aaatgcaagt tctgagtcag gaggtctggg gtggggcctc agactgcttt    30240
tctaacaagc tcccaggtga agcgatcctg ctgccccatg gaccacactt taattagcca    30300
ggttgtgtcc tcatttagag cagtgatttt tcaaccttgg ctgcacacca gaatcacctg    30360
ggagctttta aaaatcccgc tgcctgggct gcaaccaaga cctgtgaaat tagactttct    30420
gggggtggga cccaggcatc agtattcttt taaaattccc caggcaacgg ccatggggtg    30480
agagccactg actgtaactg gtggtgac atgtgagtga ttggcagcca gagtaatgga      30540
ctgggaggtt ggtaaccaag gtggtctttg cttcttagt tacaacagcg gcacctgtgt      30600
ggatggagac aactggtacc ggtgcgaatg tgccccgggt tttgctgggc ccgactgcag    30660
aataagtaag gactgtctcc gtctggtttt cccaatggct ttaccgcttc attccatgcc    30720
```

```
tcaccccaag actttcatct ttaaaaacaa agccaccatt cccctttaagt agctctcata   30780
gagcaaagga tctctctcct ccagctggga ttaagatatg ccaggctgga tcctcccagg   30840
tacctgctgg tagttccctg ggtggtgtag ccctccttgt tcttggggag agagtgccag   30900
tcacagaatc tgatgattaa tctacagtgg ggtcctgaag aaagtatgtg catttcccca   30960
tgactaacat gaaattatgg gcaagcagat gttaaccaca gctacactgg tataggataa   31020
agctaataca aacggaaggg aggacgactg tggcttccag aggcttgtct gtgctgggtc   31080
tgatcaggcc ctggagaaat gactaaaaca ggaaaatagg ggcaggcaac gcagtttttc   31140
aagaggctta aagcatatta ttttgagcct tttctctact tttttacaag ccctttctct   31200
tacagaacaa aaaaggtgct agagtagtta tggtttgatt cttgtaccca aattgtctga   31260
aattttactg gtgcttgaaa tccaagtctg ggattaacta gtcttcagca ctagatgggg   31320
gcaggttgta tctgtttcat gtttctaaat aaacagttgg caaactgtgg cccaggggcc   31380
gtatccagcc cactgtctgt ttttataaat acagttttct tggcacacag ccacacattc   31440
atttatgtat tgtctatggc tactttcatg ataccacaag agttggatag ttgtgacaga   31500
gactatatac cccacaaagc ctaagatgtt tactgtctga ccccttccag gaaactttgc   31560
caggcttgct gtaaattgca ctgtcaaagg aatcaaatta aaaattgctg cctcccaaaa   31620
tggttctcca ctgttagaac tcaggatggt ggtggtcttt gggagccagt gattggaggt   31680
ttttgcaata gatctgtttc ttcttttgga tgctgcttac ctgagtgaaa attcatcaag   31740
cttatgatga tatgcttttc ttgtatgtta tgtcaataaa acaatctca aaacattgcc   31800
acacaccatc agtccctaaa cttgaactcc atttctccta gacatcaatg aatgccagtc   31860
ttcaccttgt gcctttggag cgacctgtgt ggatgagatc aatggctacc ggtgtgtctg   31920
ccctccaggg cacagtggtg ccaagtgcca ggaaggtatg tgtgccaggc ttcagctgcc   31980
catgggtctt ctggggtgag cgagctttgc agtcaccatt tgacttttca caataagcc    32040
actgtgctca gggaagggaa cacacagtgg gactacaagg gaaagggaac gtgaagagtc   32100
ttccccaaaa caggtagctg ttgttttttgg tcagctgttg ccacaaaact gtgtaccaaa   32160
ccatcccaaa ctgctgtggc ttgcagcaag cattatttt attgctcatg atatgcagca   32220
tgggcagaga gattgcgctg tgggttgggt tcagttcgac cagtggctgt gtctgggca    32280
tattcctttc atcgccagtg ggtaggtgtg caagaggcta gtcaaaggct ctgctcacat   32340
cacatctgcc aatgttacat tggccagagc aagtcttgtg gccaagcgca gagccagcaa   32400
aggcaggaag tacacatgct gttactgtgg gaagaatgat cttaacatgg caaagggcac   32460
aggcataacc atttcataac agggaccaaa gaattgaacc ccgatccggt tcacagaaaa   32520
ataaactgct cacccgtctc cacctgtcag tttcagggag accttgcatc accatgggga   32580
gtgtgatacc agatggggcc aaatgggatg atgactgtaa tacctgccag tgcctgaatg   32640
gacggatcgc ctgctcaaag gtaggacatg atggctgccg cagttcacct gtgttctgga   32700
atcagggatg agcatgcctg ctaagctgcc agcttctgtt tttctccagg tctggtgtgg   32760
ccctcgacct tgcctgctcc acaaagggca cagcgagtgc cccagcgggc agagctgcat   32820
ccccatcctg gacgaccagt gcttcgtcca ccctgcact ggtgtgggcg agtgtcggtc    32880
ttccagtctc cagccggtga agacaaagtg cacctctgac tcctattacc aggataactg   32940
tgcgaacatc acatttacct ttaacaagga gatgatgtca ccagtatgta acaacctttg   33000
ttttttttt gaatggtgga tgtctgcttg cttgctttaa aggaggaatg ccatgagcta   33060
```

```
ggatctactt ctccctagct tacattcctg ttttataata aagtaagctt gaacttagcc   33120
agcctcaaag agaacatctc agccttttgt tcttcctctc aatcttacac gtgtgtgggt   33180
ttttaaaaat cgttttaggg tcttactacg gagcacattt gcagtgaatt gaggaatttg   33240
aatattttga agaatgtttc cgctgaatat tcaatctaca tcgcttgcga gccttcccct   33300
tcagcgaaca atgaaataca tgtggccatt gtaagtataa gacccattca cacctcatta   33360
ttcgatggca aggcagttcg gttaaccagt gtctgaatgg agcaaattca ctgacaaaaa   33420
gctttgcaga cacagattgt cgagtaattt tgaagaaagg ctgctttgag tattcctctg   33480
actctcaagt ctgacaattg ttttttccagt ctgctgaaga tatacgggat gatgggaacc   33540
cgatcaagga aatcactgac aaaataatcg atcttgttag taaacgtgat ggaaacagct   33600
cgctgattgc tgccgttgca gaagtaagag ttcagaggcg gcctctgaag aacagaacag   33660
gtaggtgtca agtgggacta gtttgtgtga tgatagtaga tgatctcatt atactattca   33720
ataaagccat caggtcgagg gattatctgg cagtgcccta ccctcgcagg agctcccaat   33780
ttaactgaga actgagggca gcctacttta ctaaggtcac atggcccatg ggaacagagg   33840
tctgcctcat attttccttc ccaacacact atgcaacgtt ccctgcagaa caggtattgt   33900
gctagatccg tgacaaagcc ctaggacact gcttgtcctt tgtccttgag tttgaagctg   33960
tacaaagcct gacttggcat tttggtgtcc tgggacagcc tagccactgc tgagctctgt   34020
gaggctcgat ggccccgcag gggtgtccag gcttccctcc tgaggatctc gagcaccgtt   34080
tcagccaagg gagagattgg gcatggagcc atggcacgtt tgagctgtct gtgctaatttt  34140
gaatcggatt tctagttctg aaaaccaact cctgtactga gctgcctcag tagccagact   34200
taacaagaca ctgctctccc catgcgaagt caaagagcct gtaggagctg ccgctccacc   34260
cagtctctcc agggataaga gtatcaaggt ctacaggggc ctgatcccag catttgctta   34320
tcaagttgtg aagtgaccat atgcaatgat gaaaagggac ttgtccctgt ggccccctc    34380
ttagggataa agggcaggag aaccactgtt ggtattcttt tgttcctgcg atgatgcttt   34440
tttctttctt tcttggagag ttaattggtt ttgtgcctgc cttacagatt tccttgttcc   34500
cttgctgagc tctgtcttaa ctgtggcttg gatctgttgc ttggtgacgg ccttctactg   34560
gtgcctgcgg aagcggcgga agccgggcag ccacacacac tcagcctctg aggacaacac   34620
caccaacaac gtgcgggagc agctgaacca gatcaaaaac cccattgaga aacatggggc   34680
caacacggtc cccatcaagg attatgagaa caagaactcc aaaatgtcta aaataaggac   34740
acacaattct gaagtagaag aggacgacat ggacaaacac cagcagaaag cccggtttgc   34800
caagcagccg gcgtacacgc tggtagacag agaagagaag cccccaacg gcacgccgac    34860
aaaacaccca aactggacaa acaaacagga caacagagac ttggaaagtg cccagagctt   34920
aaaccgaatg gagtacatcg tatagcagac cgcgggcact gccgccgcta ggtagagtct   34980
gagggcttgt agttctttaa actgtcgtgt catactcgag tctgaggccg ttgctgactt   35040
agaatccctg tgttaattta agttttgaca agctggctta cactggcaat ggtagtttct   35100
gtggttggct gggaaatcga gtgccgcatc tcacagctat gcaaaaagct agtcaacagt   35160
accctggttg tgtgtcccct tgcagccgac acggtctcgg atcaggctcc caggagcctg   35220
cccagccccc tggtctttga gctcccactt ctgccagatg tcctaatggt gatgcagtct   35280
tagatcatag ttttatttat atttattgac tcttgagttg ttttttgtata ttggttttat   35340
gatgacgtac aagtagttct gtattttgaaa gtgcctttgc agctcagaac cacagcaacg   35400
atcacaaatg actttattat ttattttttt taattgtatt tttgttgttg ggggaggga    35460
```

```
gactttgatg tcagcagttg ctggtaaaat gaagaattta agaaaaaaaa tgtcaaaagt    35520
agaactttgt atagttatgt aaataattct tttttattaa tcactgtgta tatttgattt    35580
attaacttaa taatcaagag ccttaaaaca tcattccttt ttatttatat gtatgtgttt    35640
agaattgaag gttttgata gcattgtaag cgtatggctt tattttttg aactcttctc     35700 attacttgtt gcctataagc caaaattaag gtgtttgaaa atagtttatt ttaaaacaat    35760
aggatgggct tctgtgccca gaatactgat ggaattttt tgtacgacgt cagatgttta    35820
aaacaccttc tatagcatca cttaaaacac gttttaagga ctgactgagg cagtttgagg    35880
attagtttag aacaggtttt tttgtttgtt tgtttttgt tttctgctt tagacttgaa     35940 aagagacagg caggtgatct gctgcagagc agtaagggaa caagttgagc tatgacttaa    36000
catagccaaa atgtgagtgg ttgaatatga ttaaaaatat caaattaatt gtgtgaactt    36060
ggaagcacac caatcttact ttgtaaattc tgatttcttt tcaccattcg tacataatac    36120
tgaaccactt gtagatttga ttttttttt taatctactg catttaggga gtattctaat    36180
aagctagttg aatacttgaa ccataaaatg tccagtaaga tcactgttta gatttgccat    36240
agagtacact gcctgcctta agtgaggaaa tcaaagtgct attacgaagt tcaagatcaa    36300
aaaggcttat aaaacagagt aatcttgttg gttcaccatt gagaccgtga agatactttg    36360
tattgtccta ttagtgttat atgaacatac aaatgcatct ttgatgtgtt gttcttggca    36420
ataaattttg aaaagtaata tttattaaat ttttttgtat gaaaacatgg aacagtgtgg    36480
cctcttctga gcttacgtag ttctaccggc tttgccatgt gcttctgcca ccctgctgag    36540
tctgttctgg taatcggggt ataataggct ctgcctgaca gagggatgga ggaagaactg    36600
aaaggctttt caaccacaaa actcatctgg agttctcaaa gacctgggc tgctgtgaag     36660 ctggaactgc gggagcccca tctagggggag ccttgattcc cttgttattc aacagcaagt    36720
gtgaatactg cttgaataaa caccactgga ttaatggcct gtagtgtcga ggtgaattg     36779
```

<210> SEQ ID NO 75
<211> LENGTH: 11232
<212> TYPE: DNA
<213> ORGANISM: Homo sapiens

<400> SEQUENCE: 75

```
ccagttattg gtgccaggtc tgtgccagga gggcgaggcc tgtcatttct agtaatcctc      60
tgggcagtgt gactgtacct cttgcggcaa ctcaaaggga gagggtgact tgtcccgggt    120
cacagagctg aaagggcagg tacaacaggt gacatgccgg gctgtctgag tttatgaggg    180
cccagtcttg tgtctgccgg gcaatgagca aggctccttc ctgtccaagc tccccgcccc    240
tccccagcct actgcctcca cccgaagtct acttcctggg tgggcaggaa ctgggcactg    300
tgcccagggc atgcactgcc tccacgcagc aaccctcaga gtcctgagct gaaccaagaa    360
ggaggagggg gtcgggcctc cgaggaaggc ctagccgctg ctgctgccag gaattccagg    420
ttggaggggc ggcaacctcc tgccagcctt caggccactc tcctgtgcct gccagaagag    480
acagagcttg aggagagctt gaggagagca ggaaaggtgg acattgctg ctgctgctct      540 aacccactct gatctcccag ggcggcgta agtcttcagc atcaggcatt tggggtgac      600 tcagtaaatg gtagatcttg ctaccagtgg aacagccact aaggattctg cagtgagagc    660
agagggccag ctaagtggta ctctcccaga gactgtctga ctcacgccac ccctccacc     720 ttggacacag gacgctgtgg tttctgagcc aggtacaatg actcctttcg gtaagtgcag    780
```

-continued

| | | | | | |
|---|---|---|---|---|---|
| tggaagctgt | acactgccca | ggcaaagcgt | ccgggcagcg | taggcgggcg | actcagatcc | 840 |
| cagccagtgg | acttagcccc | tgtttgctcc | tccgataact | ggggtgacct | tggttaatat | 900 |
| tcaccagcag | cctcccccgt | tgcccctctg | gatccactgc | ttaaatacgg | acgaggacag | 960 |
| ggccctgtct | cctcagcttc | aggcaccacc | actgacctgg | gacagtgaat | cgtaagtatg | 1020 |
| cctttcactg | cgagaggttc | tggagaggct | tctgagctcc | ccatggccca | ggcaggcagc | 1080 |
| aggtctgggg | caggaggggg | gttgtggagt | gggtatccgc | ctgctgaggt | gcagggcaga | 1140 |
| tggagaggct | gcagctgagc | tcctattttc | ataataacag | cagccatgag | ggttgtgtcc | 1200 |
| tgtttcccag | tcctgcccgg | tcccccctcg | gtacctcctg | gtggatacac | tggttcctgt | 1260 |
| aagcagaagt | ggatgagggt | gtctaggtct | gcagtcctgg | caccccagga | tgggggacac | 1320 |
| cagccaagat | acagcaacag | caacaaagcg | cagccatttc | tttctgtttg | cacagctcct | 1380 |
| ctgtctgtcg | ggggctcctg | tctgttgtct | cctataagcc | tcaccacctc | tcctactgct | 1440 |
| tgggcatgca | tctttctccc | cttctataga | tgaggaggtt | aaggtccaga | gaggggtggg | 1500 |
| gaggaacgcc | ggctcacatt | ctccatcccc | tccagatatg | accaggaaca | gacctgtgcc | 1560 |
| aggcctcagc | cttacatcaa | aatgggcctc | cccatgcacc | gtggacctct | gggccctcct | 1620 |
| gtcccagtgg | aggacaggaa | gctgtgaggg | gcactgtcac | ccagggctca | agctggcatt | 1680 |
| cctgaataat | cgctctgcac | caggccacgg | ctaagctcag | tgcgtgatta | agcctcataa | 1740 |
| ccctccaagg | cagttactag | tgtgattccc | attttacaga | tgaggaagat | ggggacagag | 1800 |
| aggtgaataa | ctggccccaa | atcacacacc | atccataatt | cgggctcagg | cacctggctc | 1860 |
| cagtccccaa | actcttgaac | ctggccctag | tgtcactgtt | tctcttgggt | ctcaggcgct | 1920 |
| ggatggggaa | caggaaacct | gggctggact | tgaggcctct | ctgatgctcg | gtgacttcag | 1980 |
| acagttgctc | aacctctctg | ttctcttggg | caaaacatga | taacctttga | cttctgtccc | 2040 |
| ctcccctcac | cccacccgac | cttgatctct | gaagtgttgg | aaggatttaa | tttttcctgc | 2100 |
| actgagtttt | ggagacaggt | caaaaagatg | accaaggcca | aggtggccag | tttcctatag | 2160 |
| aacgcctcta | aaagacctgc | agcaatagca | gcaagaactg | gtattctcga | gaacttgctg | 2220 |
| cgcagcaggc | acttcttggc | attttatgtg | tatttaattt | cacaatagct | ctatgacaaa | 2280 |
| gtccaccttt | ctcatctcca | ggaaactgag | gttcagagag | gttaagtaac | ttgtccaagg | 2340 |
| tcacacagct | aatagcaagt | tgacgtggag | caatctggcc | tcagagcctt | taattttagc | 2400 |
| cacagactga | tgctcccctc | ttcatttagc | caggctgcct | ctgaagtttt | ctgattcaag | 2460 |
| acttctggct | tcagctttgt | acacagagat | gattcaatgt | caggttttgg | agtgaaatct | 2520 |
| gtttaatccc | agacaaaaca | tttaggatta | catctcagtt | ttgtaagcaa | gtagctctgt | 2580 |
| gattttagt | gagttattta | atgctctttg | gggctcaatt | tttctatcta | taaaataggg | 2640 |
| ctaataattt | gcaccttata | gggtaagctt | tgaggacaga | ttagatgata | cggtgcctgt | 2700 |
| aaaacaccag | gtgttagtaa | gtgtggcaat | gatggtgacg | ctgaggctga | tgtttgctta | 2760 |
| gcatagggtt | aggcagctgg | caggcagtaa | acagttggat | aatttaatgg | aaaatttgcc | 2820 |
| aaactcagat | gctgttcact | gctgagcagg | agccccttcc | tgctgaaatg | gtcctgggga | 2880 |
| gtgcagcagg | ctctccggga | agaaatctac | catctctcgg | gcaggagctc | aacctgtgtg | 2940 |
| caggtacagg | gagggcttcc | tcacctggtg | cccactcatg | cattacgtca | gttattcctc | 3000 |
| atccctgtcc | aaaggattct | tttctccatt | gtacagctat | gaagctagtg | ctcaaagaag | 3060 |
| tgaagtcatt | taccccaggc | ccctgccag | taagtgacag | ggcctggtca | cacttgggtt | 3120 |
| tatttattgc | ccagttcaac | aggttgtttg | accataggcg | agattctctt | ccctgcaccc | 3180 |

```
tgccggggttg ctcttggtcc cttattttat gctcccgggt agaaatggtg tgagattagg    3240
cagggagtgg ctcgcttccc tgtccctggc ccgcaaaga gtgctcccac ctgccccgat      3300
cccagaaatg tcaccatgaa gccttcattc ttttggttta aagcttggcc tcagtgtccg     3360
tacaccatgg ggtacttggc cagatggcga ctttctcctc tccagtcgcc ctcccaggca    3420
ctagctttta ggagtgcagg gtgctgcctc tgatagaagg gccaggagag agcaggtttt    3480
ggagtcctga tgttataagg aacagcttgg gaggcataat gaacccaaca tgatgcttga    3540
gaccaatgtc acagcccaat tctgacattc atcatctgag atctgaggac acagctgtct    3600
cagttcatga tctgagtgct gggaaagcca agacttgttc cagctttgtc actgacttgc    3660
tgtatagcct caacaaggcc ctgaccctct ctgggcttca aactcttcac tgtgaaagga    3720
ggaaaccaga gtaggtgatg tgacaccagg aaagatggat gggtgtgggg aatgtgctc     3780
ctcccagctg tcaccccctc gccacccctcc ctgcaccagc ctctccacct cctttgagcc   3840
cagaattccc ctgtctagga gggcacctgt tcatgcctta gccatgggaa ttctccatct    3900
gttttgctac attgaaccca gatgccattc taaccaagaa tcctggctgg gtgcaggggc    3960
tctcgcctgt aaccccagca ctttgggagg ccaaggcagg cggatcaaga ggtcaggagt    4020
tcaagacctg cctggccaac acggtgaaac ctcagctcta ctaaaaatac aaaaattagc    4080
caggcgtggt ggcacacgcc tgtaatccca gctatttggg aagctgagac agaagaattt    4140
cttgaacccg ggaggtggag gtttcagtga gccgagatca cgccactgca ctccaccctg    4200
gcagataaag cgagactctg tctcaaaaaa aacccaaaaa cctatgttag tgtacagagg    4260
gccccagtga agtcttctcc cagccccact ttgcacaact ggggagagtg aggcccagg     4320
accagaggat tcttgctaaa ggccaagtgg atagtgatgg ccctgccagg gctagaagcc    4380
acaacctctg gccctgaggc cactcagcat atttagtgtc cccaccctgc agaggcccaa    4440
ctccctcctg accactgagc cctgtaatga tgggggaatt tccataagcc atgaaggact    4500
gcacaaagtt cagttgggaa gtgaaagaga aattaaaggg agatggaaat atacagcact    4560
aattttagca ccgtctttag ttctaacaac actagctagc tgaagaaaaa tacaaacatg    4620
tattatgtaa tgtgtggtct gttccatttg gattacttag aggcacgagg gccaggagaa    4680
aggtggtgga gagaaaccag cttttgcactt catttgttgc tttattggaa ggaaactttt    4740
aaaagtccaa gggggttgaa gaatctcaat atttgttatt ccagcttttt tttctccagt    4800
ttttcatttc ccaaattcaa ggacaccttt ttctttgtat tttgttaaga tgatggtttt    4860
ggttttgtga ctagtagtta acaatgtggc tgccgggcat attctcctca gctaggacct    4920
cagttttccc atctgtgaag acggcaggtt ctacctaggg ggctgcaggc tggtggtccg    4980
aagcctgggc atatctggag tagaaggatc actgtggggc agggcaggtt ctgtgttgct    5040
gtggatgacg ttgactttga ccattgctcg gcagagcctg ctctcgctgg ttcagccaca    5100
ggccccacca ctcccctattg tctcagcccc gggtatgaaa catgtattcc tcactggcct   5160
atcacctgaa gcctttgaat ttgcaacacc tgccaacccc tccctcaaaa gagttgccct    5220
ctcagatcct tttgatgtaa ggtttggtgt tgagacttat ttcactaaat tctcatacat    5280
aaacatcact ttatgtatga ggcaaaatga ggaccaggga gatgaatgac ttgtcctggc    5340
tcatacacct ggaaagtgac agagtcagat tagatcccag gtctatctga agttaaaaga    5400
ggtgtctttt cacttcccac ctcctccatc tactttaaag cagcacaaac ccctgctttc    5460
aaggagagat gagcgtctct aaagcccctg acagcaagag cccagaactg ggacaccatt    5520
```

-continued

```
agtgacccag acggcaggta agctgactgc aggagcatca gcctattctt gtgtctggga   5580
ccacagagca ttgtggggac agcccgtct cttgggaaaa aaaccctaag ggctgaggat    5640
ccttgtgagt gttgggtggg aacagctccc aggaggttta atcacagccc ctccatgctc   5700
tctagctgtt gccattgtgc aagatgcatt tcccttctgt gcagcagttt ccctggccac   5760
taaatagtgg gattagatag aagccctcca agggcttcca gcttgacatg attcttgatt   5820
ctgatctggc ccgattcctg gataatcgtg ggcaggccca ttcctcttct tgtgcctcat   5880
tttcttcttt tgtaaaacaa tggctgtacc atttgcatct tagggtcatt gcagatgtaa   5940
gtgttgctgt ccagagcctg ggtgcaggac ctagatgtag gattctggtt ctgctacttc   6000
ctcagtgaca ttgaatagct gacctaatct ctctggcttt ggtttcttca tctgtaaaag   6060
aaggatatta gcattagcac ctcacgggat tgttacaaga aagcaatgaa ttaacacatg   6120
tgagcacgga gaacagtgct tggcatatgg taagcactac gtacattttg ctattcttct   6180
gattctttca gtgttactga tgtcggcaag tacttggcac aggctggttt aataatccct   6240
aggcacttcc acgtggtgtc aatccctgat cactgggagt catcatgtgc cttgactcgg   6300
ggcctggccc ccccatctct gtcttgcagg acaatgccgt cttctgtctc gtggggcatc   6360
ctcctgctgg caggcctgtg ctgcctggtc cctgtctccc tggctgagga tccccaggga   6420
gatgctgccc agaagacaga tacatcccac catgatcagg atcacccaac cttcaacaag   6480
atcaccccca acctggctga gttcgccttc agcctatacc gccagctggc acaccagtcc   6540
aacagcacca atatcttctt ctccccagtg agcatcgcta cagcctttgc aatgctctcc   6600
ctggggacca aggctgacac tcacgatgaa atcctggagg gcctgaattt caacctcacg   6660
gagattccgg aggctcagat ccatgaaggc ttccaggaac cctccgtac cctcaaccag   6720
ccagacagcc agctccagct gaccaccggc aatggcctgt tcctcagcga gggcctgaag   6780
ctagtggata agttttttgga ggatgttaaa aagttgtacc actcagaagc cttcactgtc   6840
aacttcgggg acaccgaaga ggccaagaaa cagatcaacg attacgtgga aagggtact    6900
caagggaaaa ttgtggattt ggtcaaggag cttgacagag acacagtttt tgctctggtg   6960
aattacatct tctttaaagg taaggttgct caaccagcct gagctgttcc catagaaaca   7020
agcaaaaata ttctcaaacc atcagttctt gaactctcct tggcaatgca ttatgggcca   7080
tagcaatgct tttcagcgtg gattcttcag ttttctacac acaaacacta aatgttttc    7140
catcattgag taatttgagg aaataataga ttaaactgtc aaaactctg acagctctgc    7200
agaacttttc agagccttta atgtccttgt gtatactgta tatgtagaat atataatgct   7260
tagaactata gaacaaattg taatacactg cataaaggga tagtttcatg gaacatactt    7320
tacacgactc tagtgtccca gaatcagtat cagttttgca atctgaaaga cctgggttca   7380
aatcctgcct ctaacacaat tagcttttga caaaaacaat gcattctacc tctttgaggt   7440
gctaatttct catcttagca tggacaaaat accattcttg ctgtcaggtt tttttaggat   7500
taaacaaatg acaaagactg tggggatggt gtgtggcata cagcaggtga tggactcttc   7560
tgtatctcag gctgccttcc tgcccctgag gggttaaaat gccagggtcc tggggccc    7620
agggcattct aagccagctc ccactgtccc aggaaaacag catagggag gggaggtggg    7680
aggcaaggcc aggggctgct tcctccactc tgaggctccc ttgctcttga ggcaaaggag   7740
ggcagtggag agcagccagg ctgcagtcag cacagctaaa gtcctggctc tgctgtggcc   7800
ttagtggggg cccaggtccc tctccagccc cagtctcctc cttctgtcca atgagaaagc   7860
tgggatcagg ggtccctgag gcccctgtcc actctgcatg cctcgatggt gaagctctgt   7920
```

-continued

```
tggtatggca gaggggaggc tgctcaggca tctgcatttc ccctgccaat ctagaggatg    7980
aggaaagctc tcaggaatag taagcagaat gtttgccctg gatgaataac tgagctgcca    8040
attaacaagg ggcagggagc cttagacaga aggtaccaaa tatgcctgat gctccaacat    8100
tttatttgta atatccaaga caccctcaaa taaacatatg attccaataa aaatgcacag    8160
ccacgatggc atctcttagc ctgacatcgc cacgatgtag aaattctgca tcttcctcta    8220
gttttgaatt atccccacac aatctttttc ggcagcttgg atggtcagtt tcagcacctt    8280
ttacagatga tgaagctgag cctcgaggga tgtgtgtcgt caaggggct cagggcttct     8340 cagggagggg actcatggtt tctttattct gctacactct tccaaacctt cactcacccc    8400
tggtgatgcc caccttcccc tctctccagg caaatgggag agaccctttg aagtcaagga    8460
caccgaggaa gaggacttcc acgtggacca ggtgaccacc gtgaaggtgc ctatgatgaa    8520
gcgtttaggc atgtttaaca tccagcactg taagaagctg tccagctggg tgctgctgat    8580
gaaatacctg ggcaatgcca ccgccatctt cttcctgcct gatgagggga actacagca    8640 cctggaaaat gaactcaccc acgatatcat caccaagttc ctggaaaatg aagacagaag    8700
gtgattcccc aacctgaggg tgaccaagaa gctgcccaca cctcttagcc atgttgggac    8760
tgaggcccat caggactggc cagagggctg aggaggtga accccacatc cctgggtcac     8820
tgctactctg tataaacttg gcttccagaa tgaggccacc actgagttca ggcagcgcca    8880
tccatgctcc atgaggagga cagtacccag gggtgaggag gtaaaggtct cgtccctggg    8940
gacttcccac tccagtgtgg acactgtccc ttcccaatat ccagtgccca gggcagggac    9000
agcagcacca ccacacgttc tggcagaacc aaaaaggaac agatgggctt cctggcaaag    9060
gcagcagtgg agtgtggagt tcaagggtag aatgtccctg gggggacggg ggaagagcct    9120
gtgtggcaag gcccagaaaa gcaaggttcg gaattggaac agccaggcca tgttcgcaga    9180
aggcttgcgt ttctctgtca ctttatcggt gctgttagat tgggtgtcct gtagtaagtg    9240
atacttaaac atgagccaca cattagtgta tgtgtgtgca ttcgtgatta tgcccatgcc    9300
ctgctgatct agttcgtttt gtacactgta aaaccaagat gaaatacaa aaggtgtcgg     9360 gttcataata ggaatcgagg ctggaatttc tctgttccat gccagcacct cctgaggtct    9420
ctgctccagg ggttgagaaa gaacaaagag gctgagaggg taacggatca gagagcccag    9480
agccaagctg cccgctcaca ccagaccctg ctcagggtgg cattgtctcc ccatggaaaa    9540
ccagagagga gcactcagcc tggtgtggtc actcttctct tatccactaa acggttgtca    9600
ctgggcactg ccaccagccc cgtgtttctc tgggtgtagg gccctgggga tgttacaggc    9660
tgggggccag gtgacccaac actacagggc aagatgagac aggcttccag gacacctaga    9720
atatcagagg aggtggcatt tcaagctttt gtgattcatt cgatgttaac attctttgac    9780
tcaatgtaga agagctaaaa gtagaacaaa ccaaagccga gttcccatct tagtgtgggt    9840
ggaggacaca ggagtaagtg gcagaaataa tcagaaaaga aaacacttgc actgtggtgg    9900
gtcccagaag aacaagagga atgctgtgcc atgccttgaa tttctttttct gcacgacagg    9960 tctgccagct tacatttacc caaactgtcc attactggaa cctatgatct gaagagcgtc    10020
ctgggtcaac tggcatcac taaggtcttc agcaatgggg ctgacctctc cggggtcaca     10080
gaggaggcac ccctgaagct ctccaaggtg agatcaccct gacgaccttg ttgcaccctg    10140
gtatctgtag ggaagaatgt gtgggggctg cagctctgtc ctgaggctga ggaaggggcc    10200
gagggaaaca aatgaagacc caggctgagc tcctgaagat gcccgtgatt cactgacacg    10260
```

```
ggacgtggtc aaacagcaaa gccaggcagg ggactgctgt gcagctggca ctttcggggc  10320
ctcccttgag gttgtgtcac tgaccctgaa tttcaactt gcccaagacc ttctagacat   10380
tgggccttga tttatccata ctgacacaga aaggtttggg ctaagttgtt tcaaaggaat  10440
ttctgactcc ttcgatctgt gagatttggt gtctgaatta atgaatgatt tcagctaaag  10500
atgacactta ttttggaaaa ctaaaggcga ccaatgaaca actgcagttc catgaatggc  10560
tgcattatct tggggtctgg gcactgtgaa ggtcactgcc agggtccgtg tcctcaagga  10620
gcttcaagcc gtgtactaga aaggagagag ccctggaggc agacgtggag tgacgatgct  10680
cttccctgtt ctgagttgtg ggtgcacctg agcaggggga gaggcgcttg tcaggaagat  10740
ggacagaggg gagccagccc catcagccaa agccttgagg aggagcaagg cctatgtgac  10800
agggagggag aggatgtgca gggccagggc cgtccagggg gagtgagcgc ttcctgggag  10860
gtgtccacgt gagccttgct cgaggcctgg gatcagcctt acaacgtgtc tctgcttctc  10920
tcccctccag gccgtgcata aggctgtgct gaccatcgac gagaaaggga ctgaagctgc  10980
tggggccatg ttttagagg ccatacccat gtctatcccc cccgaggtca agttcaacaa   11040 acctttgtc ttcttaatga ttgaacaaaa taccaagtct cccctcttca tgggaaaagt    11100
ggtgaatccc acccaaaaat aactgcctct cgctcctcaa cccctcccct ccatccctgg  11160 cccctccct ggatgacatt aaagaagggt tgagctggtc cctgcctgca tgtgactgta   11220
aatccctccc at                                                     11232
```